US010844090B2

(12) United States Patent
Kline et al.

(10) Patent No.: US 10,844,090 B2
(45) Date of Patent: Nov. 24, 2020

(54) HEMIASTERLIN DERIVATIVES FOR CONJUGATION AND THERAPY

(71) Applicant: SUTRO BIOPHARMA, INC., South San Franisco, CA (US)

(72) Inventors: Toni Kline, San Francisco, CA (US); Qun Yin, Palo Alto, CA (US); Krishna Bajjuri, Fremont, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 56 days.

(21) Appl. No.: 15/011,388

(22) Filed: Jan. 29, 2016

(65) Prior Publication Data
US 2016/0257709 A1    Sep. 8, 2016

Related U.S. Application Data

(60) Provisional application No. 62/110,390, filed on Jan. 30, 2015.

(51) Int. Cl.
| | |
|---|---|
| *C07K 5/083* | (2006.01) |
| *C07K 9/00* | (2006.01) |
| *C07K 16/28* | (2006.01) |
| *C07K 16/40* | (2006.01) |
| *C07K 16/30* | (2006.01) |
| *C07K 5/02* | (2006.01) |
| *A61K 47/68* | (2017.01) |
| *C07K 5/065* | (2006.01) |
| *A61K 38/00* | (2006.01) |

(52) U.S. Cl.
CPC ........ *C07K 5/0808* (2013.01); *A61K 47/6817* (2017.08); *C07K 5/0205* (2013.01); *C07K 9/003* (2013.01); *C07K 16/28* (2013.01); *C07K 16/30* (2013.01); *C07K 16/40* (2013.01); *A61K 38/00* (2013.01); *A61K 47/6855* (2017.08); *C07K 5/06078* (2013.01); *C07K 2317/76* (2013.01)

(58) Field of Classification Search
CPC .............. A61K 38/00; A61K 47/48438; A61K 47/48584; C07K 16/28; C07K 16/30; C07K 16/40; C07K 2317/76; C07K 5/0205; C07K 5/06078; C07K 5/0808; C07K 9/003
See application file for complete search history.

(56) References Cited

U.S. PATENT DOCUMENTS

| | | | |
|---|---|---|---|
| 5,661,175 | A | 8/1997 | Kashman |
| 7,390,910 | B2 | 6/2008 | Zask et al. |
| 7,579,323 | B1 | 8/2009 | Andersen |
| 2004/0121965 | A1 | 6/2004 | Greenberger et al. |
| 2005/0171014 | A1 | 8/2005 | Tarasova et al. |
| 2008/0051434 | A1 | 2/2008 | Kowalczyk et al. |
| 2009/0264487 | A1 | 10/2009 | Andersen et al. |
| 2014/0315954 | A1 | 10/2014 | Winters et al. |
| 2016/0038606 | A1 | 2/2016 | Winters et al. |
| 2017/0246310 | A1 | 8/2017 | Rich et al. |

OTHER PUBLICATIONS

ThermoFisher Scientific, Amine-reactive crosslinker chemistry, published online Apr. 2012.*
Bai et al., "Interactions of the Sponge-Derived Antimitotic Tripeptide Hemiasterlin with Tubulin: Comparison with Dolastatin 10 and Cryptophycin 1", Biochemistry 1999, vol. 38, pp. 14302-14310.
Doronina et al., "Development of potent monoclonal antibody auristatin conjugates for cancer therapy," Nature Biotechnology, Jul. 2003, vol. 21, No. 7, pp. 778-784; and Erratum, Nature Biotechnology, Aug. 2003, vol. 21, No. 8, p. 941.
Hadaschik et al., "Targeting prostate cancer with HTI-286, a synthetic analog of the marine sponge product hemiasterlin", Int. J. Cancer, (2008), vol. 122, pp. 2368-2376.
Hsu et al., "Development of hemiasterlin derivatives as potential anticancer agents that inhibit tubulin polymerization and synergize with a stilbene tubulin inhibitor", Invest New Drugs (2012), vol. 30, pp. 1379-1388.
Kuznetsov et al., "Tubulin-based antimitotic mechanism of E7974, a novel analogue of the marine sponge natural product hemiasterlin", Molecular Cancer Therapeutics, Oct. 2009, vol. 8(10), pp. 2852-2860.
Maderna et al., "Discovery of cytotoxic Dolastatin 10 analogs with N-terminal modifications," Journal of Medicinal Chemistry, DOI: 10.1021/jm501649k, Nov. 28, 2014, 67 pages.

(Continued)

*Primary Examiner* — James H Alstrum-Acevedo
*Assistant Examiner* — Erinne R Dabkowski
(74) *Attorney, Agent, or Firm* — Squire Patton Boggs (US) LLP

(57) ABSTRACT

Provided herein are hemiasterlin derivatives, conjugates thereof, compositions comprising the derivatives or conjugates thereof, methods of producing the derivatives and conjugates thereof, and methods of using the derivatives, conjugates, and compositions for the treatment of cell proliferation. The derivatives, conjugates, and compositions are useful in methods of treatment and prevention of cell proliferation and cancer, methods of detection of cell proliferation and cancer, and methods of diagnosis of cell proliferation and cancer. In an embodiment, the hemiasterlin derivatives are according to Formula 1000:

(1000)

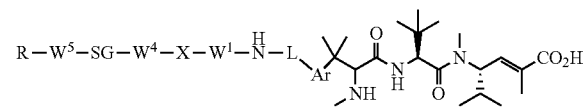

or a pharmaceutically acceptable salt, solvate, or tautomer thereof, wherein Ar, L, $W^1$, $W^4$, $W^5$, SG, and R are as described herein.

16 Claims, 4 Drawing Sheets

(56) References Cited

OTHER PUBLICATIONS

Nieman et al., "Synthesis and Antimitotic/Cytotoxic Activity of Hemiasterlin Analogues", J. Nat. Prod. 2003, vol. 66, pp. 183-199.
Qie et al., "Hemiasterlin Analogues with Unnatural Amino Acids at the N-Terminal and Their Inhibitory Activity on Tumor Cells", Int J Pept Res Ther (2009), vol. 15, pp. 187-194.
Zask et al. "Hybrids of the Hemiasterlin Analogue Taltobulin and the Dolastatins Are Potent Antimicrotubule Agents," *J. Am. Chem. Soc.*, 2005, vol. 127, pp. 17667-17671.
Zask et al. "D-piece modifications of the hemiasterlin analog HTI-286 produce potent tubulin inhibitors," *Bioorg Med Chem Lett* 14, (16), 2004, 4353-4358.
Lassalas et al., "Structure Property Relationships of Carboxylic Acid Isosteres", Journal of Medicinal Chemistry, 2016, vol. 59, pp. 3183-3203.
Lassila eat al., "Toxicity of Carboxylic Acid-Containing Drugs: The Role of Acyl Migration and CoA Conjugation Investigated", Chemical Research in Toxicology, 2015, vol. 28, pp. 2292-2303.
Uyar et al., "Antitumor activity of STRO-002, a novel anti-folate receptor-α(FolRα) antibody drug conjugate (ADC), in patient-derived xenograft (PDX) models and preliminary Phase I dose escalation safety outcomes in patients with ovarian carcinoma (OC)", 1 page.
Uyar et al., AACR-NCI-EORTC Molecular Targets and Cancer Therapeutics Conference 2019—STRO-002—Abstract, Oct. 16, 2019; 2 pages.
Coleman et al. "Cytotoxic Peptides from the Marine Sponge *Cymbastela* sp.," *Tetrahedron*, 1995, vol. 51, No. 39, pp. 10653-10662.
Gamble et al., "Cytotoxic and Tubulin-Interactive Hemiasterlins from *Auletta* sp. And *iphonochalina* spp. Sponges," Bioorganic & Medicinal Chemistry 7, 1999, pp. 1611-1615.
Loganzo et al. "HTI-286, a Synthetic Analogue of the Tripeptide Hemiasterlin, is a Potent Antimicrotubule Agent that Circumvents P-Glycoprotein-mediated Resistance in Vitro and in Vivo1," Cancer Research, Apr. 15, 2003, vol. 63, pp. 1838-1845.
Ravi et al., "Structure-Based Identification of the Binding Site for the Hemiasterlin Analogue HTI-286 on Tubulin," *Biochemistry*, 2005, vol. 44, No. 48, pp. 15871-15879.
Reddy et al. "Asymmetric Synthesis of the Highly Methylated Tryptophan Portion of the Hemiasterlin Tripeptides," *Organic Letters*, 2002, vol. 4, No. 5, pp. 695-697.
Talpir et al., "Hemiasterlin and Geodiamolide TA; Two New Cytotoxic Peptides from the Marine Sponge *Hemiasterella minor* (Kirkpatrick)," *Tetrahedron Letter*, 1994, vol. 35, No. 25, pp. 4453-4456.
Thi et al. "Synthesis of new bioisosteric hemiasterlin analogues with extremely high cytotoxicity," *Bioorganic & Medicinal Chemistry Letters 2014*, vol. 24, No. 22, pp. 5216-5218.
Vedejs et al. "A Total Synthesis of ( )-Hemiasterlin Using N-Bts Methodology," J. Org. Chem., 2001, vol. 66, pp. 7355-7364.
Yamashita et al. "Synthesis and activity of novel analogs of hemiasterlin as inhibitors of tubulin polymerization: modification of the A segment," *Bioorganic & Medicinal Chemistry Letters 14*, 2004, pp. 5317-5322.
Zask et al. "Hybrids of the Hemiasterlin Analogue Taltobulin and the Dolastatins Are Potent Antimicrotubule Agents," *J. Am. Chem. Soc.*, 2005, vol. 127, pp. 17667-1767.
Zask et al. "Synthesis and Biological Activity of Analogues of the Antimicrotubule Agent *N*,β,β-Trimethyl-L-phenylalanyl-*N*$^1$-[(1*S*,2*E*)-3-carboxy-1-isopropylbut-2-enyl]-*N*$^1$,3-dimethyl-L-valinamide (HTI-286)," *J. Med. Chem.*, 2004, vol. 47, pp. 4774-4786.
English translation of a first office action of Chinese Application No. 201680007822.X dated Jun. 3, 2020; 14 pages.
Yuan Ying-jin, "Modern pharmaceutical processes", Chemical Industry Press, vol. 2, 1st Edition, Jan. 31, 2006, pp. 165-168; together with an English translation.

* cited by examiner

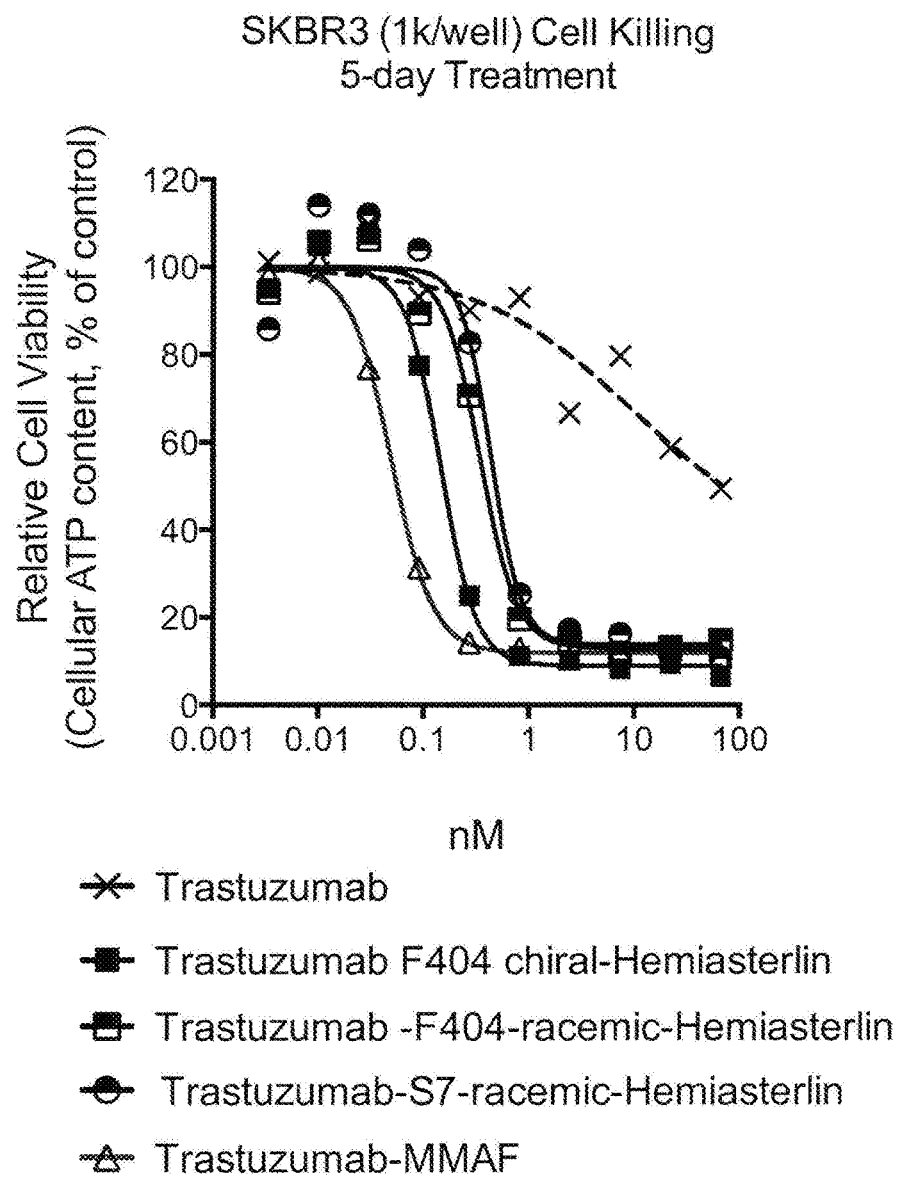

Fig. 2a
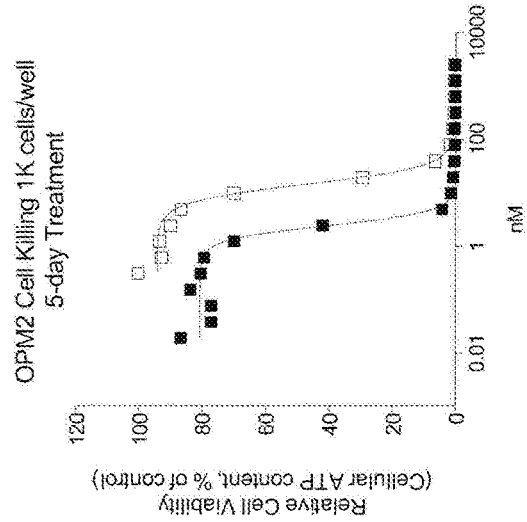
(c)
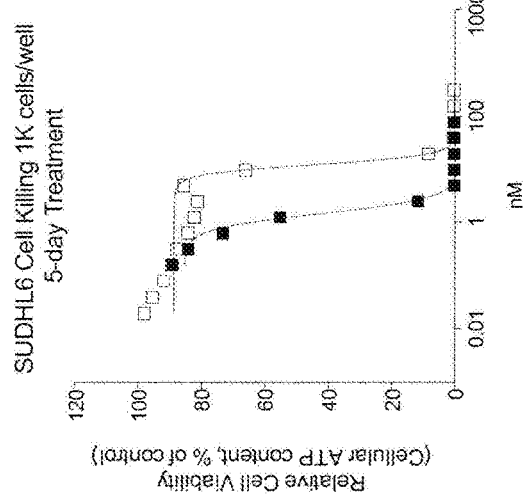
(b)
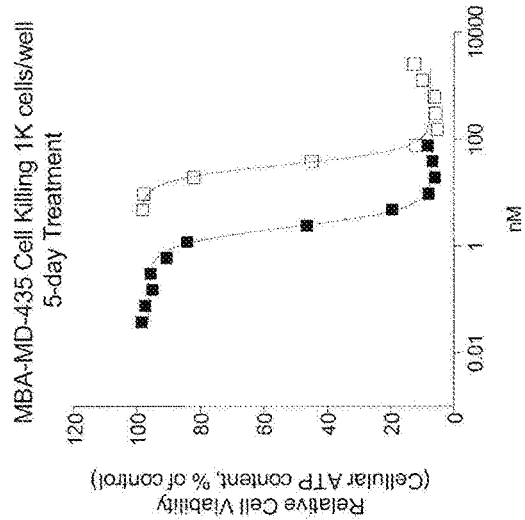
(a)

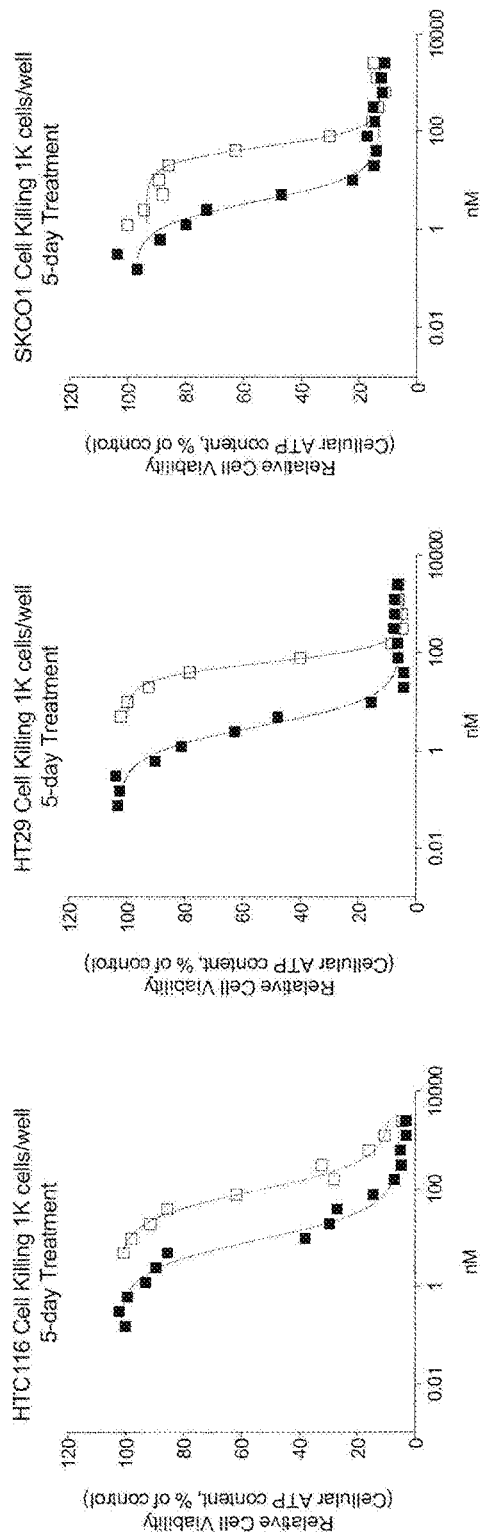

HEMIASTERLIN DERIVATIVES FOR CONJUGATION AND THERAPY

FIELD

Provided herein are hemiasterlin derivatives, conjugates thereof, compositions comprising the derivatives or conjugates thereof, methods of producing the derivatives and conjugates thereof, and methods of using the derivatives, conjugates, and compositions for the treatment of cell proliferation. The derivatives, conjugates, and compositions are useful in methods of treatment and prevention of cell proliferation and cancer, methods of detection of cell proliferation and cancer, and methods of diagnosis of cell proliferation and cancer.

BACKGROUND

Hemiasterlins are a class of tripeptides modified from the original natural product hemiasterlin. Hemiasterlin is isolated from marine sponges *Cymbastela* sp., *Hemiasterella minor*, *Siphonochalina* sp., and *Auletta* sp. (Talpir et al., *Tetrahedron Letters*, vol. 35, no. 25, pp. 4453-4456, 1994).

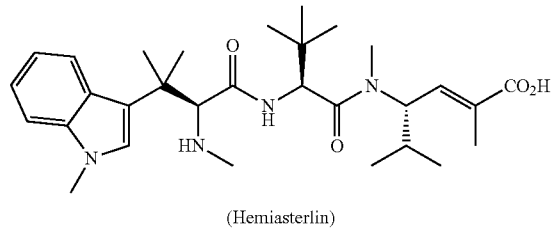 [SMILES: CN[C@H](C(=O)N[C@H](C(=O)N(C)[C@H](/C=C(\C)C(=O)O)C(C)C)C(C)(C)C)C(C)(C)c1cn(C)c2ccccc12]

(Hemiasterlin)

Hemiasterlins are pseudopeptides which are inhibitors of tubulin polymerization, sharing an antimitotic mechanism of action with dolastatins and cryptophycins. Noncompetitive binding at the vinblastine site on tubulin has been demonstrated. Hemiasterlins are in general poor permeability glycoprotein (pGP) substrates, rendering them effective against tumors that overexpress pGP as a resistance mechanism. (Loganzo et al., *Cancer Research*, vol 63, pp. 1838-1845, 15 Apr. 2003).

Extensive modification of natural hemiasterlin demonstrated key features contributing to the nanomolar activity of this class against a wide variety of tumor cell lines. Two derivatives, E7974, an N-terminal piperidine derivative developed at Eisai, and HTI-286, an N-terminal phenyl developed at Wyeth, entered Phase I trials. Encouraging results were presented in 2007 for E7974. (Madajewicz et al., "A phase I trial of E7974 administered on days 1 and 15 of a 28-day cycle in patients with solid malignancies," presented at American Society of Clinical Oncology Annual Meeting; Jun. 1-5, 2007; Chicago, Ill.; and Zojwalla et al., "A phase I trial of E7974 administered on days 1, 8, and 15 of a 28-day cycle in patients with solid malignancies," presented at American Society of Clinical Oncology Annual Meeting; Jun. 1-5, 2007; Chicago, Ill.; both summarized in Rocha-Lima et al., *Cancer*, Sep. 1, 2012 pp. 4262-4270). However, no results have been reported for HTI-286 to date.

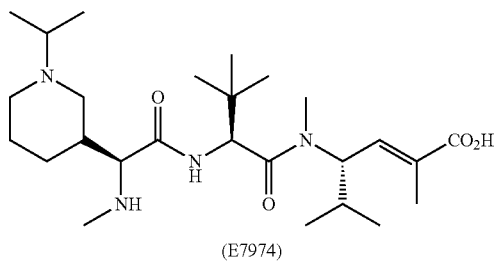

(E7974)

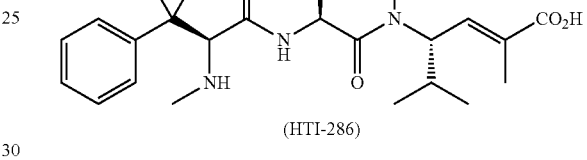

(HTI-286)

In addition, conjugation of HTI-286 at the C-terminus to a gastrin decapeptide VLALAEEEAYGWNleDF-NH$_2$ for tumor targeting is described in Tarsova et al., United States patent application publication number US 2005/0171014 A1. Reported activity, however, was very weak.

SUMMARY

Provided herein are hemiasterlin derivatives, conjugates thereof, compositions comprising the derivatives or conjugates thereof, methods of producing the derivatives and conjugates thereof, and methods of using the derivatives, conjugates, and compositions for the treatment of cell proliferation. The derivatives, conjugates, and compositions are useful in methods of treatment and prevention of cell proliferation and cancer, methods of detection of cell proliferation and cancer, and methods of diagnosis of cell proliferation and cancer.

In one aspect, provided herein is a compound according to Formula 1000:

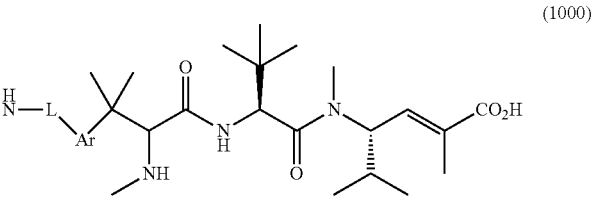

(1000)

or a pharmaceutically acceptable salt, solvate, stereoisomer, or tautomer thereof, wherein:

Ar is a divalent five- or six-membered, substituted or unsubstituted, monocyclic aryl or heteroaryl ring or a divalent eight-, nine- or ten-membered, substituted or unsubstituted, fused bicyclic aryl or heteroaryl ring;

L is absent or —CH$_2$—;

X is

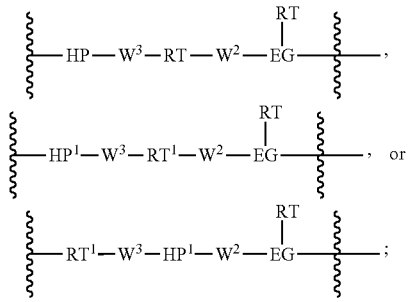

$W^1$, $W^2$, $W^3$, $W^4$, and $W^5$ are each independently a single bond, absent, or a divalent attaching group;

EG is absent or an eliminator group;

each RT is a release trigger group, in the backbone of Formula 1000 or bonded to EG, wherein each RT is optional;

$RT^1$ is a release trigger group, or a cleavable linker, or $RT^1$ is absent;

HP is a single bond, absent, or a divalent hydrophilic group;

$HP^1$ is a single bond, absent, a divalent hydrophilic group, or

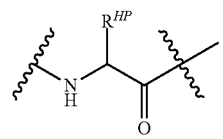

where $R^{HP}$ is a monovalent hydrophilic group;

SG is a single bond, absent, or a divalent spacer group; and

R is hydrogen, a terminal conjugating group, or a divalent residue of a terminal conjugating group;

or, in the alternative, $W^1$, $W^2$, $W^3$, $W^4$, $W^5$, EG, RT, HP, SG, and R combine to form —H.

In one aspect, provided herein is a conjugate comprising a compound described herein (e.g., a compound according to any of Formulas 1000-1000b, 1001-1001b, 1002-1002b, and I-XIXb-2, 101-111b, or 1-8b) linked to a second compound.

In an aspect, provided herein is a pharmaceutical composition comprising:

a compound (e.g., a compound according to any of Formulas 1000-1000b, 1001-1001b, 1002-1002b, and I-XIXb-2, 101-111b, or 1-8b) or conjugate (e.g., a conjugate according to any of Formulas C1-C17b, E1, F1-F17b, and G1-G17b) as described herein; and a pharmaceutically acceptable excipient, carrier, or diluent.

In an aspect, provided herein is a method of inhibiting tubulin polymerization in a subject in need thereof comprising administering an effective amount of a compound (e.g., a compound according to any of Formulas 1000-1000b, 1001-1001b, 1002-1002b, and I-XIXb-2, 101-111b, or 1-8b), conjugate (e.g., a conjugate according to any of Formulas C1-C17b, E1, F1-F17b, and G1-G17b), or composition comprising a compound or conjugate, as described herein, to the subject.

In an aspect, provided herein is a method of treating cell proliferation or cancer in a subject in need thereof comprising administering an effective amount of a compound (e.g., a compound according to any of Formulas 1000-1000b, 1001-1001b, 1002-1002b, and I-XIXb-2, 101-111b, or 1-8b), conjugate (e.g., a conjugate according to any of Formulas C1-C17b, E1, F1-F17b, and G1-G17b), or composition comprising a compound or conjugate, as described herein, to the subject.

In an aspect, provided herein is a method of producing a conjugate, comprising contacting a compound described herein (e.g., a compound according to any of Formulas 1000-1000b, 1001-1001b, 1002-1002b, and I-XIXb-2 or 101-111b) with a second compound under conditions suitable for conjugating the second compound with the compound described herein (e.g., a compound according to any of Formulas 1000-1000b, 1001-1001b, 1002-1002b, and I-XIXb-2 or 101-111b); wherein the second compound comprises a modified amino acid comprising an alkyne, strained alkene, tetrazine, thiol, maleimide, carbonyl, oxyamine, or azide.

BRIEF DESCRIPTION OF THE FIGURES

FIG. 1 provides results of a cell killing assay described in detail herein. Racemic [R/S,S,S] Compound 1 is evaluated as a conjugate on the trastuzumab heavy chain at F404 and also on the light chain at S7. All other conjugates in FIG. 1 are on the trastuzumab heavy chain at F404. The relative cell viability of SKBR3 cells is plotted against concentration for trastuzumab (exes), trastuzumab F404 [S,S,S] Compound 1 conjugate (filled squares), trastuzumab F404 racemic [R/S,S,S] Compound 1 conjugate (split squares), trastuzumab S7 racemic [R/S,S,S] Compound 1 conjugate (split circles), and a trastuzumab auristatin (MMAF) conjugate (open triangles).

FIG. 2a provides results of a cell killing assay described in detail herein. In FIG. 2a relative cell viability is plotted against concentration of [S,S,S] Compound 1 (filled squares) and [R,S,S] Compound 1 (open squares) for SKBR3 cells in panel (a), MDA-MB-453 cells in panel (b), and MDA-MB-468 cells in panel (c).

FIG. 2b provides results of a cell killing assay described in detail herein. In FIG. 2b relative cell viability is plotted against concentration of [S,S,S] Compound 1 (filled squares) and [R,S,S] Compound 1 (open squares) for HTC116 cells in panel (a), HT29 cells in panel (b), and SKCO1 cells in panel (c).

In FIG. 2c relative cell viability is plotted against concentration of [S,S,S] Compound 1 (filled squares) and [R,S,S] Compound 1 (open squares) for MDA-MB-435 cells in panel (a), SUDHL6 cells in panel (b), and OMP2 cells in panel (c).

DESCRIPTION OF EXEMPLARY EMBODIMENTS

Figure 2C:
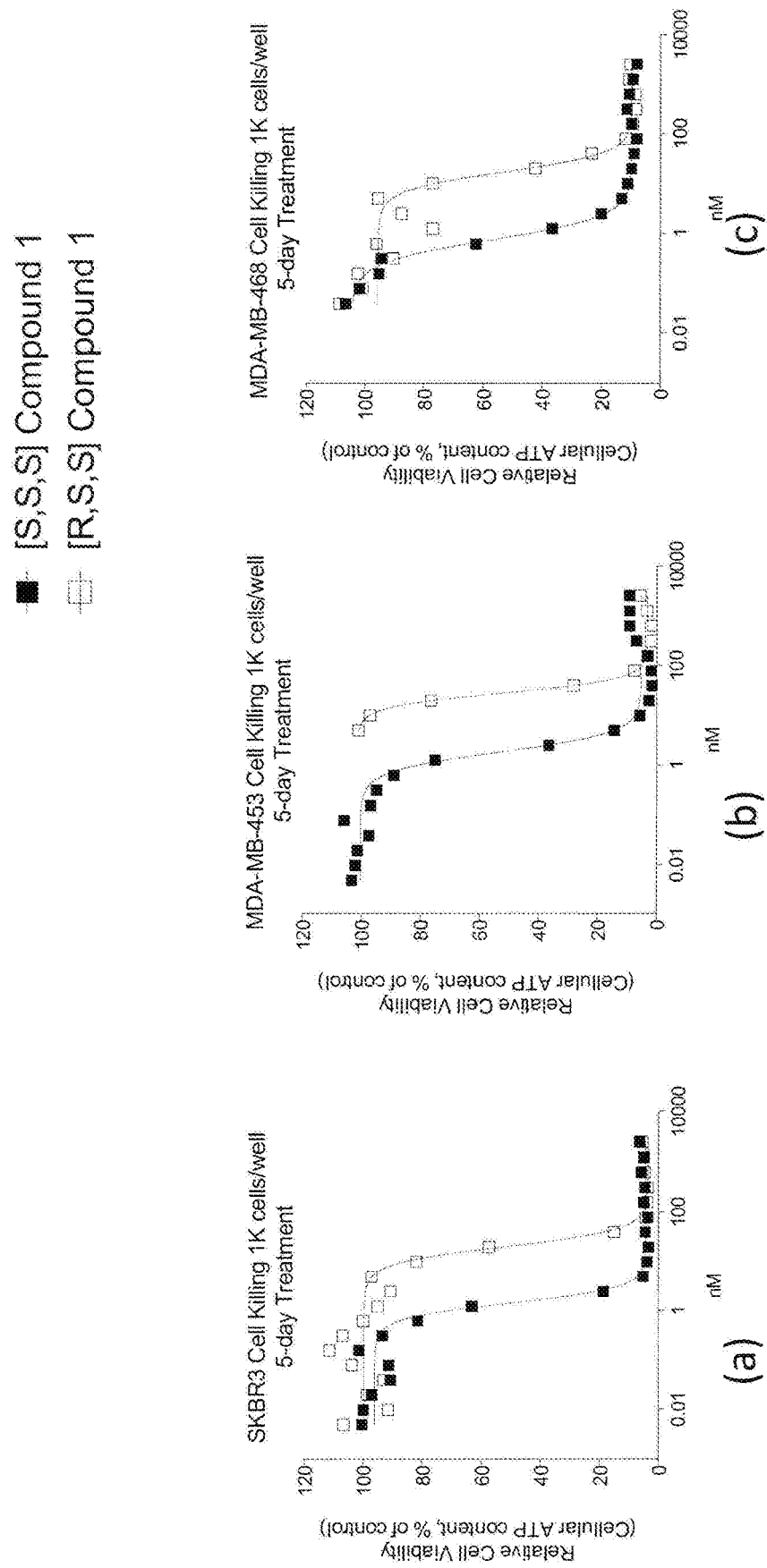
FIG. 2c provides results of a cell killing assay described in detail herein.

Provided herein are compounds (e.g., according to any of Formulas 1000-1000b, 1001-1001b, 1002-1002b, and I-XIXb-2, 101-111b, or 1-8b), conjugates thereof (e.g., according to any of Formulas C1-C17b, E1, F1-F17b, and G1-G17b), compositions comprising the compounds or conjugates thereof, methods of producing the compounds and conjugates thereof, and methods of using the compounds, conjugates, and compositions. The compounds, conjugates, and compositions are useful in methods of treatment and prevention of cell proliferation and cancer, methods of detection of cell proliferation and cancer, and methods of diagnosis of cell proliferation and cancer.

DEFINITIONS

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise. Unless specified otherwise, where a term is defined as being unsubstituted or substituted, the groups in the list of substituents are unsubstituted. For example, an alkyl group can be substituted with a cycloalkyl group and the cycloalkyl group is not further substituted.

The term "alkyl," as used herein, unless otherwise specified, refers to a saturated straight or branched hydrocarbon which can be substituted with halo groups. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group is, for example, methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, or 2,3-dimethylbutyl. The term includes both substituted and unsubstituted alkyl groups, including halogenated alkyl groups. In certain embodiments, the alkyl group is a fluorinated alkyl group. In certain embodiments, the alkyl group can be substituted with at least one (in another example with 1, 2, 3, 4, or 5) halogen (fluoro, chloro, bromo or iodo), oxo, epoxy, hydroxyl, alkylcarbonyl, cycloalkylcarbonyl, arylcarbonyl, cycloalkyl, aralkyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g. alkylamino, dialkylamino, arylamino, etc.), alkoxy, aryloxy, nitro, cyano, sulfonic acid, sulfate, sulfonate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl," as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties.

The term "upper alkyl," as used herein, and unless otherwise specified, refers to a saturated straight or branched hydrocarbon having seven to thirty carbon atoms, i.e., $C_7$ to $C_{30}$ alkyl. In certain embodiments, the upper alkyl group is a primary, secondary, or tertiary hydrocarbon. The term includes both substituted and unsubstituted moieties.

The term "alkylcarbonyl" refers to the group —C(O)(alkyl) where alkyl is as defined herein.

The term "alkylsulfanyl" refers to the group —S(alkyl) where alkyl is as defined herein.

The term "carboxylene" refers to a —C(O)O— or —OC(O)— group.

The term "cycloalkylsulfanyl" refers to the group —S(cycloalkyl) where cycloalkyl is as defined herein.

The term "arylsulfanyl" refers to the group —S(aryl) where aryl is as defined herein.

The term "alkylsulfonyl" refers to the group —S(O)$_2$(alkyl) where alkyl is as defined herein.

The term "cycloalkylsulfonyl" refers to the group —S(O)$_2$(cycloalkyl) where cycloalkyl is as defined herein.

The term "arylsulfonyl" refers to the group —S(O)$_2$(aryl) where aryl is as defined herein.

The term "cycloalkyl," as used herein, unless otherwise specified, refers to a saturated monocyclic or polycyclic hydrocarbon. In certain embodiments, cycloalkyl includes fused, bridged, and spiro ring systems. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is, for example, cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl or adamantyl. The term includes both substituted and unsubstituted cycloalkyl groups, including halogenated cycloalkyl groups. In certain embodiments, the cycloalkyl group is a fluorinated cycloalkyl group. In certain embodiments, the cycloalkyl group can be substituted with at least one (in another example with 1, 2, 3, 4, or 5) halogen (fluoro, chloro, bromo or iodo), oxo, epoxy, hydroxyl, alkylcarbonyl, cycloalkylcarbonyl, arylcarbonyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g alkylamino, dialkylamino, arylamino, etc.), alkoxy, aryloxy, nitro, cyano, sulfonic acid, sulfate, sulfonate, phosphonic acid, phosphate, or phosphonate, either unprotected, or protected as necessary.

The term "cycloalkylalkyl" refers to an alkyl group as defined herein substituted with at least one (in some embodiments, one or two) cycloalkyl groups as defined herein.

The term "cycloalkylcarbonyl" refers to the group —C(O)(cycloalkyl) where cycloalkyl is as defined herein.

"Alkylene" refers to divalent saturated aliphatic hydrocarbon groups, including those having from one to eleven carbon atoms which can be straight-chained or branched. In certain embodiments, the alkylene group contains 1 to 10 carbon atoms. The term includes both substituted and unsubstituted moieties. In certain embodiments, alkylene is, for example, methylene (—CH$_2$—), ethylene (—CH$_2$CH$_2$—), the propylene isomers (e.g., —CH$_2$CH$_2$CH$_2$— and —CH(CH$_3$)CH$_2$—) and the like. The term includes halogenated alkylene groups. In certain embodiments, the alkylene group is a fluorinated alkylene group. In certain embodiments, the alkylene group can be substituted with at least one (in another example with 1, 2, 3, 4, or 5) halogen (fluoro, chloro, bromo or iodo), oxo, epoxy, hydroxyl, alkylcarbonyl, cycloalkylcarbonyl, arylcarbonyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g. alkylamino, dialkylamino, arylamino, etc.), alkylaryl, alkoxy, aryloxy, nitro, cyano, sulfonic acid, sulfate, sulfonate, phosphonic acid, phosphate, and phosphonate, either unprotected, or protected as necessary.

"Alkenyl" refers to monovalent olefinically unsaturated hydrocarbon groups, in certain embodiments, having up to about 11 carbon atoms, including from 2 to 8 carbon atoms, or from 2 to 6 carbon atoms, which can be straight-chained or branched and having at least 1, including from 1 to 2, site of olefinic unsaturation. The term includes both substituted and unsubstituted moieties. In certain embodiments, alkenyl is, for example, ethenyl (i.e., vinyl, or —CH=CH$_2$), n-propenyl (—CH$_2$CH=CH$_2$), isopropenyl (—C(CH$_3$)=CH$_2$), and the like. The term includes halogenated alkenyl groups. In certain embodiments, the alkenyl group is a fluorinated alkenyl group. In certain embodiments, the alkenyl group can be substituted with at least one (in another example with 1, 2, 3, 4, or 5) halogen (fluoro, chloro, bromo or iodo), oxo, epoxy, hydroxyl, alkylcarbonyl, cycloalkylcarbonyl, arylcarbonyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g. alkylamino, dialkylamino, arylamino, etc.), alkoxy, aryloxy, nitro, cyano, sulfonic acid, sulfate, sulfonate, phosphonic acid, phosphate, or phosphonate, either unprotected, or protected as necessary.

The term "cycloalkenyl," as used herein, unless otherwise specified, refers to an unsaturated (but not aromatic) cyclic hydrocarbon. In certain embodiments, cycloalkenyl refers to mono- or multicyclic ring systems that include at least one double bond. In certain embodiments, cycloalkyl includes fused, bridged, and spiro ring systems. In certain embodiments, the cycloalkyl group includes at least three carbon atoms, including three to ten carbon atoms, i.e., $C_3$ to $C_{10}$ cycloalkyl. In some embodiments, the cycloalkenyl has from 3 to 10 ($C_{3-10}$), or from 4 to 7 ($C_{4-7}$) carbon atoms. The term includes both substituted and unsubstituted cycloalkenyl groups, including halogenated cycloalkenyl groups. In certain embodiments, the cycloalkenyl group is a fluorinated cycloalkenyl group. In certain embodiments, the cycloalkenyl group can be substituted with at least one (in another example with 1, 2, 3, 4, or 5) halogen (fluoro, chloro, bromo or iodo), oxo, epoxy, hydroxyl, alkylcarbonyl, cycloalkylcarbonyl, arylcarbonyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g. alkylamino, dialkylamino, arylamino, etc.), alkoxy, aryloxy, nitro, cyano, sulfonic acid, sulfate, sulfonate, phosphonic acid, phosphate, or phosphonate, either unprotected, or protected as necessary.

"Alkenylene" refers to divalent olefinically unsaturated hydrocarbon groups, in certain embodiments, having up to about 11 carbon atoms or from 2 to 6 carbon atoms which can be straight-chained or branched and having at least 1 or from 1 to 2 sites of olefinic unsaturation. In certain embodiments, alkenylene is, for example, ethenylene (—CH=CH—), the propenylene isomers (e.g., —CH=CHCH$_2$— and —C(CH$_3$)=CH— and —CH=C (CH$_3$)—) and the like. The term includes both substituted and unsubstituted alkenylene groups, including halogenated alkenylene groups. In certain embodiments, the alkenylene group is a fluorinated alkenylene group. Non-limiting examples of moieties with which the alkenylene group can be substituted with at least one (in another example with 1, 2, 3, 4, or 5) halogen (fluoro, chloro, bromo or iodo), oxo, epoxy, hydroxyl, alkylcarbonyl, cycloalkylcarbonyl, arylcarbonyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g. alkylamino, dialkylamino, arylamino, etc.), alkoxy, aryloxy, nitro, cyano, sulfonic acid, sulfate, sulfonate, phosphonic acid, phosphate, or phosphonate, either unprotected, or protected as necessary.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. In certain embodiments, alkynyl is, for example, acetylenic, ethynyl (—C≡CH), propargyl (—CH$_2$C≡CH), and the like. The term includes both substituted and unsubstituted alkynyl groups, including halogenated alkynyl groups. In certain embodiments, the alkynyl group is a fluorinated alkynyl group. In certain embodiments, the alkynyl group can be substituted with at least one (in another example with 1, 2, 3, 4, or 5) halogen (fluoro, chloro, bromo or iodo), oxo, epoxy, hydroxyl, alkylcarbonyl, cycloalkylcarbonyl, arylcarbonyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g. alkylamino, dialkylamino, arylamino, etc.), alkoxy, aryloxy, nitro, cyano, sulfonic acid, sulfate, sulfonate, phosphonic acid, phosphate, or phosphonate, either unprotected, or protected as necessary.

The term "aryl," as used herein, and unless otherwise specified, refers to a monovalent six- to fourteen-membered, mono-, bi-, or tri-carbocyclic ring, wherein the monocyclic ring is aromatic and at least one of the rings in the bicyclic and tricyclic ring is aromatic. The aryl group can be bonded to the rest of the molecule through any carbon in the ring system. In an embodiment, an aryl group is a $C_6$-$C_{12}$ aryl group. In an embodiment, an aryl group is phenyl, indanyl, or naphthyl. The term includes both substituted and unsubstituted moieties. In certain embodiments, an aryl group can be substituted with one or more (for example 1, 2, 3, 4, or 5) moieties independently selected from the group halogen (fluoro, chloro, bromo or iodo), alkyl, haloalkyl, hydroxyl, alkylcarbonyl, cycloalkylcarbonyl, arylcarbonyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g. alkylamino, dialkylamino, arylamino, etc.), alkoxy, aryloxy, nitro, cyano, sulfonic acid, sulfate, sulfonate, phosphonic acid, phosphate, and phosphonate, either unprotected, or protected as necessary, as known to those skilled in the art, for example, as taught in Greene, et al., *Protective Groups in Organic Synthesis*, John Wiley and Sons, Second Edition, 1991.

The term "arylcarbonyl" refers to the group —C(O)(aryl) where aryl is as defined herein.

The term "aryloxy" refers to the group —OR' where R' is aryl, as defined herein.

The term "aryloxyalkyl" refers to an alkyl group as defined herein substituted with at least one (in some embodiments one or two) aryloxy groups as defined herein.

"Alkoxy" and "alkoxyl" refer to the group —OR' where R' is alkyl or cycloalkyl as defined herein. In certain embodiments, alkoxy and alkoxyl groups include, by way of example, methoxy, ethoxy, n-propoxy, isopropoxy, cyclopropoxy, n-butoxy, tert-butoxy, sec-butoxy, n-pentoxy, n-hexoxy, 1,2-dimethylbutoxy, and the like.

The term "alkoxyalkyl" refers to an alkyl group substituted with at least one (in another embodiment, one or two) alkoxy groups as defined herein.

"Alkoxycarbonyl" refers to a radical —C(O)-alkoxy where alkoxy is as defined herein.

"Alkoxycarbonylalkyl" refers to an alkyl group substituted with at least one, in another example 1 or 2, alkoxycarbonyl groups, as defined herein.

"Amino" refers to the group —NR$^{1'}$R$^{2'}$ or —NR$^{1'}$—, wherein R$^{1'}$ and R$^{2'}$ are independently hydrogen, alkyl, alkenyl, alkynyl, cycloalkyl, cycloalkenyl, heterocyclic, aryl, or heteroaryl, each of which is as defined herein. In an embodiment, "Amino" is —NH$_2$ or —NH—.

"Carboxyl" or "carboxy" refers to the radical —C(O)OH.

The term "alkylamino" or "arylamino" refers to an amino group that has one alkyl or aryl substituent, respectively, e.g. —NHCH$_3$, and —NH(phenyl). In certain embodiments, the alkyl substituent is lower alkyl. In another embodiment, the alkyl or lower alkyl is unsubstituted.

The term "dialkylamino" refers to an amino group that has two alkyl substituents, e.g. —N(CH$_3$)$_2$. In certain embodiments, the alkyl substituent is lower alkyl. In another embodiment, the alkyl or lower alkyl is unsubstituted.

The term "diarylamino" refers to an amino group that has two aryl substituents.

"Halogen" or "halo" refers to chloro, bromo, fluoro, or iodo.

"Thioalkoxy" refers to the group —SR' where R' is alkyl or cycloalkyl.

The term "heterocyclo" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N and the remaining ring atoms are carbon atoms and where the multicyclic ring system further comprises a carbocyclic or heterocyclic, aromatic or nonaromatic ring. In certain embodiments, the heterocyclo or heterocyclic group has from 3 to 20, from 3 to 15, from 3 to 10, from 3 to 8, from 4 to 7, or from 5 to 6 ring atoms. Heterocyclo groups are bonded to the rest of the molecule through a non-aromatic ring. In certain embodiments, the heterocyclo is a monocyclic, bicyclic, tricyclic, or tetracyclic ring system, which may include a fused, spirocyclic, or bridged ring system, and in which the nitrogen or sulfur atoms may be optionally oxidized, the nitrogen atoms may be optionally quaternized, and some rings may be partially or fully saturated, or aromatic. The heterocyclo may be attached to the main structure at any heteroatom or carbon atom of the non-aromatic ring which results in the creation of a stable compound. In certain embodiments, heterocyclic is azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, O-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein. In certain embodiments, the heterocyclic group can be substituted with at least one (in another example with 1, 2, 3, 4, or 5) halogen (fluoro, chloro, bromo or iodo), oxo, epoxy, hydroxyl, alkylcarbonyl, cycloalkylcarbonyl, arylcarbonyl, alkoxycarbonyl, alkoxycarbonylalkyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g., alkylamino, dialkylamino, arylamino, etc.), alkoxy, aryloxy, nitro, cyano, sulfonic acid, sulfate, sulfonate, phosphonic acid, phosphate, or phosphonate, either unprotected, or protected as necessary.

The term "heteroaryl" refers to a monovalent monocyclic aromatic group and/or multicyclic group that contains at least one aromatic ring, wherein the monocyclic ring contains one or more heteroatoms independently selected from O, S and N in the ring and where the multicyclic ring system comprises at least one aromatic ring and further comprises a carbocyclic or heterocyclic, aromatic or nonaromatic ring and where one or more of the ring atoms in the multicyclic ring system is a heteroatom independently selected from O, S and N. Heteroaryl groups are bonded to the rest of the molecule through an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl and triazolyl. In certain embodiments, bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In certain embodiments, tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl and xanthenyl. In certain embodiments, the heteroaryl group can be substituted with at least one (in another example with 1, 2, 3, 4, or 5) group halogen (fluoro, chloro, bromo or iodo), alkyl, haloalkyl, hydroxyl, alkylcarbonyl, cycloalkylcarbonyl, arylcarbonyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g. alkylamino, dialkylamino, arylamino, etc.), alkoxy, aryloxy, nitro, cyano, sulfonic acid, sulfate, sulfonate, phosphonic acid, phosphate, and phosphonate, either unprotected, or protected as necessary.

The term "alkylaryl" refers to an aryl group with an alkyl substituent, wherein aryl and alkyl are as defined herein. The term "aralkyl" or "arylalkyl" refers to an alkyl group with an aryl substituent, wherein aryl and alkyl are as defined herein.

The term "phenylene," as used herein, and unless otherwise specified, refers to a divalent phenyl group and includes both substituted and unsubstituted moieties. In certain embodiments, phenylene group can be substituted with one or more (for example 1, 2, 3, 4, or 5) moieties independently selected from the group halogen (fluoro, chloro, bromo or iodo), alkyl, haloalkyl, hydroxyl, alkylcarbonyl, cycloalkylcarbonyl, arylcarbonyl, sulfanyl, alkylsulfanyl, cycloalkylsulfanyl, arylsulfanyl, alkylsulfonyl, cycloalkylsulfonyl, arylsulfonyl, aminocarbonyl, carbamoyl, sulfonamido, amino (as defined herein, e.g. alkylamino, dialkylamino, arylamino, etc.), alkoxy, aryloxy, nitro, cyano, sulfonic acid, sulfate, sulfonate, phosphonic acid, phosphate, and phosphonate, either unprotected, or protected as necessary, as known to those skilled in the art, for example, as taught in Greene, et al., *Protective Groups in Organic Synthesis*, John Wiley and Sons, Second Edition, 1991. When phenylene is used in the context of an EG group, the phenylene is substituted with 1, 2, 3, or 4 $R^{EG}$ groups, as defined herein, and/or with 1 or 2-O-[RT] groups, and/or with 1 or 2-CH$_2$OC(O)[RT] groups, where RT is as defined herein.

The term "protecting group" as used herein and unless otherwise defined refers to a group that is added to an oxygen, nitrogen or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "acyl" refers to a group of the formula —C(O)R', wherein R' is alkyl (including lower alkyl); cycloalkyl; cycloalkylalkyl; cycloalkenyl; aryl; arylalkyl (including benzyl); substituted alkyl (including lower alkyl and for example alkoxyalkyl and aryloxyalkyl); heterocyclo; heterocycloalkyl; heteroaryl; and heteroarylalkyl; where the cycloalkyl, cycloalkenyl, aryl, heterocyclo, and heteroaryl may be substituted. In certain embodiments, aryl groups in the acyl or esters comprise a phenyl group. In certain embodiments, acyl groups include, for example, acetyl, trifluoroacetyl, methylacetyl, cyclopropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoroheptanoyl, 7H-dodeca-fluoroheptanoyl, 7-chlorododecafluoro-heptanoyl, 7-chloro-dodecafluoro-heptanoyl, 7H-dodecafluoroheptanoyl, 7H-dodeca-fluoroheptanoyl, nonafluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxybenzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenylcarbonyl, isovaleryl, 1-pyrrolidinecarbonyl, and 4-phenylbenzoyl.

The term "amino acid" refers to naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, or β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, a compound described herein comprises an amino acid derivative, wherein the amino acid derivative is —NR$^X$-G(S$_C$)—C(O)-Q$^1$-, wherein Q$^1$ is —S—, —NR$^Y$—, or —O—, R$^Y$ is hydrogen or alkyl, S$_C$ is a side chain of a naturally occurring or non-naturally occurring amino acid, G is C$_1$-C$_2$ alkylene, and R$^X$ is hydrogen or R$^X$ and S$_C$, together with the atoms to which they are attached, combine to form a five-membered heterocyclic ring. In an embodiment, an amino acid derivative is provided as a substituent of a compound described herein, wherein the substituent is —O—C(O)-G(S$_C$)—NH-Q$^2$-, wherein Q$^2$ is a single bond or —O—, S$_C$ is a side chain of a naturally occurring or non-naturally occurring amino acid and G is C$_1$-C$_2$ alkylene. In certain embodiments, Q$^2$ and S$_C$, together with the atoms to which they are attached, combine to form a five-membered heterocyclic ring. In certain embodiments, G is C$_1$ alkylene and S$_C$ is hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoyl alkyl, alkylsulfanylalkyl, or hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "alkylheterocyclo" refers to a heterocyclo group with an alkyl substituent. The term "heterocycloalkyl" refers to an alkyl group with a heterocyclo substituent.

As used herein, the term "carboxylalkyl" refers to an alkyl substituted with at least 1, in another example 1 or 2, carboxy, where alkyl is as described herein.

The term "alkylheteroaryl" refers to a heteroaryl group with an alkyl substituent. The term "heteroarylalkyl" refers to an alkyl group with a heteroaryl substituent.

As used herein, the term "aminoalkyl" refers to an alkyl group substituted with at least 1, in another example 1 or 2, amino substituent(s), where alkyl and amino are as described herein.

As used herein, the terms "hydroxylalkyl" and "hydroxyalkyl" refer to an alkyl group substituted with at least 1, in another example 1 or 2, hydroxyl, where alkyl is as described herein.

As used herein, the term "aminoiminoaminoalkyl" refers to an alkyl substituted with at least 1, in another example 1 or 2, -amino-C(NH)-amino, where alkyl and amino are as described herein.

The term aminocarbonyl refers to the group —C(O)(amino) where amino is as defined herein.

As used herein, the term "aminocarbonylalkyl" refers to an alkyl substituted with at least 1, in another example 1 or 2, —C(O)-amino, where alkyl and amino are as described herein.

As used herein, the term "sulfanylalkyl" refers to an alkyl substituted with at least 1, in another example 1 or 2, —SH, where alkyl is as described herein.

The term "carbamoyl" refers to a —NRC(OR', where R is hydrogen or alkyl and R' is alkyl, cycloalkyl, heterocyclo, heteroaryl, or aryl, as defined herein.

As used herein, the term "carbamoylalkyl" refers to an alkyl substituted with at least 1, in another example 1 or 2, carbamoyl groups, as defined herein.

As used herein, the term "alkylsulfanylalkyl" refers to an alkyl substituted with at least 1, in another example 1 or 2, —S— alkyl, where alkyl is as described herein.

As used herein, the term "hydroxylarylalkyl" refers to the group-alkyl-aryl-OH, where alkyl and aryl are as described herein.

The term "sulfonic acid" refers to the group —S(O)$_2$OH.

The term "sulfate" refers to the group —OS(O)$_2$OR where R is alkyl or arylalkyl.

The term "sulfonate" refers to the group —S(O)$_2$OR where R is alkyl or arylalkyl.

The term "sulfonamido" refers to the group —S(O)$_2$NRR' where R is hydrogen or alkyl and R' is alkyl, cycloalkyl, heterocyclo, heteroaryl, or aryl, as defined herein.

The term "phosphate" refers to the group —OP(O)(OR)$_2$ where each R is independently alkyl or arylalkyl.

The term "phosphonic acid" refers to —P(O)(OH)$_2$.

The term "phosphonate" refers to the group —P(O)(OR)$_2$ where each R is independently alkyl or arylalkyl.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a modified amino acid. Additionally, such "polypeptides," "peptides" and "proteins" include amino acid chains of any length, including full length proteins, wherein the amino acid residues are linked by covalent peptide bonds.

Many of the compounds and conjugates described herein have chiral centers. The present disclosure encompasses each stereoisomer of each compound or conjugate with each possible stereochemistry at each chiral center. Certain compounds are identified by stereochemical notation that is known to those of skill. In particular embodiments, stereochemistry is identified with R and S notation for each chiral center, from left to right as depicted in formula 1000, 1001, 1002, and (I), etc. or formula (C1), F1, and G1, etc. For instance, the notation [R,S,S] indicates R, S and S stereochemistry at the chiral centers of formula (I) from left to right, beginning with the methylamino substituent position and ending with the isopropyl substituent position. Similarly, the notation [S,S,S] indicates S, S and S stereochemistry at the chiral centers of formula (I) from left to right. Further, the notation racemic [R/S,S,S] indicates a mixture of [R,S,S] and [S,S,S] compounds. For other compounds and conjugates herein, the notation can be applied to corresponding structures.

The term "substantially free of" or "substantially in the absence of," when used in connection with an article (including, but not limited to, a compound, a salt thereof, a solvate thereof, a solid form thereof, and the like), refers to the article that includes at least 85% or 90% by weight, in certain embodiments, 95%, 98%, 99%, or 100% by weight, of the designated article. For example, the term "substantially free of" or "substantially in the absence of" with respect to a composition can refer to a composition that includes at least 85% or 90% by weight, in certain embodiments, 95%, 98%, 99%, or 100% by weight, of a designated stereoisomer of a compound. In certain embodiments, in the methods and compounds provided herein, the compounds are substantially free of undesignated stereoisomers or other compounds. For another example, the term "substantially free of" or "substantially in the absence of" with respect to a solid form can refer to a solid form that includes at least 85% or 90% by weight, in certain embodiments, 95%, 98%, 99%, or 100% by weight, of the designated solid form. In certain embodiments, in the methods and compounds provided herein, the solid form is substantially free of other solid forms.

Similarly, the term "isolated" with respect to a composition refers to a composition that includes at least 85%, 90%, 95%, 98%, or 99% to 100% by weight, of a designated compound, the remainder comprising other chemical species or stereoisomers. Similarly, the term "isolated" with respect to a solid form of a compound refers to a solid that includes at least 85%, 90%, 95%, 98%, or 99% to 100% by weight, of such solid form of the compound, the remainder comprising other solid forms of the compound, other compounds, solvents, and/or other impurities.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkenyl," "cycloalkenyl," "alkynyl," "aryl," "alkoxy," "alkoxycarbonyl," "amino," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise deuterium at one or more positions where hydrogen atoms are present, and wherein the deuterium composition of the atom or atoms is other than the natural isotopic composition.

Also as used herein, "alkyl," "cycloalkyl," "alkenyl," "cycloalkenyl," "alkynyl," "aryl," "alkoxy," "alkoxycarbonyl," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise carbon-13 at an amount other than the natural isotopic composition.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: colon (colon carcinoma, colon adenocarcinoma, colorectal adenocarcinoma), esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pineal oma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], platinum-resistant ovarian, granulosa-thecal cell tumors, Sertoli-Leydig cell tumors, dysgerminoma, malignant teratoma, ovarian adenocarcinoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: melanoma, malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma; a lymphoma; large cell lymphoma; diffuse mixed histiocytic and lymphocytic lymphoma; follicular B cell lymphoma; and breast (breast cancer which overexpresses Her2, triple-negative breast cancer). Thus, the term "cancerous cell" as provided herein, includes a cell afflicted by any one of the above-identified conditions. As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey, a chimpanzee, and a human), and for example, a human. In certain embodiments, the subject is refractory or non-responsive to current treatments for cell proliferation and/or cancer. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disease or condition, or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a or condition, or one or more symptoms thereof.

"Therapeutically effective amount" refers to an amount of a compound or composition that, when administered to a subject for treating a disease or condition, is sufficient to effect such treatment for the disease or condition. A "therapeutically effective amount" can vary depending on, inter alia, the compound, the disease or condition and its severity, and the age, weight, etc., of the subject to be treated.

"Treating" or "treatment" of any disease or condition refers, in certain embodiments, to ameliorating a disease or condition that exists in a subject. In another embodiment, "treating" or "treatment" includes ameliorating at least one physical parameter, which may be indiscernible by the subject. In yet another embodiment, "treating" or "treatment" includes modulating the disease or condition, either physically (e.g., stabilization of a discernible symptom) or physiologically (e.g., stabilization of a physical parameter) or both. In yet another embodiment, "treating" or "treatment" includes delaying the onset of the disease or condition.

As used herein, the terms "prophylactic agent" and "prophylactic agents" as used refer to any agent(s) which can be used in the prevention of a disease or condition, or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression and/or severity of a disease or condition.

As used herein, the phrase "prophylactically effective amount" refers to the amount of a therapy (e.g., prophylactic agent) which is sufficient to result in the prevention or reduction of the development, recurrence or onset of one or more symptoms associated with a disease or condition, or to enhance or improve the prophylactic effect(s) of another therapy (e.g., another prophylactic agent).

The term "antibody" refers to any macromolecule that would be recognized as an antibody by those of skill in the art. Antibodies share common properties including binding and at least one polypeptide chain that is substantially identical to a polypeptide chain that can be encoded by any of the immunoglobulin genes recognized by those of skill in the art. The immunoglobulin genes include, but are not limited to, the κ, λ, α, γ (IgG1, IgG2, IgG3, and IgG4), δ, ε and μ constant region genes, as well as the immunoglobulin variable region genes. The term includes full-length antibodies and antibody fragments recognized by those of skill in the art, and variants thereof.

The term "antibody fragment" refers to any form of an antibody other than the full-length form. Antibody fragments herein include antibodies that are smaller components that exist within full-length antibodies, and antibodies that have been engineered. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDR's, variable regions, framework regions, constant regions, and the like (Maynard & Georgiou, 2000, *Annu. Rev. Biomed. Eng.* 2:339-76; Hudson, 1998, *Curr. Opin. Biotechnol.* 9:395-402).

The term "immunoglobulin (Ig)" refers to a protein consisting of one or more polypeptides substantially encoded by one of the immunoglobulin genes, or a protein substantially identical thereto in amino acid sequence. Immunoglobulins include but are not limited to antibodies. Immunoglobulins may have a number of structural forms, including but not limited to full-length antibodies, antibody fragments, and individual immunoglobulin domains including but not limited to $V_H$, Cγ1, Cγ2, Cγ3, $V_L$, and $C_L$.

The term "immunoglobulin (Ig) domain" refers to a protein domain consisting of a polypeptide substantially encoded by an immunoglobulin gene. Ig domains include but are not limited to $V_H$, Cγ1, Cγ2, Cγ3, $V_L$, and $C_L$.

The term "variable region" of an antibody refers to a polypeptide or polypeptides composed of the $V_H$ immunoglobulin domain, the $V_L$ immunoglobulin domains, or the $V_H$ and $V_L$ immunoglobulin domains. Variable region may refer to this or these polypeptides in isolation, as an Fv fragment, as a scFv fragment, as this region in the context of a larger antibody fragment, or as this region in the context of a full-length antibody or an alternative, non-antibody scaffold molecule.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies. It is concentrated in three segments called Complementarity Determining Regions (CDRs) both in the light chain and the heavy chain variable domains. The more highly conserved portions of the variable domains are called the framework regions (FR). The variable domains of native heavy and light chains each comprise four FR regions, largely adopting a β-sheet configuration, connected by three or four CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)).

The constant domains are not typically involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and several of these may be further divided into subclasses (isotypes), e.g. IgG1, IgG2, IgG3, and IgG4; IgA1 and IgA2. The heavy chain constant regions that correspond to the different classes of immunoglobulins are called α, δ, ε, γ, and μ, respectively. Of the various human immunoglobulin classes, only human IgG1, IgG2, IgG3 and IgM are known to activate complement.

The term "conjugate" refers to any compound that can be formed by conjugating a compound described herein to a second compound. The second compound can be a small molecule or a macromolecule. In some embodiments, the second compound is a bioactive molecule including, but not limited to, a protein, a peptide, a nucleic active or a hybrid thereof. In some embodiments, the second compound is a polymer such as polyethylene glycol. In some embodiments, the second compound is a therapeutic agent, including a commercially available drug. In some embodiments, the second compound is a label that can recognize and bind to specific targets, such as a molecular payload that is harmful to target cells or a label useful for detection or diagnosis. In some embodiments, the compound described herein is connected to the second compound via a linker. In some embodiments, the compound described herein is directly connected to the second compound without a linker. In another embodiment the second compound is a small molecule; a macromolecule; bioactive molecule including, but not limited to, a protein, a peptide, a nucleic active or a hybrid thereof; a polymer such as polyethylene glycol; a therapeutic agent, including a commercially available drug; or a label that can recognize and bind to specific targets, such as a molecular payload that is harmful to target cells or a label useful for detection or diagnosis. In another embodiment, the second compound comprises a modified amino acid comprising an alkyne, strained alkene, tetrazine, thiol, maleimide, carbonyl, oxyamine, or azide.

The term "variant protein sequence" refers to a protein sequence that has one or more residues that differ in amino acid identity from another similar protein sequence. Said similar protein sequence may be the natural wild type protein sequence, or another variant of the wild type sequence. Variants include proteins that have one or more amino acid insertions, deletions or substitutions. Variants also include proteins that have one or more post-translationally modified amino acids.

The term "parent antibody" refers to an antibody known to those of skill in the art that is modified according to the description provided herein. The modification can be physical, i.e., chemically or biochemically replacing or modifying one or more amino acids of the parent antibody to yield an antibody within the scope of the present description. The modification can also be conceptual, i.e., using the sequence of one or more polypeptide chains of the parent antibody to design an antibody comprising one or more site-specific modified amino acids according to the present description. Parent antibodies can be naturally occurring antibodies or antibodies designed or developed in a laboratory. Parent antibodies can also be artificial or engineered antibodies, e.g., chimeric or humanized antibodies.

The term "conservatively modified variant" refers to a protein that differs from a related protein by conservative substitutions in amino acid sequence. One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

See, e.g., Creighton, *Proteins: Structures and Molecular Properties*, W H Freeman & Co.; 2nd edition (December 1993).

The terms "identical" or "identity," in the context of two or more polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. The identity can exist over a region that is at least about 50 amino acids or nucleotides in length, or over a region that is 75-100 amino acids or nucleotides in length, or, where not specified, across the entire sequence or a polypeptide. In the case of antibodies, identity can be measured outside the variable CDRs. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection (see, e.g., Ausubel et al., Current Protocols in Molecular Biology (1995 supplement)).

Examples of algorithms that are suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off. In some embodiments, the BLAST algorithm is typically performed with the "low complexity" filter turned on.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, in another embodiment less than about 0.01, and in another embodiment less than about 0.001.

The term "amino acid" refers to naturally occurring and non-naturally occurring amino acids, as well as amino acids such as proline, amino acid analogs and amino acid mimetics that function in a manner similar to naturally occurring amino acids.

Naturally encoded amino acids are the proteinogenic amino acids known to those of skill in the art. They include the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and the less common pyrrolysine and selenocysteine. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids and acylated amino acids.

The term "modified amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

The term "strained alkene" refers to a molecule comprising an alkene moiety that is capable of reacting with tetrazine in a tetrazine ligation. Exemplary tetrazine ligations are described in Blackman et al., 2008, *J. Am. Chem. Soc.* 130:13518-13519. Examples include trans-cyclooctenes and norbornenes. Useful compounds include, but are not limited to, trans-cyclooctene, (E)-cyclooct-4-enol, (E)-cyclooct-4-enyl 2,5-dioxo-1-pyrrolidinyl carbonate, 5-norbornene-2-acetic acid succinimidyl ester, and 5-norbornene-2-endo-acetic acid.

The term "tetrazine" refers to a compound or group comprising the following structure:

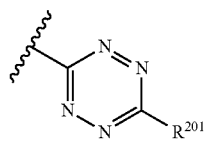

wherein $R^{201}$ is lower alkyl. For example, $R^{201}$ can be methyl, ethyl, or propyl. In certain aspects, $R^{201}$ is methyl.

Compounds

In certain embodiments, the compound is not of formula (101), (101a), or (101b) and the conjugate does not comprise the compound of formula (101), (101a), or (101b). In certain embodiments, the compound is not of formula (101a), and the conjugate does not comprise the compound of formula (101a). In certain embodiments where X is

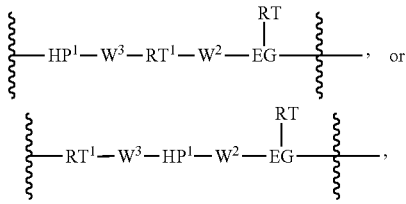

the compound is not the compound of formula (101), (101a), or (101b) and the conjugate does not comprise the compound of formula (101), (101a), or (101b). In certain embodiments where X is

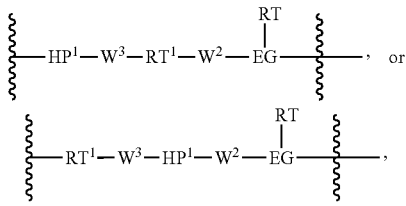

the compound is not the compound of formula (101a), and the conjugate does not comprise the compound of formula (101a). In certain embodiments, the compound is not of formula (101), (101a), or (101b). In certain embodiments, the compound is not of formula (101a). In certain embodiments where X is

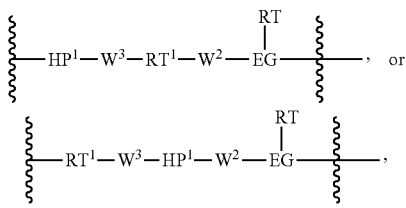

the compound is not the compound of formula (101), (101a), or (101b). In certain embodiments where X is

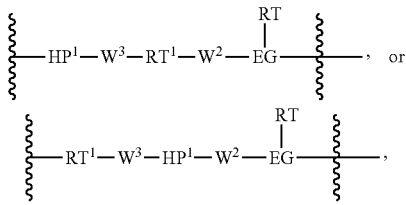

the compound is not the compound of formula (101a). In certain embodiments, the conjugate does not comprise the compound of formula (101), (101a), or (101b). In certain embodiments, the conjugate does not comprise the compound of formula (101a). In certain embodiments where X is

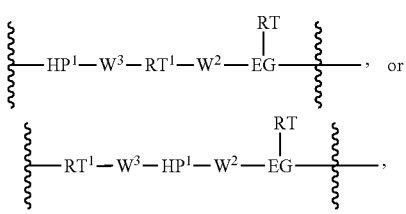

the conjugate does not comprise the compound of formula (101), (101a), or (101b). In certain embodiments where X is

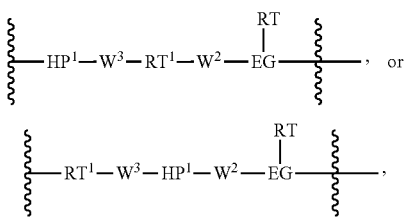

the conjugate does not comprise the compound of formula (101a).

When a range of formula are used, for example I-XIXb-2, each formula within that range is included and is as if it were explicitly listed, including where the roman numeral is followed by, for example, "a," "-1," etc. For example, I-XIXb-2 includes Va, XIV, and XIXa-1, etc.

In an embodiment, provided herein is a compound according to Formula I:

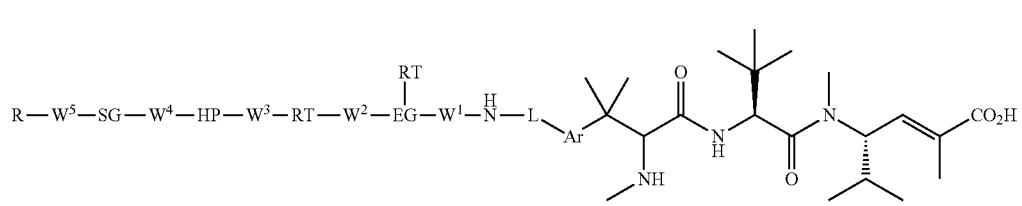

or a pharmaceutically acceptable salt, solvate, stereoisomer, or tautomer thereof, wherein:

Ar is a divalent five- or six-membered, substituted or unsubstituted, monocyclic aryl or heteroaryl ring or a divalent eight-, nine- or ten-membered, substituted or unsubstituted, fused bicyclic aryl or heteroaryl ring;

L is absent or —CH$_2$—;

W$^1$, W$^2$, W$^3$, W$^4$, and W$^5$ are each independently a single bond, absent, or a divalent attaching group;

EG is an eliminator group;

each RT is a release trigger group, in the backbone of Formula (I) or bonded to EG, wherein one RT is optional;

HP is a single bond, absent, or a divalent hydrophilic group;

SG is a single bond, absent, or a divalent spacer group; and

R is hydrogen, a terminal conjugating group, or a divalent residue of a terminal conjugating group;

or, in the alternative, W$^1$, W$^2$, W$^3$, W$^4$, W$^5$, EG, RT, HP, SG, and R combine to form —H.

In one embodiment, provided herein is a compound of Formula 1000 according to 1001:

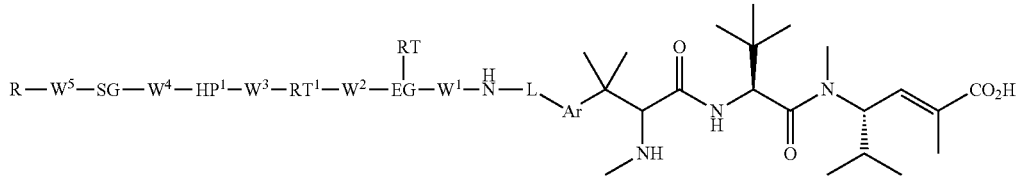

or a pharmaceutically acceptable salt, solvate, stereoisomer, or tautomer thereof, wherein:

Ar is a divalent five- or six-membered, substituted or unsubstituted, monocyclic aryl or heteroaryl ring or a divalent eight-, nine- or ten-membered, substituted or unsubstituted, fused bicyclic aryl or heteroaryl ring;

L is absent or —CH$_2$—;

W$^1$, W$^2$, W$^3$, W$^4$, and W$^5$ are each independently a single bond, absent, or a divalent attaching group;

EG is absent or an eliminator group;

RT$^1$ is a release trigger group or a cleavable linker;

RT is a release trigger group bonded to EG; and wherein RT is optional;

HP$^1$ is single bond, absent, a divalent hydrophilic group, or

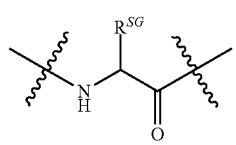

where R$^{SG}$ is a monovalent hydrophilic group;

SG is a single bond, absent, or a divalent spacer group; and

R is hydrogen, a terminal conjugating group, or a divalent residue of a terminal conjugating group.

In one embodiment, provided herein is a compound of Formula 1000 according to 1002:

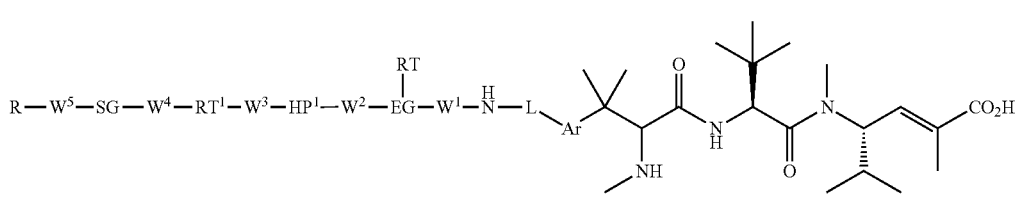

(1002)

or a pharmaceutically acceptable salt, solvate, stereoisomer, or tautomer thereof, wherein:
- Ar is a divalent five- or six-membered, substituted or unsubstituted, monocyclic aryl or heteroaryl ring or a divalent eight-, nine- or ten-membered, substituted or unsubstituted, fused bicyclic aryl or heteroaryl ring;
- L is absent or —CH$_2$—;
- $W^1$, $W^2$, $W^3$, $W^4$, and $W^5$ are each independently a single bond, absent, or a divalent attaching group;
- EG is absent or an eliminator group;
- $RT^1$ is a release trigger group or a cleavable linker;
- RT is a release trigger group bonded to EG; and wherein RT is optional;
- $HP^1$ is single bond, absent, a divalent hydrophilic group, or

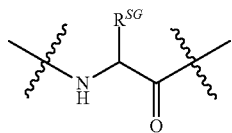

where $R^{SG}$ is a monovalent hydrophilic group;
SG is a single bond, absent, or a divalent spacer group; and
R is hydrogen, a terminal conjugating group, or a divalent residue of a terminal conjugating group.

In certain embodiments, a conjugating group can be used to conjugate a modified Hemiasterlin as described herein (e.g., according to any of Formulas 1000-1000b, 1001-1001b, 1002-1002b, and I-XIXb-2, 101-111b, or 1-8b) to any molecular entity capable of reacting with the conjugating group to form the conjugate. In certain embodiments, the conjugating group is designated R herein. The conjugating group can be directly or indirectly linked to the modified Hemiasterlin as described herein (e.g., according to any of Formulas 1000-1000b, 1001-1001b, 1002-1002b, and I-XIXb-2, 101-111b, or 1-8b) via one or more attaching groups, eliminator groups, release trigger groups, hydrophobic groups, and/or spacer groups.

Attaching Groups

Attaching groups facilitate incorporation of eliminator groups, release trigger groups, hydrophobic groups, spacer groups, and/or conjugating groups into a compound, such as a modified Hemiasterlin as described herein (e.g., according to any of Formulas 1000-1000b, 1001-1001b, 1002-1002b, and I-XIXb-2, 101-111b, or 1-8b). Useful attaching groups are known to, and are apparent to, those of skill in the art. Examples of useful attaching groups are provided herein. In certain embodiments, attaching groups are designated $W^1$, $W^2$, $W^3$, $W^4$, or $W^5$. In certain embodiments, an attaching group can comprise a divalent ester, divalent ether, divalent amide, divalent amine, alkylene, arylene, sulfide, disulfide, —C(O)—, or a combination thereof. In certain embodiments an attaching group can comprise —C(O)—, —O—, —C(O)O—, —OC(O)—, —C(O)NH—, —C(O)NH-alkyl-, —OC(O)NH—, —SC(O)NH—, —NH—, —N(alkyl)-, —N(R)-alkylene-N(R)— (where each R is independently H or alkyl), —N(CH$_3$)CH$_2$CH$_2$N(CH$_3$)—, —CH$_2$—, —CH$_2$CH$_2$—, —CH(CH$_3$)—, —C(CH$_3$)$_2$—, —CH$_2$CH$_2$CH$_2$—, phenylene, —NHCH$_2$CH$_2$C(O)—, —C(O)CH$_2$CH$_2$NH—, —S—, —S—S—, —OCH$_2$CH$_2$O—, or the reverse (e.g. —NHC(O)—) thereof, or a combination thereof.

Eliminator Groups

Eliminator groups facilitate separation of a biologically active portion of a compound or conjugate described herein from the remainder of the compound or conjugate in vivo and/or in vitro. Eliminator groups can also facilitate separation of a biologically active portion of a compound or conjugate described herein in conjunction with a release trigger group. For example, the eliminator group and the release trigger group can react in a Releasing Reaction to release a biologically active portion of a compound or conjugate described herein from the compound or conjugate in vivo and/or in vitro. Upon initiation of the releasing reaction by the release trigger, the eliminator group cleaves the biologically active moiety, or a prodrug form of the biologically active moiety, and forms a stable, non-toxic entity that has no further effect on the activity of the biologically active moiety.

In certain embodiments, the eliminator group is designated EG herein. Useful eliminator groups include those described herein. In certain embodiments, the eliminator group comprises a phenylene, a —C(O)—, an amino, or a combination thereof In certain embodiments, the eliminator group is:

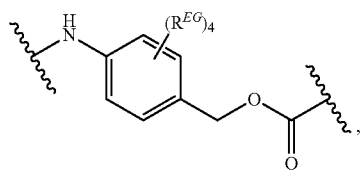

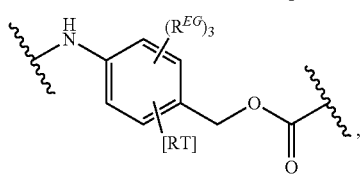

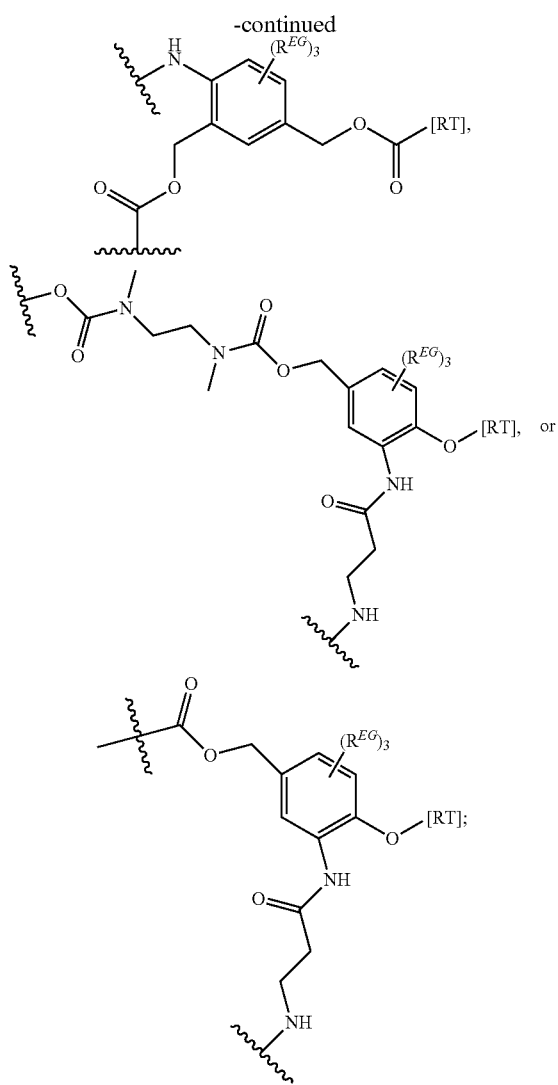

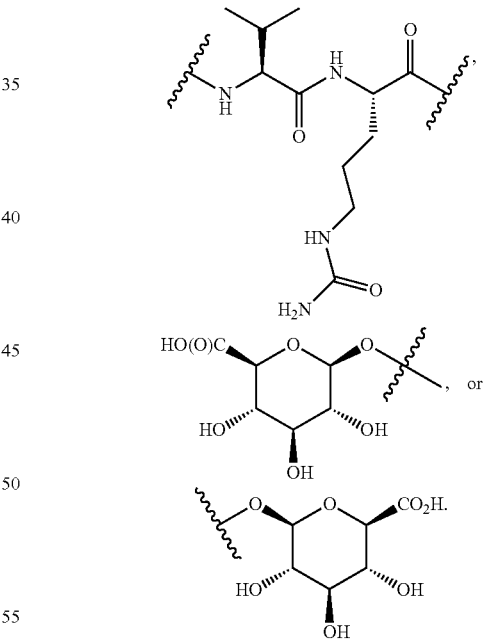

wherein each $R^{EG}$ is independently selected from the group consisting of hydrogen, alkyl, biphenyl, —$CF_3$, —$NO_2$, —CN, fluoro, bromo, chloro, alkoxyl, alkylamino, dialkylamino, alkyl-C(O)O—, alkylamino-C(O)— and dialkylamino-C(O)—. In the second and third structures, those of skill will recognize that EG is bonded to an RT that is not within the backbone of the e.g. formula 1000, or (I), as indicated in the above description of formula 1000 and (I). In some embodiments, each $R^{EG}$ is independently selected from the group consisting of hydrogen, alkyl, biphenyl, —$CF_3$, alkoxyl, alkylamino, dialkylamino, alkyl-C(O)O—, alkylamino-C(O)— and dialkylamino-C(O)—. In further embodiments, each $R^{EG}$ is independently selected from the group consisting of hydrogen, —$NO_2$, —CN, fluoro, bromo, and chloro.

Release Trigger Groups and Cleavable Linkers

In certain embodiments, release trigger groups facilitate separation of a biologically active portion of a compound or conjugate described herein from the remainder of the compound or conjugate in vivo and/or in vitro. In certain embodiments, release trigger groups can also facilitate separation of a biologically active portion of a compound or conjugate described herein in conjunction with an eliminator group. In some embodiments, the eliminator group and the release trigger group can react in a Releasing Reaction to release a biologically active portion of a compound or conjugate described herein from the compound or conjugate in vivo and/or in vitro. In certain embodiments, the release trigger can act through a biologically-driven reaction with high tumor:nontumor specificity, such as the proteolytic action of an enzyme overexpressed in a tumor environment.

In certain embodiments, the release trigger group is designated RT herein. In certain embodiments, RT is divalent and bonded within the backbone of formula (I) or 1000. In other embodiments, RT is monovalent and bonded to EG as depicted above. Useful release trigger groups include those described herein. In certain embodiments, the release trigger group comprises a residue of a natural or non-natural amino acid or residue of a sugar ring. In certain embodiments, the release trigger group comprises a residue of a natural or non-natural amino acid or residue of a sugar ring.

In some embodiments, the release trigger group is derived from a linker precursor selected from the group consisting of dipeptides, tripeptides, tetrapeptides, and pentapeptides, each of which comprises one citrulline. Exemplary dipeptides include, but are not limited to, valine-citrulline (vc or val-cit), and N-methyl-valine-citrulline (Me-val-cit). Exemplary tripeptides include, but are not limited to, glycine-valine-citrulline (gly-val-cit). In some embodiments, the release trigger group is derived from a linker precursor selected from the group consisting of valine-citrulline, N-methyl-valine-citrulline, and glycine-valine-citrulline, In certain embodiments, the release trigger group is:

Those of skill will recognize that the first structure is divalent and can be bonded within the backbone of formula (I) or 1000, and that the second structure is monovalent and can be bonded to EG as depicted in formula (I) and 1000 above.

Cleavable linkers facilitate separation of a biologically active portion of a compound or conjugate described herein from the remainder of the compound or conjugate in vivo and/or in vitro. In certain embodiments, the release trigger can act through a biologically-driven reaction with high tumor:nontumor specificity, such as the proteolytic action of an enzyme overexpressed in a tumor environment. In certain embodiments, the cleavable linker is designated $RT^1$ herein. Useful cleavable linkers include those described herein. In some embodiments, the cleavable linker is derived from a linker precursor selected from the group consisting of dipeptides, tripeptides, tetrapeptides, and pentapeptides. In such embodiments, the linker can be cleaved by a protease. Exemplary dipeptides include, but are not limited to, valine-alanine (VA or Val-Ala); valine-glutamic acid (Val-Glu); alanine-phenylalanine (AF or Ala-Phe); phenylalanine-lysine (FK or Phe-Lys); and phenylalanine-homolysine (Phe-homoLys). Exemplary tripeptides include, but are not limited to glycine-glycine-glycine (Gly-Gly-Gly). In certain embodiments, the cleavable linker is derived from a linker precursor selected from the group consisting of dipeptides and tripeptides. In certain embodiments, the cleavable linker is derived from a dipeptide. In certain embodiments, the cleavable linker is derived from a tripeptide. In certain embodiments the cleavable linker is derived from a linker precursor derived from valine-alanine, valine-glutamic acid, phenylalanine-homolysine, phenylalanine-lysine, phenylalanine-homolysine, or glycine-glycine-glycine.

In certain embodiments the cleavable linker is derived from a linker precursor selected from the group consisting of dipeptides, tripeptides, tetrapeptides, and pentapeptides; or is

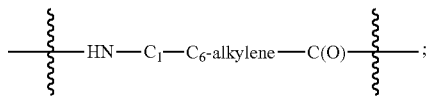

or is

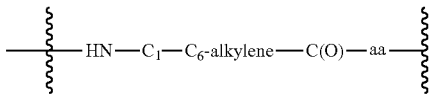

where aa is a natural or non-natural amino acid residue; or is

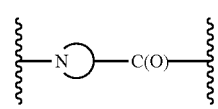

where the

ring is a 4-7 membered heterocyclic ring comprising 3-6 carbon atoms. In certain embodiments the cleavable linker is derived from a linker precursor selected from the group consisting of dipeptides and tripeptides; or is

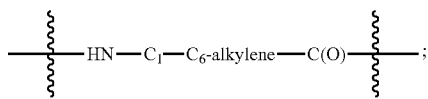

or is

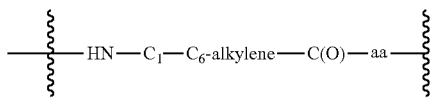

where aa is a natural or non-natural amino acid residue; or is

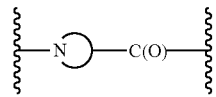

where the

ring is a 4-7 membered heterocyclic ring comprising 3-6 carbon atoms.

In certain embodiments the cleavable linker is derived from a linker precursor selected from valine-alanine, valine-glutamic acid, alanine-phenylalanine; phenylalanine-lysine; phenylalanine-homolysine; and glycine-glycine-glycine (Gly-Gly-Gly); or is

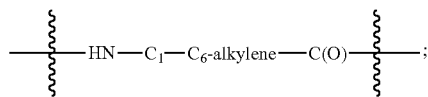

or is

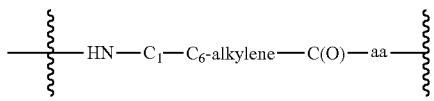

where aa is a natural or non-natural amino acid residue; or is

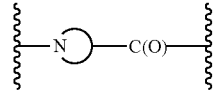

where the

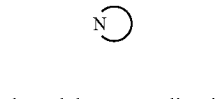

ring is a 4-7 membered heterocyclic ring comprising 3-6 carbon atoms.

In certain embodiments the cleavable linker is

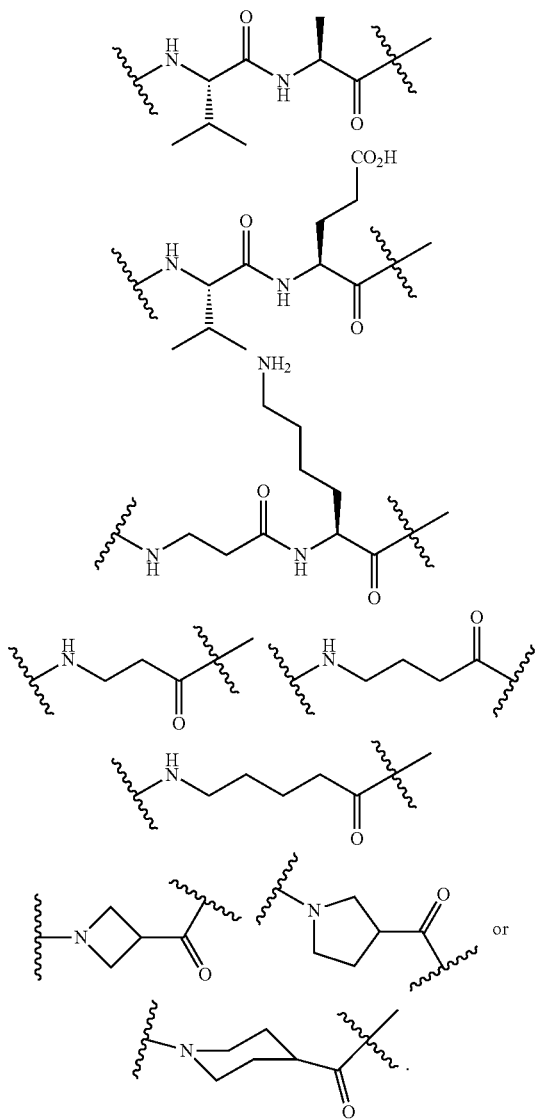

Hydrophilic Groups

Hydrophilic groups facilitate increasing the hydrophilicity of the compounds described herein. It is believed that increased hydrophilicity allows for greater solubility in aqueous solutions, such as aqueous solutions found in biological systems. Hydrophilic groups can also function as spacer groups or substituents, which are described in further detail herein.

In certain embodiments, the hydrophilic group is designated HP and $HP^1$ herein. Useful hydrophilic groups include those described herein. In certain embodiments, the HP hydrophilic group is a divalent poly(ethylene glycol). In certain embodiments, the HP hydrophilic group is a divalent poly(ethylene glycol) according to the formula:

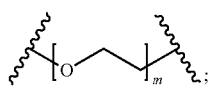

wherein m is an integer from 1 to 12, optionally 1 to 4, optionally 2 to 4. In certain embodiments, the $HP^1$ hydrophilic group is a divalent hydrophilic group or a

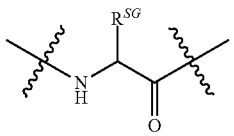

where $R^{SG}$ is a monovalent hydrophilic group. In certain embodiments, $R^{SG}$ is a monovalent poly(ethylene glycol). In certain embodiments, $R^{SG}$ is a monovalent poly(ethylene glycol) according to the formula:

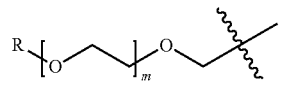

wherein R is —H or —$CH_3$ and m is an integer from 1 to 12, optionally 1 to 4, optionally 2 to 4. In certain embodiments, $R^{SG}$ is a monovalent poly(ethylene glycol) according to the formula:

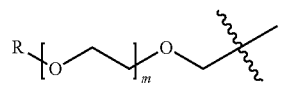

wherein R is —H or —$CH_3$ and m is an integer from 1 to 12, optionally 1 to 4, optionally 2 to 4; $R^{SG}$ or is —$C_1$-$C_6$-alkylene-S(O)$_3$—. In certain embodiments, $R^{SG}$ is a monovalent poly(ethylene glycol) according to the formula:

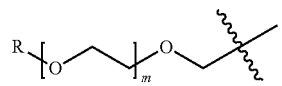

wherein R is —H or —$CH_3$ and m is 2 to 4; or is —$CH_2CH_2$—S(O)$_3$—. In certain embodiments, $R^{SG}$ is a monovalent poly(ethylene glycol) according to the formula:

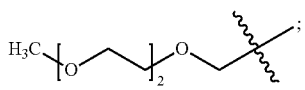

or $R^{SG}$ is —$CH_2CH_2$—S(O)$_3$—. In certain embodiments, $R^{SG}$ is —$C_1$-$C_6$-alkylene-S(O)$_3$—. In certain embodiments, $R^{SG}$ is —$CH_2CH_2$—S(O)$_3$—.

Spacer Groups

Spacer groups facilitate spacing of the conjugating group from the other groups of the compounds described herein. This spacing can lead to more efficient conjugation of the compounds described herein to a second compound. The spacer group can also stabilize the conjugating group.

In certain embodiments, the spacer group is designated SG herein. Useful spacer groups include those described herein. In certain embodiments, the spacer group is:

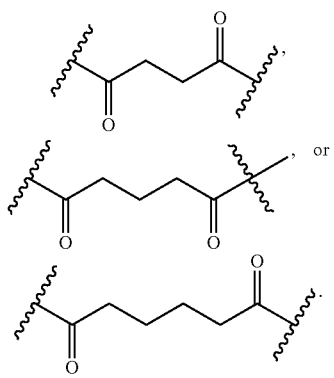

In certain embodiments, SG, W⁴, and the HP or HP¹ group combine to form a divalent poly(ethylene glycol) according to the formula:

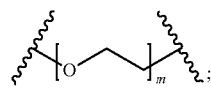

wherein m is an integer from 1 to 12, optionally 1 to 4, optionally 2 to 4.

Conjugating Groups and Residues Thereof

Conjugating groups facilitate conjugation of the compounds described herein to a second compound, such as a targeting moiety. In certain embodiments, the conjugating group is designated R herein. Conjugating groups can react via any suitable reaction mechanism known to those of skill in the art. In certain embodiments, a conjugating group reacts through a [3+2] alkyne-azide cycloaddition reaction, inverse-electron demand Diels-Alder ligation reaction, thiol-electrophile reaction, or carbonyl-oxyamine reaction, as described in detail herein. In certain embodiments, the conjugating group comprises an alkyne, strained alkene, tetrazine, thiol, para-acetyl-phenylalanine residue, oxyamine, maleimide, or azide. In certain embodiments, the conjugating group is:

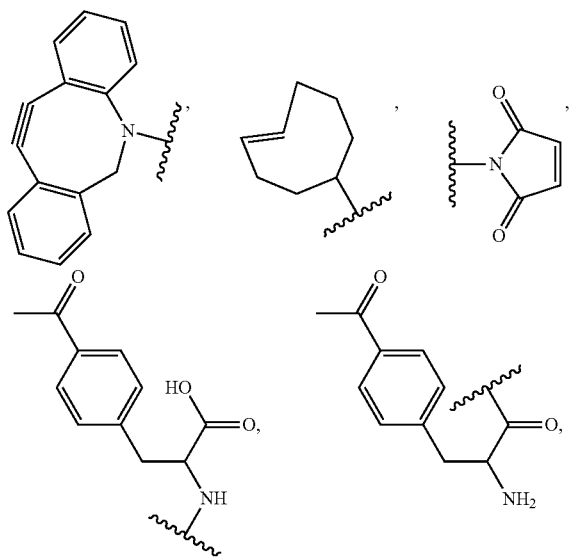

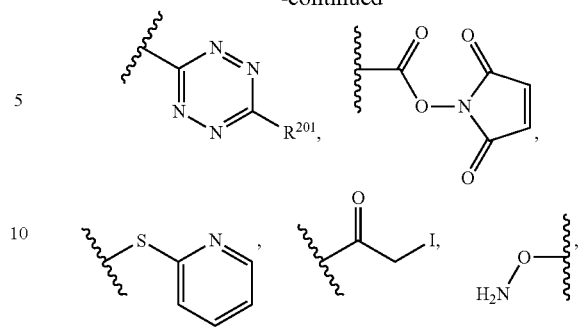

—N₃, or —SH; wherein $R^{201}$ is lower alkyl. In an embodiment, $R^{201}$ is methyl, ethyl, or propyl. In an embodiment, $R^{201}$ is methyl.

After conjugation, a divalent residue of the conjugating group is formed and is bonded to the residue of a second compound. The structure of the divalent residue is determined by the type of conjugation reaction employed to form the conjugate.

In certain embodiments when a conjugate is formed through a [3+2] alkyne-azide cycloaddition reaction, the divalent residue of the conjugating group comprises a triazole ring or fused cyclic group comprising a triazole ring. In certain embodiment when a conjugate is formed through a [3+2] alkyne-azide cycloaddition reaction, the divalent residue of the conjugating group is:

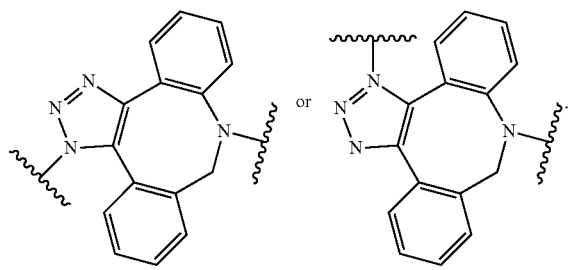

In certain embodiments when a conjugate is formed through a tetrazine inverse electron demand Diels-Alder ligation reaction, the divalent residue of the conjugating group comprises a fused bicyclic ring having at least two adjacent nitrogen atoms in the ring. In certain embodiments when a conjugate is formed through a tetrazine inverse electron demand Diels-Alder ligation reaction, the divalent residue of the conjugating group is:

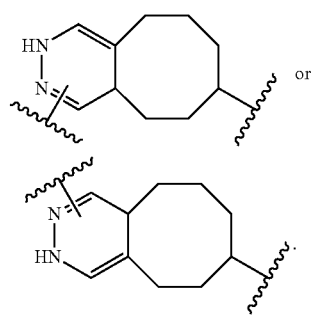

In certain embodiments when a conjugate is formed through a thiol-maleimide reaction, the divalent residue of the conjugating group comprises succinimidylene and a sulfur linkage. In certain embodiments when a conjugate is formed through a thiol-maleimide reaction, the divalent residue of the conjugating group is:

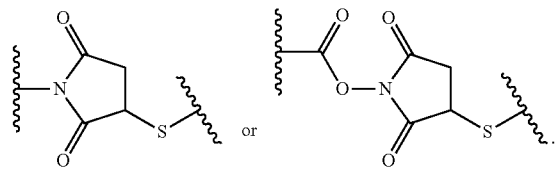 [SMILES: *SC1CC(=O)N(*)C1=O ; "or" ; *SC1CC(=O)N(OC(*)=O)C1=O]

In certain embodiments when a conjugate is formed through a carbonyl-oxyamine reaction, the divalent residue of the conjugating group comprises a divalent residue of a non-natural amino acid. In certain embodiments when a conjugate is formed through a carbonyl-oxyamine reaction, the divalent residue of the conjugating group is:

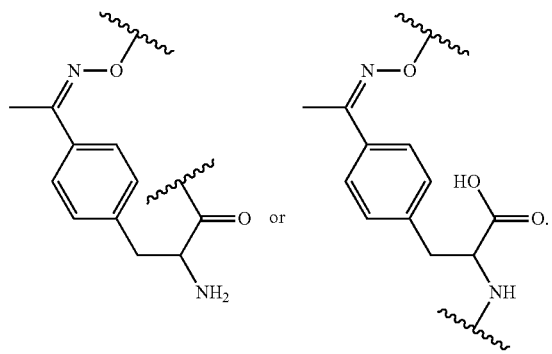 [SMILES: *O/N=C(/C)c1ccc(CC(N)C(*)=O)cc1 ; "or" ; *NC(Cc1ccc(/C(C)=N\O*)cc1)C(=O)O]

In certain embodiments when a conjugate is formed through a carbonyl-oxyamine reaction, the divalent residue of the conjugating group comprises an oxime linkage. In certain embodiments when a conjugate is formed through a carbonyl-oxyamine reaction, the divalent residue of the conjugating group is:

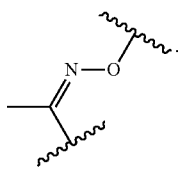 [SMILES: *O/N=C(\*)C]

In an embodiment, provided herein is a compound according to any of Formulas 1000-1002b, I-Ib, or X-XIXb-2, or a pharmaceutically acceptable salt, solvate, stereoisomer, or tautomer thereof; wherein Ar is a divalent five- or six-membered, substituted or unsubstituted, monocyclic aryl or heteroaryl ring. In an embodiment, provided herein is a compound according to any of Formulas XVIb1000-1002b, I-Ib, or X-XIXb-2, or a pharmaceutically acceptable salt, solvate, stereoisomer, or tautomer thereof; wherein Ar is a divalent six-membered, substituted or unsubstituted, monocyclic aryl or heteroaryl ring. In an embodiment, provided herein is a compound according to any of Formulas XVIb1000-1002b, I-Ib, or X-XIXb-2, or a pharmaceutically acceptable salt, solvate, stereoisomer, or tautomer thereof; wherein Ar is a divalent eight-, nine- or ten-membered, substituted or unsubstituted, fused bicyclic aryl or heteroaryl ring. In an embodiment, provided herein is a compound according to any of Formulas XVIb1000-1002b, I-Ib, or X-XIXb-2, or a pharmaceutically acceptable salt, solvate, stereoisomer, or tautomer thereof; wherein Ar is a divalent nine-membered, substituted or unsubstituted, fused bicyclic heteroaryl ring. In an embodiment, provided herein is a compound according to any of Formulas XVIb1000-1002b, I-Ib, or X-XIXb-2, or a pharmaceutically acceptable salt, solvate, stereoisomer, or tautomer thereof; wherein Ar is phenylene or indolylene, each of which is unsubstituted or substituted. In an embodiment, provided herein is a compound according to any of Formulas XVIb1000-1002b, I-Ib, or X-XIXb-2, or a pharmaceutically acceptable salt, solvate, stereoisomer, or tautomer thereof; wherein Ar is any of the following:

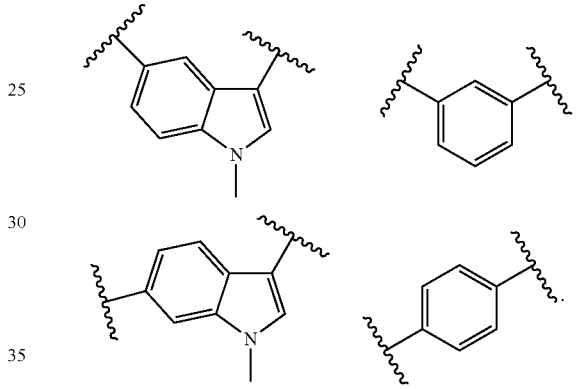

In an embodiment, provided herein is a compound according to any of Formulas XVIb1000-1002b, I-Ib, or X-XIXb-2, or a pharmaceutically acceptable salt, solvate, stereoisomer, or tautomer thereof; wherein L is absent. In an embodiment, provided herein is a compound according to any of Formulas XVIb1000-1002b, I-Ib, or X-XIXb-2, or a pharmaceutically acceptable salt, solvate, stereoisomer, or tautomer thereof; wherein L is —CH$_2$—.

In an embodiment, provided herein is a compound according to any of Formulas 1000-1002b and I-XIXb-2 in which the group "EG" is present in the formula, or a pharmaceutically acceptable salt, solvate, stereoisomer, or tautomer thereof; wherein EG comprises phenylene, carboxylene, amino, or a combination thereof. In an embodiment, provided herein is a compound according to any of Formulas I 1000-1002b and I-XIXb-2 in which the group "EG" is present in the formula, or a pharmaceutically acceptable salt, solvate, stereoisomer, or tautomer thereof; wherein EG is:

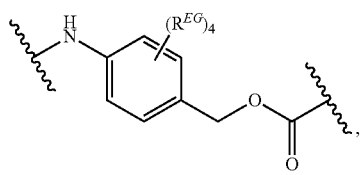

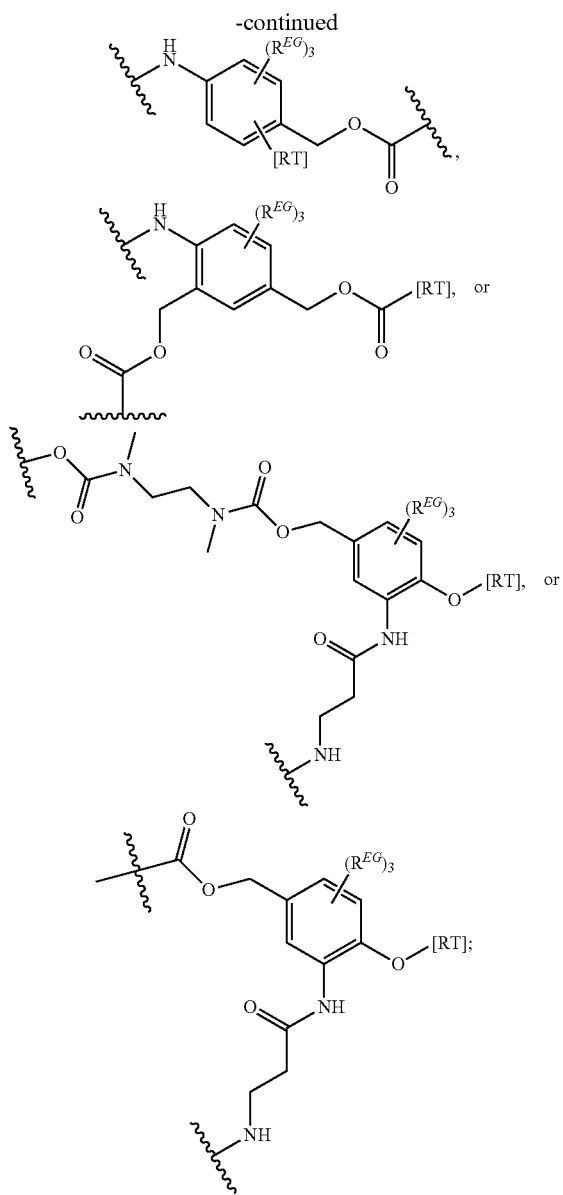

wherein each $R^{EG}$ is independently selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylaminoC(O)—. In the second and third structures, those of skill will recognize that EG is bonded to an RT that is not within the backbone of formula 1000 or (I) as indicated in the above description of formula 1000 and (I). In some embodiments, each $R^{EG}$ is independently selected from the group consisting of hydrogen, alkyl, biphenyl, —CF$_3$, alkoxyl, alkylamino, dialkylamino, alkyl-C(O)O—, alkylamino-C(O)— and dialkylaminoC(O)—. In further embodiments, each $R^{EG}$ is independently selected from the group consisting of hydrogen, —NO$_2$, —CN, fluoro, bromo, and chloro.

In an embodiment, provided herein is a compound according to any of Formulas 1000-1002b and I-XIXb-2 in which the group "RT" is present in the formula, or a pharmaceutically acceptable salt, solvate, stereoisomer, or tautomer thereof; wherein RT comprises a residue of a natural or non-natural amino acid or a residue of a sugar. In an embodiment, provided herein is a compound according to any of Formulas I1000-1002b and I-XIXb-2 in which the group "RT" is present in the formula, or a pharmaceutically acceptable salt, solvate, stereoisomer, or tautomer thereof; wherein RT is:

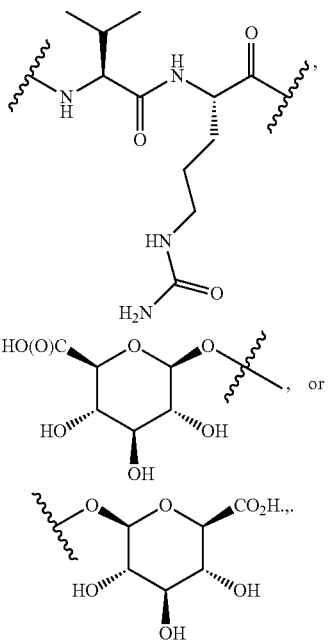

Those of skill will recognize that the first structure is divalent and can be bonded within the backbone of formula 1000 or (I), and that the second structure is monovalent and can be bonded to EG as depicted in formula 1000 and (I) above.

In an embodiment, provided herein is a compound according to any of Formulas 1000-1002b and I-XIXb-2 in which the group "HP" is present in the formula, or a pharmaceutically acceptable salt, solvate, stereoisomer, or tautomer thereof; wherein HP comprises poly(ethylene glycol). In an embodiment, provided herein is a compound according to any of Formulas 1000-1002b and I-XIXb-2 in which the group "HP" is present in the formula, or a pharmaceutically acceptable salt, solvate, stereoisomer, or tautomer thereof; wherein HP is:

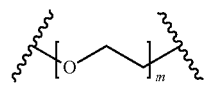

wherein m is an integer from 1 to 12.

In an embodiment, provided herein is a compound according to any of Formulas 1000-1002b and I-XIXb-2 in which the group "SG" is present in the formula, or a pharmaceutically acceptable salt, solvate, stereoisomer, or tautomer thereof; wherein SG com comprises $C_1$-$C_{10}$ alkylene, $C_4$-$C_6$ alkylene, —C(O)—, or combination thereof. In an embodiment, provided herein is a compound according to any of Formulas 1000-1002b and I-XIXb-2 in which the group "SG" is present in the formula, or a pharmaceutically acceptable salt, solvate, stereoisomer, or tautomer thereof; wherein SG is:

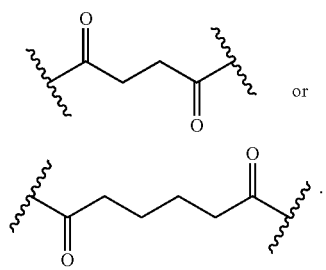 or

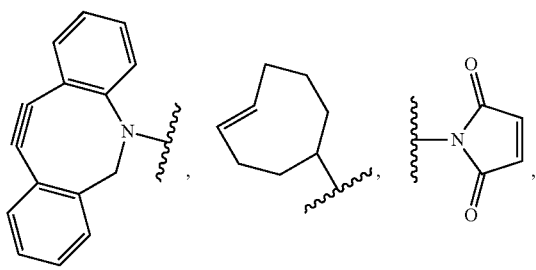.

In an embodiment, provided herein is a compound according to any of Formulas 1000-1002b and I-XIXb-2 in which the group "$W^1$," "$W^2$," "$W^3$," "$W^4$," and/or "$W^5$" is present in the formula, or a pharmaceutically acceptable salt, solvate, stereoisomer, or tautomer thereof wherein $W^1$, $W^2$, $W^3$, $W^4$, and $W^5$ are each independently a single bond, absent, or comprise a divalent ketone, divalent ester, divalent ether, divalent amide, divalent amine, alkylene, arylene, sulfide, disulfide, —C(O)—, or a combination thereof. In an embodiment, provided herein is a compound according to any of Formulas 1000-1002b and I-XIXb-2 in which the group "$W^1$," "$W^2$," "$W^3$," "$W^4$," and/or "$W^5$" is present in the formula, or a pharmaceutically acceptable salt, solvate, stereoisomer, or tautomer thereof; wherein $W^1$, $W^2$, $W^3$, $W^4$, and $W^5$ are each independently a single bond, absent, or comprise —C(O)—, —O—, —C(O)NH—, —C(O)NH-alkyl-, —OC(O)NH—, —SC(O)NH—, —NH—, —NH-alkyl-, —N(CH$_3$)CH$_2$CH$_2$N(CH$_3$)—, —S—, —S—S—, —OCH$_2$CH$_2$O—, or a combination thereof.

In an embodiment, provided herein is a compound according to any of Formulas 1000-1002b and I-XIXb-2 in which the group "R" is present in the formula, or a pharmaceutically acceptable salt, solvate, stereoisomer, or tautomer thereof; wherein R is a conjugating group or a residue of a conjugating group. In an embodiment, provided herein is a compound according to any of Formulas 1000-1002b and I-XIXb-2 in which the group "R" is present in the formula, or a pharmaceutically acceptable salt, solvate, stereoisomer, or tautomer thereof; wherein R comprises an alkyne, strained alkene, tetrazine, thiol, para-acetyl-phenyl-alanine residue, oxyamine, maleimide, carbonyl alkyl halide, aryl sulfide, or azide. In an embodiment, provided herein is a compound according to any of Formulas 1000-1002b and I-XIXb-2 in which the group "R" is present in the formula, or a pharmaceutically acceptable salt, solvate, stereoisomer, or tautomer thereof; wherein R is:

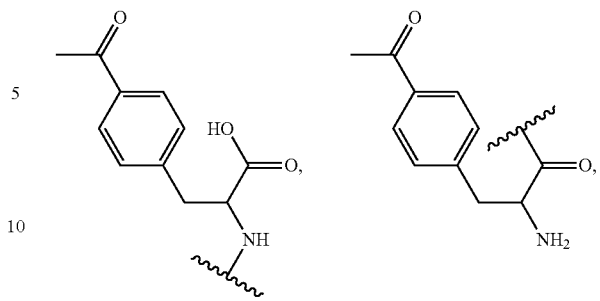

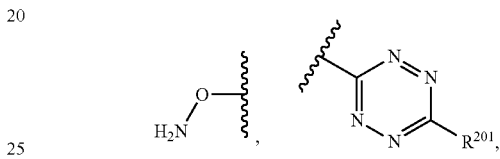,

—N$_3$, or —SH; wherein $R^{201}$ is lower alkyl. In an embodiment, provided herein is a compound according to any of Formulas 1000-1002b and I-XIXb-2 in which the group "R" is present in the formula, or a pharmaceutically acceptable salt, solvate, stereoisomer, or tautomer thereof; wherein R is:

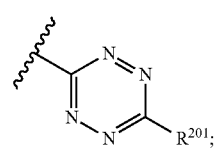

and $R^{201}$ is methyl, ethyl, or propyl. In an embodiment, provided herein is a compound according to any of Formulas 1000-1002b and I-XIXb-2 in which the group "R" is present in the formula, or a pharmaceutically acceptable salt, solvate, stereoisomer, or tautomer thereof; wherein R is:

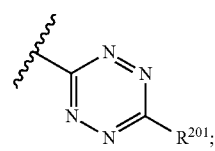

and $R^{201}$ is methyl.

In an embodiment, provided herein is a compound according to any of Formulas I-IXb, or a pharmaceutically acceptable salt, solvate, stereoisomer, or tautomer thereof; wherein $W^1$, $W^2$, $W^3$, $W^4$, $W^5$, EG, RT, HP, SG, and R combine to form —H.

In an embodiment, provided herein is a compound according to Formula 1000a or Formula 1000b:

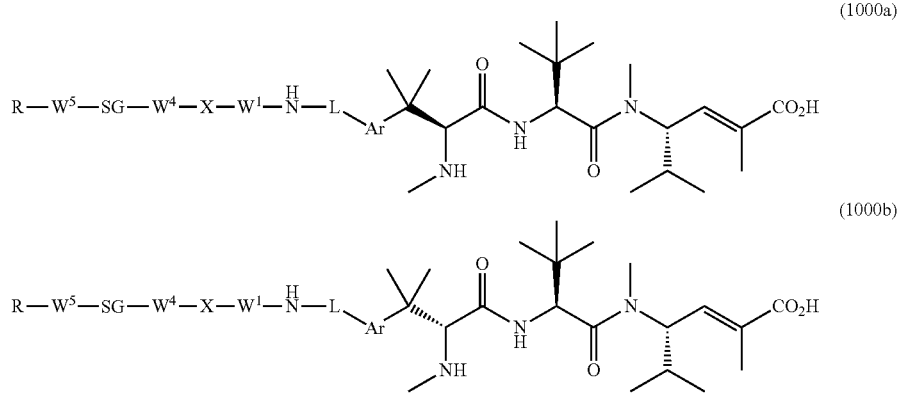

(1000a)

(1000b)

or a pharmaceutically acceptable salt, solvate, stereoisomer, or tautomer thereof; wherein X, EG, RT, HP, SG, $W^1$, $W^2$, $W^3$, $W^4$, $W^5$, R, L, and Ar are as described in the context of Formula 1000 and/or any of the embodiments described herein.

In an embodiment, provided herein is a compound according to Formula Ia or Formula Ib:

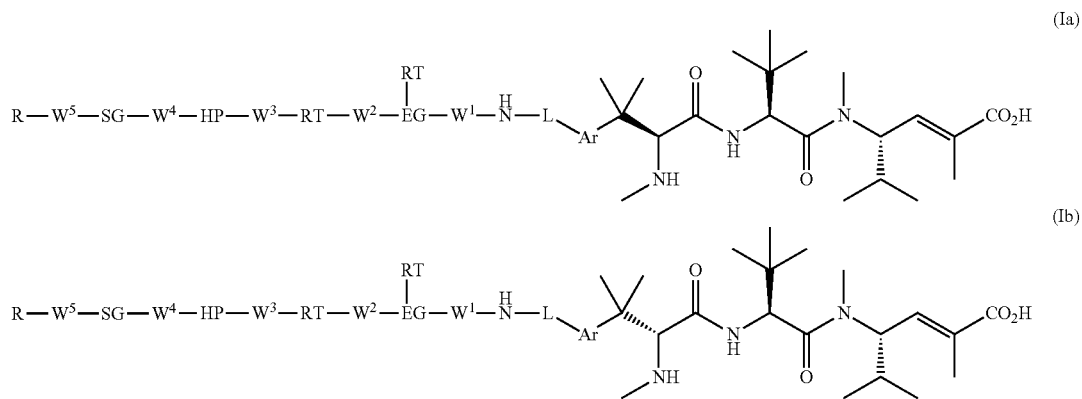

(Ia)

(Ib)

or a pharmaceutically acceptable salt, solvate, stereoisomer, or tautomer thereof; wherein EG, RT, HP, SG, $W^1$, $W^2$, $W^3$, $W^4$, $W^5$, R, L, and Ar are as described in the context of Formula I and/or any of the embodiments described herein.

In an embodiment, provided herein is a compound according to Formula 1001a or Formula 1001b:

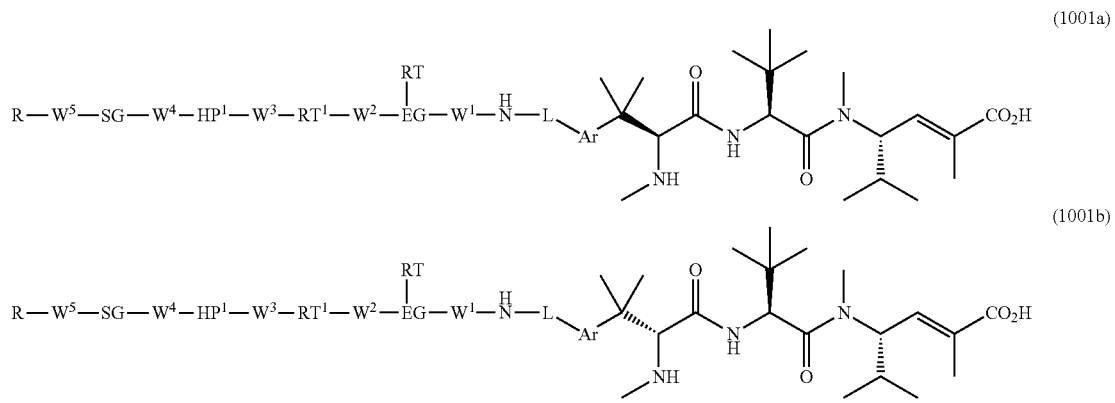

(1001a)

(1001b)

or a pharmaceutically acceptable salt, solvate, stereoisomer, or tautomer thereof; wherein EG, RT¹, HP¹, SG, W¹, W², W³, W⁴, W⁵, R, L, and Ar are as described in the context of Formula 1001 and/or any of the embodiments described herein.

In an embodiment, provided herein is a compound according to Formula 1002a or Formula 1002b:

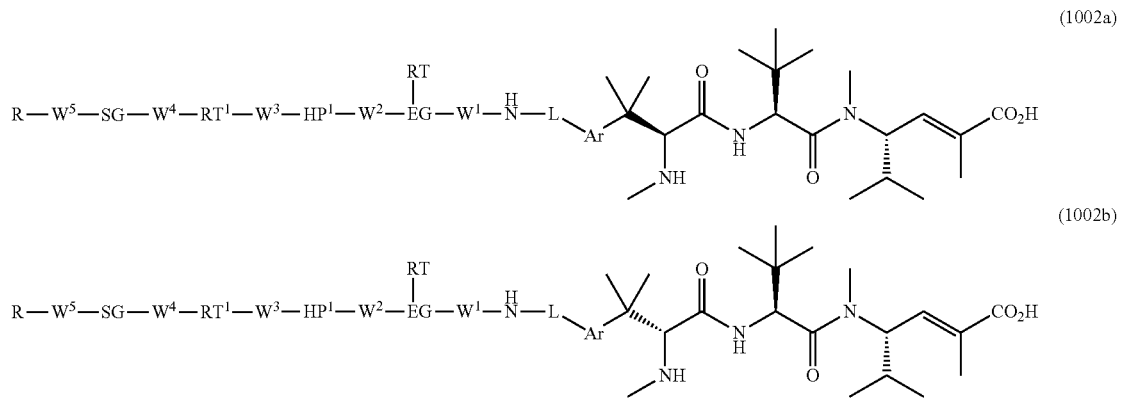

or a pharmaceutically acceptable salt, solvate, stereoisomer, or tautomer thereof; wherein EG, RT¹, HP¹, SG, W¹, W², W³, W⁴, W⁵, R, L, and Ar are as described in the context of Formula 1002 and/or any of the embodiments described herein.

In an embodiment, provided herein is a compound according to any of Formulas II-IX-1:

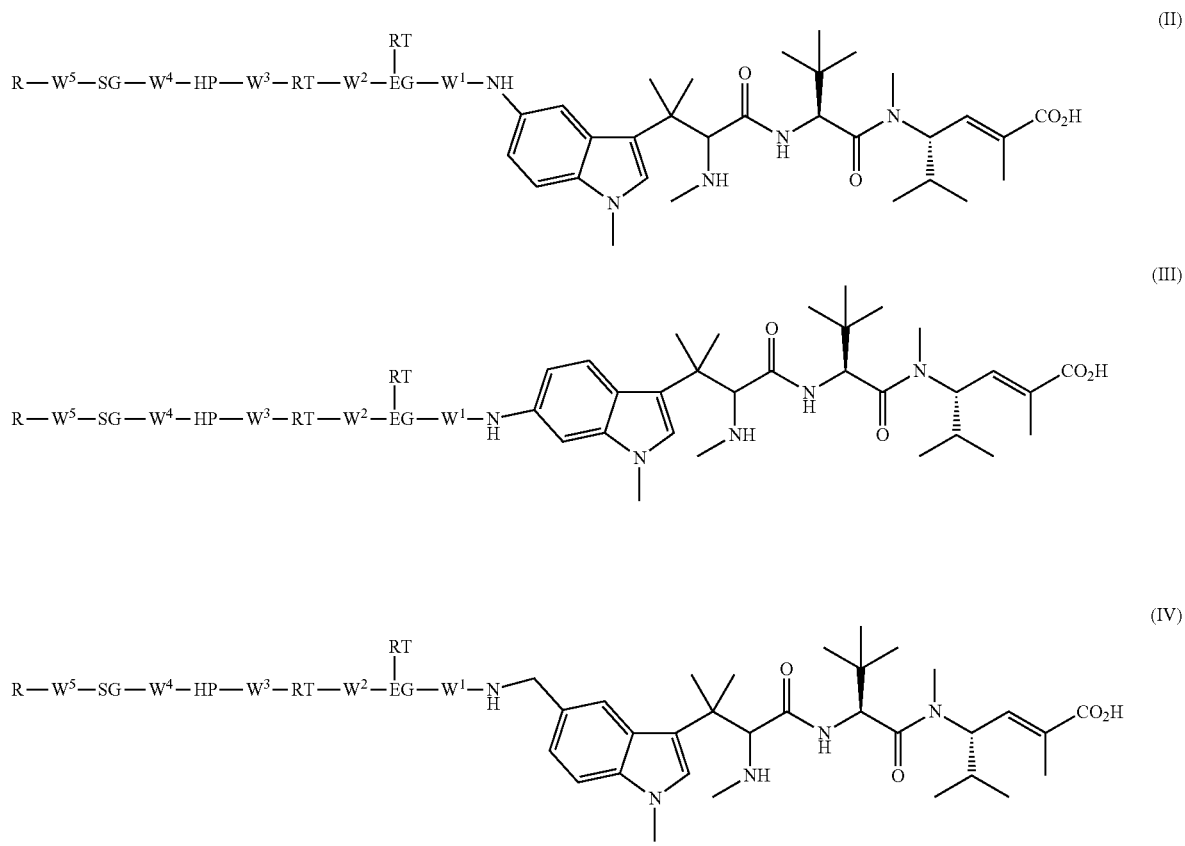

(V)
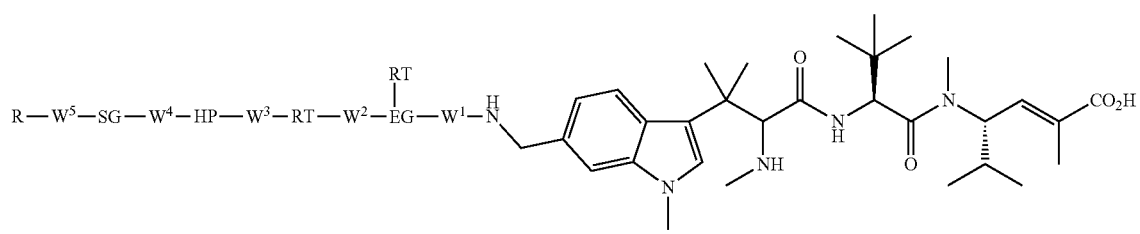
(VI)
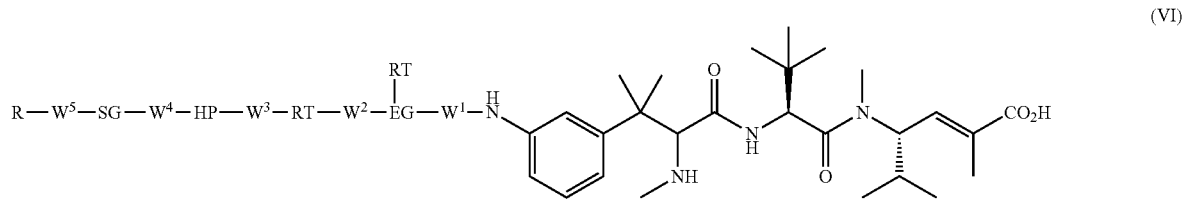
(VII)
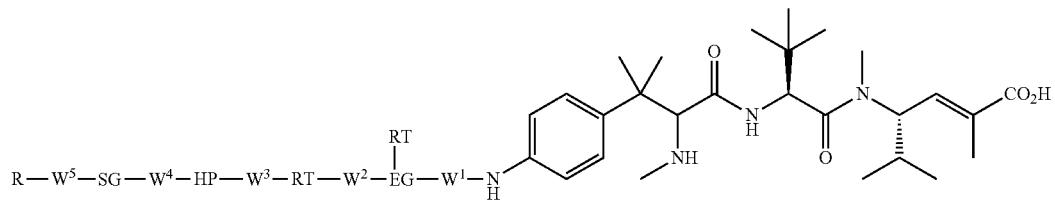
(VIII)
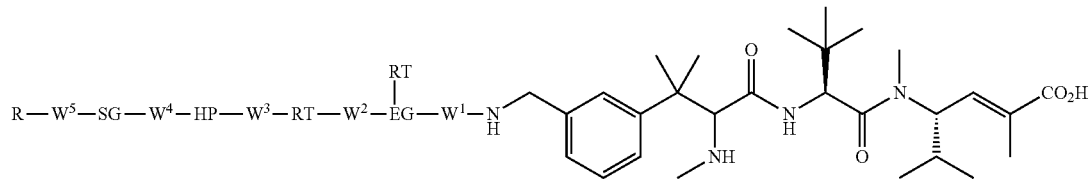
(IX)
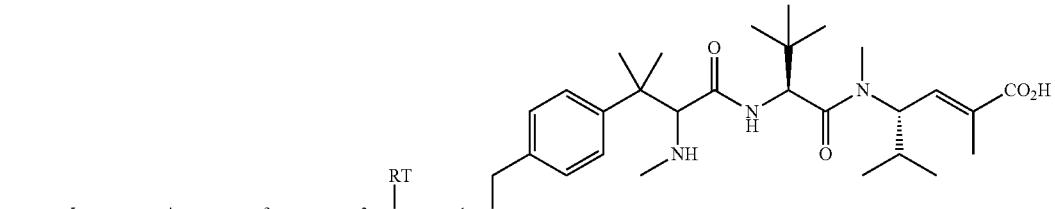
(II-1)
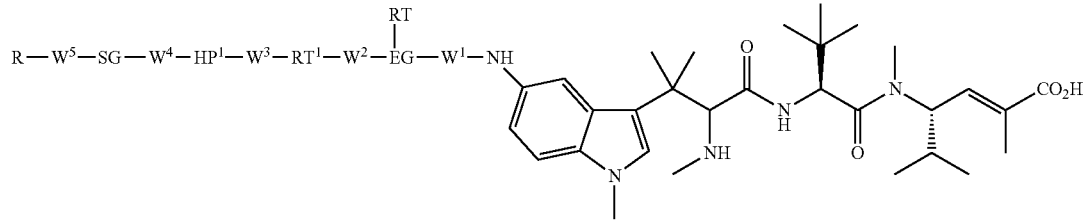
(III-1)
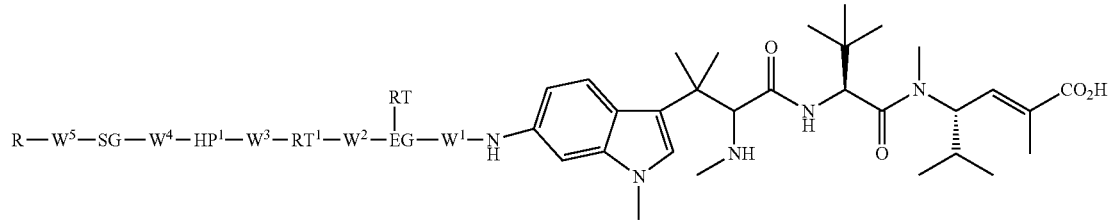

-continued
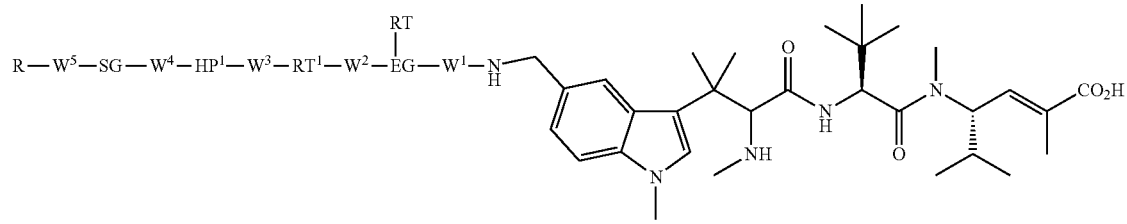
(IV-1)
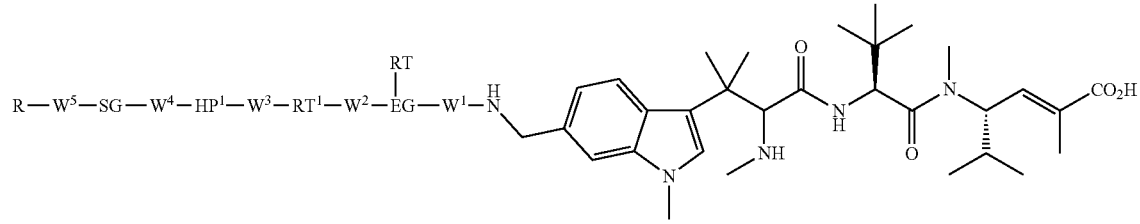
(V-1)
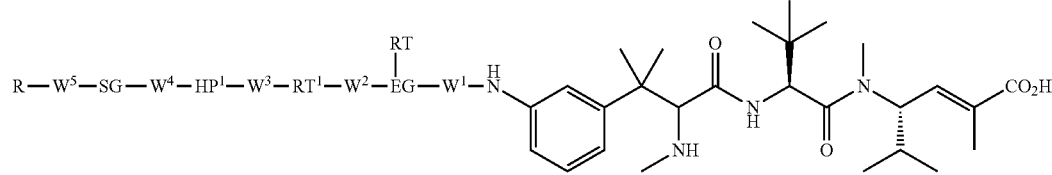
(VI-1)
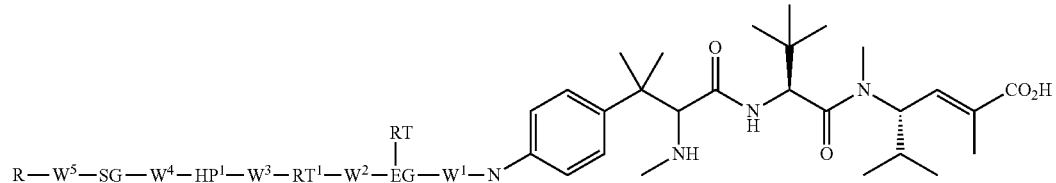
(VII-1)
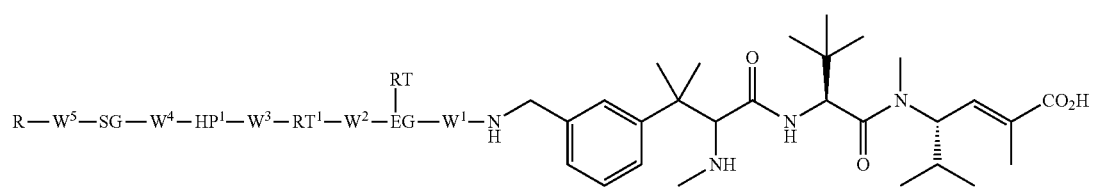
(VIII-1)
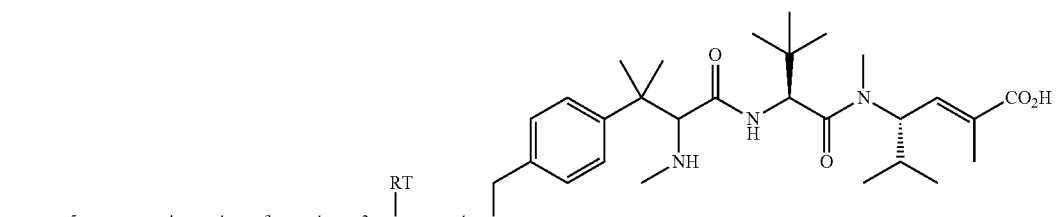
(IX-1)
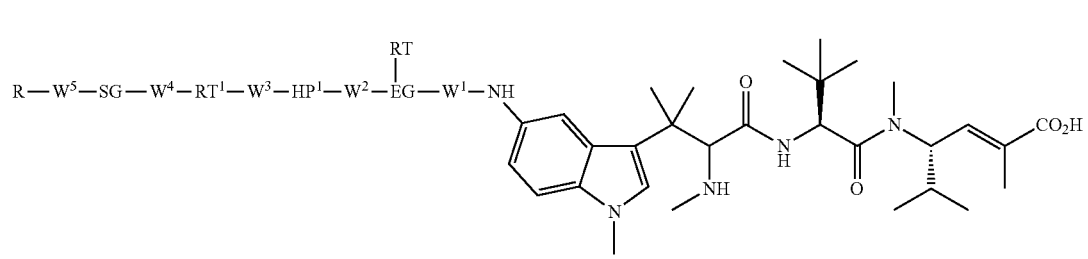
(II-2)

-continued
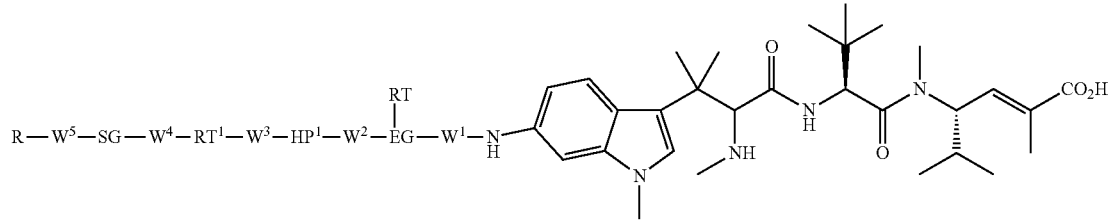
(III-2)
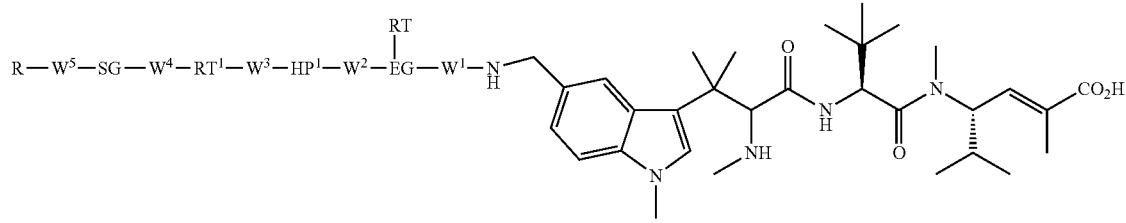
(IV-2)
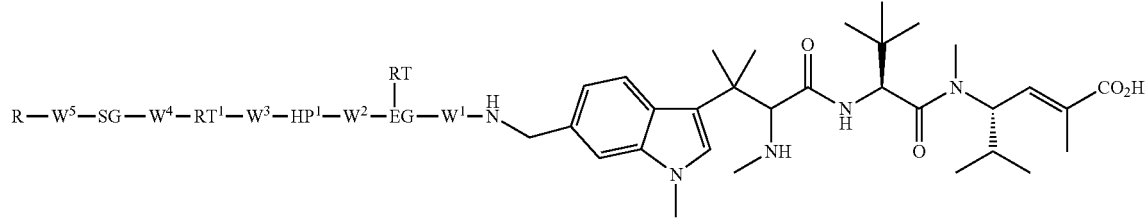
(V-2)
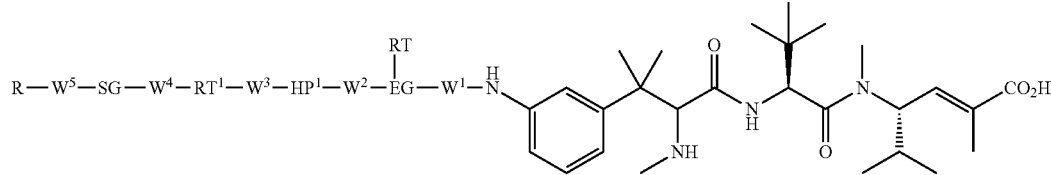
(VI-2)
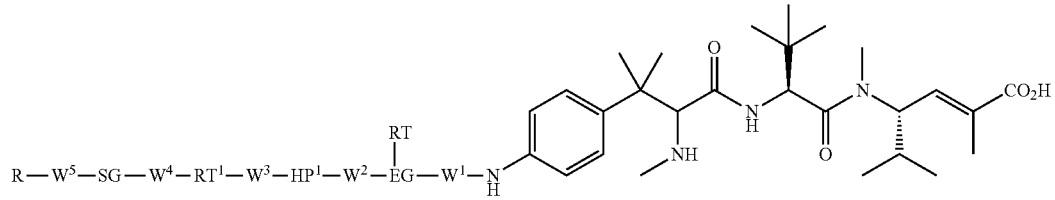
(VII-2)
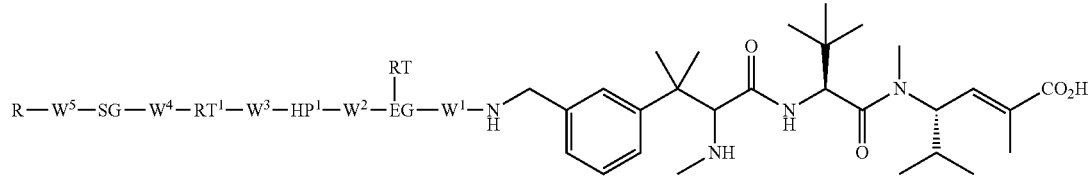
(VIII-2)

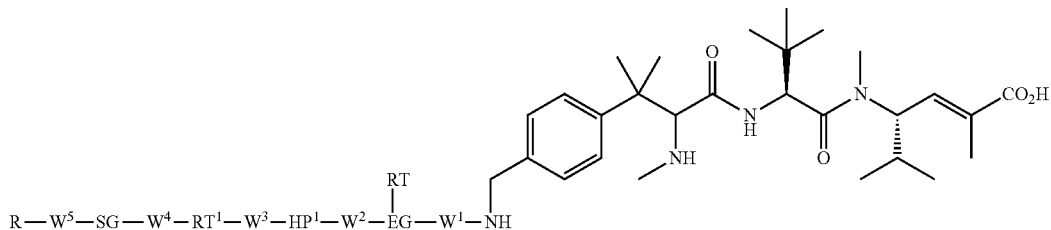
(IX-2)
or a pharmaceutically acceptable salt, solvate, stereoisomer, or tautomer thereof; wherein EG, RT, HP, RT¹, HP¹, SG, W¹, W², W³, W⁴, W⁵, and R are as described in the context of Formula 1000, I, 1001, and/or any of the embodiments described herein.
In an embodiment, provided herein is a compound according to any of Formulas IIa-IXa-1:
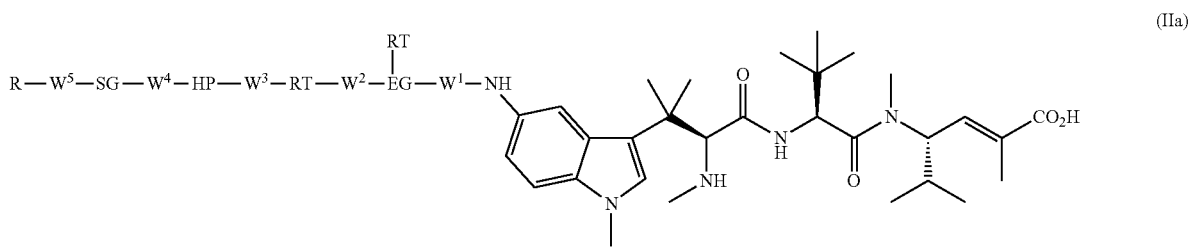
(IIa)
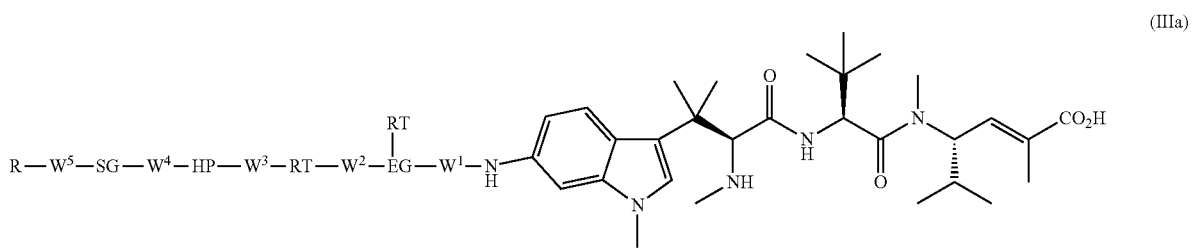
(IIIa)
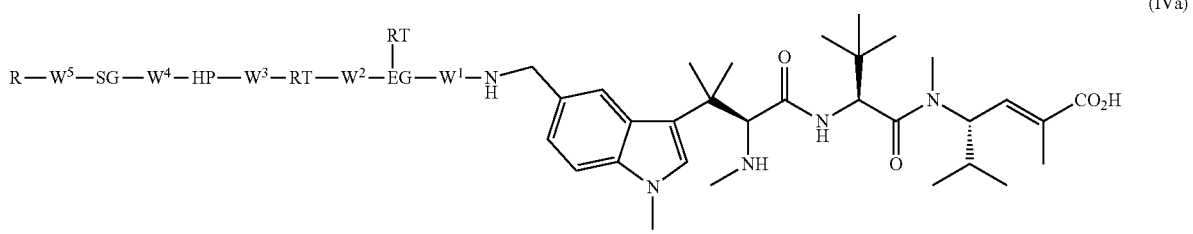
(IVa)
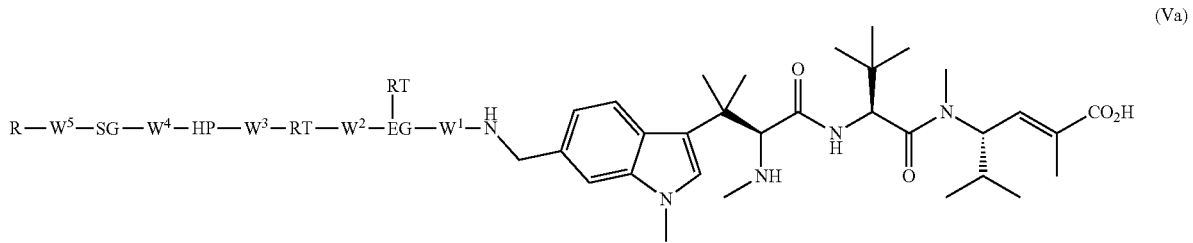
(Va)
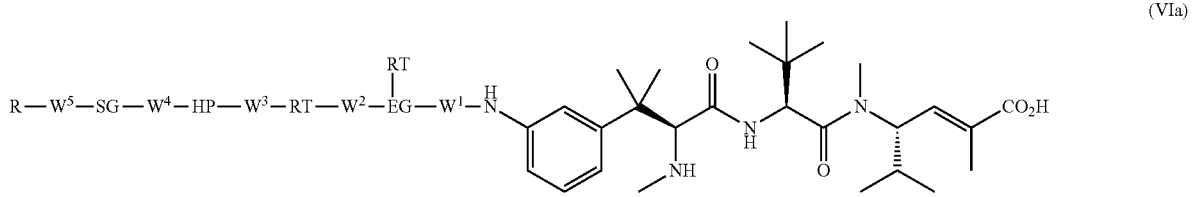
(VIa)

(VIIa)
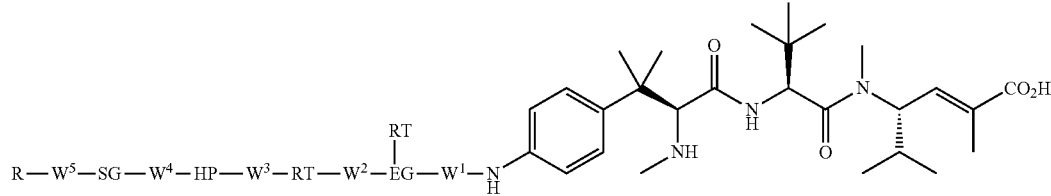
(VIIIa)
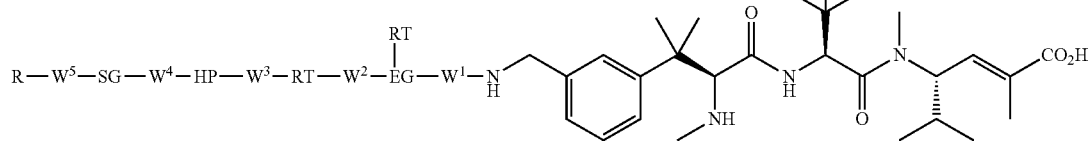
(IXa)
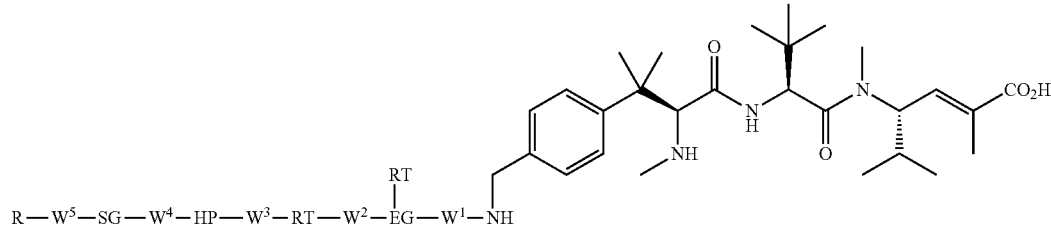
(IIa-1)
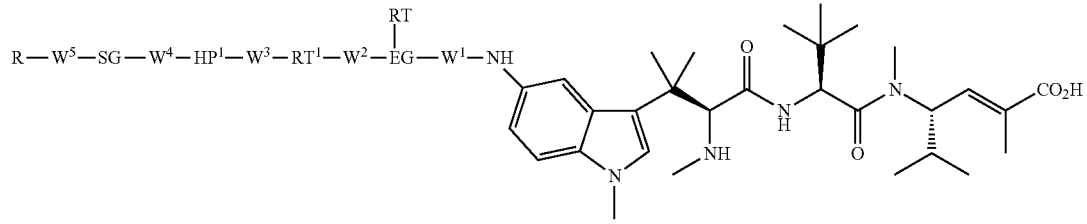
(IIIa-1)
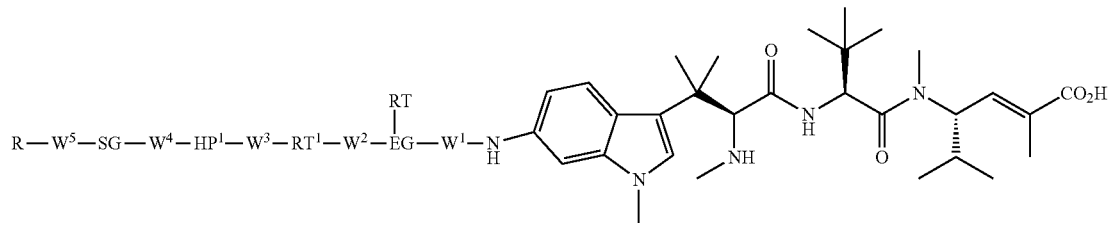
(IVa-1)
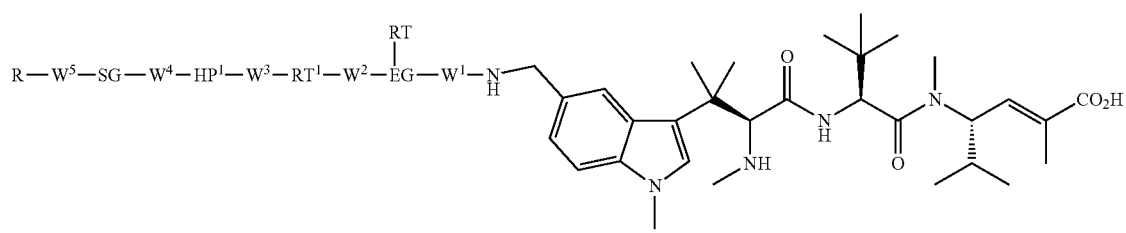
(Va-1)
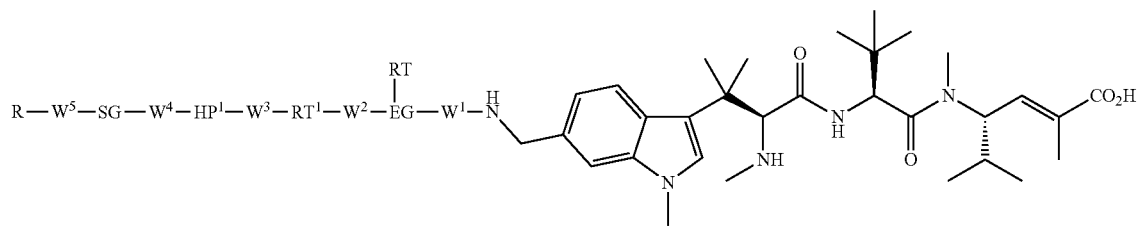

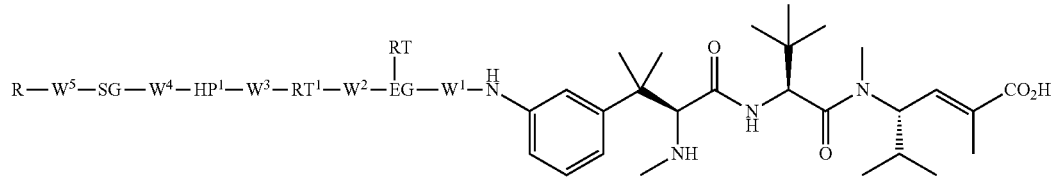
(Via-1)
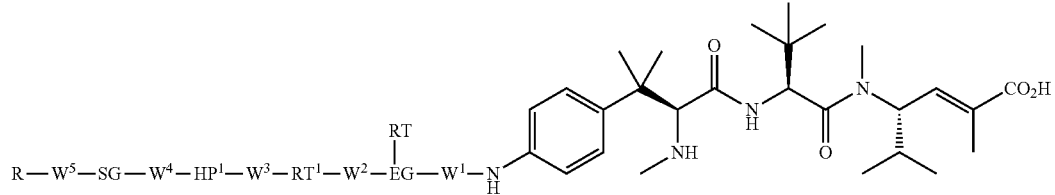
(VIIa-1)
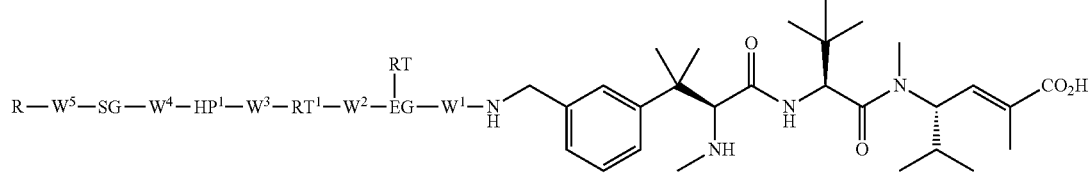
(VIIIa-1)
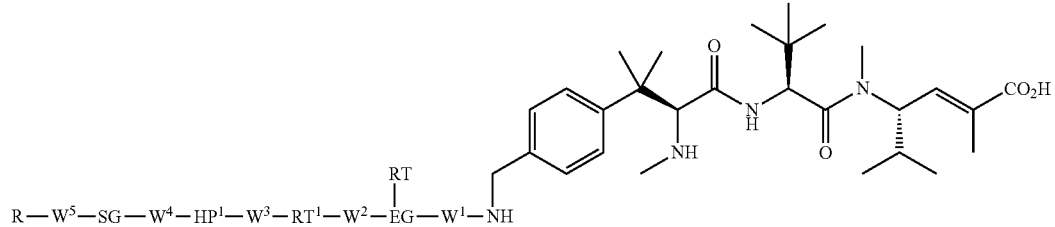
(IXa-1)
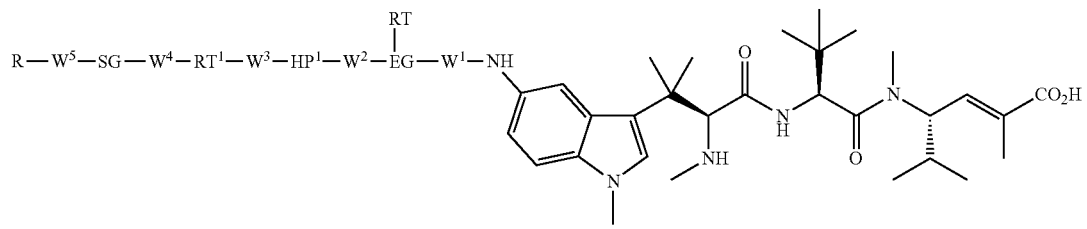
(IIa-2)
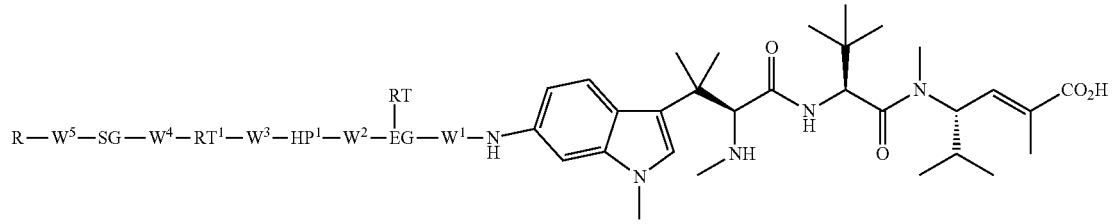
(IIIa-2)
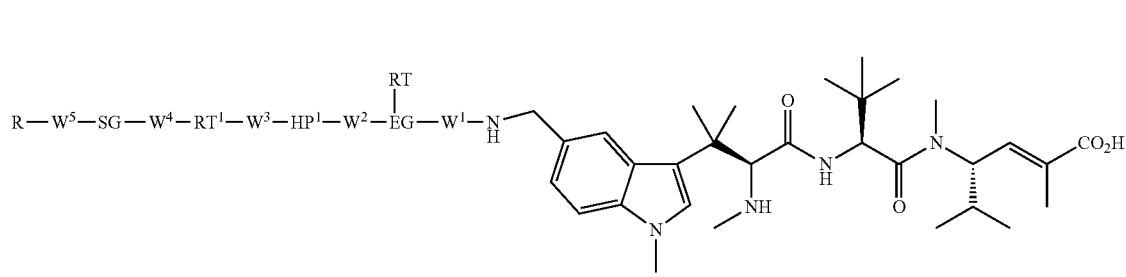
(IVa-2)

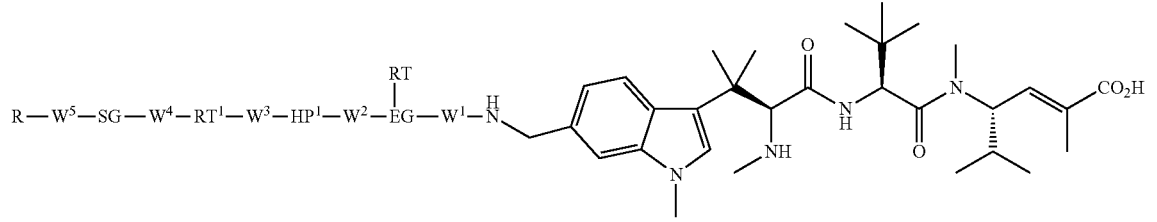
(Va-2)
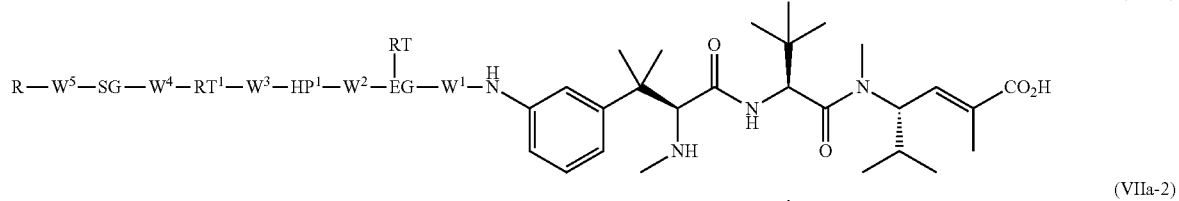
(VIa-2)
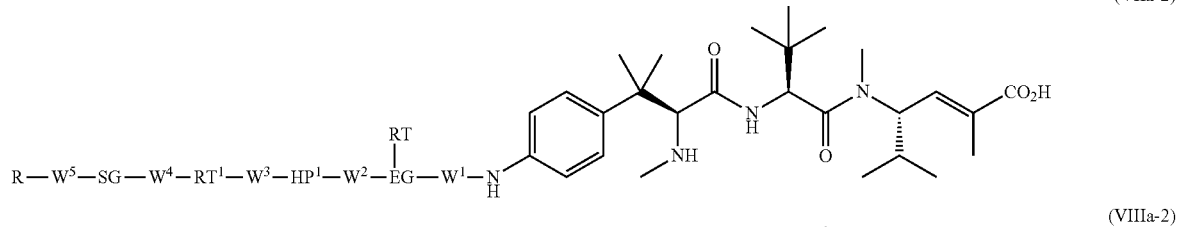
(VIIa-2)
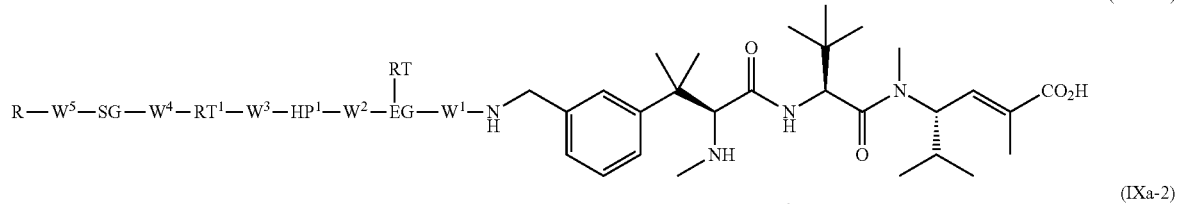
(VIIIa-2)
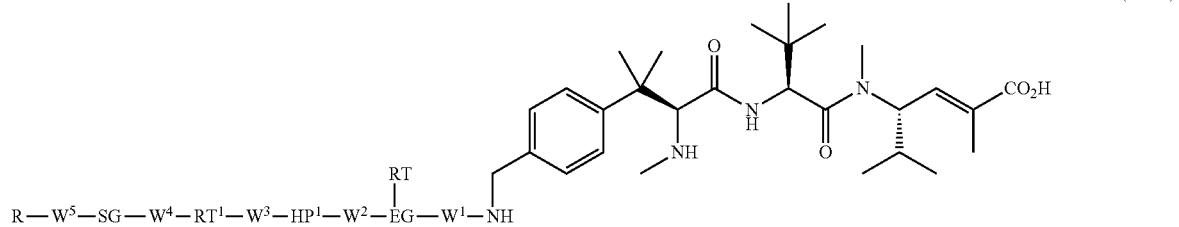
(IXa-2)
or a pharmaceutically acceptable salt, solvate, stereoisomer, or tautomer thereof; wherein EG, RT, HP, RT$^1$, HP$^1$, SG, W$^1$, W$^2$, W$^3$, W$^4$, W$^5$, and R are as described in the context of Formula 1000, I, 1001, and/or any of the embodiments described herein.
In an embodiment, provided herein is a compound according to any of Formulas IIb-IXb-1:
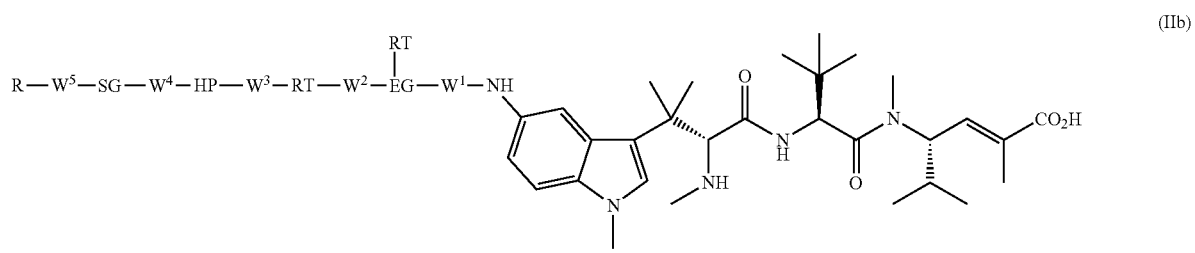
(IIb)

-continued
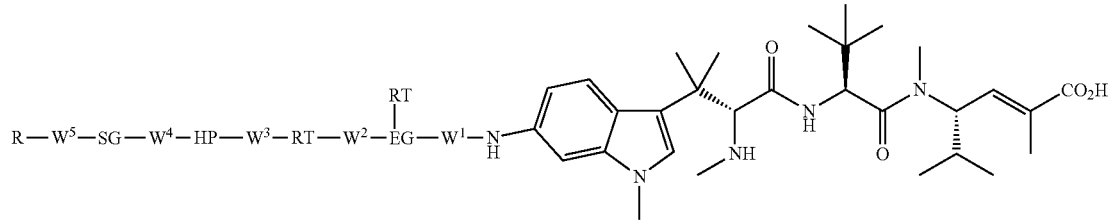
(IIIb)
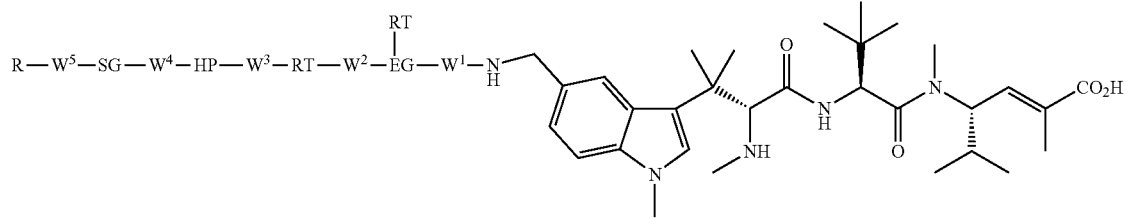
(IVb)
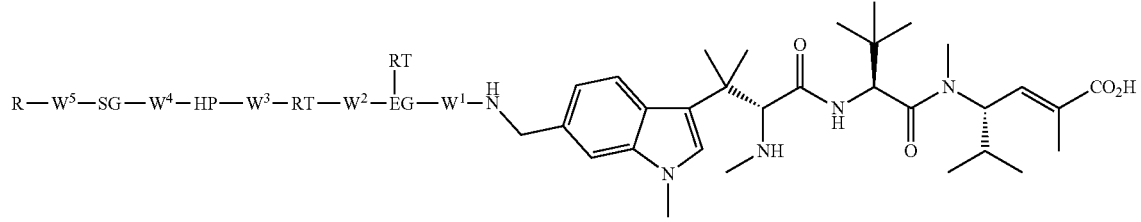
(Vb)
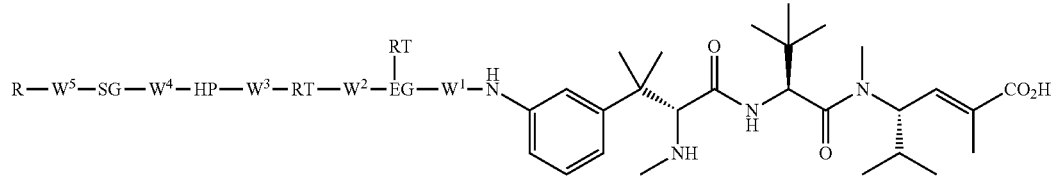
(VIb)
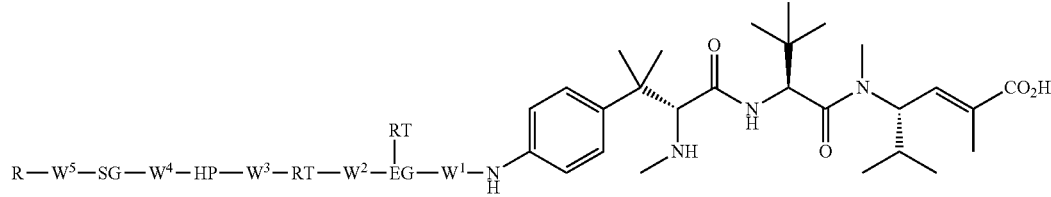
(VIIb)
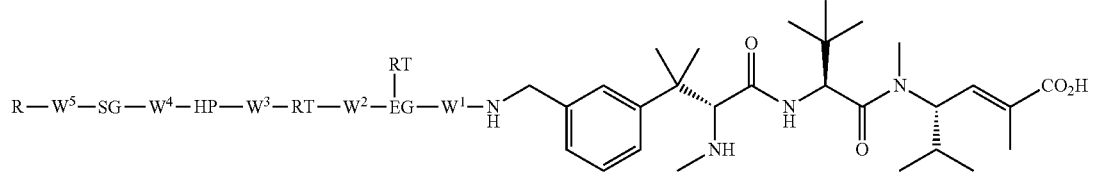
(VIIIb)
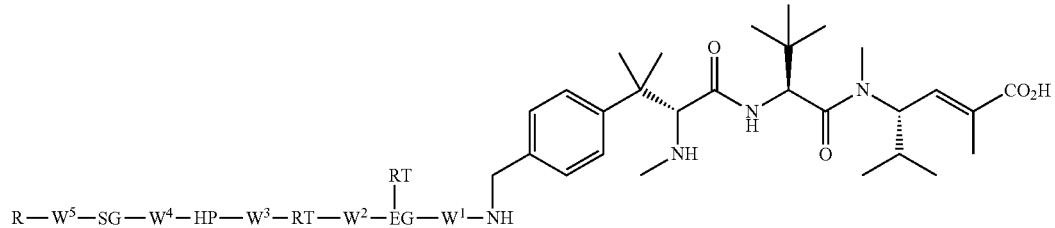
(IXb)

-continued
(IIb-1)
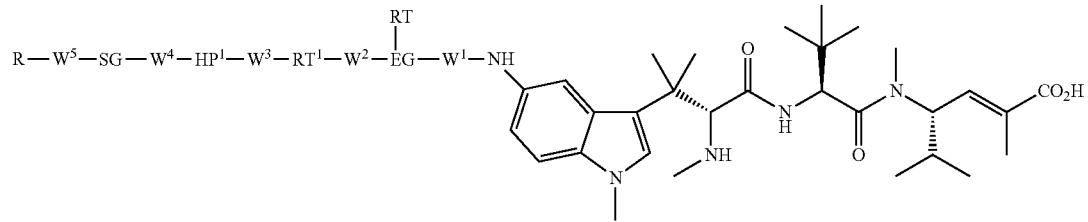
(IIIb-1)
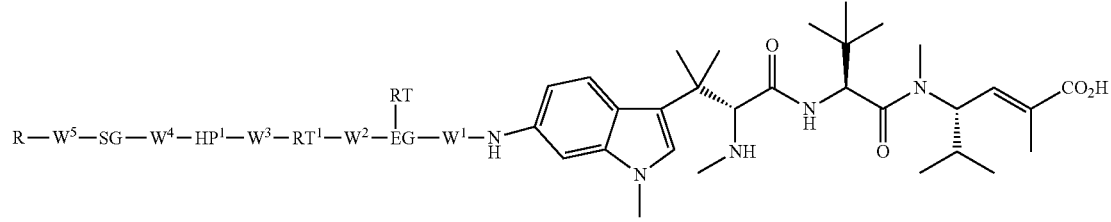
(IVb-1)
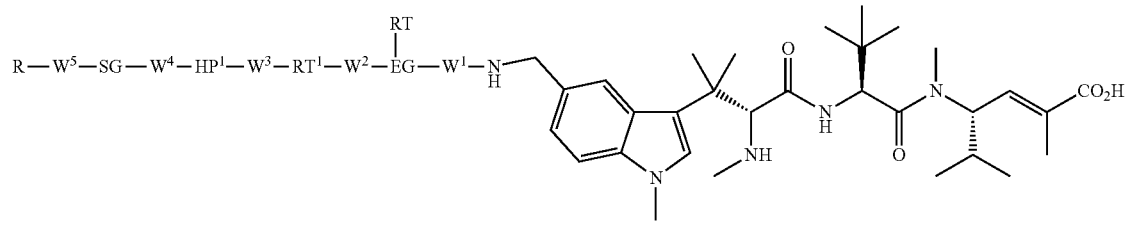
(Vb-1)
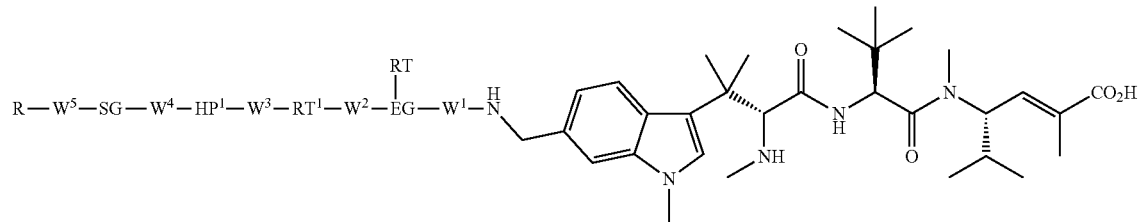
(VIb-1)
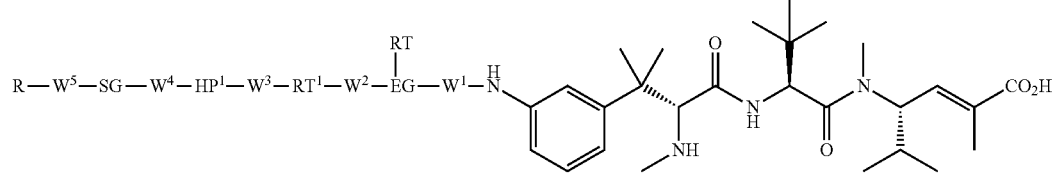
(VIIb-1)
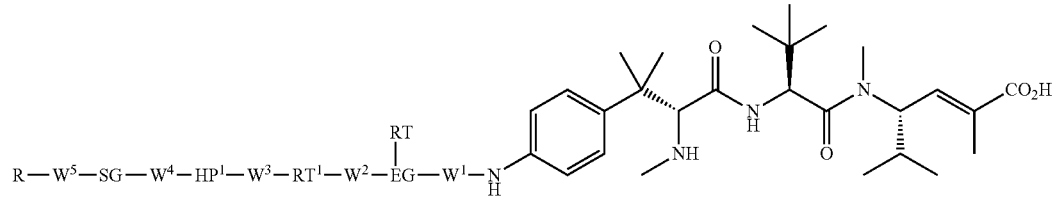
(VIIIb-1)
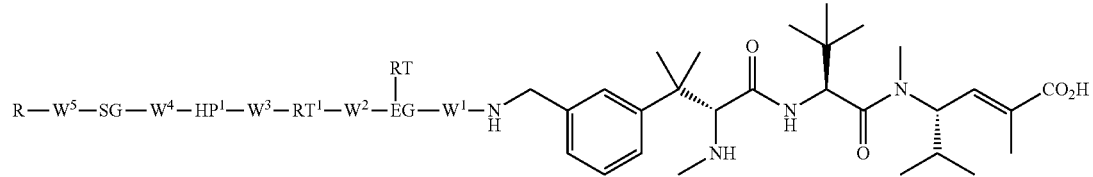

-continued
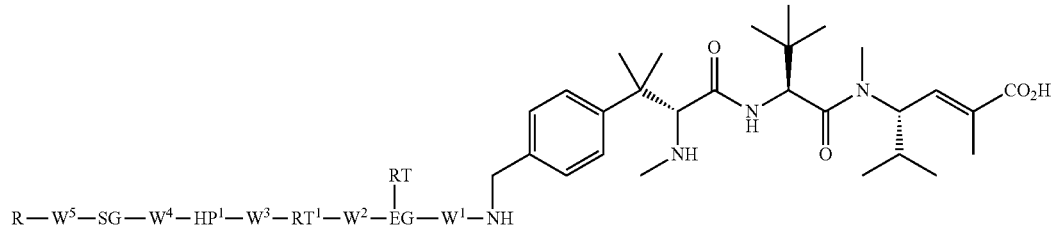
(IXb-1)
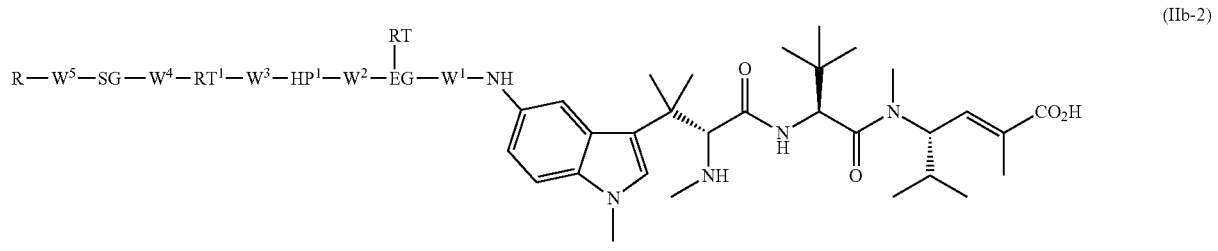
(IIb-2)
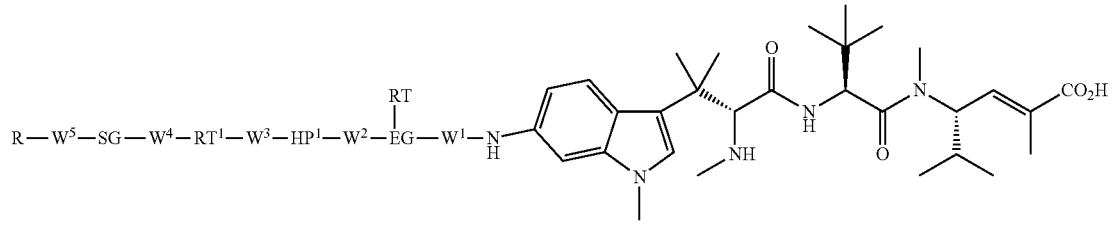
(IIIb-2)
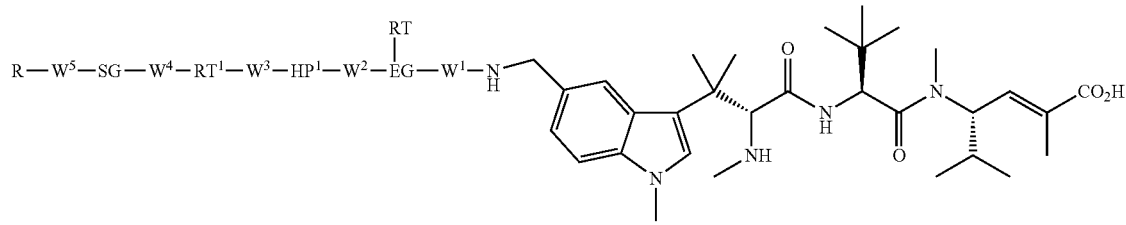
(IVb-2)
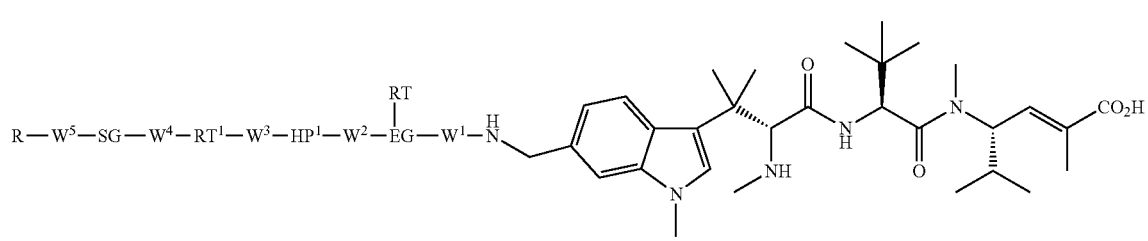
(Vb-2)
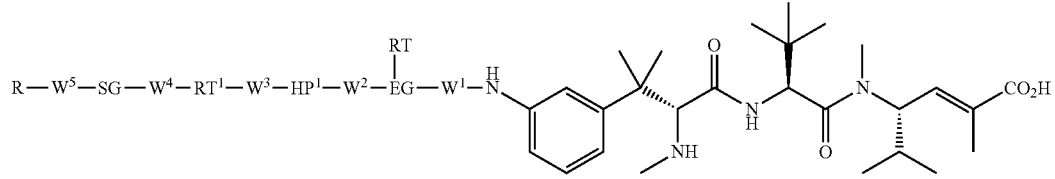
(VIb-2)
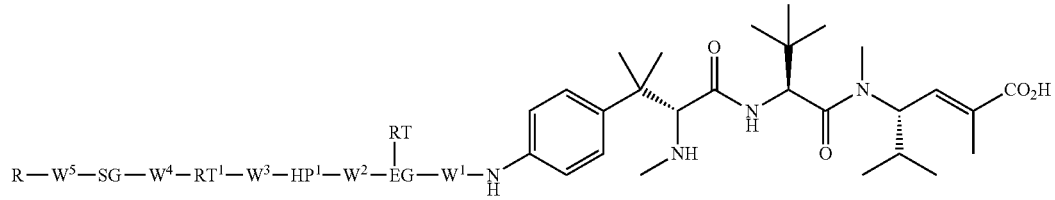
(VIIb-2)

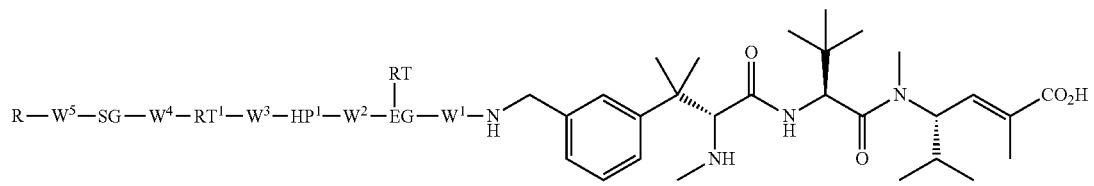

(VIIIb-2)

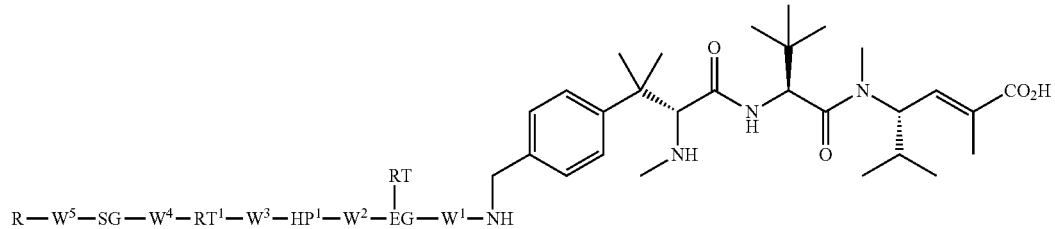

(IXb-2)

or a pharmaceutically acceptable salt, solvate, stereoisomer, or tautomer thereof; wherein EG, RT, HP, RT$^1$, HP$^1$, SG, W$^1$, W$^2$, W$^3$, W$^4$, W$^5$, and R are as described in the context of Formula 1000, I, 1001, and/or any of the embodiments described herein.

In an embodiment, provided herein is a compound according to Formula X:

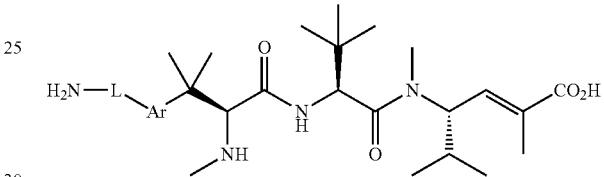

(X)

or a pharmaceutically acceptable salt, solvate, stereoisomer, or tautomer thereof; wherein L and Ar are as described in the context of Formula I.

In an embodiment, provided herein is a compound according to Formula Xa or Xb:

(Xa)

(Xb)

or a pharmaceutically acceptable salt, solvate, stereoisomer, or tautomer thereof; wherein L and Ar are as described in the context of Formula I.

In an embodiment, provided herein is a compound according to any of Formulas XI-XVI-1:

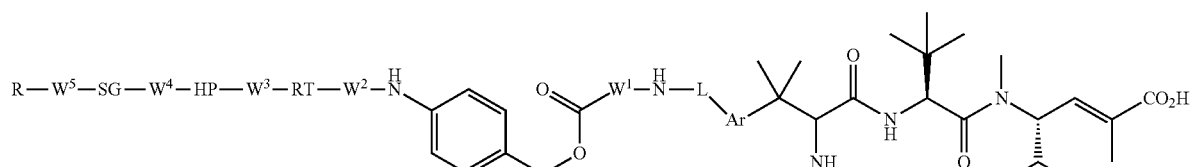

(XI)

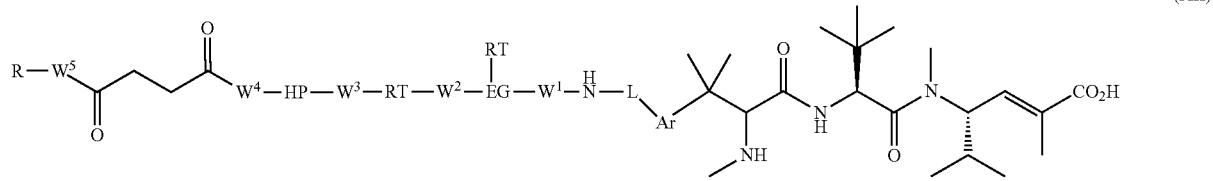

(XII)

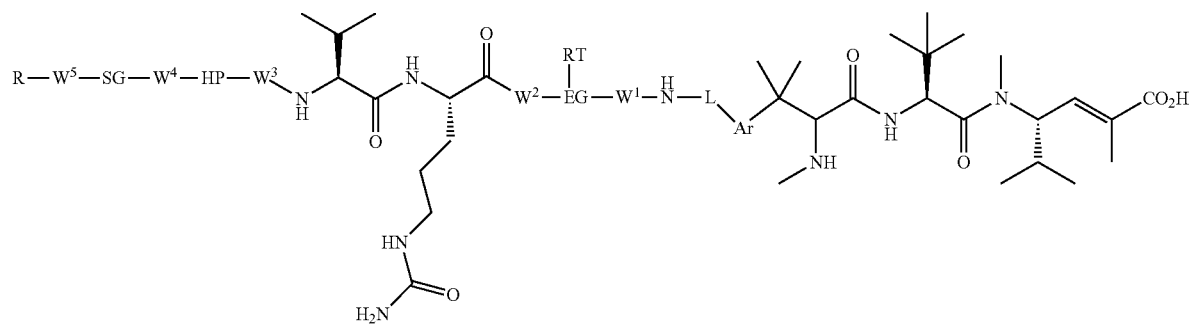
(XIII)
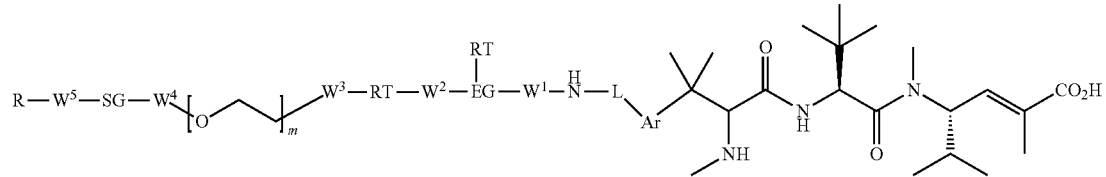
(XIV)
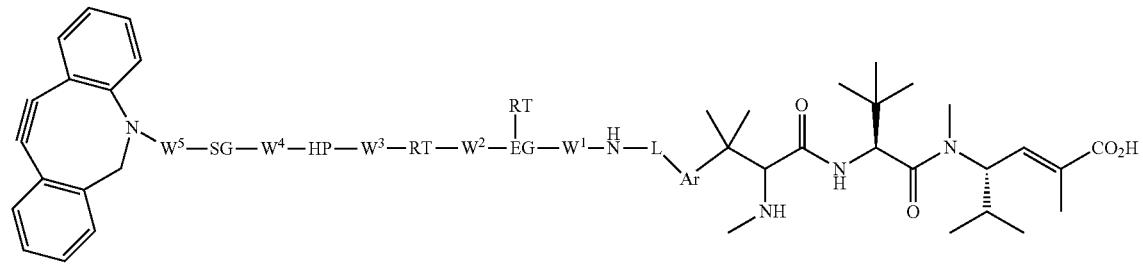
(XV)
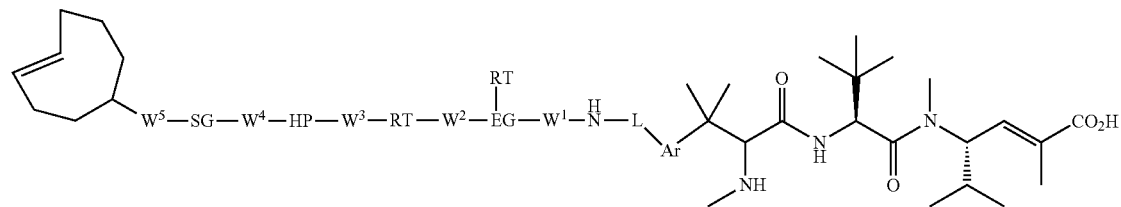
(XVI)
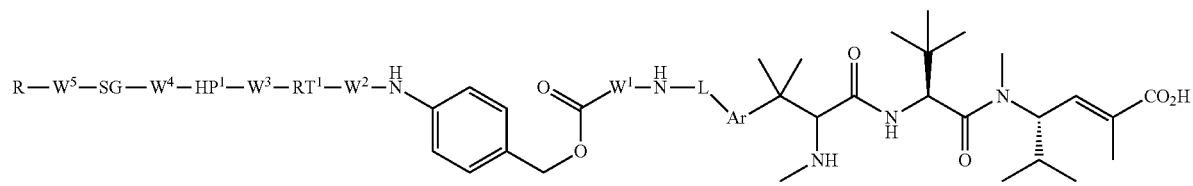
(XI-1)
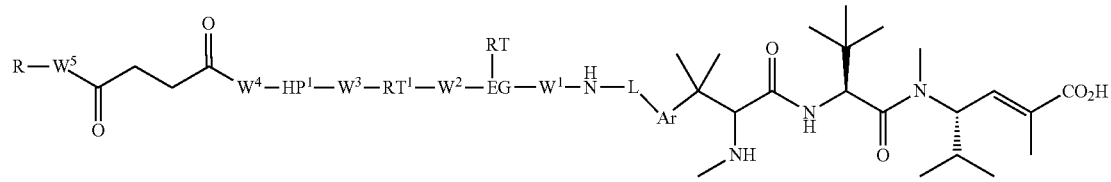
(XII-1)

(XIII-1)
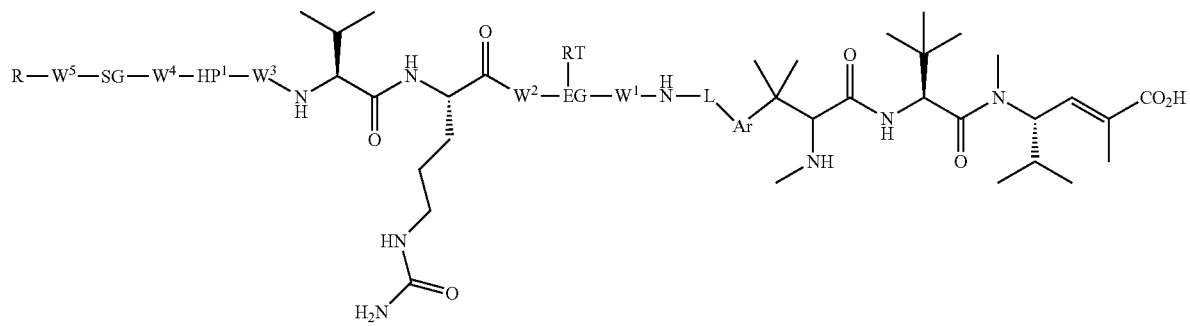
(XIV-1)
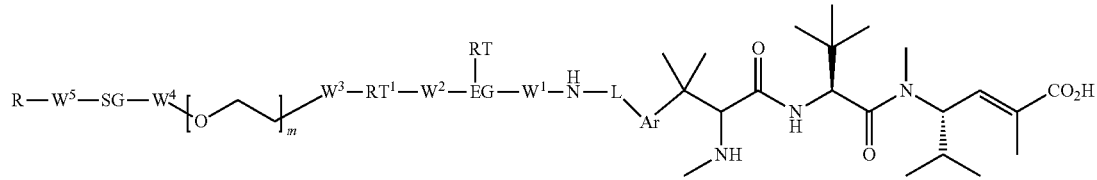
(XV-1)
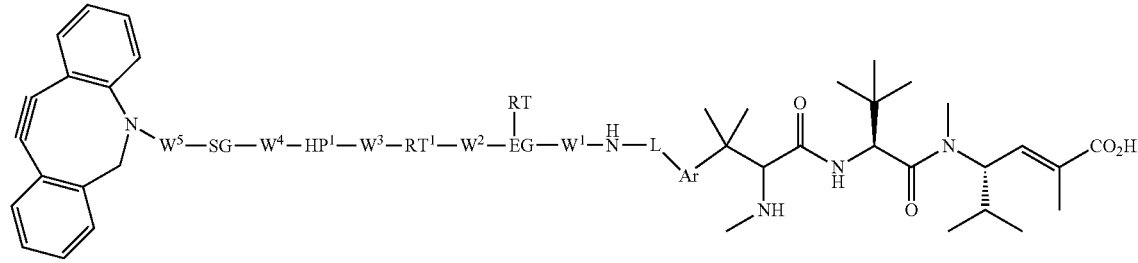
(XVI-1)
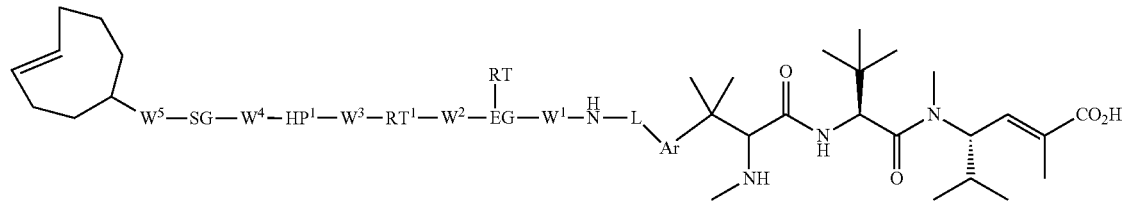
(XIX-1)
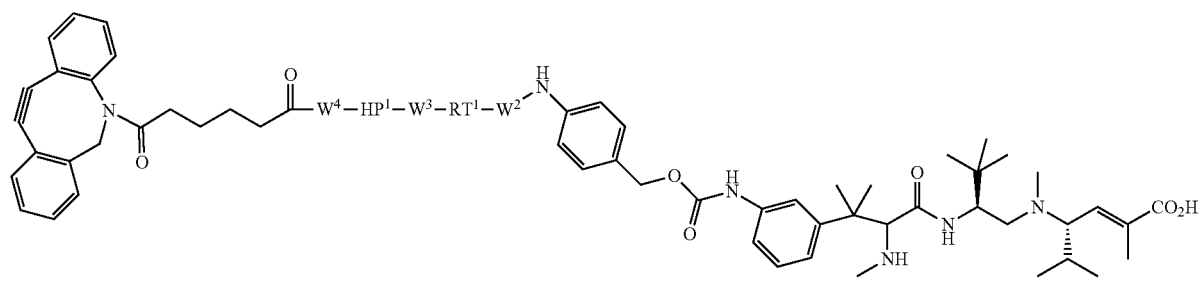
(XI-2)
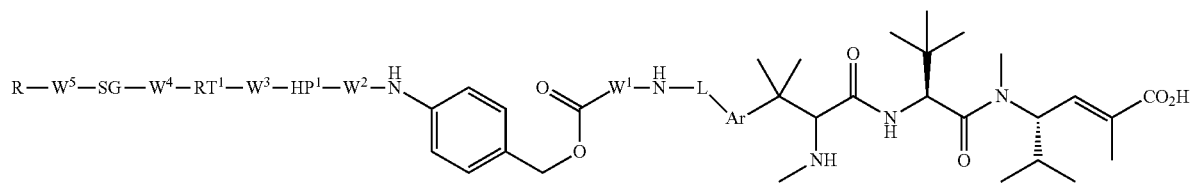

-continued
(XII-2)
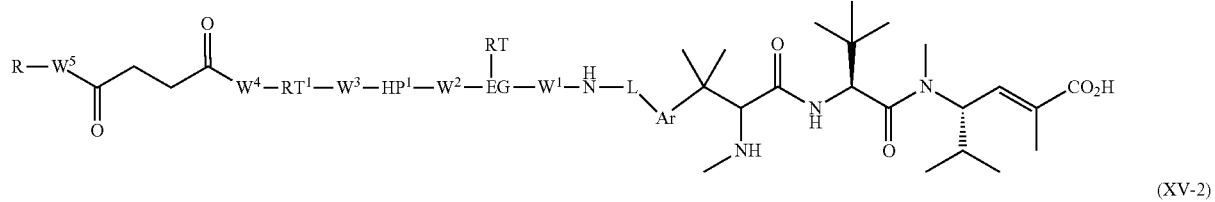
(XV-2)
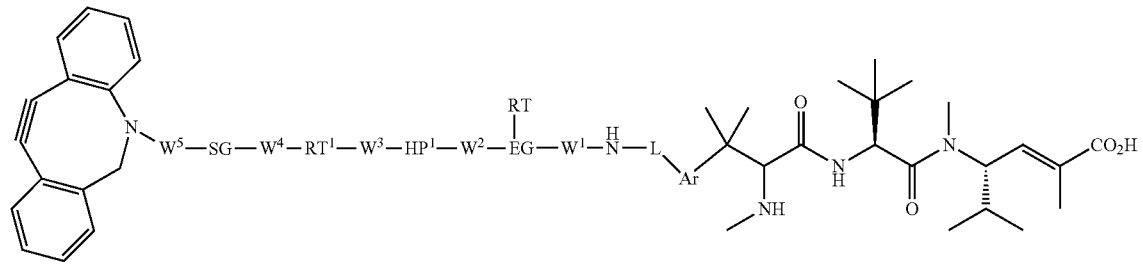
(XVI-2)
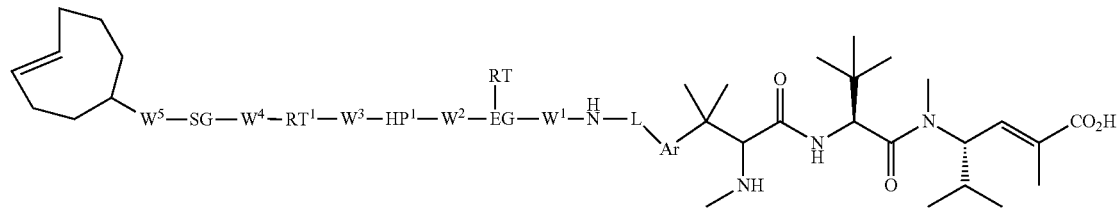
(XIX-2)
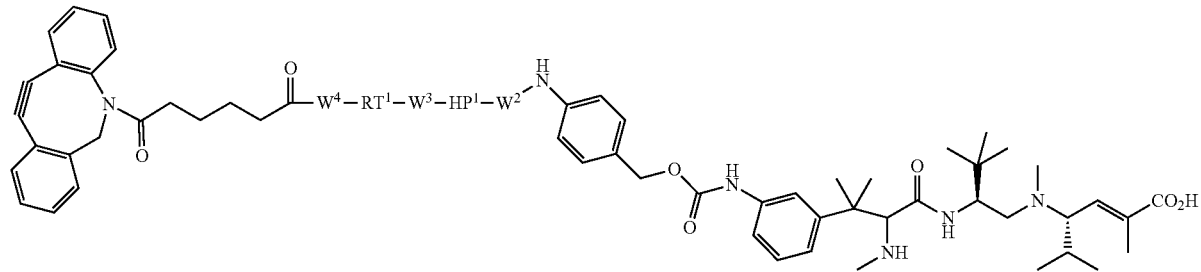
or a pharmaceutically acceptable salt, solvate, stereoisomer, or tautomer thereof; wherein EG, RT, HP, RT$^1$, HP$^1$, SG, W$^1$, W$^2$, W$^3$, W$^4$, W$^5$, R, L, and Ar are as described in the context of Formula 1000, I, 1001, and/or any of the embodiments described herein.
In an embodiment, provided herein is a compound according to any of Formulas XIa-XVIa-1:
(XIa)
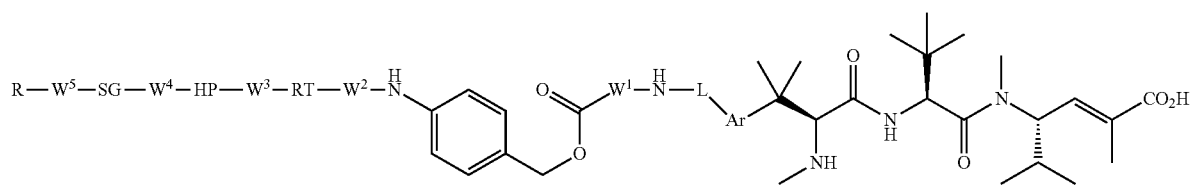

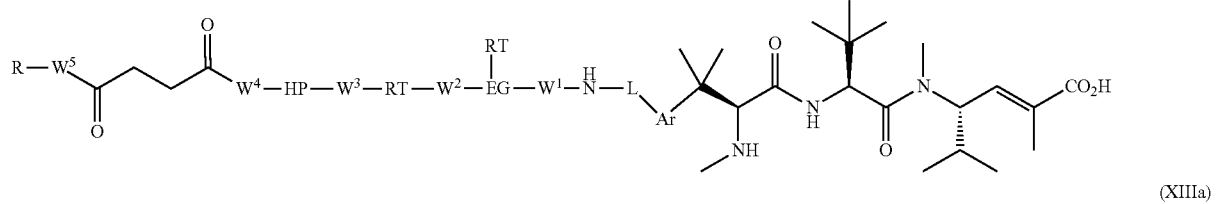
(XIIa)
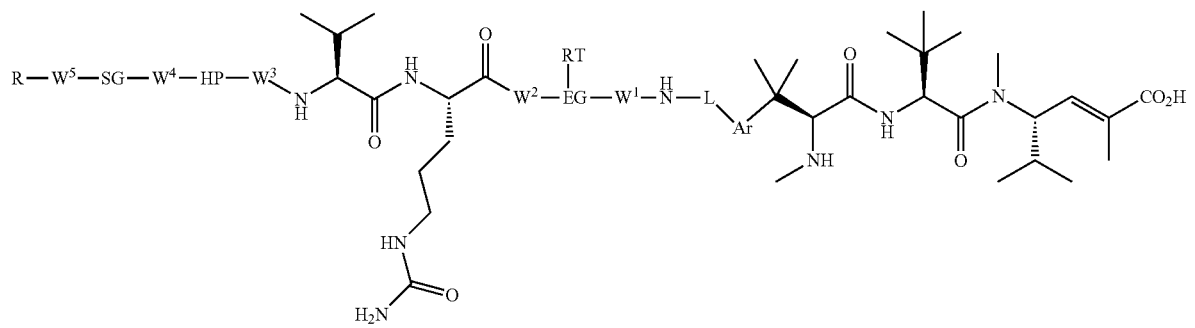
(XIIIa)
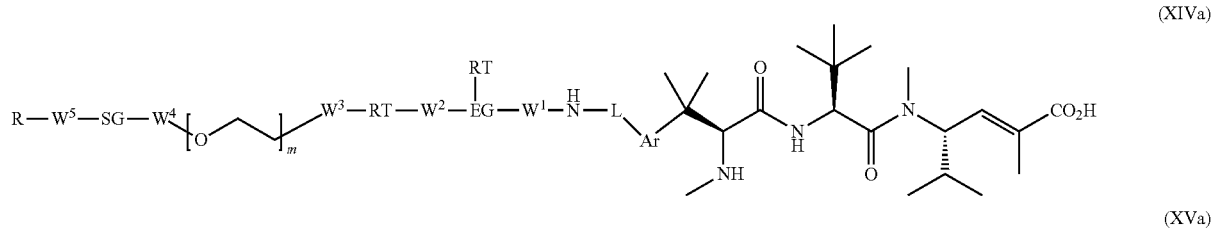
(XIVa)
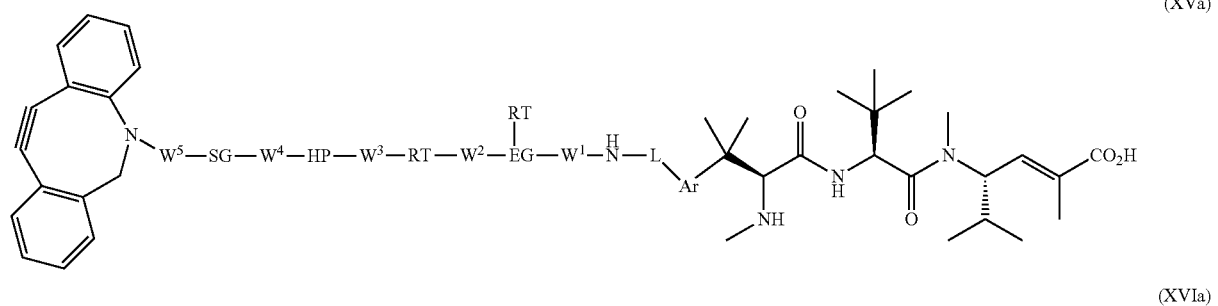
(XVa)
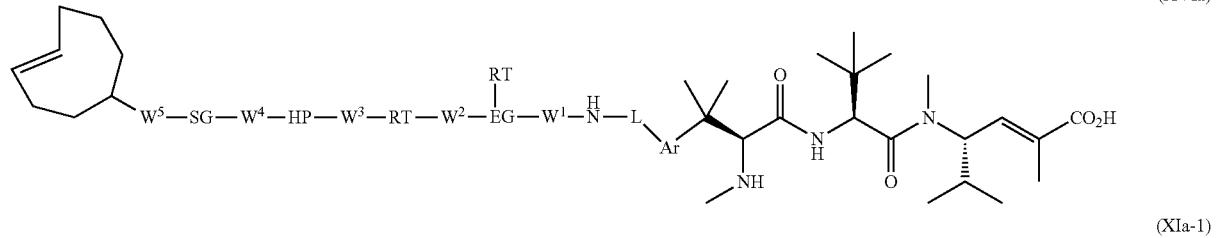
(XVIa)
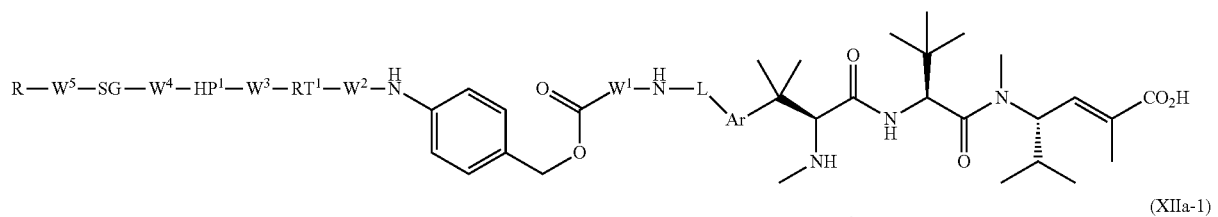
(XIa-1)
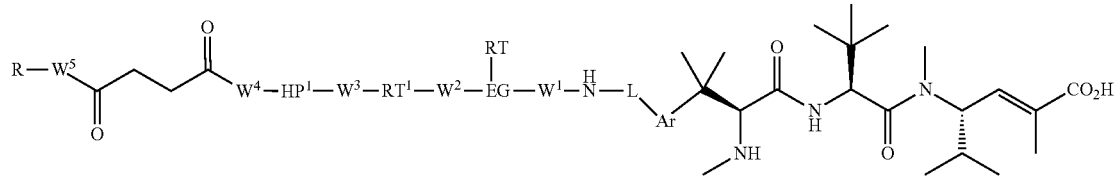
(XIIa-1)

-continued
(XIIIa-1)
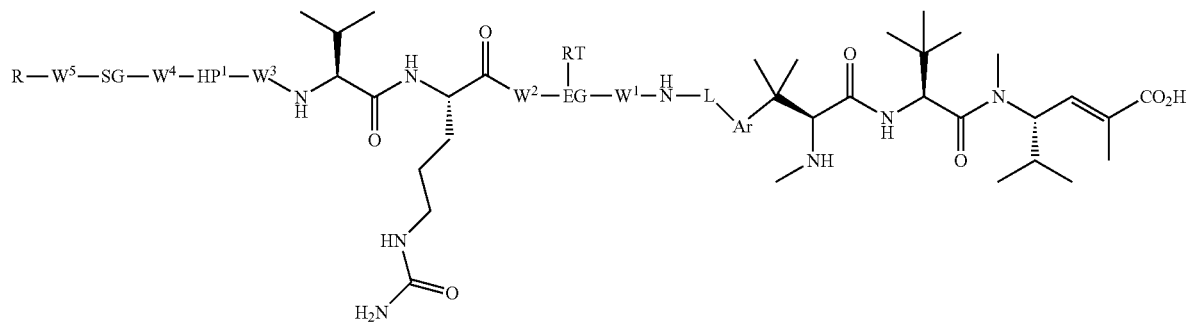
(XIVa-1)
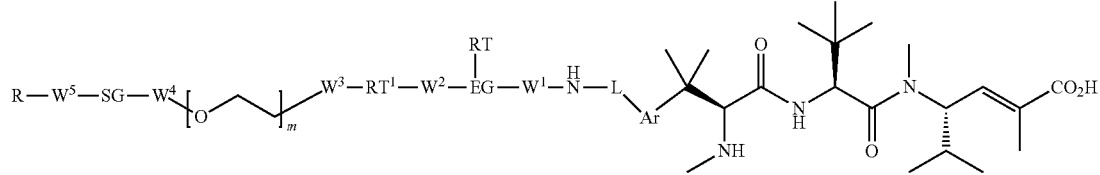
(XVa-1)
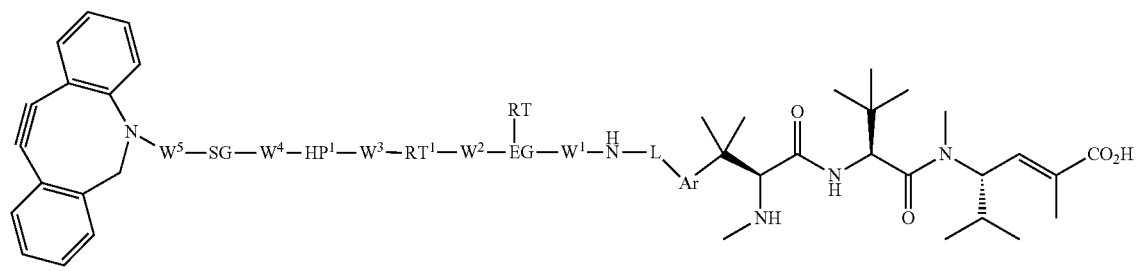
(XVIa-1)
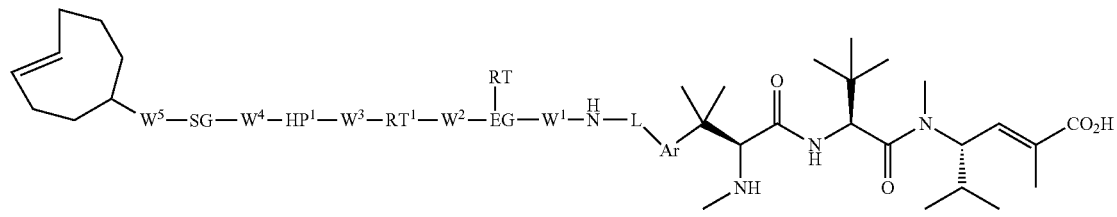
(XIXa-1)
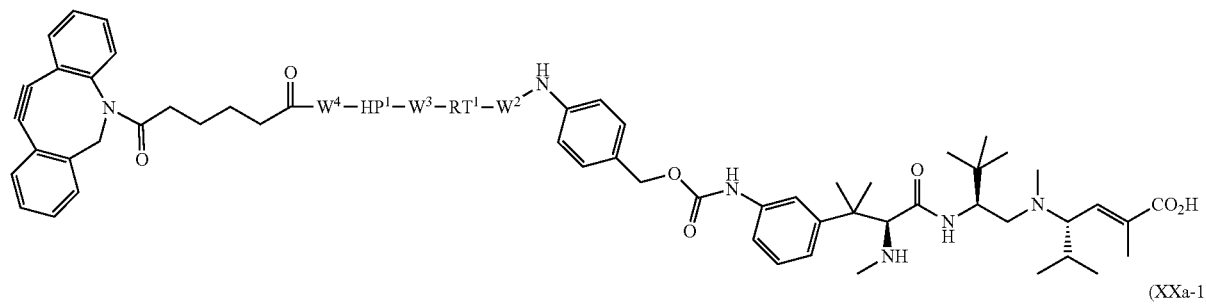
(XXa-1)
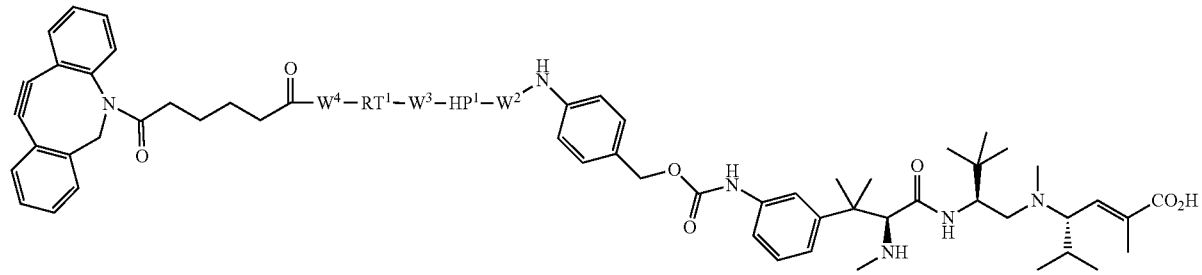

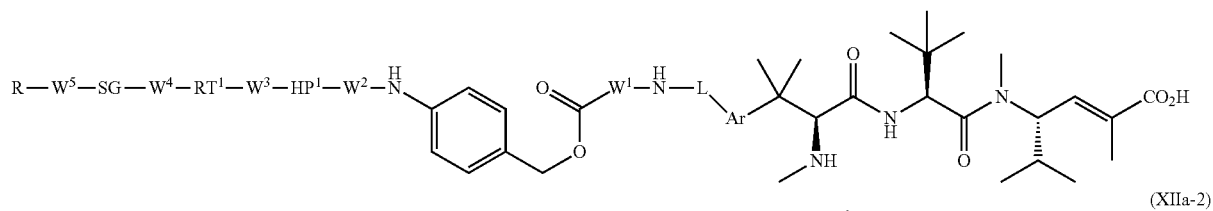
(XIa-2)
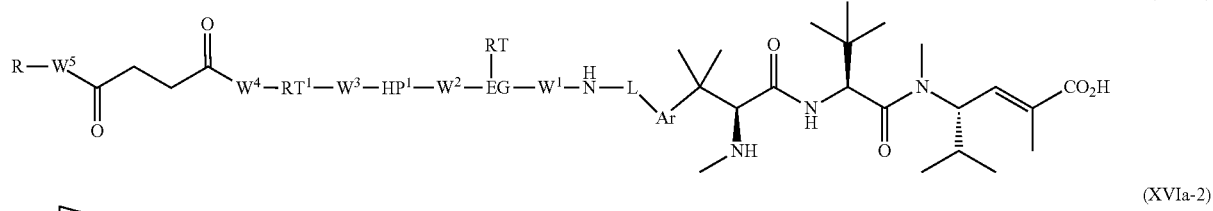
(XIIa-2)
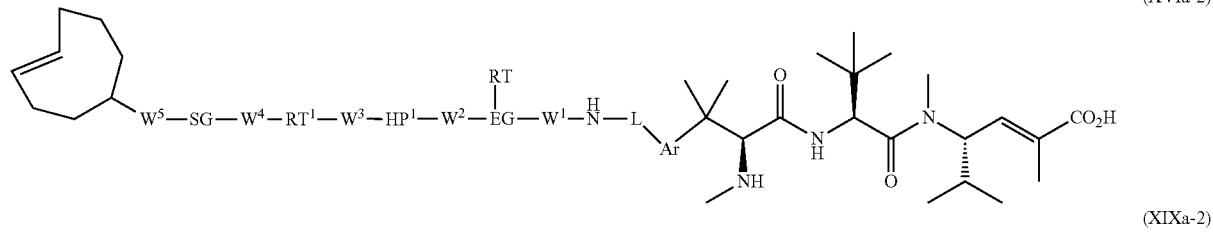
(XVIa-2)
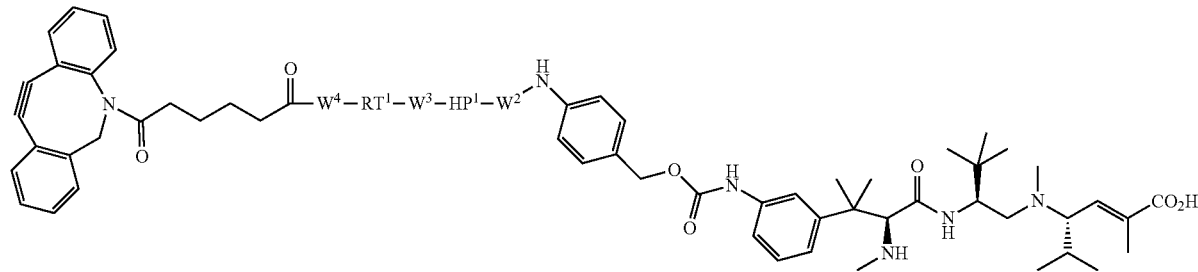
(XIXa-2)
or a pharmaceutically acceptable salt, solvate, stereoisomer, or tautomer thereof; wherein EG, RT, HP, $RT^1$, $HP^1$, SG, $W^1$, $W^2$, $W^3$, $W^4$, $W^5$, R, L, and Ar are as described in the context of Formula 1000, I, 1001, and/or any of the embodiments described herein.
In an embodiment, provided herein is a compound according to any of Formulas XIb-XIVb-1:
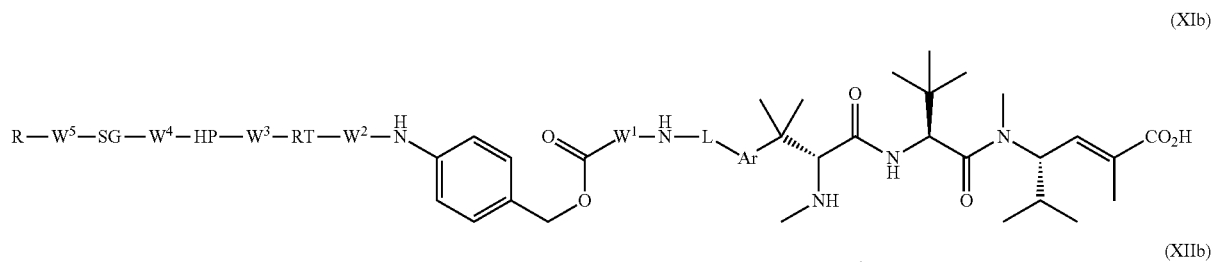
(XIb)
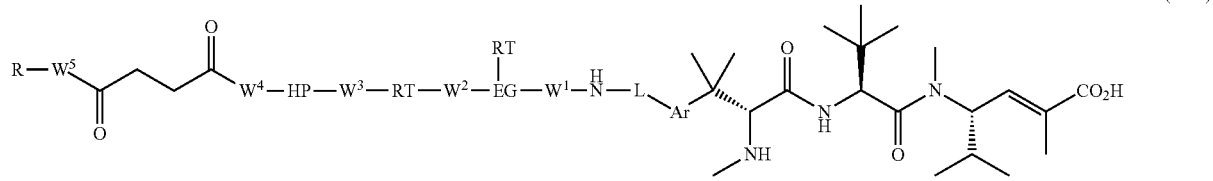
(XIIb)

-continued
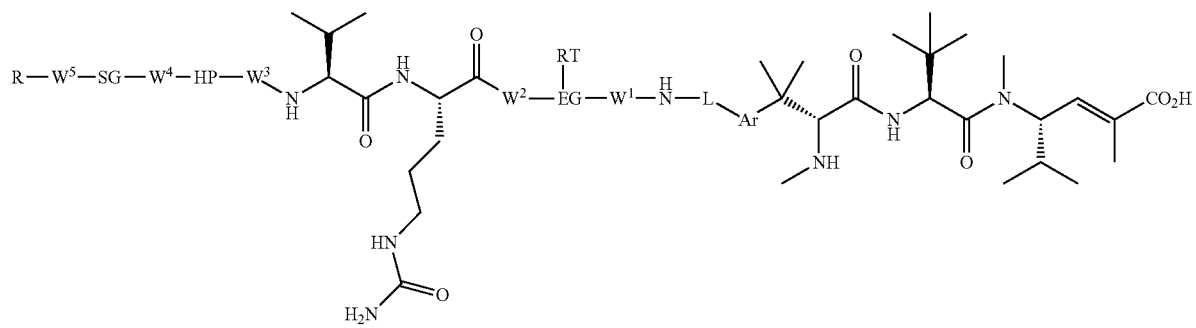
(XIIIb)
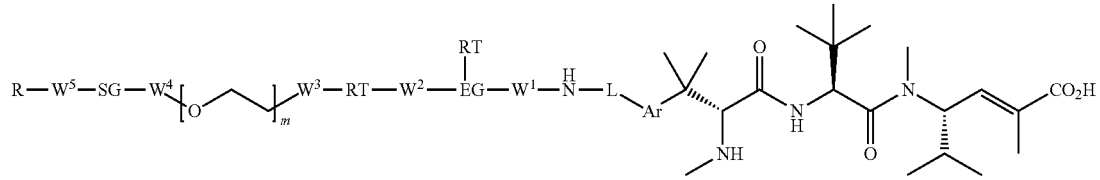
(XIVb)
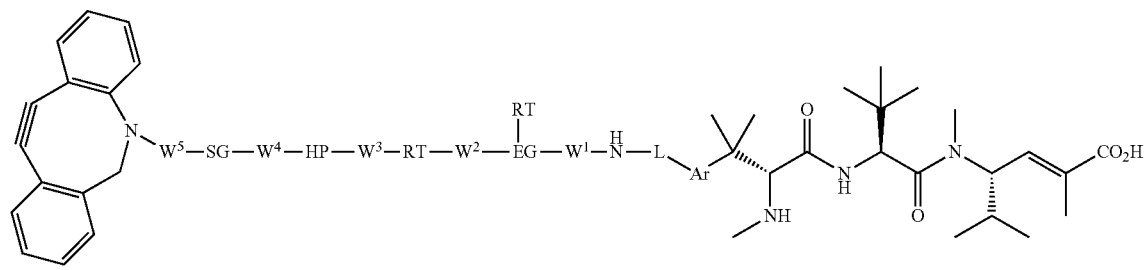
(XVb)
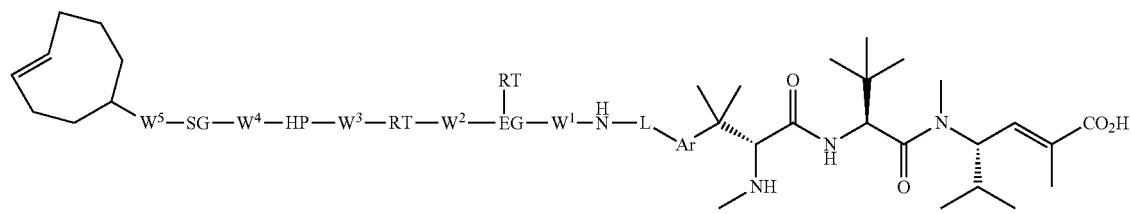
(XVIb)
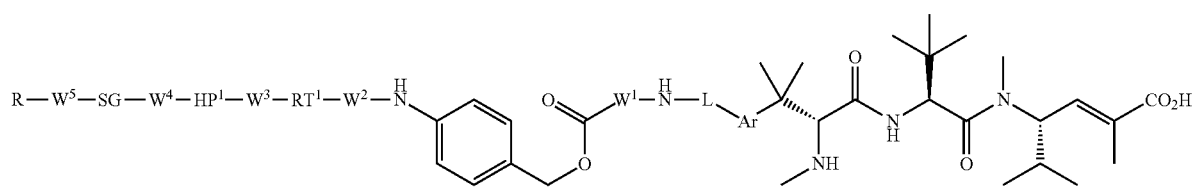
(XIb-1)
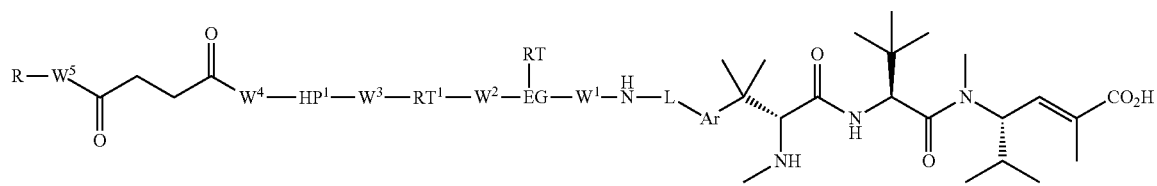
(XIIb-1)

-continued
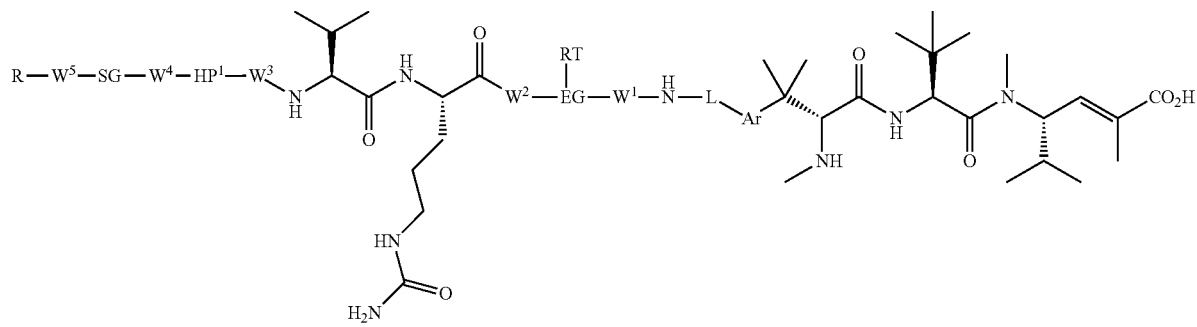
(XIIIb-1)
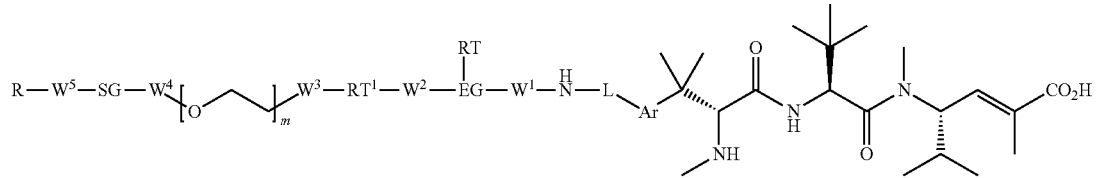
(XIVb-1)
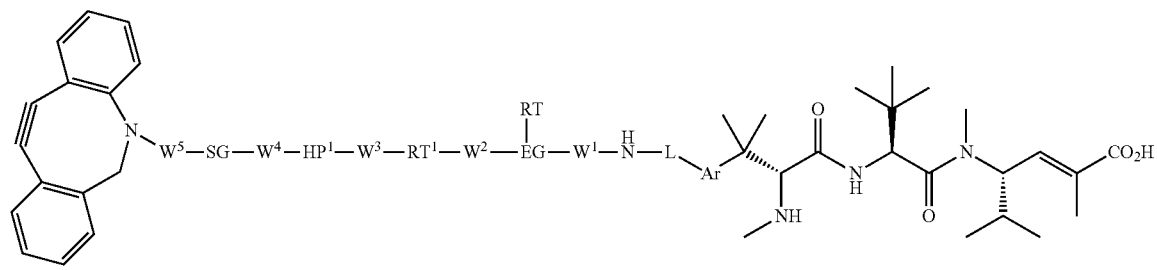
(XVb-1)
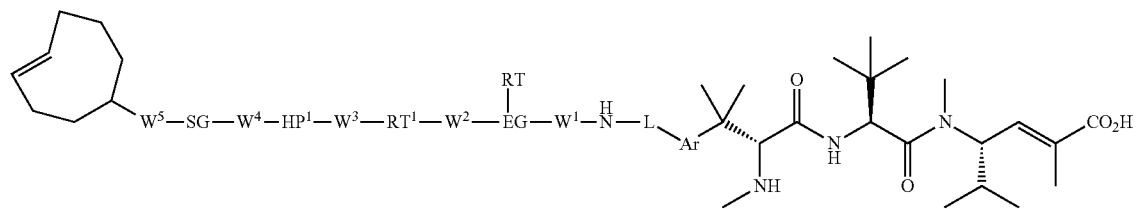
(XVIb-1)
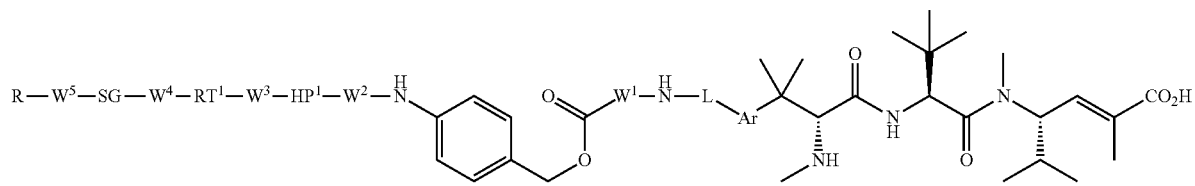
(XIb-2)
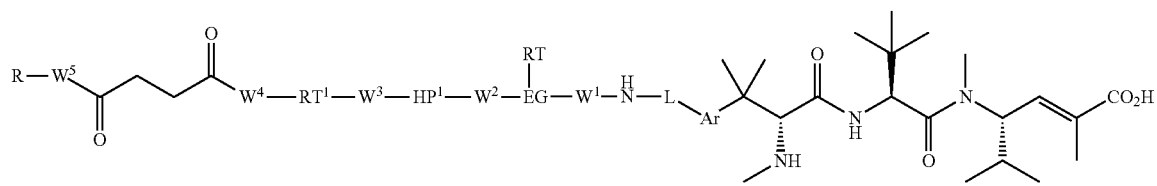
(XIIb-2)

-continued (XVb-2)
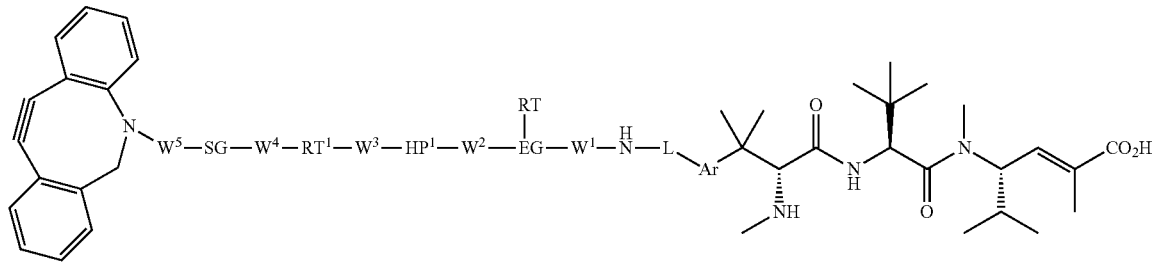

(XVIb-2)
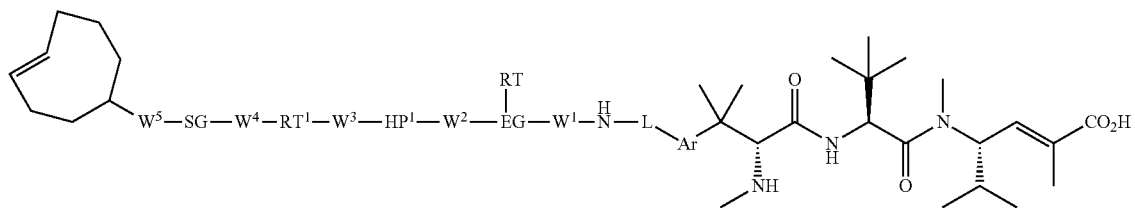

(XIXb-2)
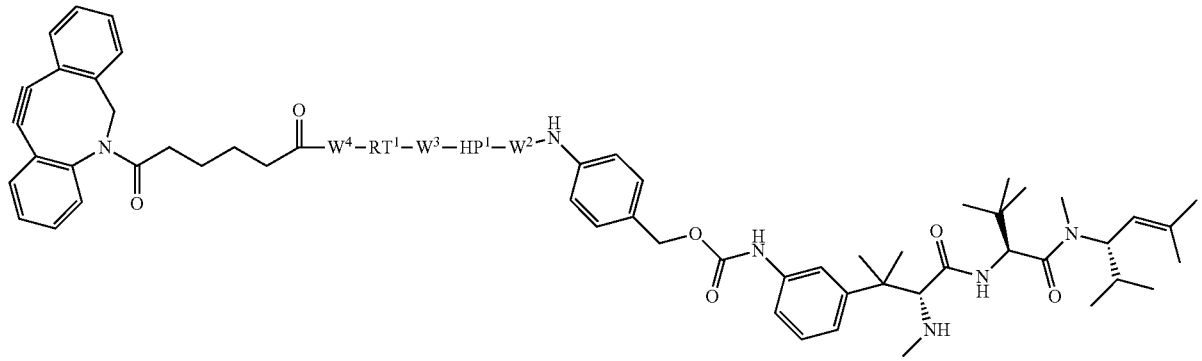

or a pharmaceutically acceptable salt, solvate, stereoisomer, or tautomer thereof; wherein EG, RT, HP, $RT^1$, $HP^1$, SG, $W^1$, $W^2$, $W^3$, $W^4$, $W^5$, R, L, and Ar are as described in the context of Formula 1000, I, 1001, and/or any of the embodiments described herein.

In one embodiment, the compound of Formula 1000 or 1001 is that where X is

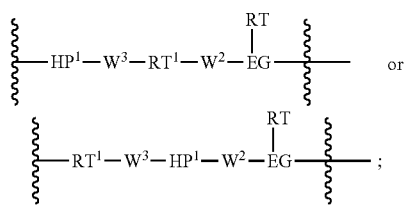

$HP^1$ is

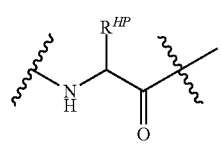

and $RT^1$ is a release trigger group, or a cleavable linker; or $HP^1$ is absent and $RT^1$ is a cleavable linker; and all other groups are as defined for Formula 1000, 1001, and/or any embodiments described herein. In one embodiment, the compound of Formula 1000 or 1001 is that where X is

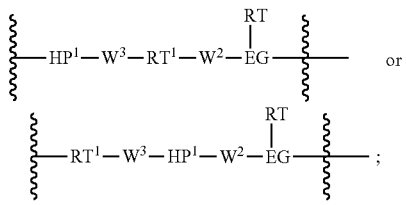

$HP^1$ is

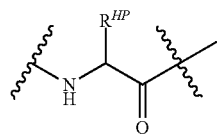

and $RT^1$ is a release trigger group, or a cleavable linker; or $HP^1$ is absent and $RT^1$ is a cleavable linker; EG

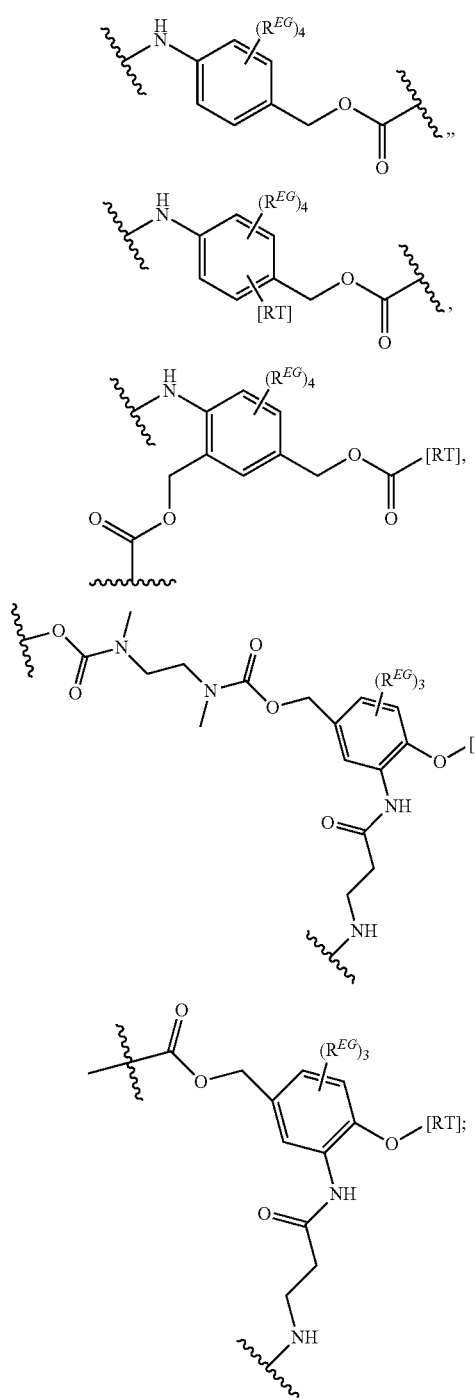
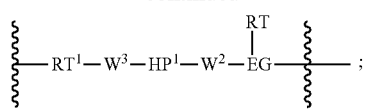
HP$^1$ is
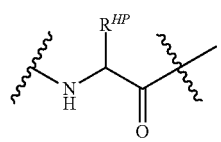
and RT$^1$ is a release trigger group, or a cleavable linker; or HP$^1$ is absent and RT$^1$ is a cleavable linker; EG is
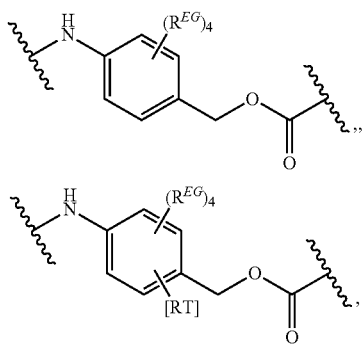
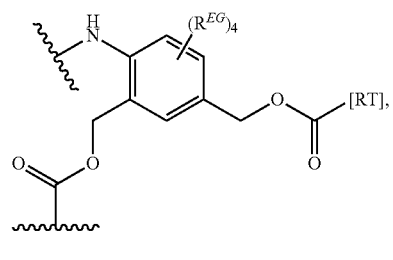
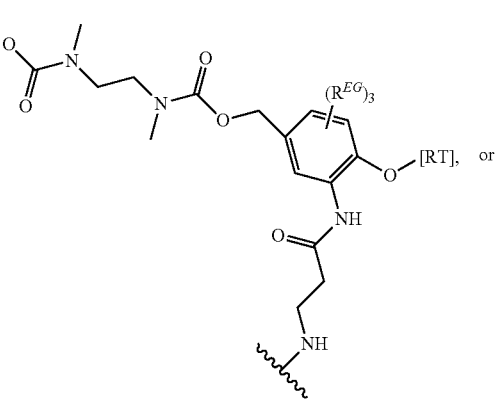
and all other groups are as defined for Formula 1000, 1001, and/or any embodiments described herein. In one embodiment, the compound of Formula 1000 or 1001 is that where X is
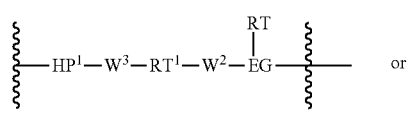

-continued

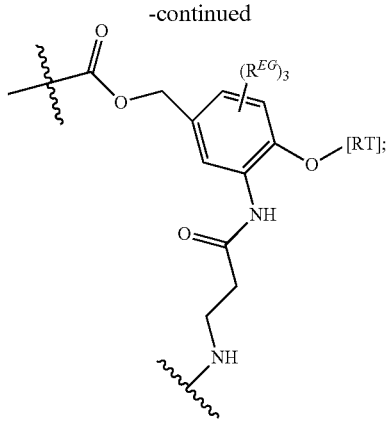

W¹-W⁵ are absent; and all other groups are as defined for Formula 1000, 1001, and/or any embodiments described herein. In certain embodiments, L is absent.

In one embodiment, provided herein is a compound according to Formula 1000:

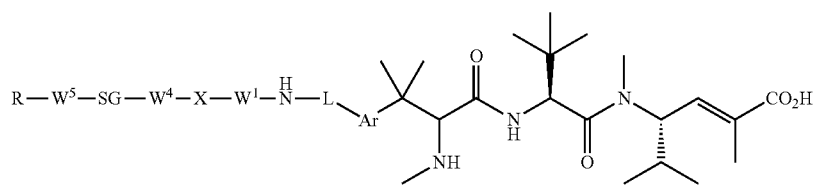

(1000)

or a pharmaceutically acceptable salt, solvate, stereoisomer, or tautomer thereof, wherein:

Ar is a substituted or unsubstituted indolylene or substituted or unsubstituted phenylene ring;

L is absent or —CH$_2$—;

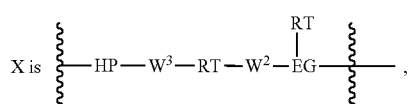

X is

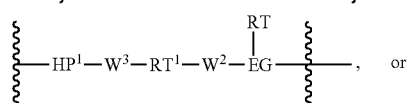

, or

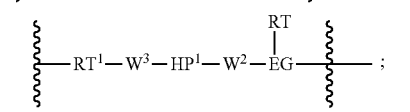

;

W¹, W², W³, W⁴, W⁵ are each independently a single bond, absent, —C(O)—, —O—, —C(O)O—, —OC(O)—, —C(O)NH—, —C(O)NH-alkyl-, —OC(O)NH—, —SC(O)NH—, —NH—, —N(alkyl)-, —N(R)-alkylene-N(R)— (where each R is independently H or alkyl), —N(CH$_3$)CH$_2$CH$_2$N(CH$_3$)—, —CH$_2$—, —CH$_2$CH$_2$—, —CH(CH$_3$)—, —C(CH$_3$)$_2$—, —CH$_2$CH$_2$CH$_2$—, phenylene, —NHCH$_2$CH$_2$C(O)—, —C(O)CH$_2$CH$_2$NH—, —S—, —S—S—, —OCH$_2$CH$_2$O—, or the reverse thereof;

EG is absent, or EG is selected from

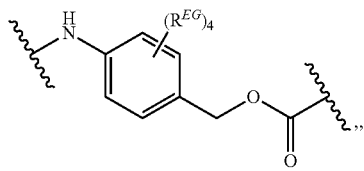

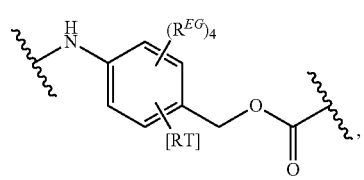

-continued

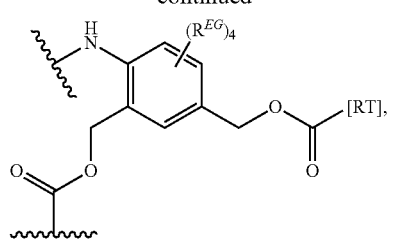

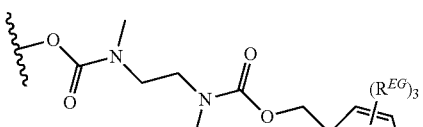

[RT], and

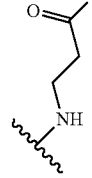

-continued

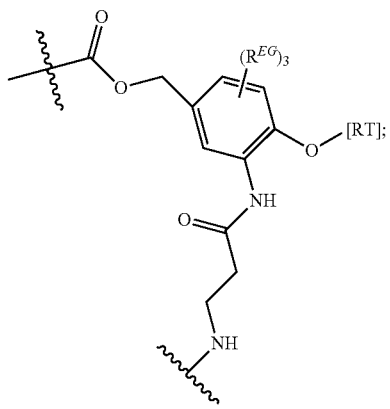

wherein each $R^{EG}$ is independently selected from the group consisting of hydrogen, alkyl, biphenyl, —$CF_3$, —$NO_2$, —CN, fluoro, bromo, chloro, alkoxyl, alkylamino, dialkylamino, alkyl-C(O)O—, alkylamino-C(O)— and dialkylamino-C(O)—;

RT when in the backbone is

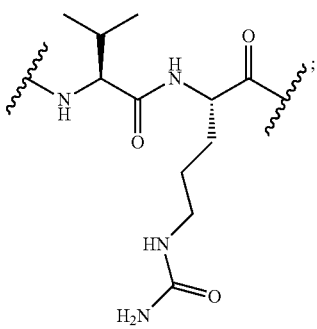 [SMILES: *N[C@H](C(=O)N[C@@H](CCCNC(N)=O)C(*)=O)C(C)C]

and RT when bonded to an EG group is

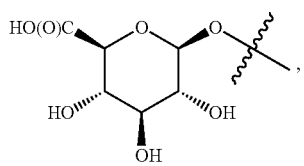, or

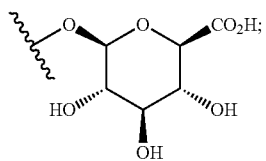

wherein each RT is optional;

$RT^1$ is absent,

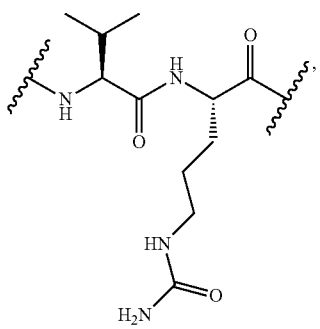 [SMILES: *N[C@H](C(=O)N[C@@H](CCCNC(N)=O)C(*)=O)C(C)C], valine-alanine, valine-glutamic acid, alanine-phenylalanine; phenylalanine-lysine; phenylalanine-homolysine; and glycine-glycine-glycine (gly-gly-gly),

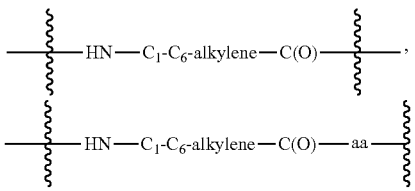

where aa is a natural or non-natural amino acid residue, or

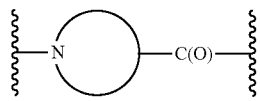

where the

ring is a 4-7 membered heterocyclic ring comprising 3-6 carbon atoms;

HP is absent or

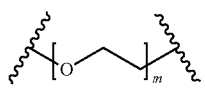

wherein m is an integer from 1 to 12;

$HP^1$ is absent or

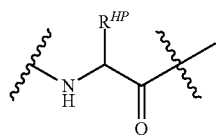

where $R^{HP}$ is

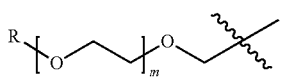

wherein R is —H or —CH$_3$ and m is an integer from 1 to 12 or $R^{HP}$ is -alkylene-S(O)$_3^-$.

SG is absent,

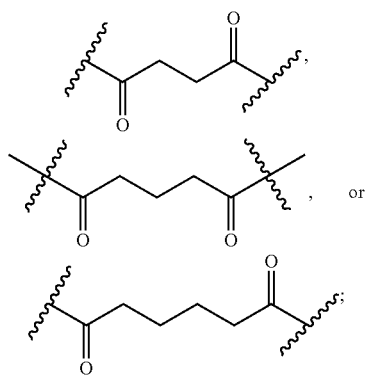

and

R is a terminal conjugating group;

or, in the alternative, $W^1$, $W^2$, $W^3$, $W^4$, $W^5$, EG, RT, HP, SG, and R combine to form —H.

In some embodiments, the compound is that where X is -HP$^1$-RT$^1$-EG-, -HP$^1$—RT$^1$- where RT$^1$ is a release trigger group, -HP$^1$-RT$^1$- where RT$^1$ is a cleavable linker, -HP$^1$-RT$^1$- where RT$^1$ is a release trigger group, -RT$^1$-, -RT-, -RT-EG-, RT$^1$-EG-, or -EG(RT)-; and all other groups are as defined in any of the Formula and/or embodiments described herein. In some embodiments, the compound is that where X is -HP$^1$-RT$^1$-EG-, -HP$^1$-RT$^1$- where RT$^1$ is a release trigger group, -HP$^1$-RT$^1$- where RT$^1$ is a cleavable linker, -HP$^1$-RT$^1$- where RT$^1$ is a release trigger group, -RT$^1$-, -RT-, -RT-EG-, RT$^1$-EG-, or -EG(RT)-; the release trigger group facilitates separation of a biologically active portion of a compound or conjugate in conjunction with an eliminator group; and all other groups are as defined in any of the Formula and/or embodiments described herein. In some embodiments, the compound is that where X is -HP$^1$-RT$^1$-EG-, -HP$^1$-RT$^1$- where RT$^1$ is a release trigger group, -HP$^1$-RT$^1$- where RT$^1$ is a cleavable linker, -HP$^1$-RT$^1$- where RT$^1$ is a release trigger group, -RT$^1$-, -RT-, -RT-EG-, RT$^1$-EG-, or -EG(RT)-; $W^1$, $W^4$, $W^5$, and L are independently a single bond or absent; the release trigger group facilitates separation of a biologically active portion of a compound or conjugate in conjunction with an eliminator group; and all other groups are as defined in any of the Formula and/or embodiments described herein. In some embodiments, the compound is that where X is -HP$^1$-RT$^1$-EG-, -HP$^1$-RT$^1$- where RT$^1$ is a release trigger group, -HP$^1$-RT$^1$- where RT$^1$ is a cleavable linker, -HP$^1$-RT$^1$- where RT$^1$ is a release trigger group, -RT$^1$-, -RT-, -RT-EG-, RT$^1$-EG-, or -EG(RT)-; $W^1$, $W^4$, $W^5$, and L are independently a single bond or absent; SG is

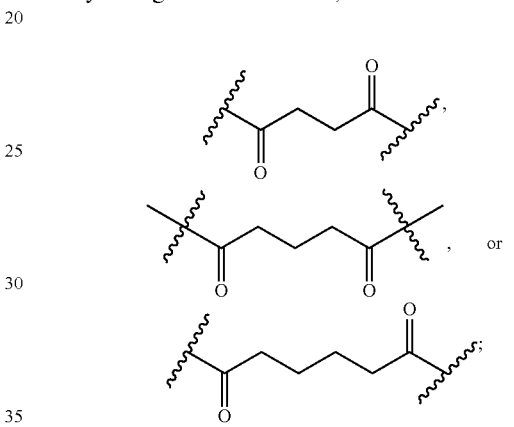

the release trigger group facilitates separation of a biologically active portion of a compound or conjugate in conjunction with an eliminator group; and all other groups are as defined in any of the Formula and/or embodiments described herein.

In an embodiment, provided herein is a compound according to any of Formulas 101-108 or 1-8:

(101)

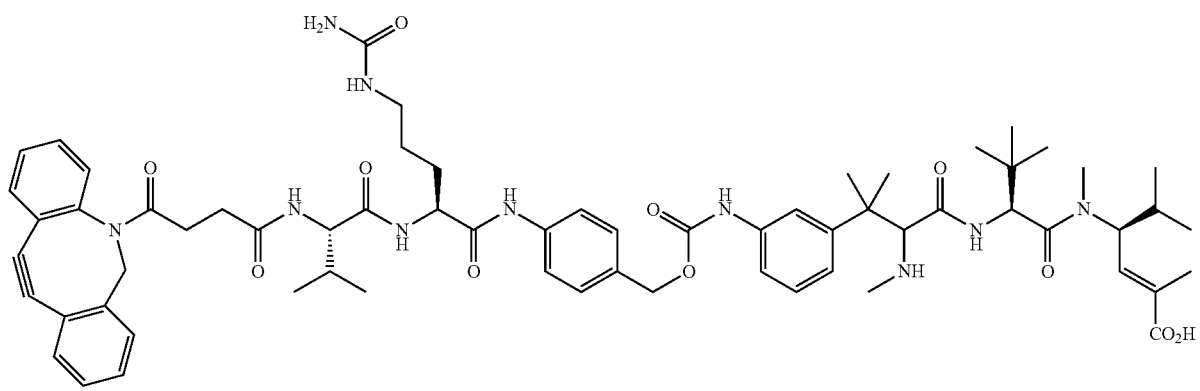

(102)
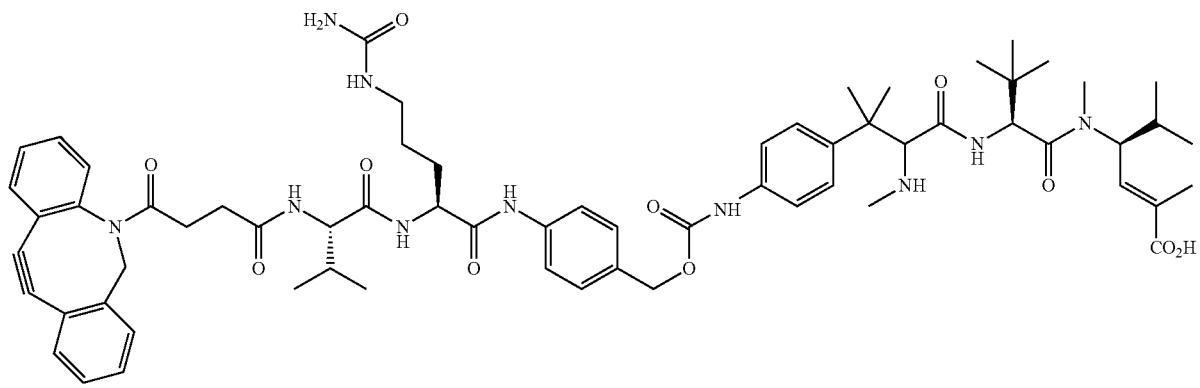
(103)
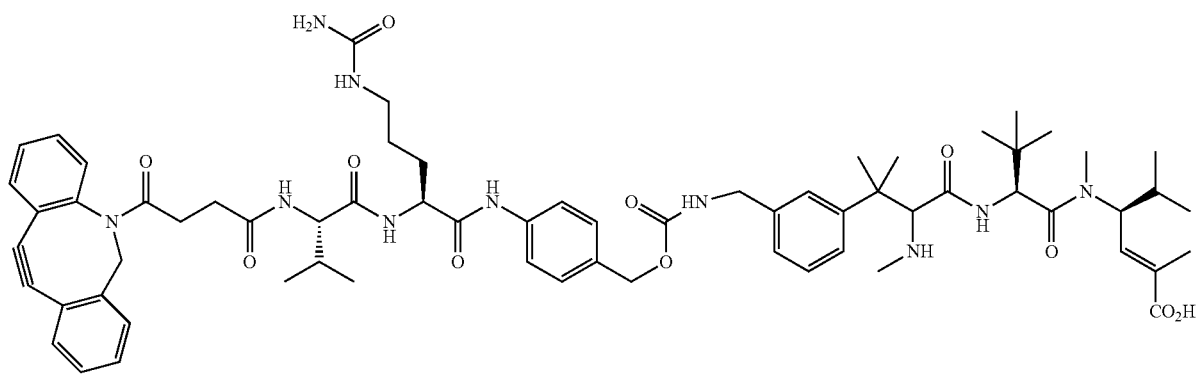
(104)
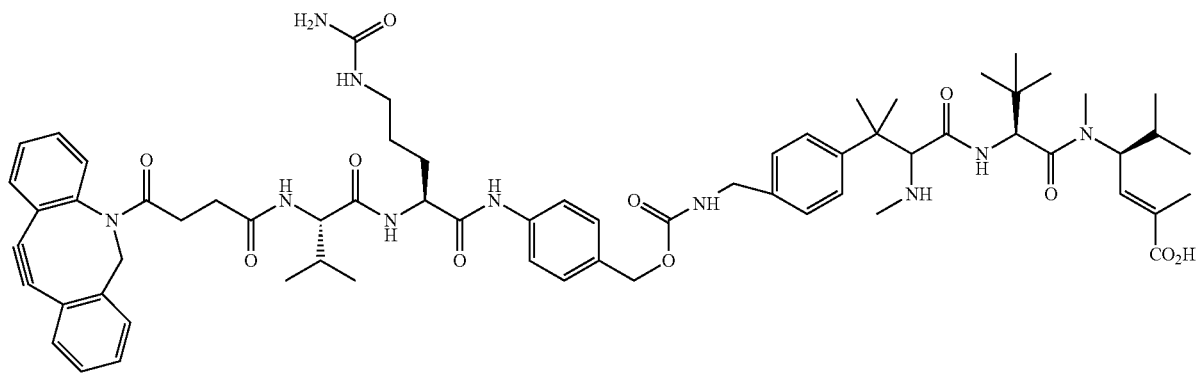
(105)
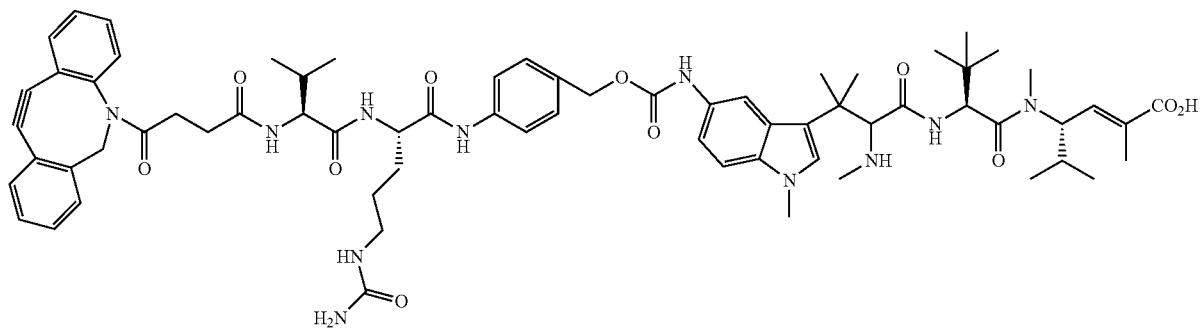

(106)
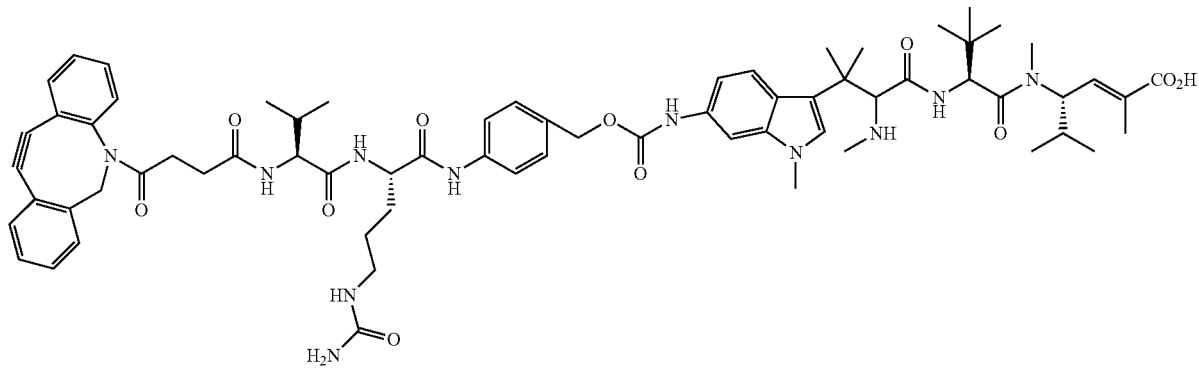
(107)
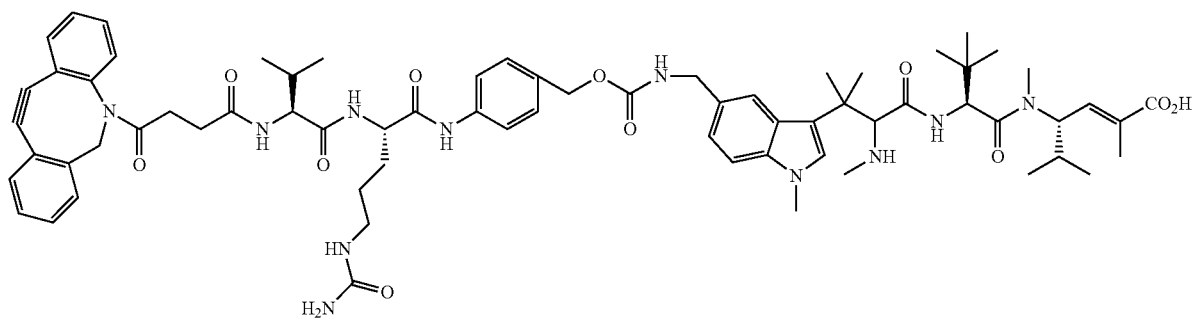
(108)
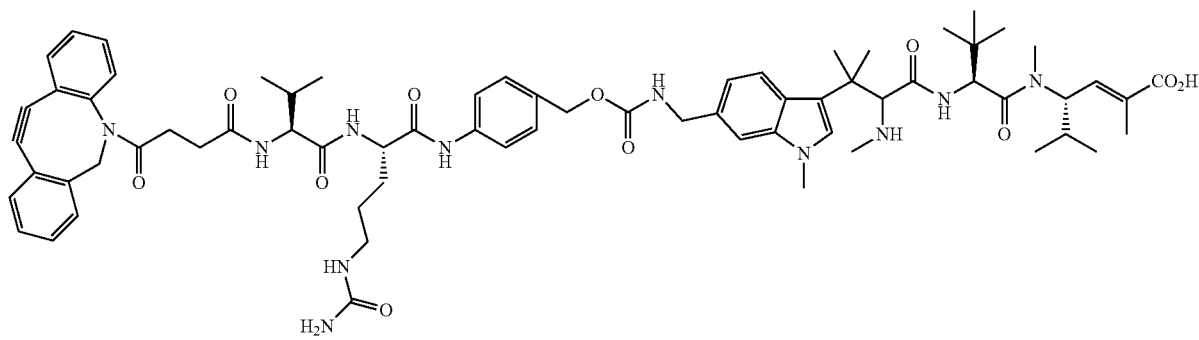
(109)
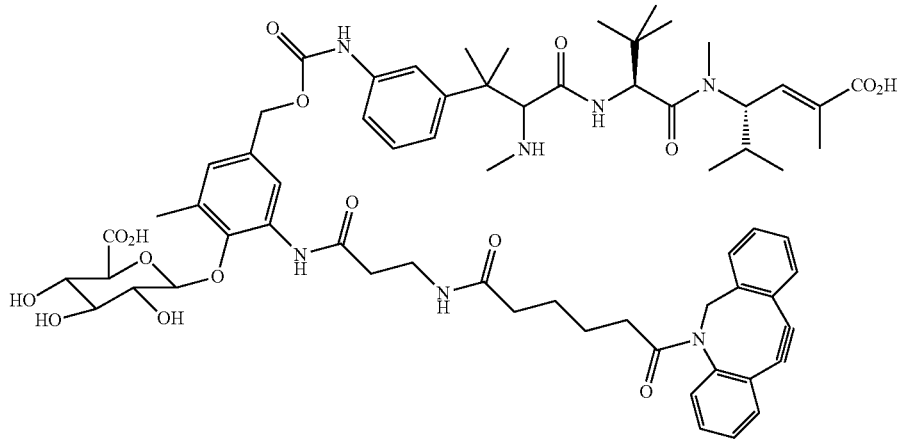

(110)
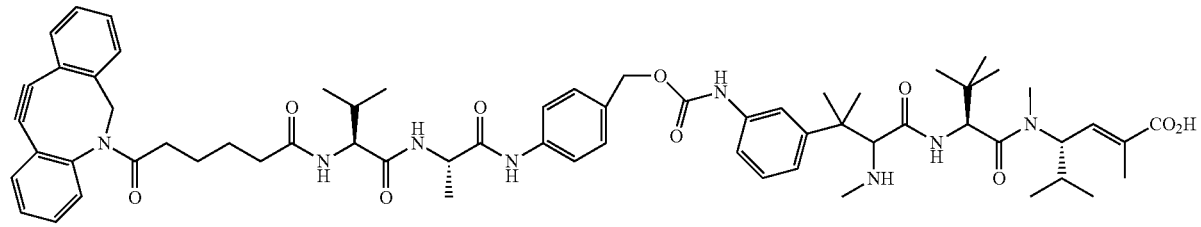
(111)
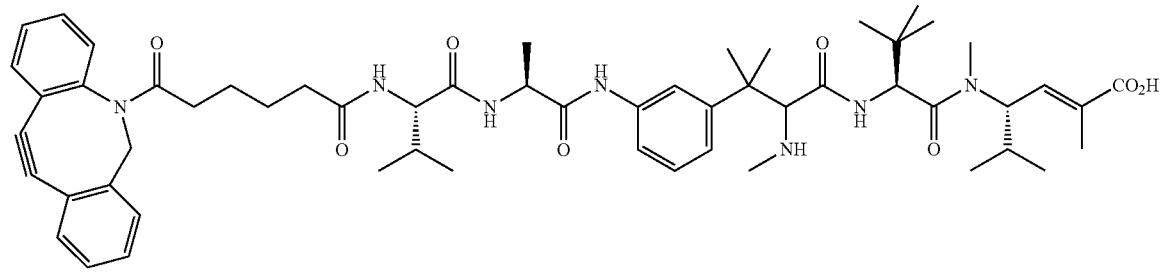
(1) (2)
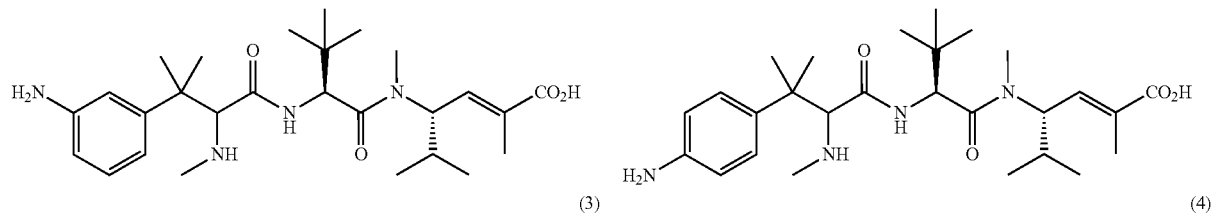
(3) (4)
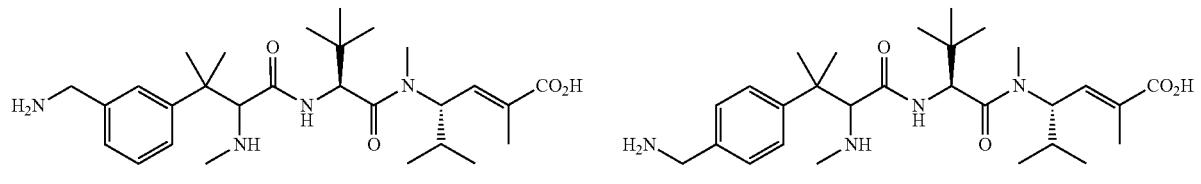
(5) (6)
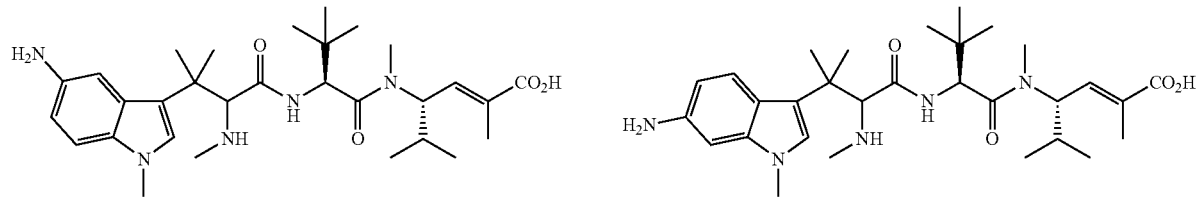
(7) (8)
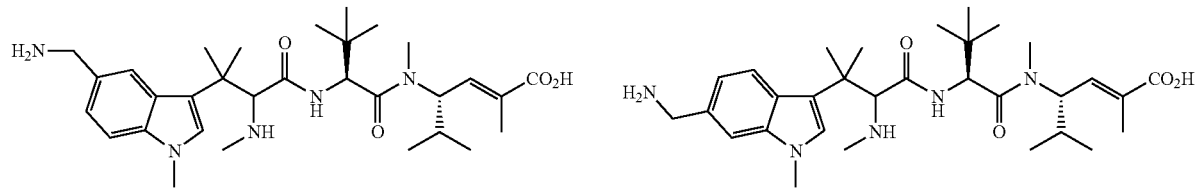
or a pharmaceutically acceptable salt, solvate, stereoisomer, or tautomer thereof.

In an embodiment, provided herein is a compound according to any of Formulas 101a-108a or 1a-8a:
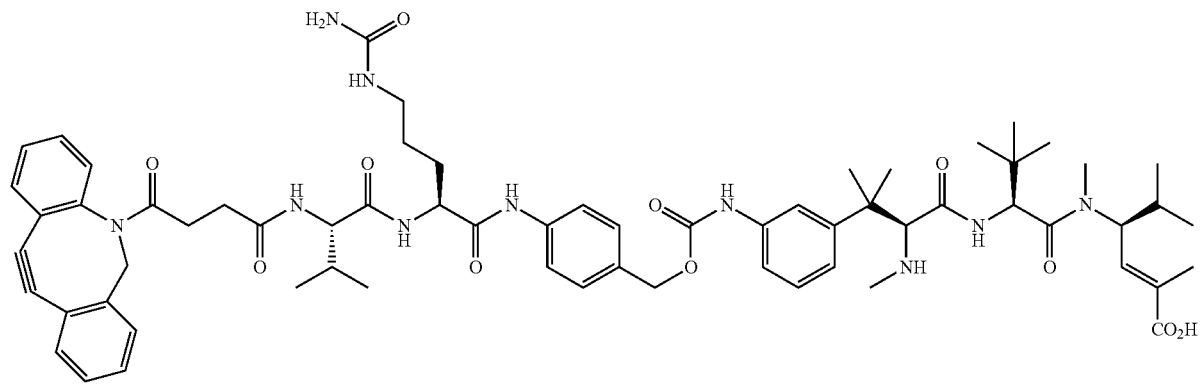
(101a)
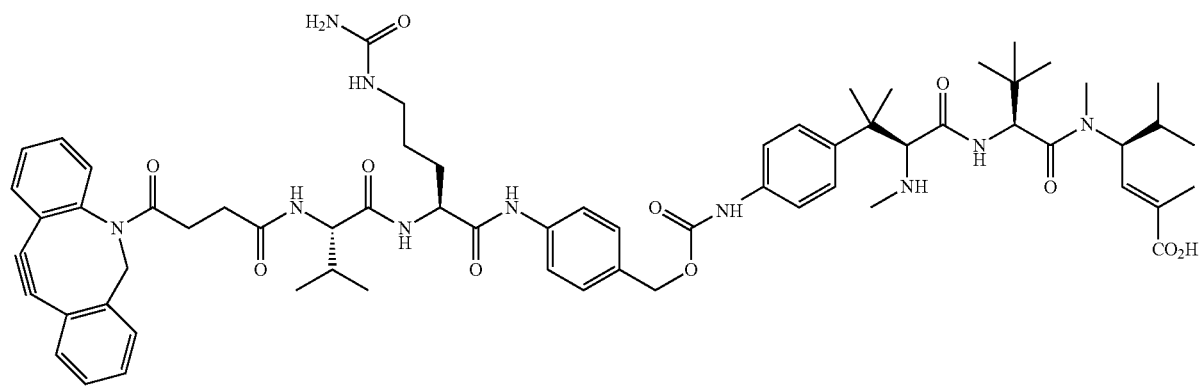
(102a)
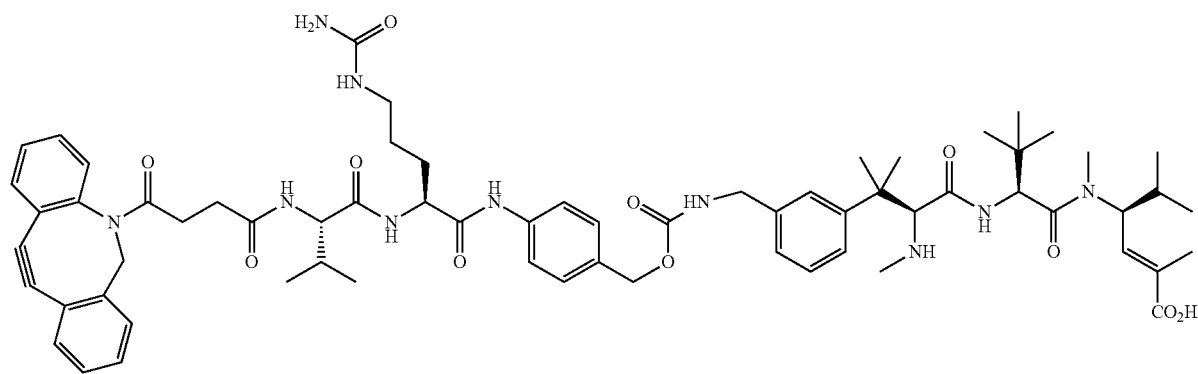
(103a)
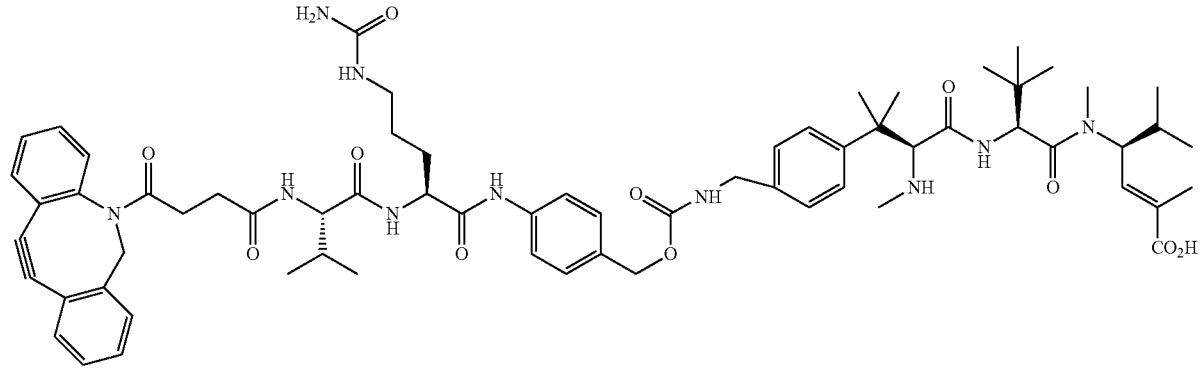
(104a)

(105a)
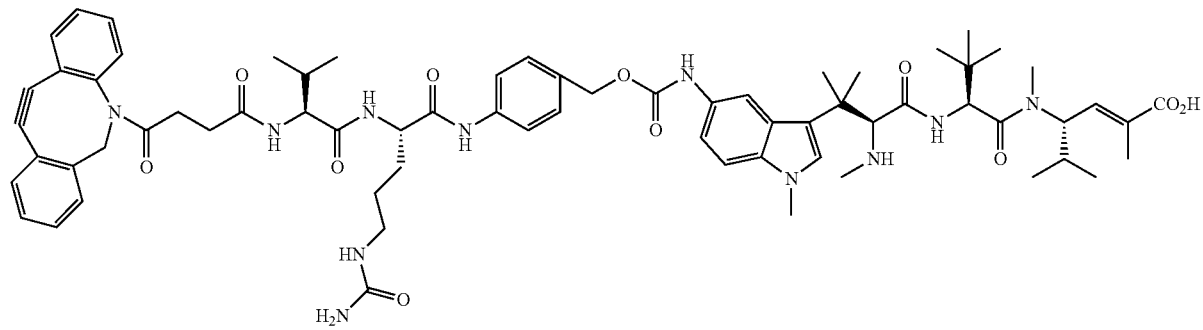
(106a)
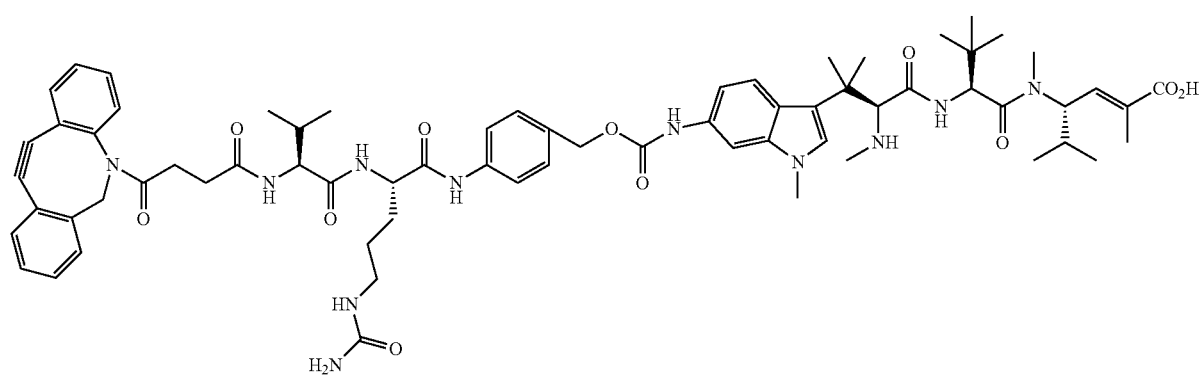
(107a)
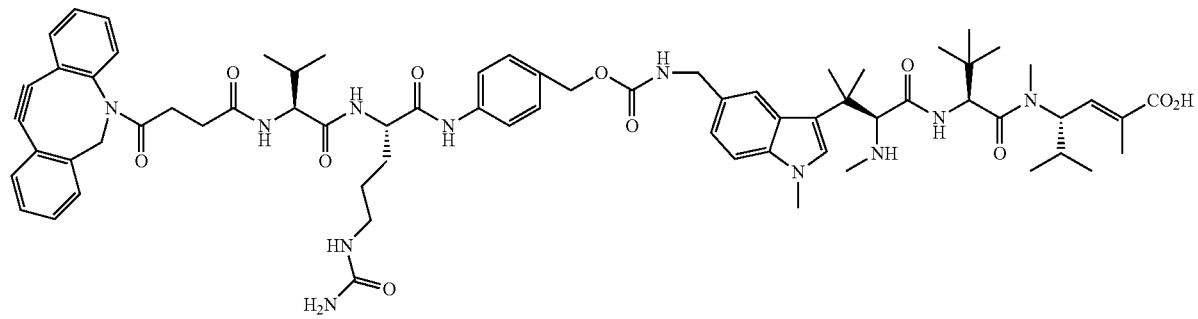
(108a)
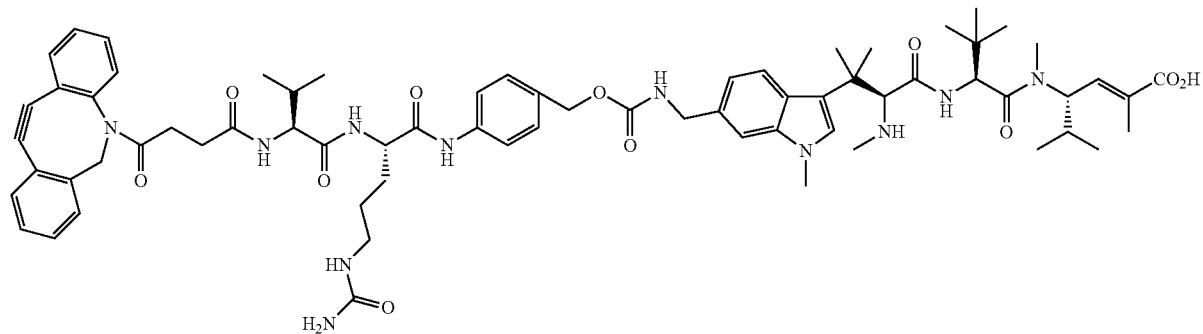

(109a)
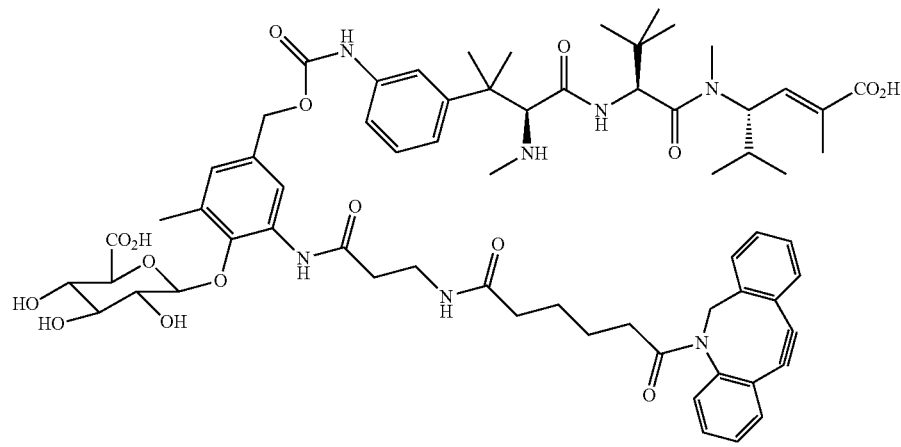
(110a)
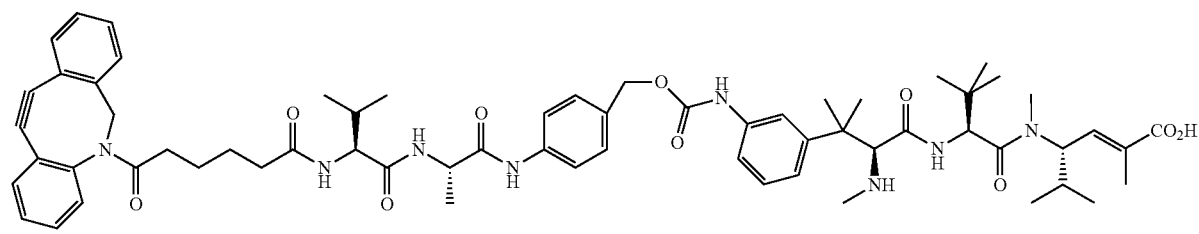
(111a)
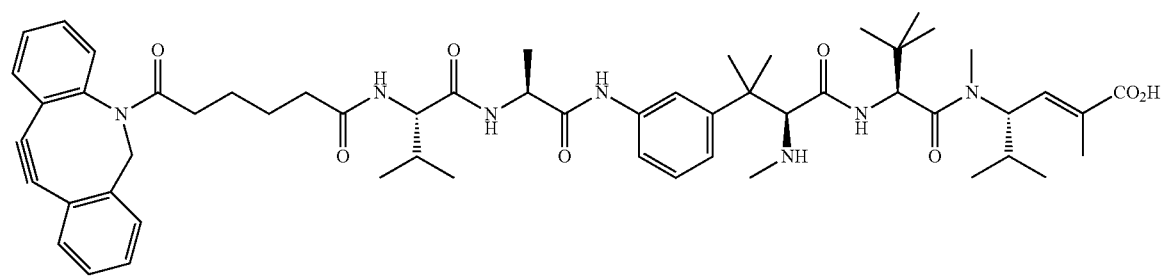
(1a)
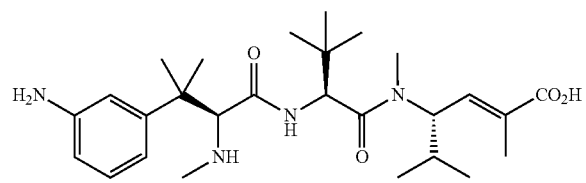
(2a)
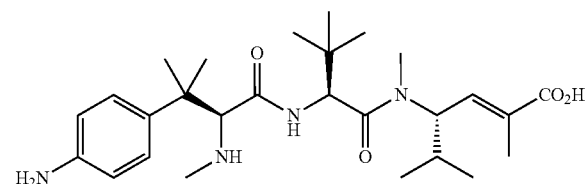
(3a)
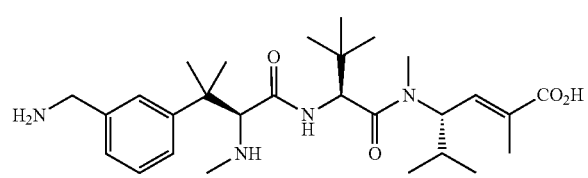
(4a)
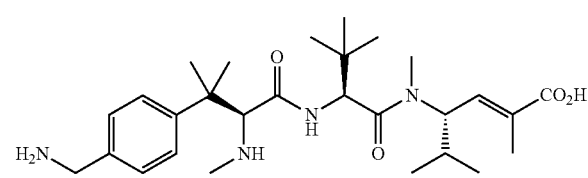
(5a)
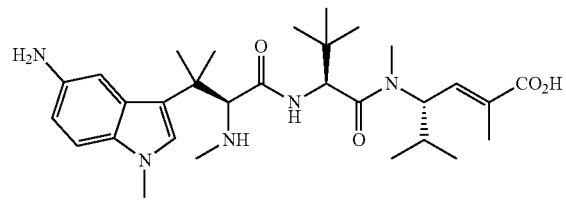
(6a)
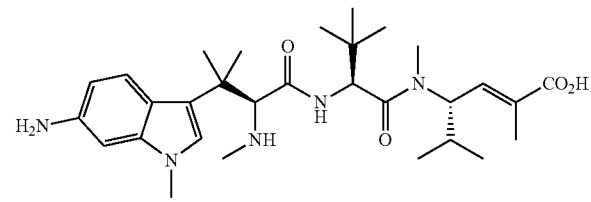

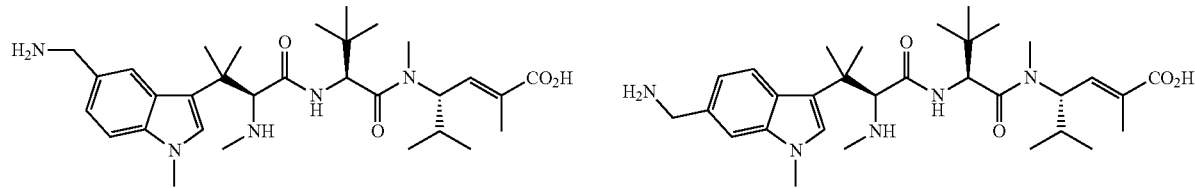
(7a)
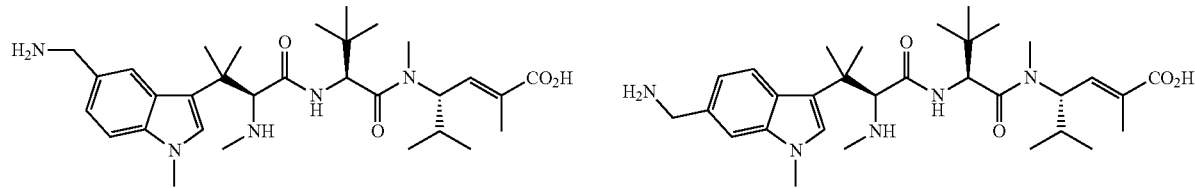
(8a)
or a pharmaceutically acceptable salt, solvate, stereoisomer, or tautomer thereof.
In an embodiment, provided herein is a compound according to any of Formulas 101b-108b or 1-8b:
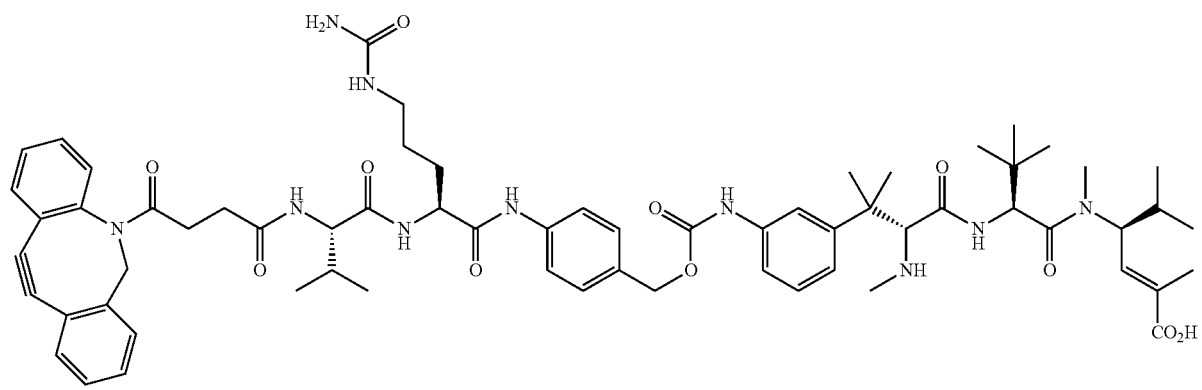
(101b)
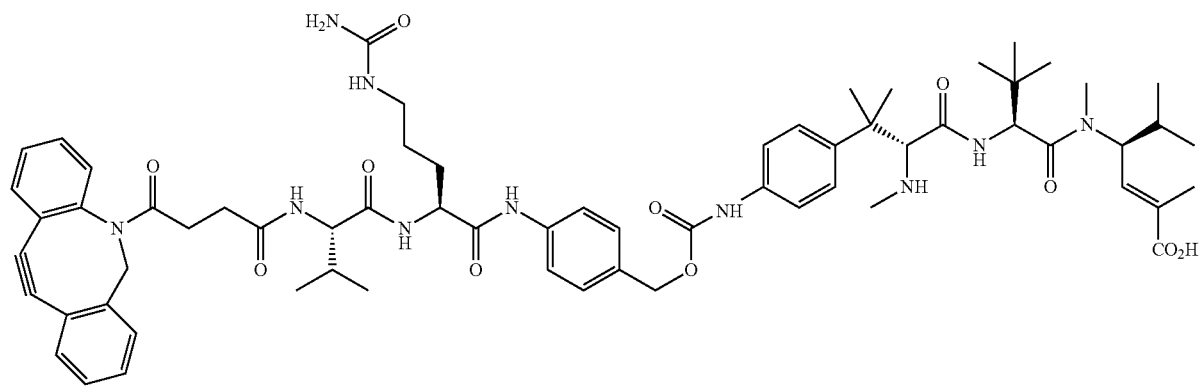
(102b)
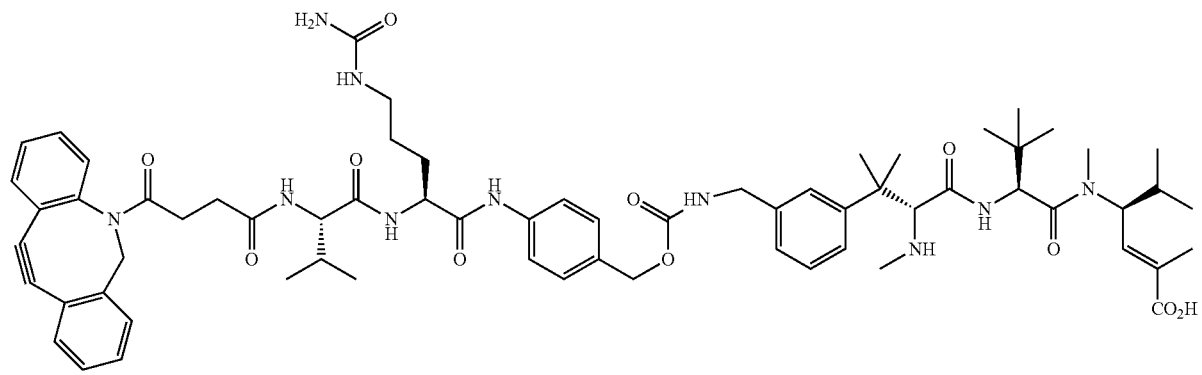
(103b)

(104b)
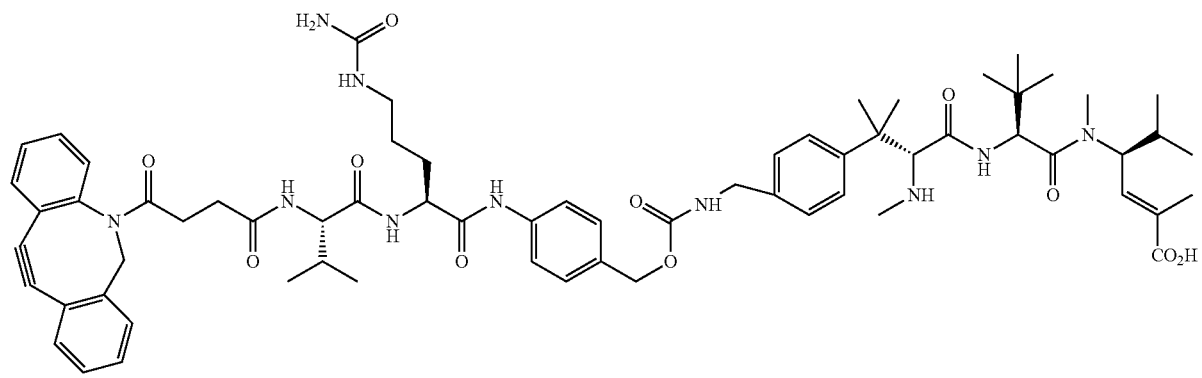
(105b)
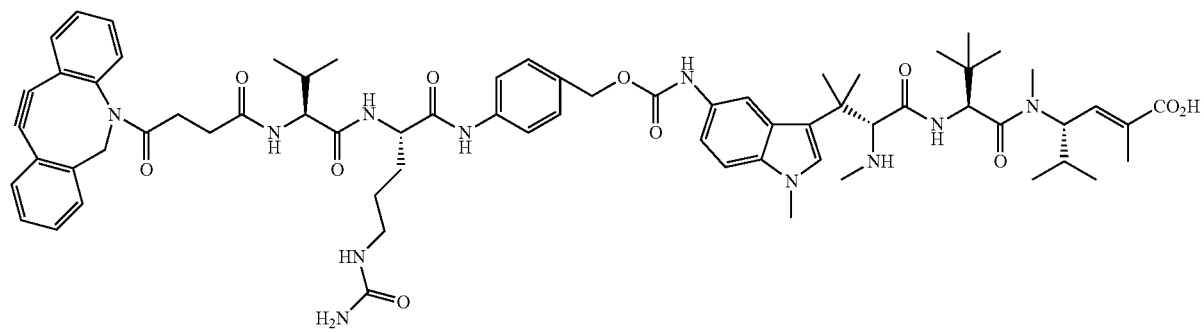
(106b)
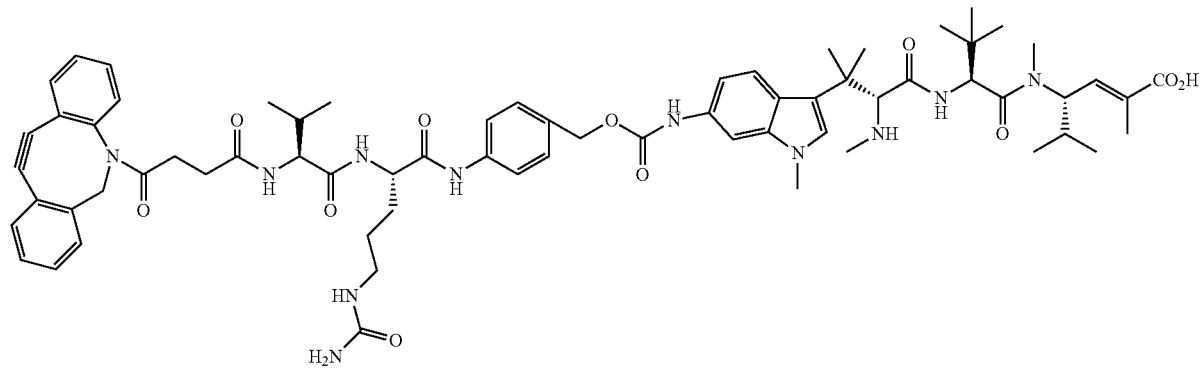
(107b)
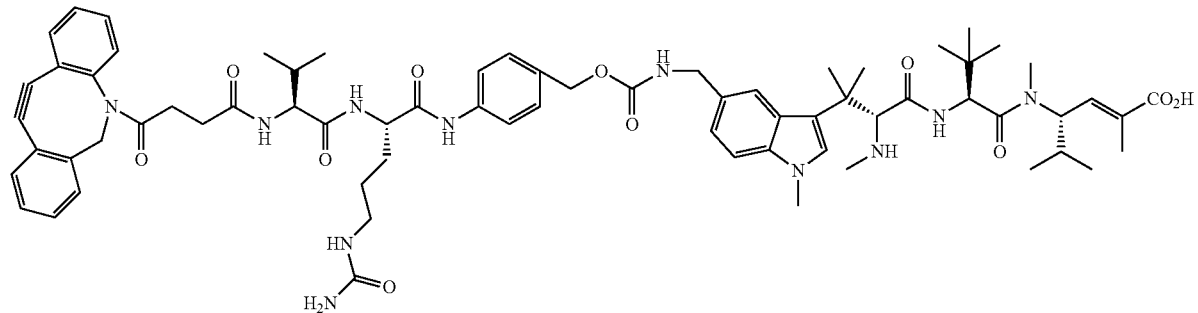

(108b)
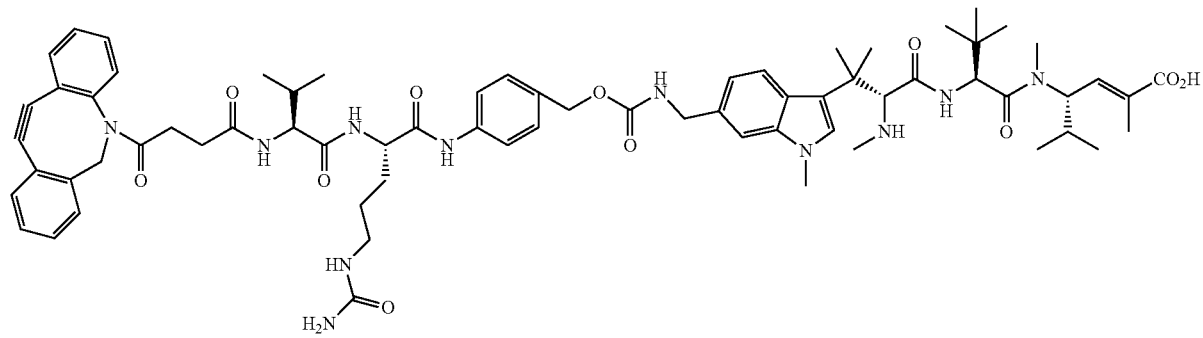
(109b)
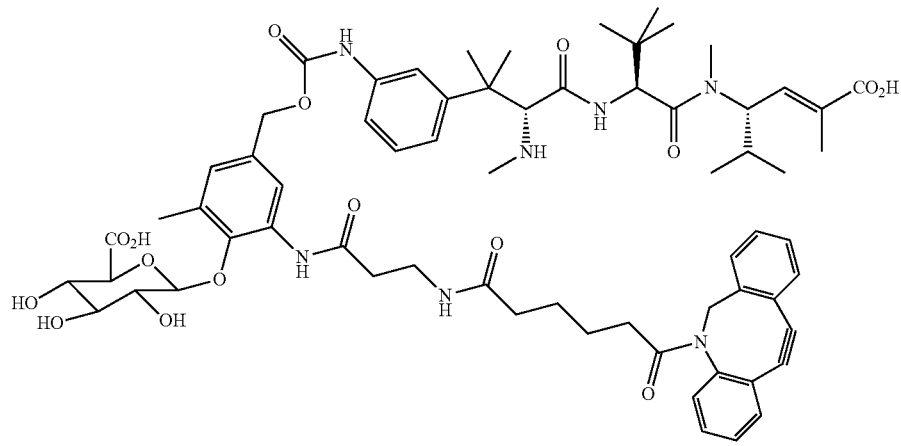
(110b)
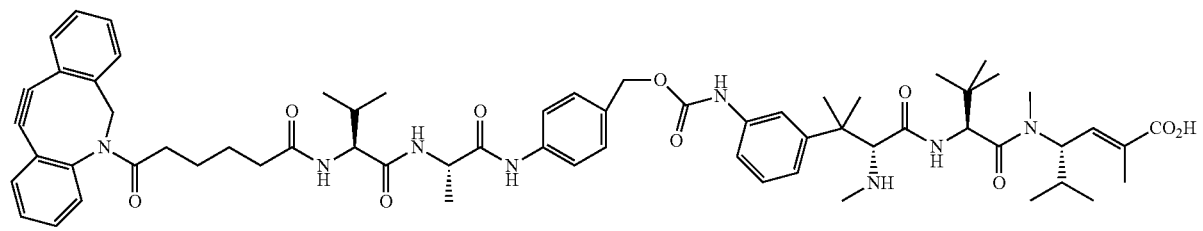
(111b)
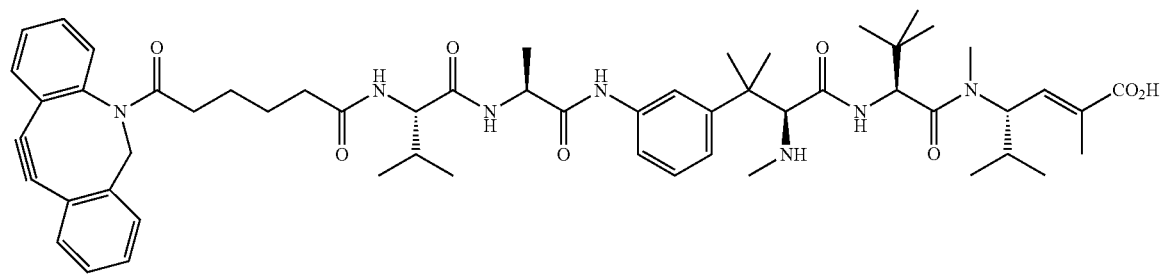
(1b) (2b)
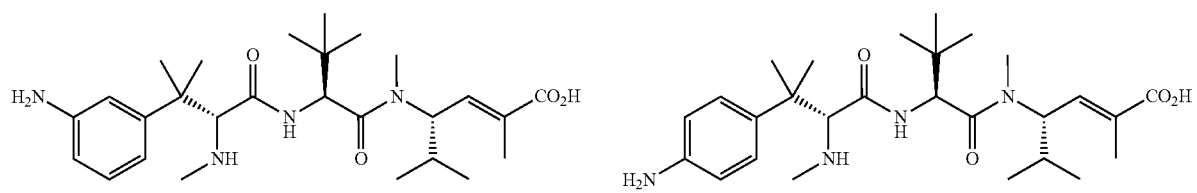

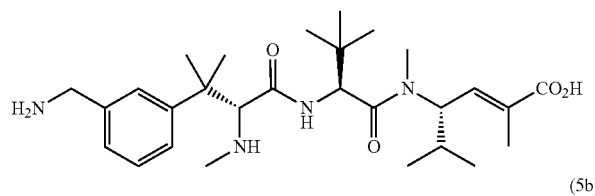 (3b)

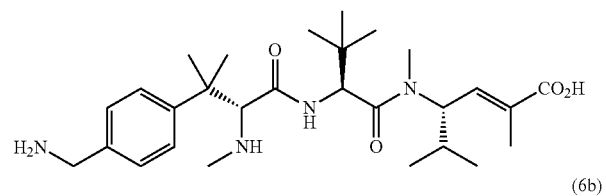 (4b)

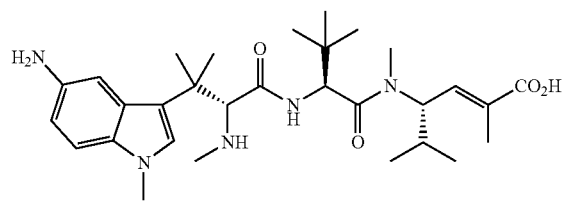 (5b)

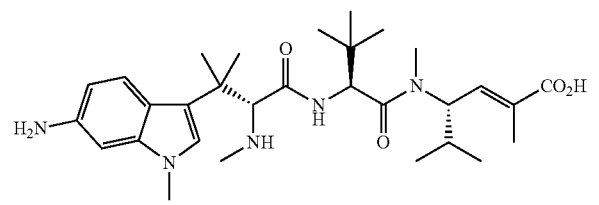 (6b)

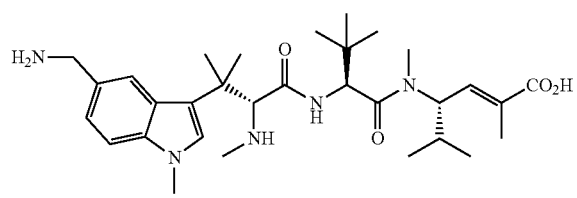 (7b)

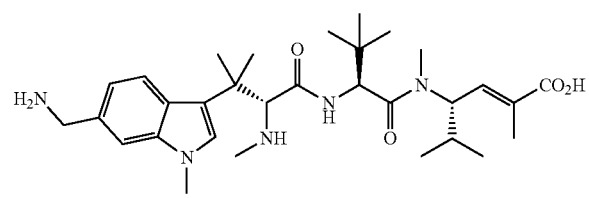 (8b)

or a pharmaceutically acceptable salt, solvate, stereoisomer, or tautomer thereof.

Conjugates

The compounds described herein (e.g., a compound according to any of Formulas 1000-1000b, 1001-1001b, 1002-1002b, and I-XIXb-2, 101-111b, or 1-8b, or a pharmaceutically acceptable salt, solvate, stereoisomer, or tautomer thereof) can be reacted with a second compound (e.g., a polypeptide or antibody) to form a conjugate. The second compound can be any compound known to be useful for conjugation to the compounds described herein (e.g., a compound according to any of Formulas 1000-1000b, 1001-1001b, 1002-1002b, and I-XIXb-2, 101-111b, or 1-8b, or a pharmaceutically acceptable salt, solvate, stereoisomer, or tautomer thereof). Useful second compounds include polypeptides and antibodies.

Therefore, in an aspect, provided herein is a conjugate comprising a compound described herein (e.g., a compound according to any of Formulas 1000-1000b, 1001-1001b, 1002-1002b, and I-XIXb-2, 101-111b, or 1-8b, or a pharmaceutically acceptable salt, solvate, stereoisomer, or tautomer thereof) linked to a second compound.

In an embodiment, the conjugate is according to the following Formula E1:

or a pharmaceutically acceptable salt, solvate, stereoisomer, or tautomer thereof, wherein:

Ar is a divalent five- or six-membered, substituted or unsubstituted, monocyclic aryl or heteroaryl ring or a divalent eight-, nine- or ten-membered, substituted or unsubstituted, fused bicyclic aryl or heteroaryl ring;

L is absent or —$CH_2$—;

X is

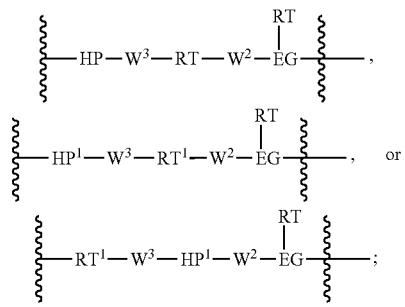

$W^1$, $W^2$, $W^3$, $W^4$, $W^5$ are each independently a single bond, absent, or a divalent attaching group;

EG is absent or an eliminator group;

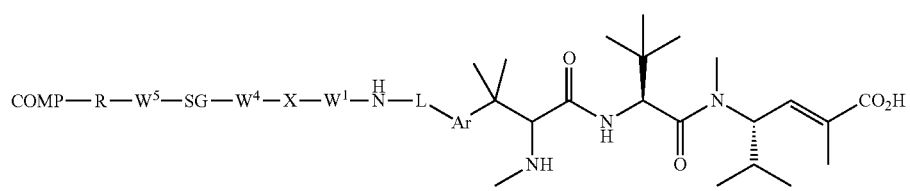 (E1)

each RT is a release trigger group, in the backbone of Formula 1000 or bonded to EG, wherein each RT is optional;

$RT^1$ is a release trigger group, or a cleavable linker, or $RT^1$ is absent;

HP is a single bond, absent, or a divalent hydrophilic group;

$HP^1$ is a single bond, absent, a divalent hydrophilic group, or

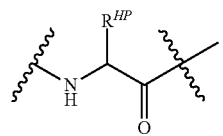

where $R^{HP}$ is a monovalent hydrophilic group;

SG is a single bond, absent, or a divalent spacer group; and

R is a divalent residue of a terminal conjugating group; or, in the alternative, $W^1$, $W^2$, $W^3$, $W^4$, $W^5$, EG, RT, HP, SG, and R combine to form —H.

In an embodiment, the conjugate is according to the following Formula C1:

Ar is a divalent five- or six-membered, substituted or unsubstituted, monocyclic aryl or heteroaryl ring or a divalent eight-, nine- or ten-membered, substituted or unsubstituted, fused bicyclic aryl or heteroaryl ring;

L is absent or —$CH_2$—;

$W^1$, $W^2$, $W^3$, $W^4$, and $W^5$ are each independently a single bond, absent, or a divalent attaching group;

EG is an eliminator group;

each RT is a release trigger group, and one RT is optional;

HP is a single bond, absent, or a divalent hydrophilic group;

SG is a single bond, absent, or a divalent spacer group; and

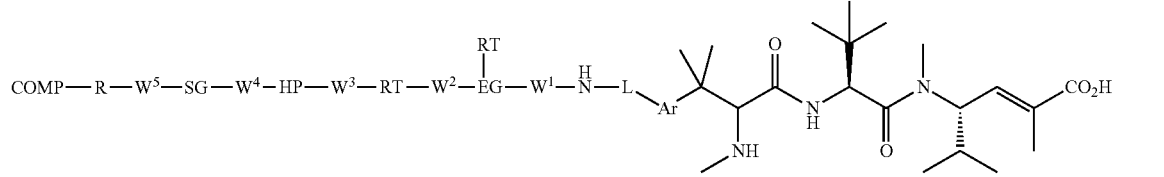

or a pharmaceutically acceptable salt, solvate, stereoisomer, or tautomer thereof, wherein:

COMP is a residue of a second compound;

R is a divalent residue of a terminal conjugating group.

In one embodiment, provided herein is a conjugate according to Formula (F1) or (G1):

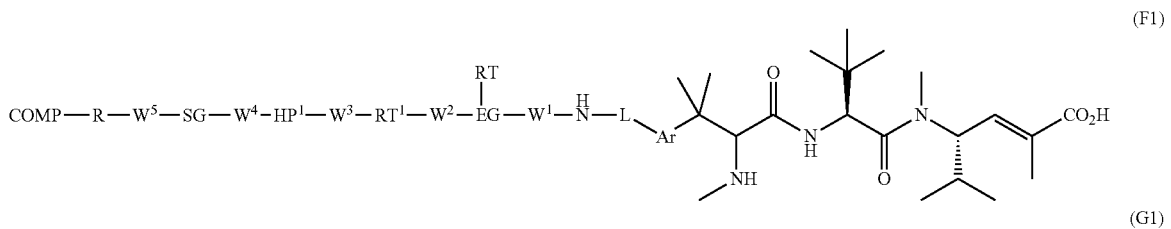

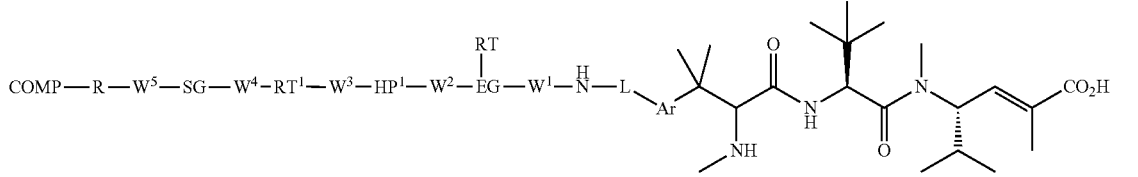

or a pharmaceutically acceptable salt, solvate, stereoisomer, or tautomer thereof, wherein:

COMP is a residue of a second compound;

Ar is a divalent five- or six-membered, substituted or unsubstituted, monocyclic aryl or heteroaryl ring or a divalent eight-, nine- or ten-membered, substituted or unsubstituted, fused bicyclic aryl or heteroaryl ring;

L is absent or —CH$_2$—;

$W^1$, $W^2$, $W^3$, $W^4$, and $W^5$ are each independently a single bond, absent, or a divalent attaching group;

EG is absent or an eliminator group;

$RT^1$ is a release trigger group or a cleavable linker; RT is a release trigger group bonded to EG; and wherein RT and $RT^1$ are optional;

$HP^1$ is single bond, absent, a divalent hydrophilic group, or

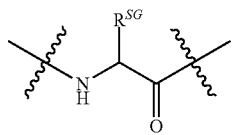

where $R^{SG}$ is a monovalent hydrophilic group;

SG is a single bond, absent, or a divalent spacer group; and

R is a divalent residue of a terminal conjugating group.

In an embodiment, provided herein is a conjugate according to any of Formulas C1-C17b, E1, F1-F17b, and G1-G17b or a pharmaceutically acceptable salt, solvate, stereoisomer, or tautomer thereof; wherein Ar is a divalent five- or six-membered, substituted or unsubstituted, monocyclic aryl or heteroaryl ring. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein Ar is a divalent six-membered, substituted or unsubstituted, monocyclic aryl or heteroaryl ring. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein Ar is a divalent eight-, nine- or ten-membered, substituted or unsubstituted, fused bicyclic aryl or heteroaryl ring. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein Ar is a divalent eight-, nine-membered, substituted or unsubstituted, fused bicyclic heteroaryl ring. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein Ar is phenylene or indolylene, each of which is unsubstituted or substituted. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein Ar is any of the following:

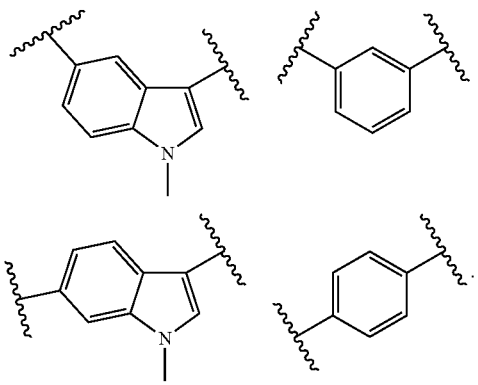

In an embodiment, provided herein is a conjugate according to any of Formulas C1-C17b, E1, F1-F17b, and G1-G17b, or a pharmaceutically acceptable salt, solvate, stereoisomer, or tautomer thereof; wherein L is absent. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein L is —CH$_2$—.

In an embodiment, provided herein is a conjugate according to any of Formulas C1-C17b, E1, F1-F17b, and G1-G17b or a pharmaceutically acceptable salt, solvate, stereoisomer, or tautomer thereof; wherein EG comprises phenylene, carboxylene, amine, or a combination thereof. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein EG is:

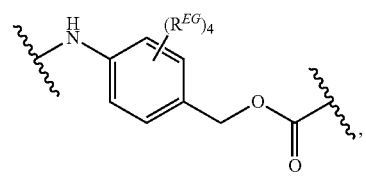

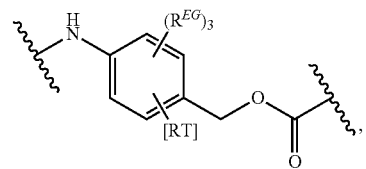

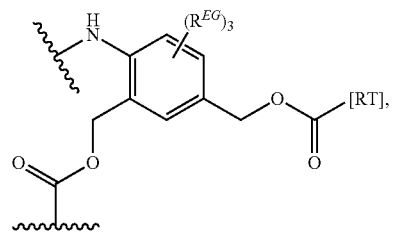

117

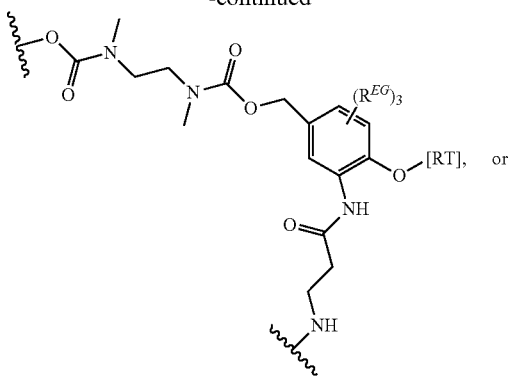

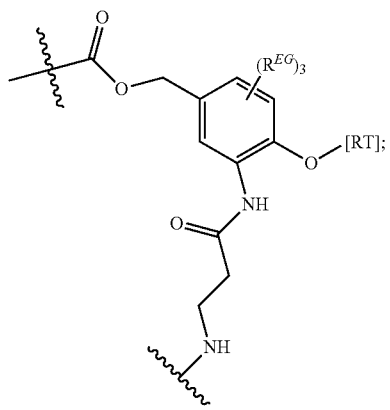

wherein each $R^{EG}$ is independently selected from the group consisting of hydrogen, alkyl, biphenyl, —$CF_3$, —$NO_2$, —CN, fluoro, bromo, chloro, alkoxyl, alkylamino, dialkylamino, alkyl-C(O)O—, alkylamino-C(O)— and dialkylaminoC(O)—. In the second and third structures, those of skill will recognize that EG is bonded to an RT that is not within the backbone of formula (I) as indicated in the above description of formula (I). In some embodiments, each $R^{EG}$ is independently selected from the group consisting of hydrogen, alkyl, biphenyl, —$CF_3$, alkoxyl, alkylamino, dialkylamino, alkyl-C(O)O—, alkylamino-C(O)— and dialkylaminoC(O)—. In further embodiments, each $R^{EG}$ is independently selected from the group consisting of hydrogen, —$NO_2$, —CN, fluoro, bromo, and chloro.

In an embodiment, provided herein is a conjugate according to any of Formulas C1-C17b, E1, F1-F17b, and G1-G17b, or a pharmaceutically acceptable salt, solvate, stereoisomer, or tautomer thereof wherein RT comprises a residue of a natural or non-natural amino acid or a residue of a sugar. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein RT is:

118

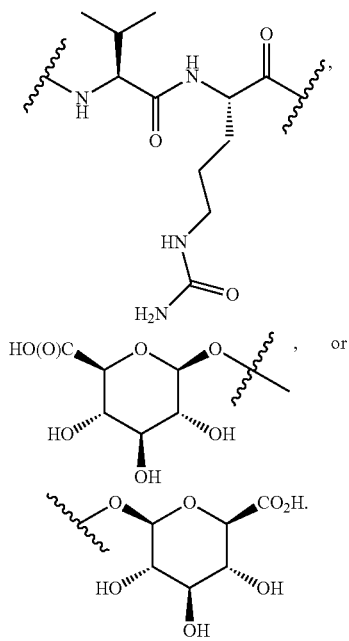

Those of skill will recognize that the first structure is divalent and can be bonded within the backbone of formula 1000 or (I), and that the second structure is monovalent and can be bonded to EG as depicted in formula (I) and 1000 above.

In an embodiment, provided herein is a conjugate according to any of Formulas C1-C17b, E1, F1-F17b, and G1-G17b, or a pharmaceutically acceptable salt, solvate, stereoisomer, or tautomer thereof; wherein HP comprises poly(ethylene glycol). In an embodiment, provided herein is a conjugate according to any of Formulas C1-C17b, E1, F1-F17b, and G1-G17b, or a pharmaceutically acceptable salt, solvate, stereoisomer, or tautomer thereof; wherein HP is:

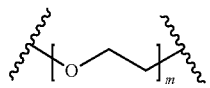

wherein m is an integer from 1 to 12.

In an embodiment, provided herein is a conjugate according to any of Formulas C1-C17b, E1, F1-F17b, and G1-G17b, or a pharmaceutically acceptable salt, solvate, stereoisomer, or tautomer thereof; wherein SG comprises $C_1$-$C_{10}$ alkylene, $C_4$-$C_6$ alkylene, —C(O)—, or combination thereof. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein SG is:

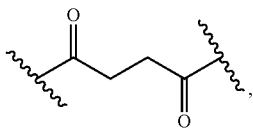

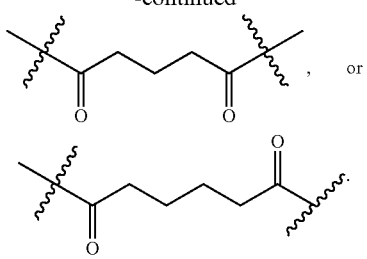

In an embodiment, provided herein is a conjugate according to any of Formulas C1-C17b, E1, F1-F17b, and G1-G17b, or a pharmaceutically acceptable salt, solvate, stereoisomer, or tautomer thereof; wherein $W^1$, $W^2$, $W^3$, $W^4$, and $W^5$ are each independently a single bond, absent, or comprise a divalent ketone, divalent ester, divalent ether, divalent amide, divalent amine, alkylene, arylene, sulfide, disulfide, —C(O)—, or a combination thereof. In an embodiment, provided herein is a conjugate according to any of Formulas C1-C17b, E1, F1-F17b, and G1-G17b, or a pharmaceutically acceptable salt, solvate, stereoisomer, or tautomer thereof; wherein $W^1$, $W^2$, $W^3$, $W^4$, and $W^5$ are each independently a single bond, absent, or comprise —C(O)—, —O—, —C(O)NH—, —C(O)NH-alkyl-, —OC(O)NH—, —SC(O)NH—, —NH—, —NH-alkyl-, —N(CH$_3$)CH$_2$CH$_2$N(CH$_3$)—, —S—, —S—S—, —OCH$_2$CH$_2$O—, or a combination thereof.

In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R comprises a triazole ring. In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R is a triazole ring or fused cyclic group comprising a triazole ring. In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R is:

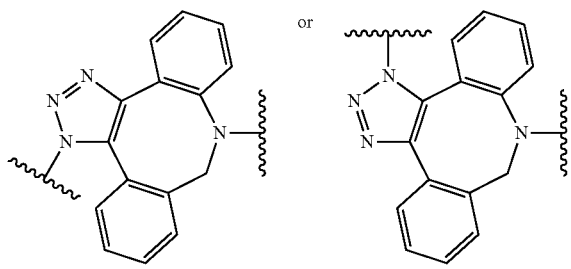

In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R comprises a fused bicyclic ring having at least two adjacent nitrogen atoms in the ring. In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R is:

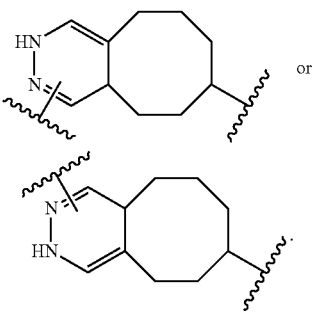

In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R comprises a sulfur linkage. In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R is:

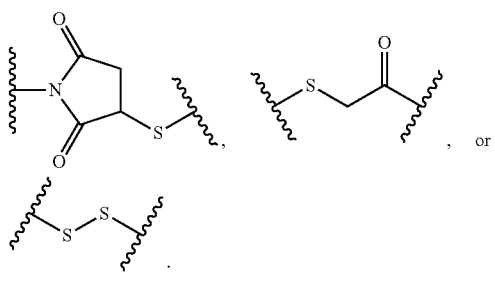

In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R comprises a divalent residue of a non-natural amino acid. In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R is:

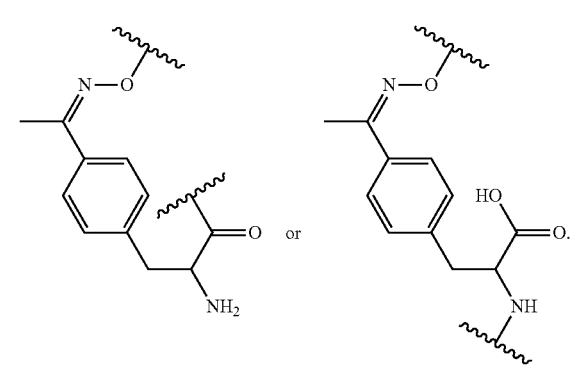 [SMILES: *O/N=C(/C)c1ccc(CC(N)C(*)=O)cc1 ; *NC(Cc1ccc(/C(C)=N\O*)cc1)C(=O)O]

In an embodiment, provided herein is a conjugate according to any of Formulas C1-C13b, E1, F1-F13b, and G1-G13b, or a pharmaceutically acceptable salt, solvate, stereoisomer, or tautomer thereof; wherein comprises an oxime linkage. In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R is:

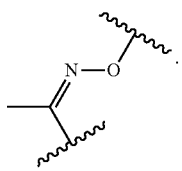 [SMILES: *O/N=C(\*)C]

In an embodiment, provided herein is a conjugate according to any of Formulas C1-C13b, E1, F1-F13b, and G1-G13b, or a pharmaceutically acceptable salt, solvate, stereoisomer, or tautomer thereof; wherein R is:

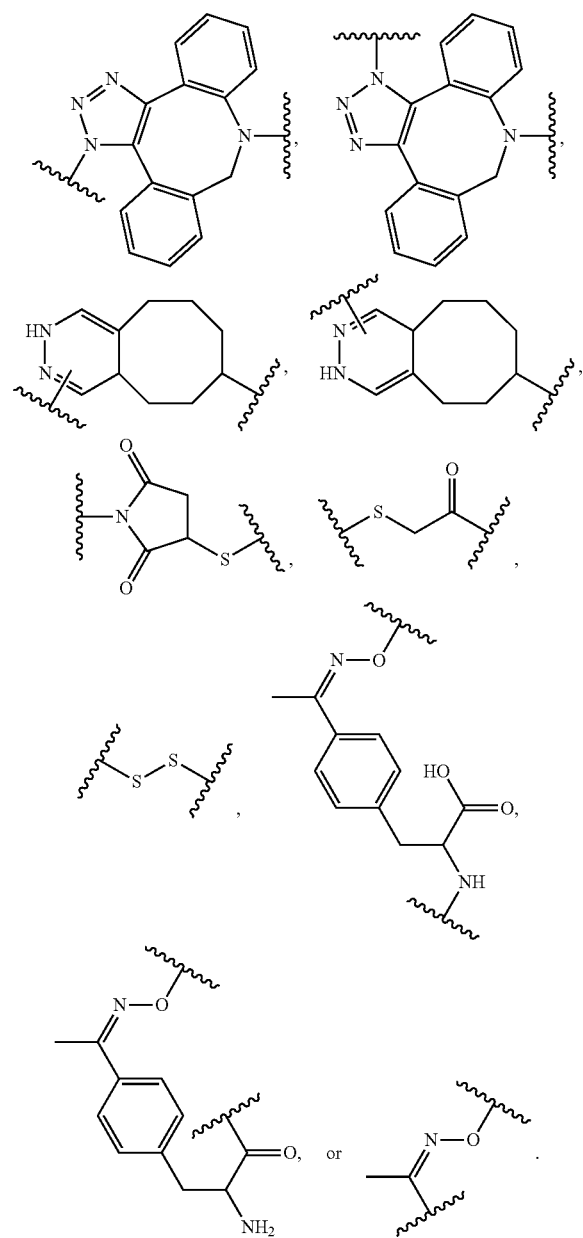

In an embodiment, provided herein is a compound according to any of Formulas C1-C17b, E1, F1-F17b, and G1-G17b, or a pharmaceutically acceptable salt, solvate, stereoisomer, or tautomer thereof; wherein COMP is a residue of any compound known to be useful for conjugation to the modified Hemiasterlin compounds described herein (e.g., a compound according to any of Formulas 1000-1000b, 1001-1001b, 1002-1002b, and I-XIXb-2, 101-111b, or 1-8b, or a pharmaceutically acceptable salt, solvate, stereoisomer, or tautomer thereof). In an embodiment, provided herein is a compound according to any of Formulas C1-C17b, E1, F1-F17b, and G1-G17b, or a pharmaceutically acceptable salt, solvate, stereoisomer, or tautomer thereof; wherein COMP is a residue of a polypeptide, antibody, or antibody chain. In an embodiment, provided herein is a compound according to any of Formulas C1-C17b, E1, F1-F17b, and G1-G17b, or a pharmaceutically acceptable salt, solvate, stereoisomer, or tautomer thereof; wherein COMP is a residue of a polypeptide. In an embodiment, provided herein is a compound according to any of Formulas C1-C17b, E1, F1-F17b, and G1-G17b, or a pharmaceutically acceptable salt, solvate, stereoisomer, or tautomer thereof; wherein COMP is a residue of an antibody. In an embodiment, provided herein is a compound according to any of Formulas C1-C17b, E1, F1-F17b, and G1-G17b, or a pharmaceutically acceptable salt, solvate, stereoisomer, or tautomer thereof; wherein COMP is a residue of an antibody chain.

In an aspect, provided herein is a polypeptide conjugate comprising a compound described herein (e.g., a compound according to any of Formulas 1000-1000b, 1001-1001b, 1002-1002b, and I-XIXb-2, 101-111b, or 1-8b, or a pharmaceutically acceptable salt, solvate, stereoisomer, or tautomer thereof) linked to a polypeptide, wherein the polypeptide conjugate is according to any of Formulas C1-C17b, E1, F1-F17b, and G1-G17b, or a pharmaceutically acceptable salt, solvate, stereoisomer, or tautomer thereof, wherein COMP is a residue of the polypeptide. In an embodiment, provided herein is a polypeptide conjugate according to any of Formulas C1-C15b, or a pharmaceutically acceptable salt, solvate, stereoisomer, or tautomer thereof, wherein: COMP is a residue of the polypeptide; and R comprises a triazole ring or fused cyclic group comprising a triazole ring. In an embodiment, provided herein is a polypeptide conjugate according to any of Formulas C1-C13b, E1, F1-F13b, and G1-G13b, or a pharmaceutically acceptable salt, solvate, stereoisomer, or tautomer thereof, wherein: COMP is a residue of the polypeptide; and R is:

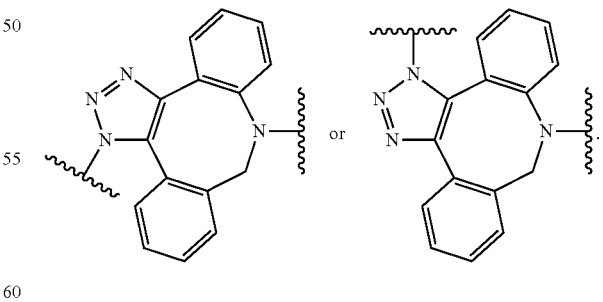

In an embodiment, provided herein is a polypeptide conjugate according to any of Formulas C1-C13b, E1, F1-F13b, and G1-G13b, or a pharmaceutically acceptable salt, solvate, stereoisomer, or tautomer thereof, wherein: COMP is a residue of the polypeptide; and R comprises a fused bicyclic ring, wherein the fused bicyclic ring has at least two adjacent nitrogen atoms in the ring. In an embodiment, provided herein is a polypeptide conjugate according to any of Formulas C1-C13b, E1, F1-F13b, and G1-G13b, or a pharmaceutically acceptable salt, solvate, stereoisomer, or tautomer thereof, wherein: COMP is a residue of the polypeptide; and R is:

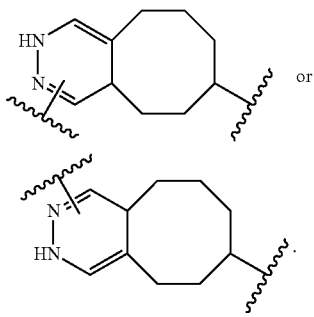

or

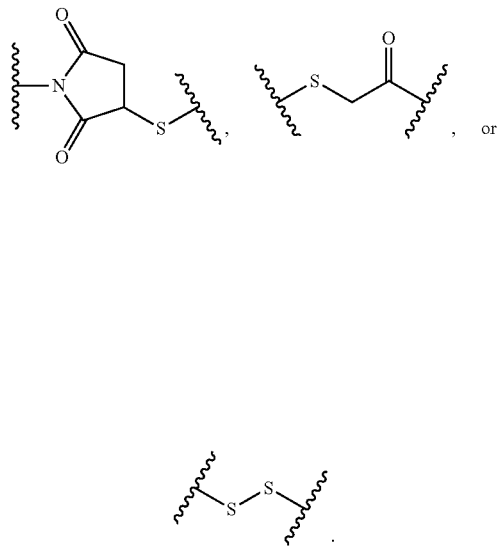

In an embodiment, provided herein is a polypeptide conjugate according to any of Formulas C1-C13b, E1, F1-F13b, and G1-G13b, or a pharmaceutically acceptable salt, solvate, stereoisomer, or tautomer thereof, wherein: COMP is a residue of the polypeptide; and R comprises a sulfur linkage. In an embodiment, provided herein is a polypeptide conjugate according to any of Formulas C1-C13b, E1, F1-F13b, and G1-G13b, or a pharmaceutically acceptable salt, solvate, stereoisomer, or tautomer thereof, wherein: COMP is a residue of the polypeptide; and R is:

In an embodiment, provided herein is a polypeptide conjugate according to any of Formulas C1-C13b, E1, F1-F13b, and G1-G13b, or a pharmaceutically acceptable salt, solvate, stereoisomer, or tautomer thereof, wherein: COMP is a residue of the polypeptide; and R comprises a divalent residue of a non-natural amino acid. In an embodiment, provided herein is a polypeptide conjugate according to any of Formulas C1-C13b, E1, F1-F13b, and G1-G13b, or a pharmaceutically acceptable salt, solvate, stereoisomer, or tautomer thereof, wherein: COMP is a residue of the polypeptide; and R is:

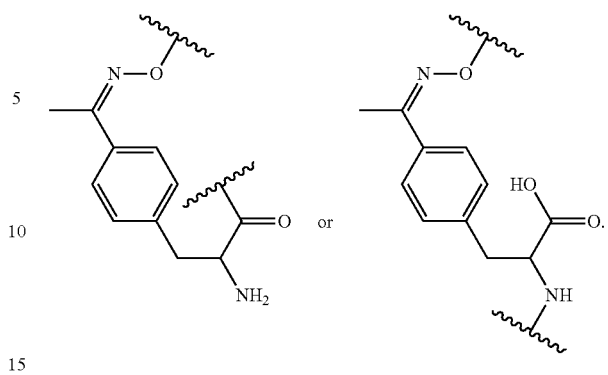

In an embodiment, provided herein is a polypeptide conjugate according to any of Formulas C1-C13b, E1, F1-F13b, and G1-G13b, or a pharmaceutically acceptable salt, solvate, stereoisomer, or tautomer thereof, wherein: COMP is a residue of the polypeptide; and R comprises an oxime linkage. In an embodiment, provided herein is a polypeptide conjugate according to any of Formulas C1-C13b, E1, F1-F13b, and G1-G13b, or a pharmaceutically acceptable salt, solvate, stereoisomer, or tautomer thereof, wherein: COMP is a residue of the polypeptide; and R is:

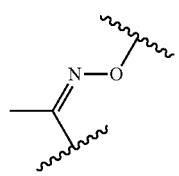

In an aspect, provided herein is an antibody conjugate comprising a compound described herein (e.g., a compound according to any of Formulas 1000-1000b, 1001-1001b, 1002-1002b, and I-XIXb-2, 101-111b, or 1-8b, or a pharmaceutically acceptable salt, solvate, stereoisomer, or tautomer thereof) linked to an antibody according to any of Formulas C1-C17b, E1, F1-F17b, and G1-G17b, or a pharmaceutically acceptable salt, solvate, stereoisomer, or tautomer thereof, wherein COMP is a residue of the antibody. In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R comprises a triazole ring or fused cyclic group comprising a triazole ring. In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R is:

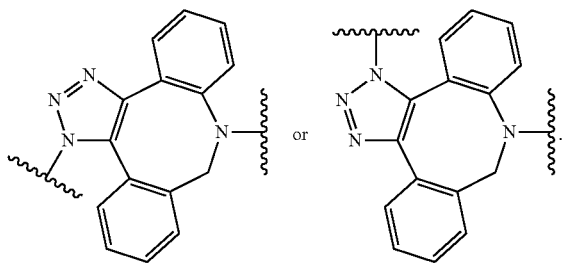 [SMILES: *N1Cc2ccccc2-c2c(nnn2*)-c2ccccc21 ; *N1Cc2ccccc2-c2nnn(*)c2-c2ccccc21]

In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R comprises a fused bicyclic ring, wherein the fused bicyclic ring has at least two adjacent nitrogen atoms in the ring. In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R is:

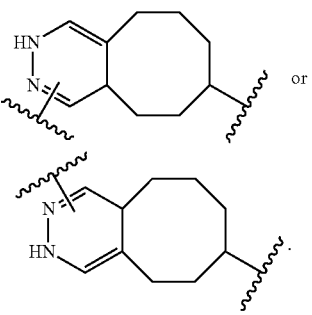

In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R comprises a sulfur linkage. In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R is:

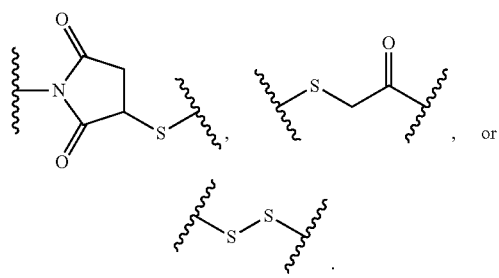

In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R comprises a divalent residue of a non-natural amino acid. In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R is:

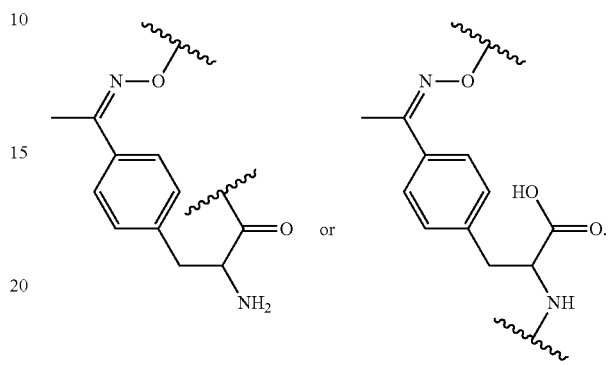

In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R comprises an oxime linkage. In an embodiment, provided herein is an antibody conjugate according to any of Formulas C1-C13b, E1, F1-F13b, and G1-G13b, or a pharmaceutically acceptable salt, solvate, stereoisomer, or tautomer thereof, wherein: COMP is a residue of the antibody; and R is:

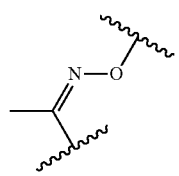

In an aspect, provided herein is an antibody chain conjugate comprising a compound described herein (e.g., a compound according to any of Formulas 1000-1000b, 1001-1001b, 1002-1002b, and I-XIXb-2, 101-111b, or 1-8b, or a pharmaceutically acceptable salt, solvate, stereoisomer, or tautomer thereof) linked to an antibody chain according to any of Formulas C1-C17b, E1, F1-F17b, and G1-G17b, or a pharmaceutically acceptable salt, solvate, stereoisomer, or tautomer thereof, wherein COMP is a residue of the antibody chain.

In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R comprises a triazole ring or fused cyclic group comprising a triazole ring. In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R is:

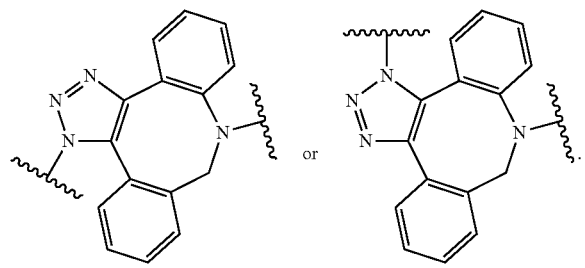 [SMILES: *N1Cc2ccccc2-c2c(nnn2*)-c2ccccc21 ; *N1Cc2ccccc2-c2nnn(*)c2-c2ccccc21]

In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R comprises a fused bicyclic ring, wherein the fused bicyclic ring has at least two adjacent nitrogen atoms in the ring. In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R is:

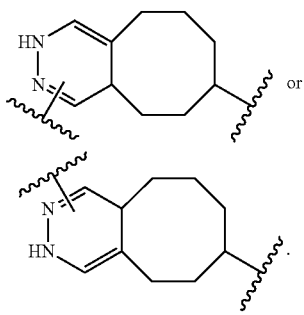

In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R comprises a sulfur linkage. In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R is:

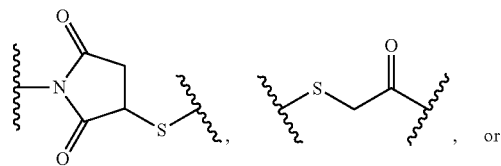 or

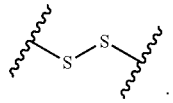

In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R comprises a divalent residue of a non-natural amino acid. In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R is:

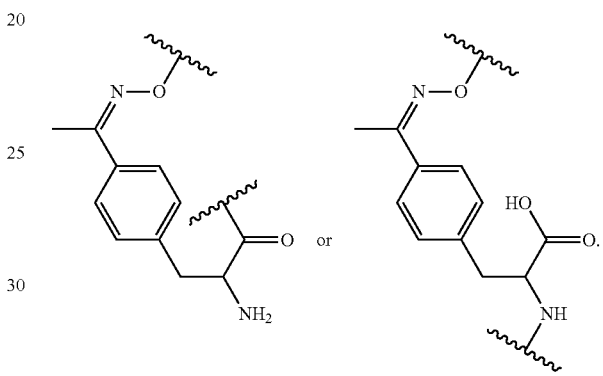

In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R comprises an oxime linkage. In an embodiment, provided herein is an antibody chain conjugate according to any of Formulas C1-C13b, E1, F1-F13b, and G1-G13b, or a pharmaceutically acceptable salt, solvate, stereoisomer, or tautomer thereof, wherein: COMP is a residue of the antibody chain; and R is:

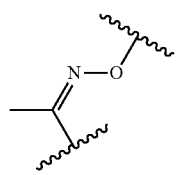

In an embodiment, provided herein is a conjugate according to Formula C1a or Formula C1b:

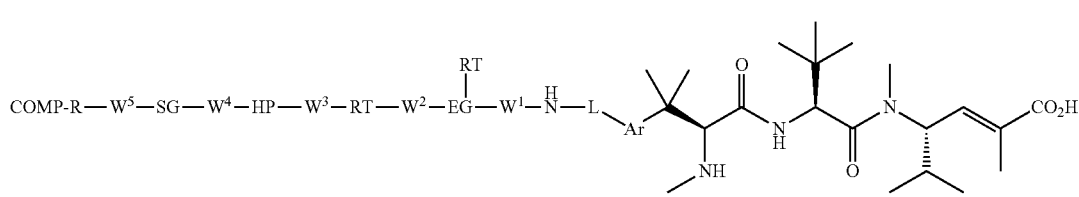

(C1a)

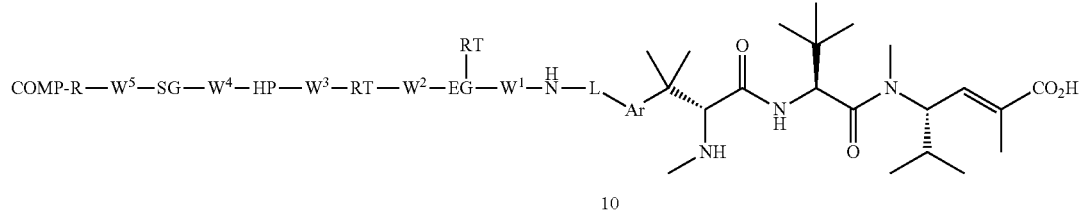

(C1b)

or a pharmaceutically acceptable salt, solvate, stereoisomer, or tautomer thereof, wherein COMP, R, SG, HP, RT, EG, $W^1$, $W^2$, $W^3$, $W^4$, $W^5$, L, and Ar are a described in the context of Formulas C1 and I-XVIb.

In an embodiment, provided herein is a conjugate according to the following Formula:

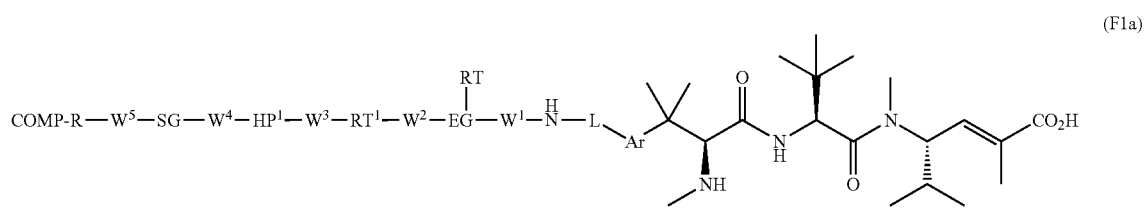

(F1a)

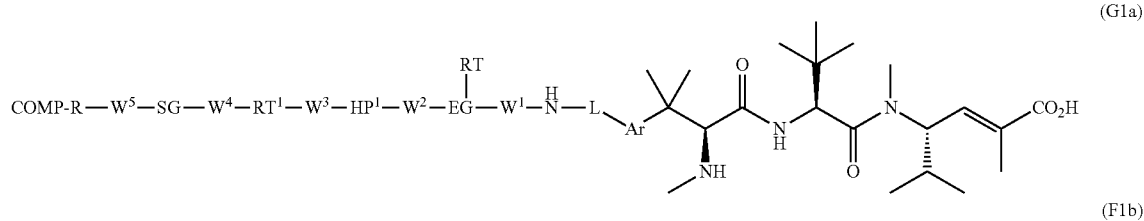

(G1a)

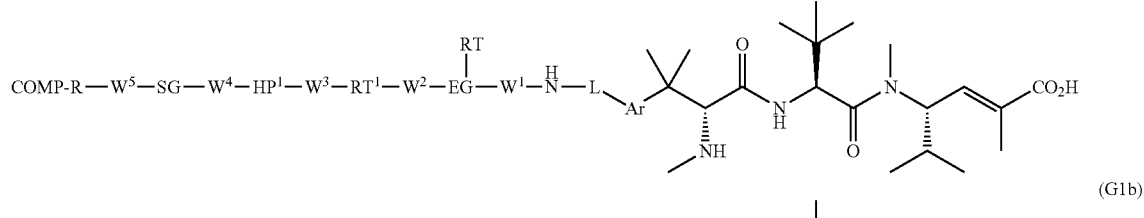

(F1b)

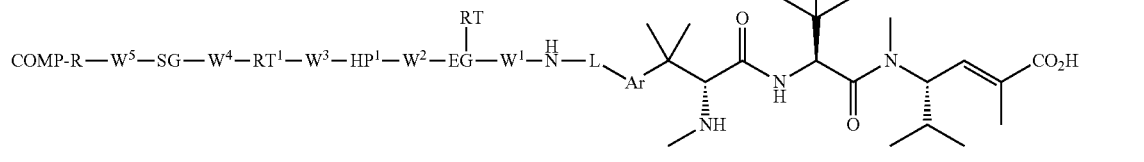

(G1b)

or a pharmaceutically acceptable salt, solvate, stereoisomer, or tautomer thereof, wherein all other groups are as defined in any of the Formulas and/or embodiments described herein.

In an embodiment, provided herein is a compound according to any of Formulas C2-C9:

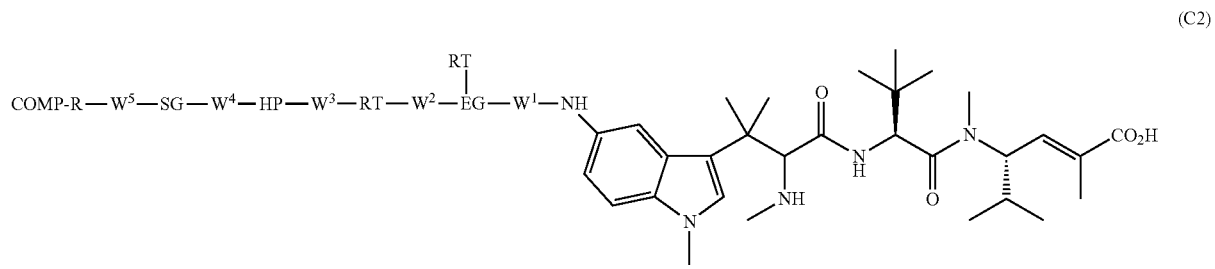

(C2)

-continued
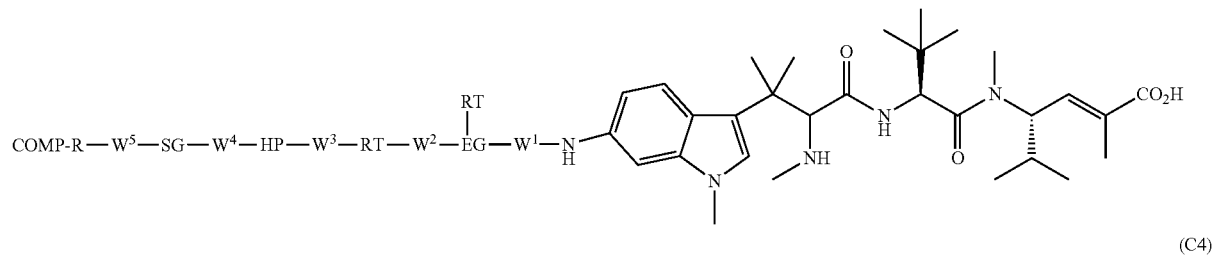
(C3)
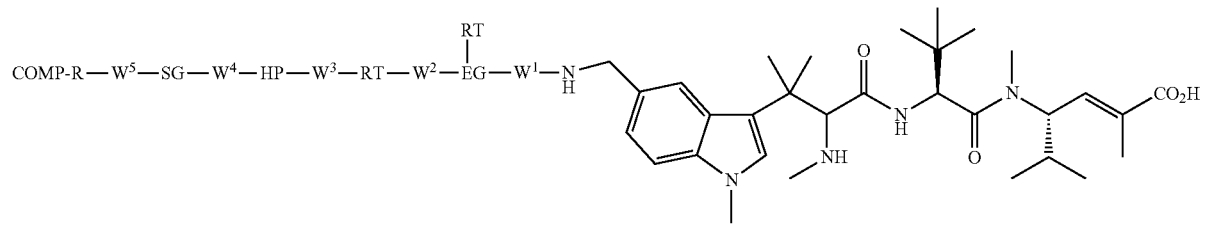
(C4)
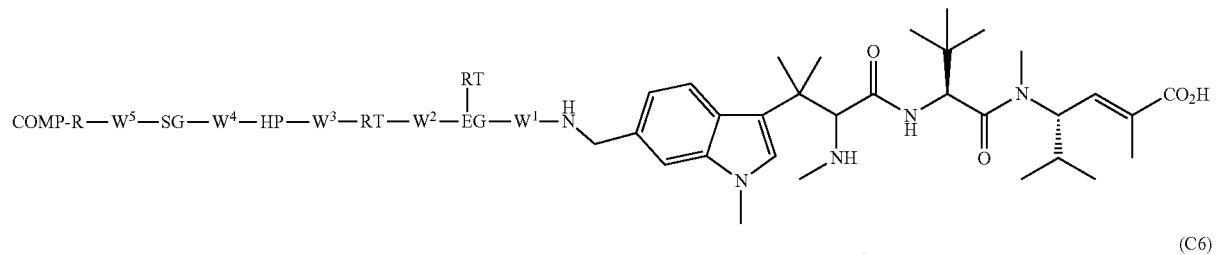
(C5)
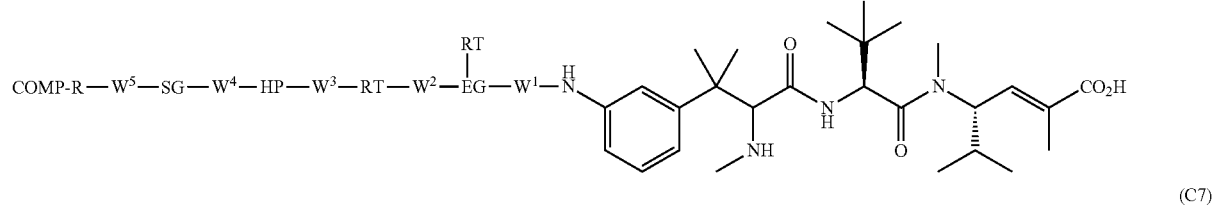
(C6)
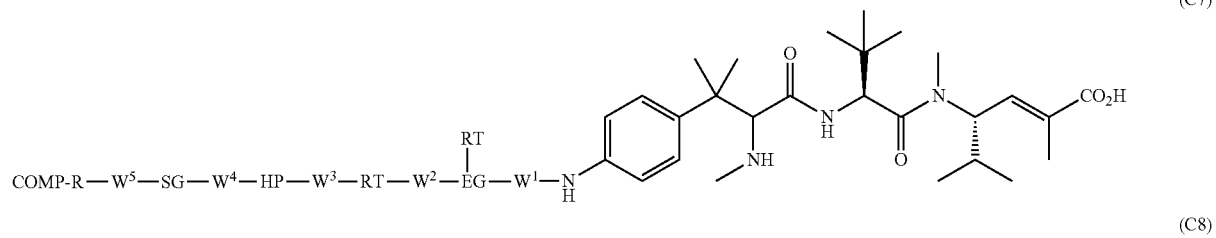
(C7)
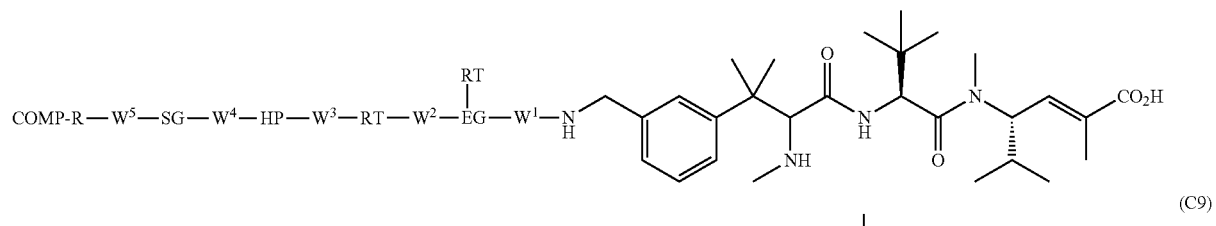
(C8)
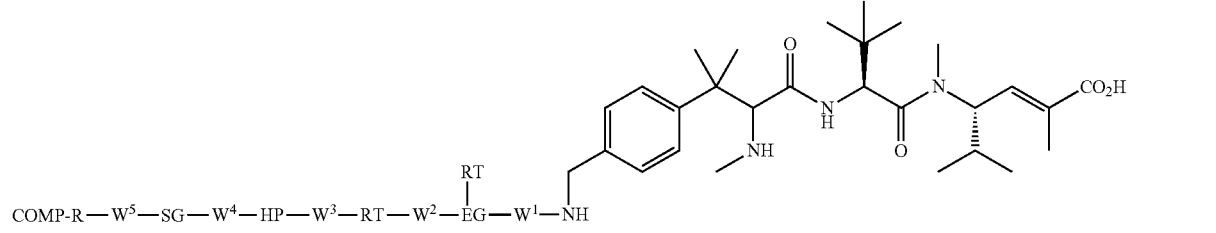
(C9)

or a pharmaceutically acceptable salt, solvate, stereoisomer, or tautomer thereof, wherein COMP, R, SG, HP, RT, EG, $W^1$, $W^2$, $W^3$, $W^4$, $W^5$, L, and Ar are a described in the context of Formulas C1 and I-XVIb.
In an embodiment, provided herein is a compound according to any of the following Formula:

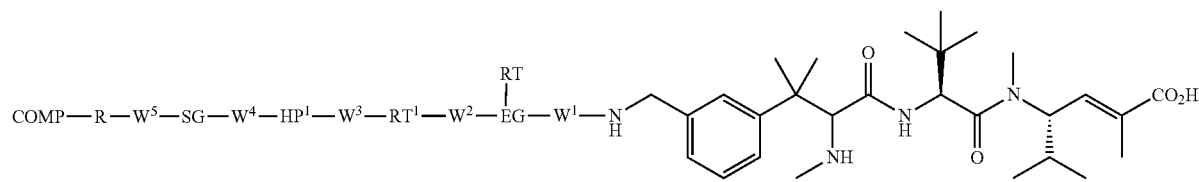
(F8)
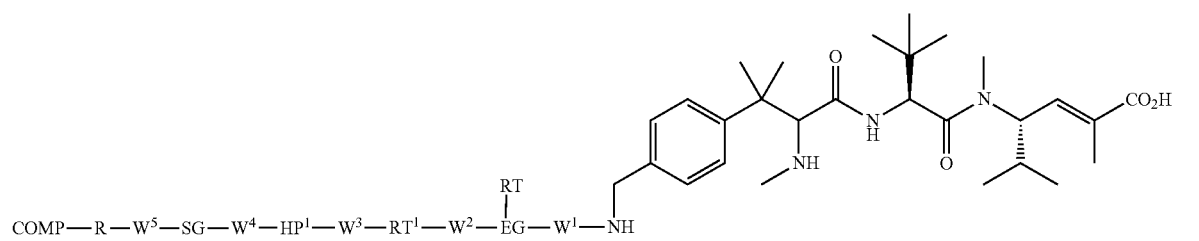
(F9)
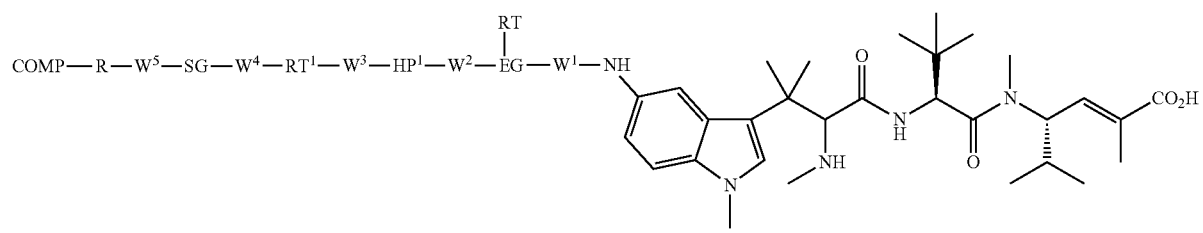
(G2)
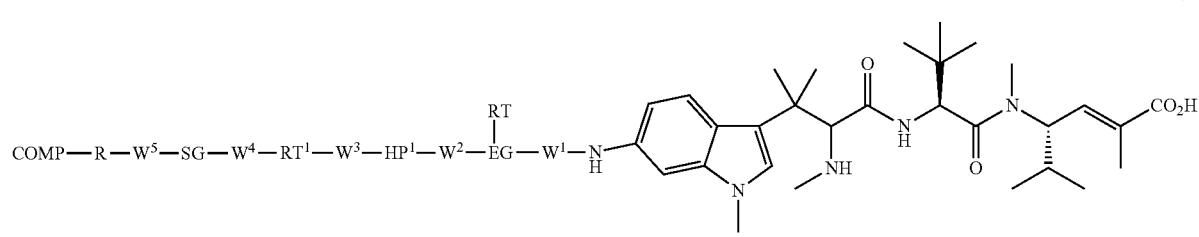
(G3)
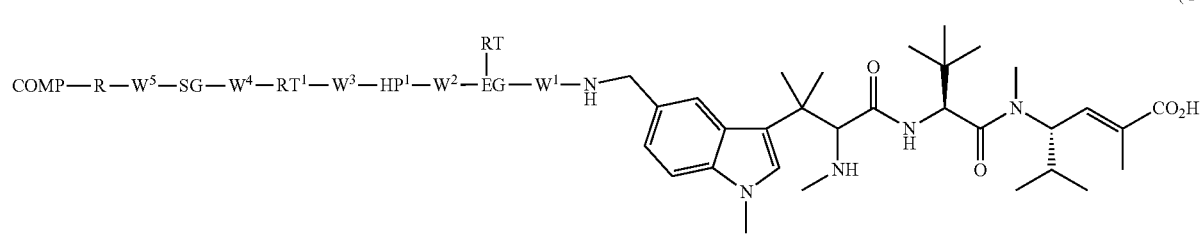
(G4)
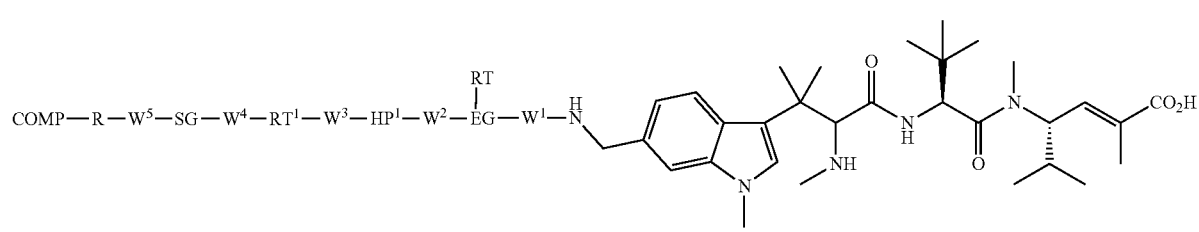
(G5)

(G6)
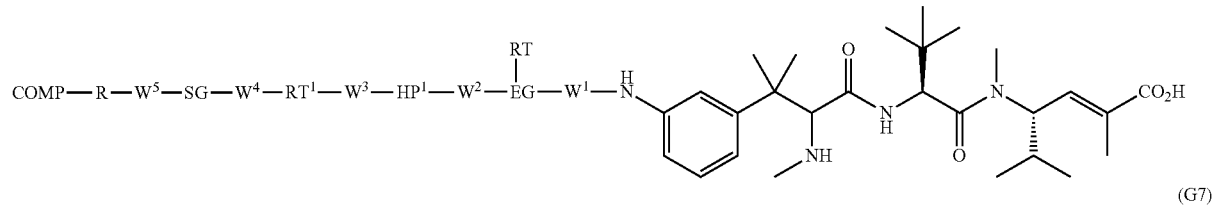
(G7)
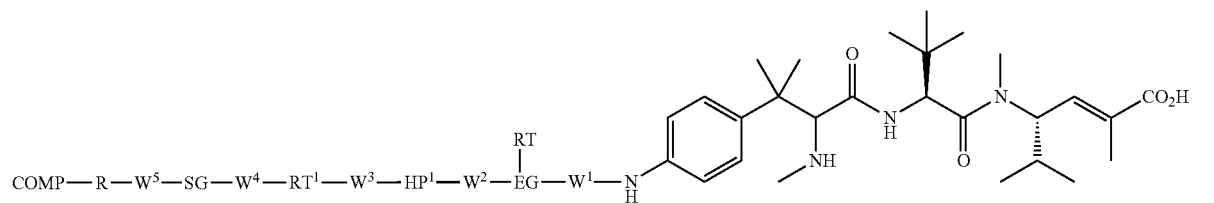
(G8)
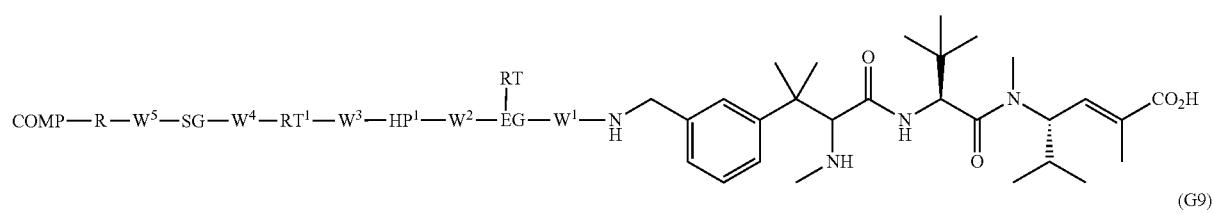
(G9)
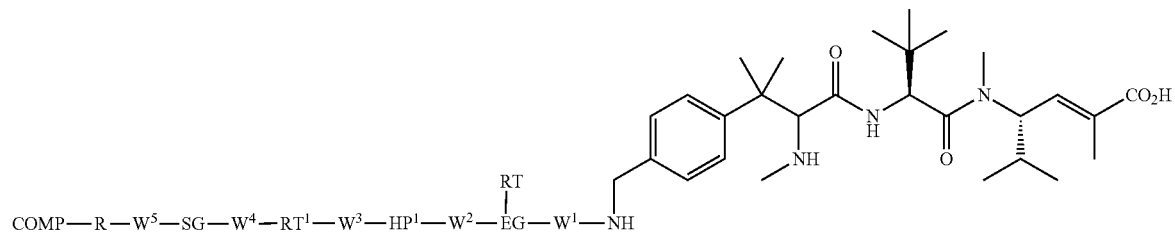
or a pharmaceutically acceptable salt, solvate, stereoisomer, or tautomer thereof, wherein all other groups are a described in the context of any of the Formulas or embodiments described herein.
In an embodiment, provided herein is a compound according to any of Formulas C2a-C9a:
(C2a)
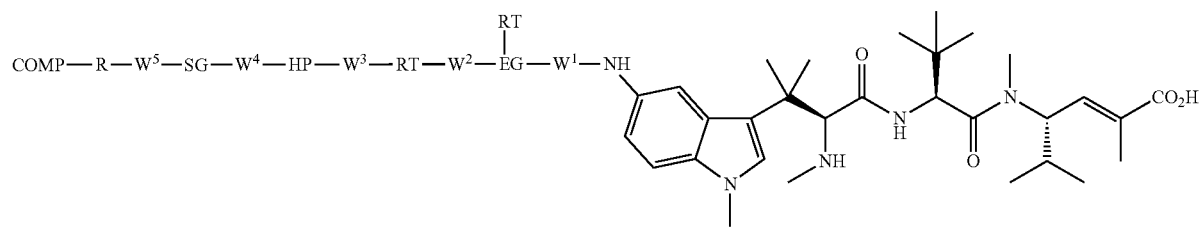
(C3a)
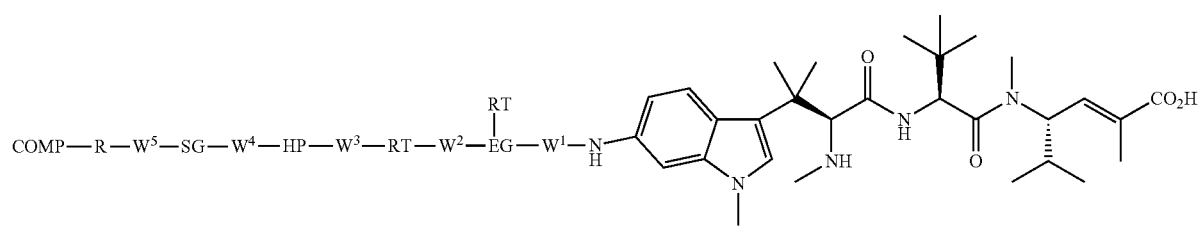

-continued
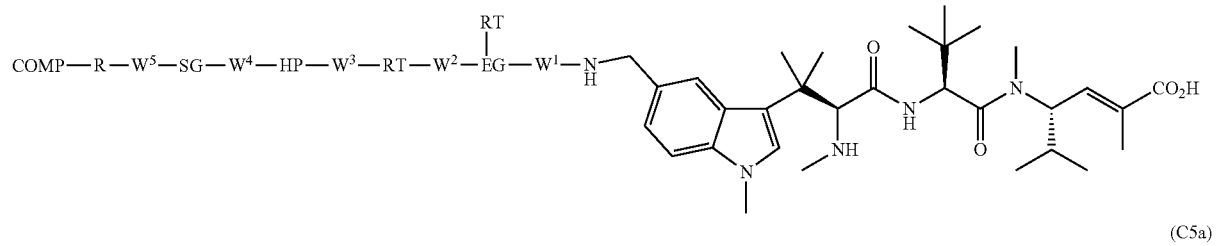
(C4a)
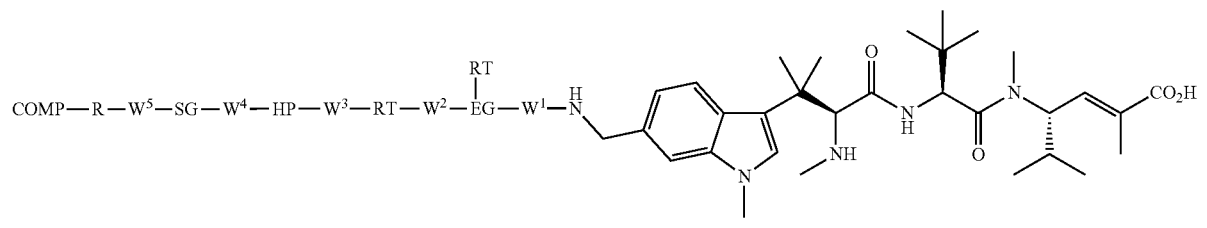
(C5a)
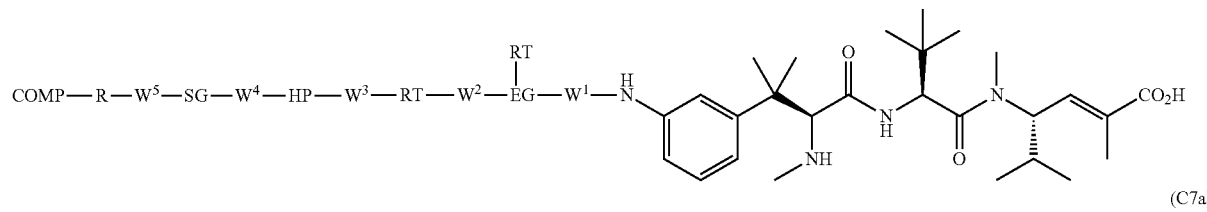
(C6a)
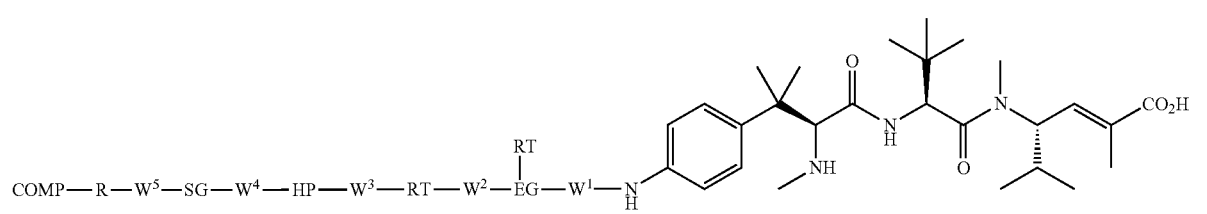
(C7a)
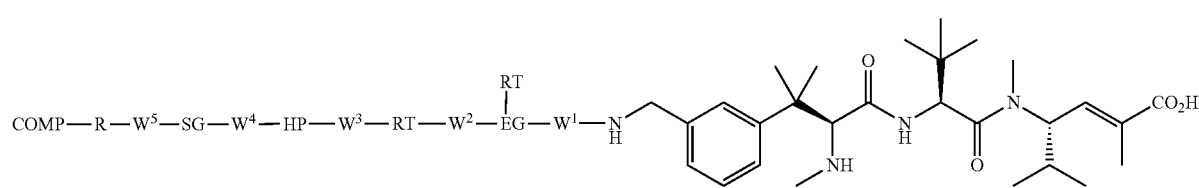
(C8a)
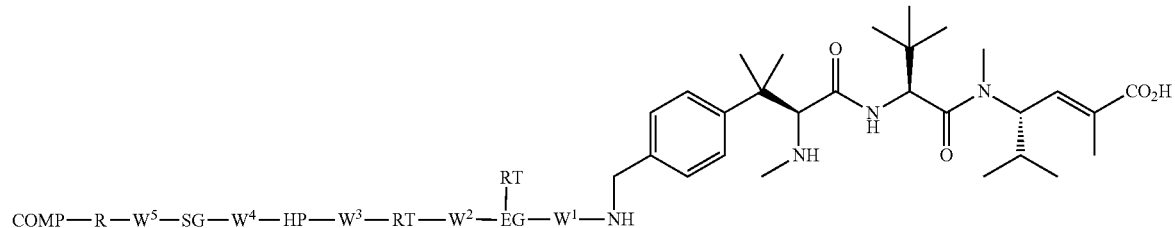
(C9a)
or a pharmaceutically acceptable salt, solvate, stereoisomer, or tautomer thereof, wherein COMP, R, SG, HP, RT, EG, $W^1$, $W^2$, $W^3$, $W^4$, $W^5$, L, and Ar are a described in the context of Formulas C1 and I-XVIb.

In an embodiment, provided herein is a compound according to any of the following Formula:
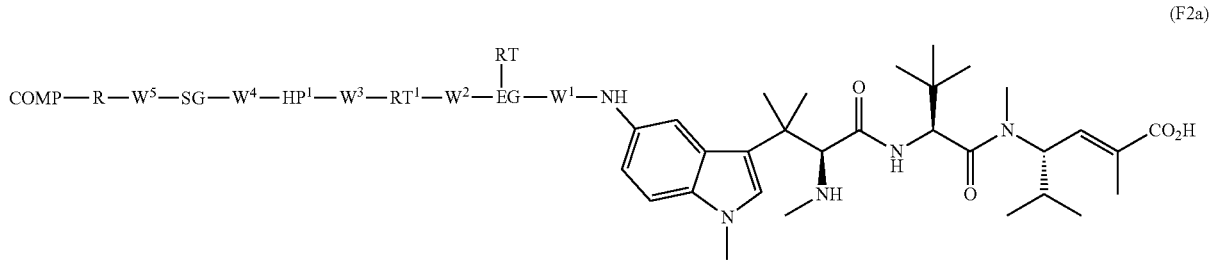
(F2a)
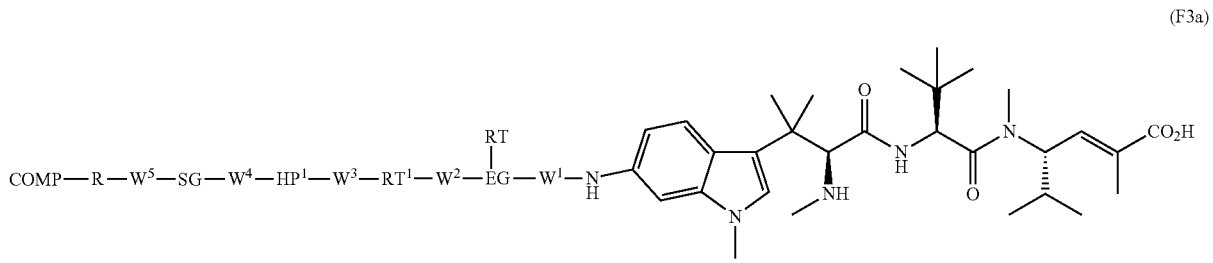
(F3a)
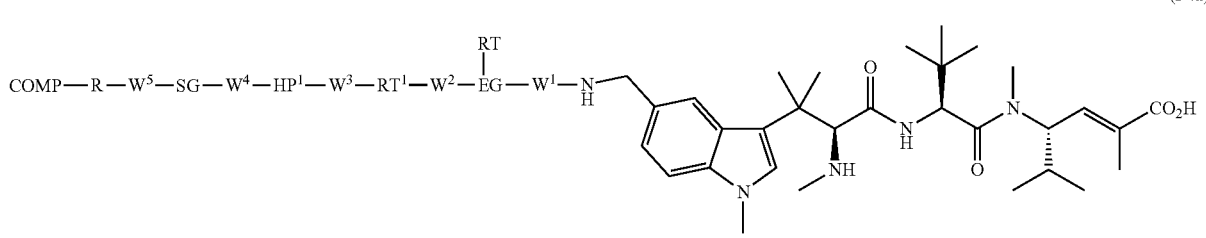
(F4a)
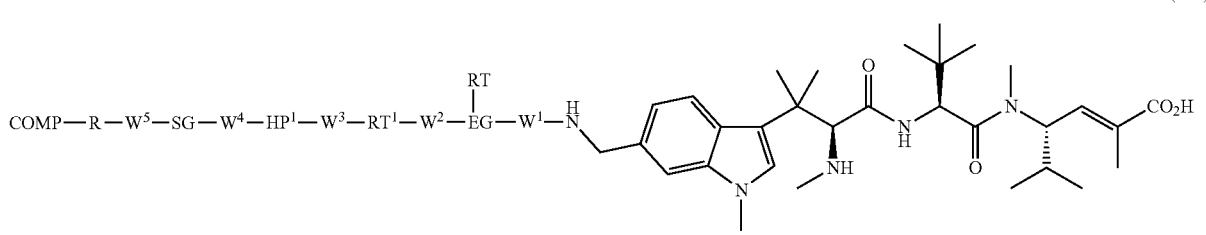
(F5a)
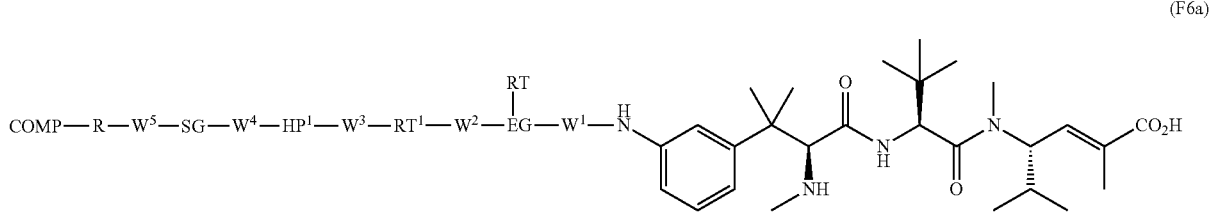
(F6a)
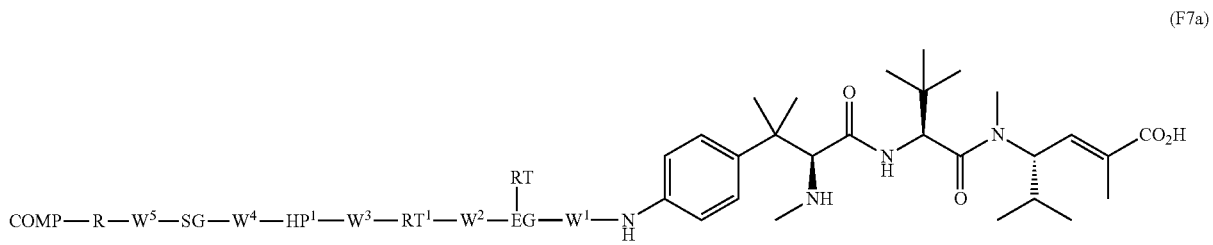
(F7a)

-continued
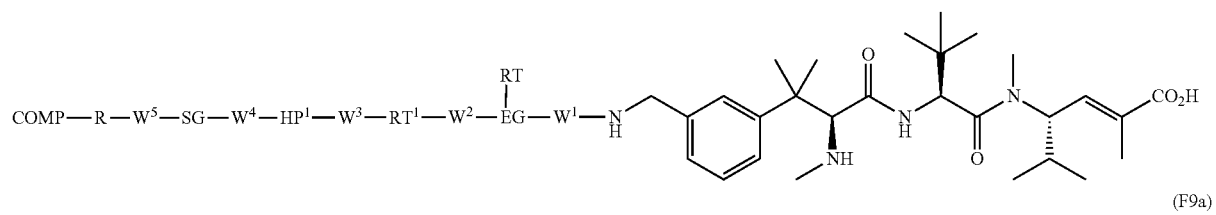
(F8a)
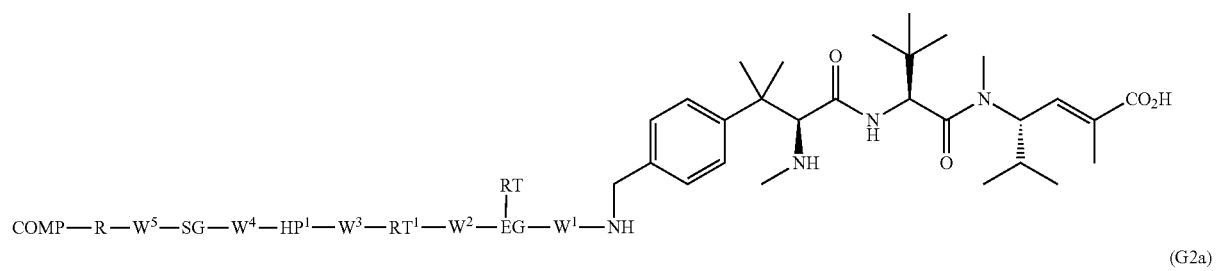
(F9a)
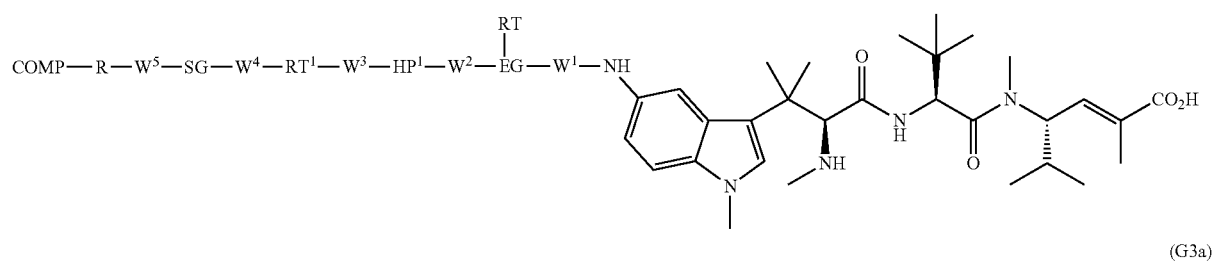
(G2a)
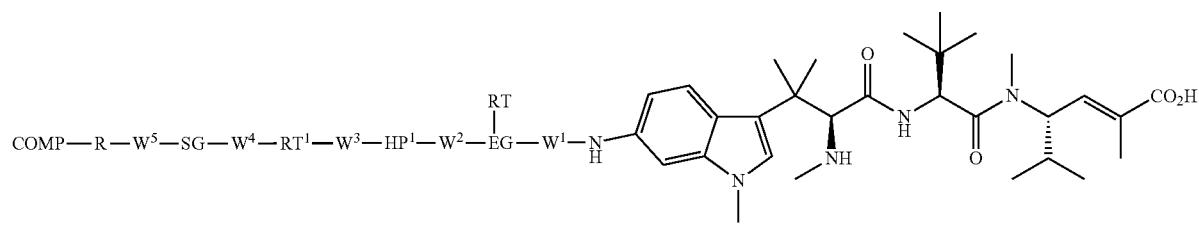
(G3a)
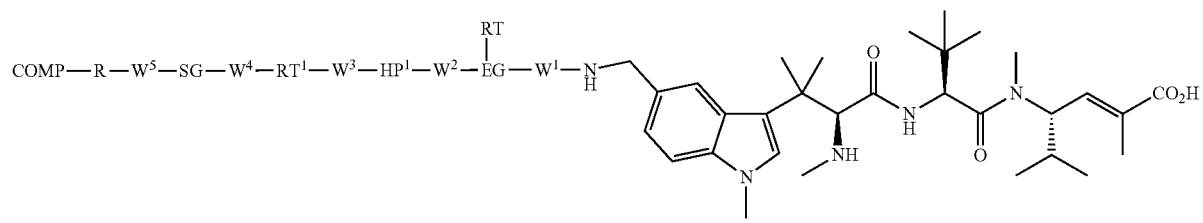
(G4a)
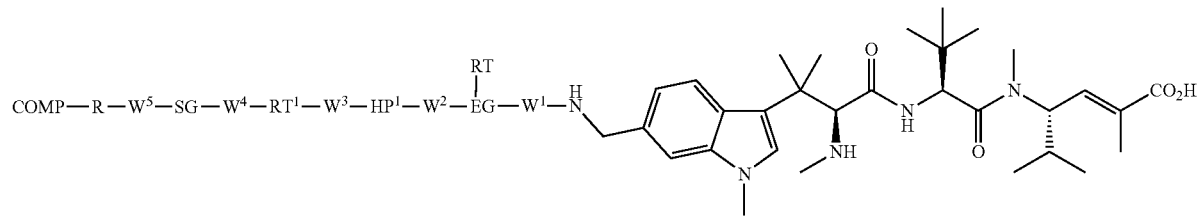
(G5a)

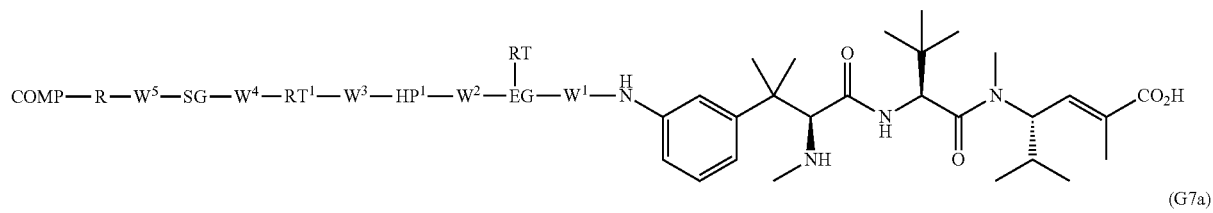
(G6a)
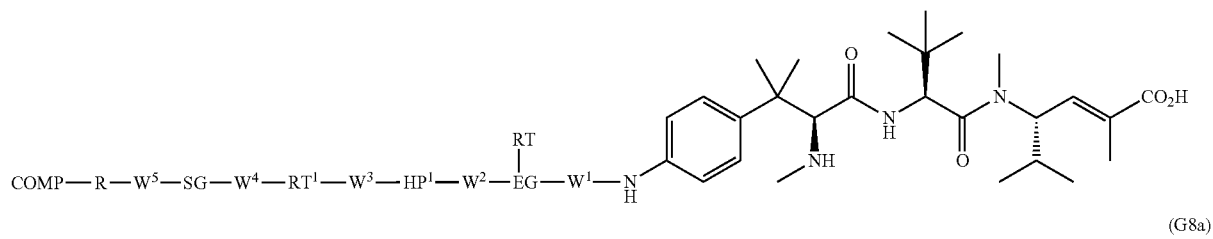
(G7a)
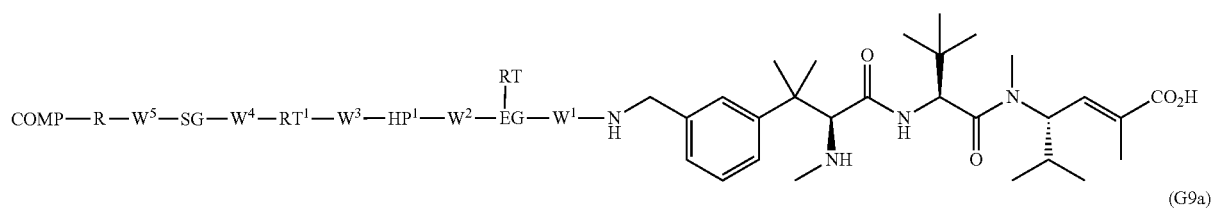
(G8a)
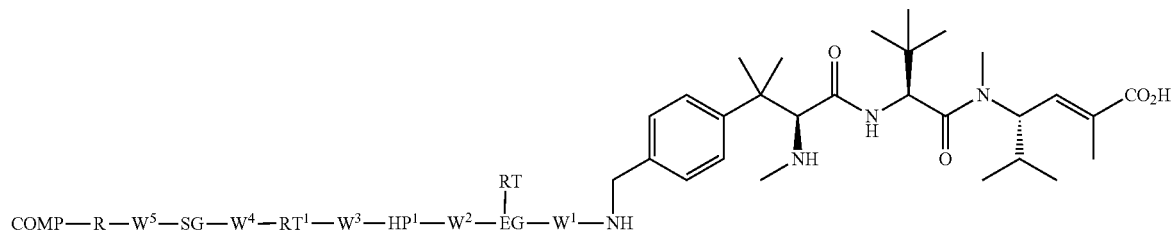
(G9a)
or a pharmaceutically acceptable salt, solvate, stereoisomer, or tautomer thereof, wherein all other groups are a described in the context of any of the Formulas or embodiments described herein.
In an embodiment, provided herein is a compound according to any of Formulas C2b-C9b:
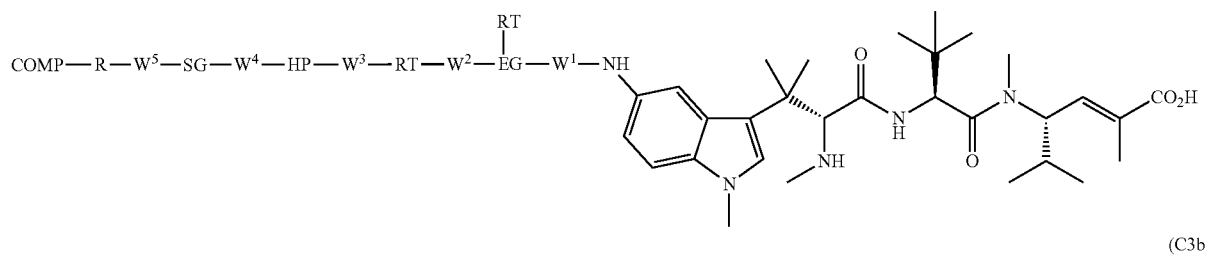
(C2b)
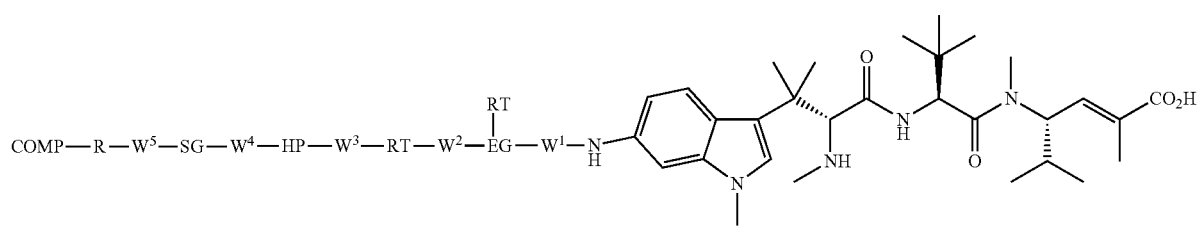
(C3b)

-continued
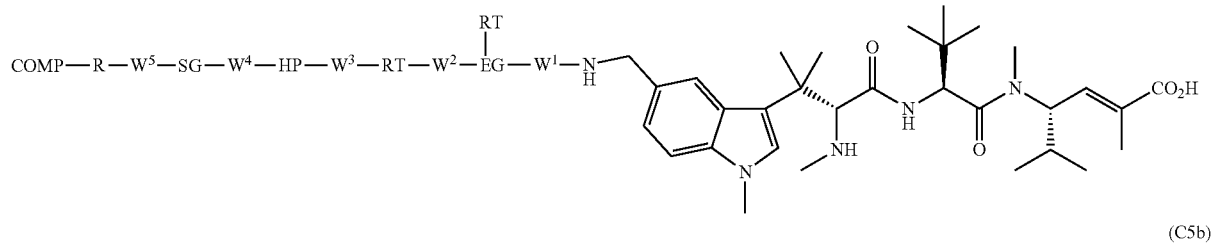
(C4b)
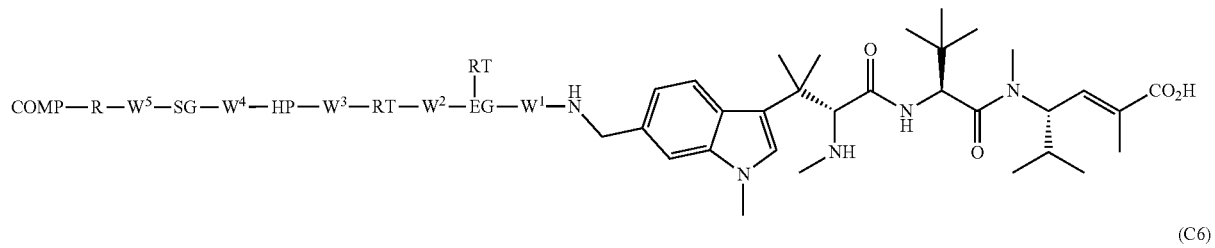
(C5b)
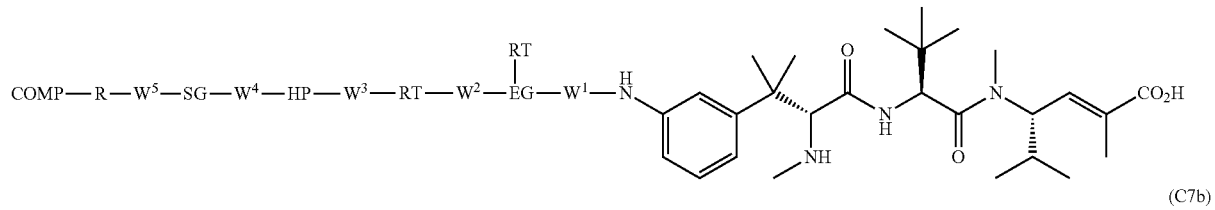
(C6)
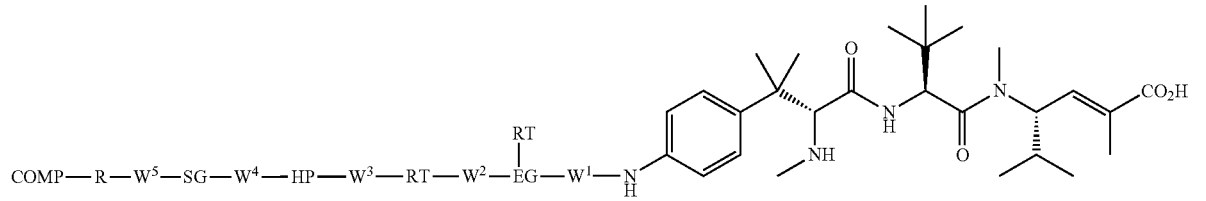
(C7b)
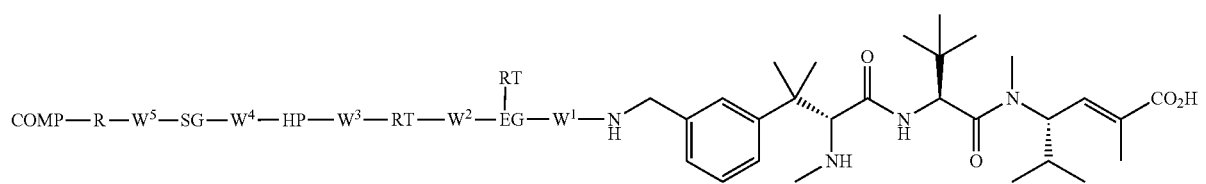
(C8b)
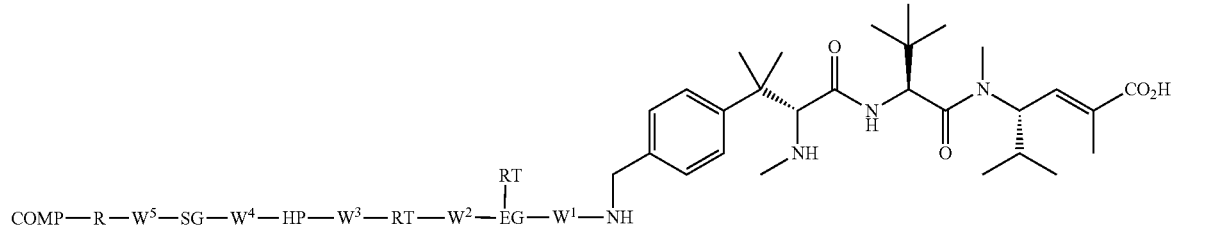
(C9b)
or a pharmaceutically acceptable salt, solvate, stereoisomer, or tautomer thereof, wherein COMP, R, SG, HP, RT, EG, $W^1$, $W^2$, $W^3$, $W^4$, $W^5$, L, and Ar are a described in the context of Formulas C1 and I-XVIb.

In an embodiment, provided herein is a compound according to any of the following Formula:
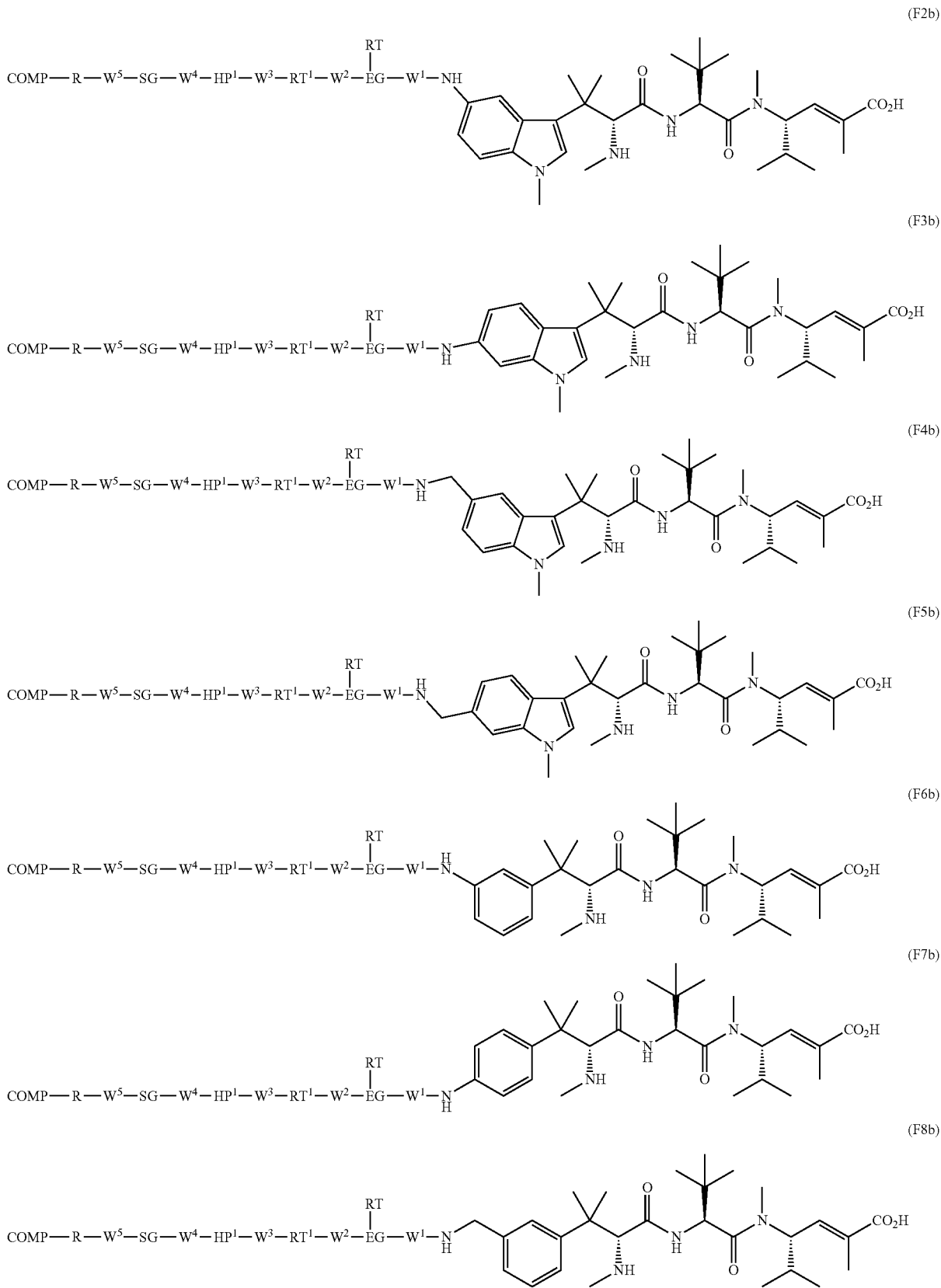

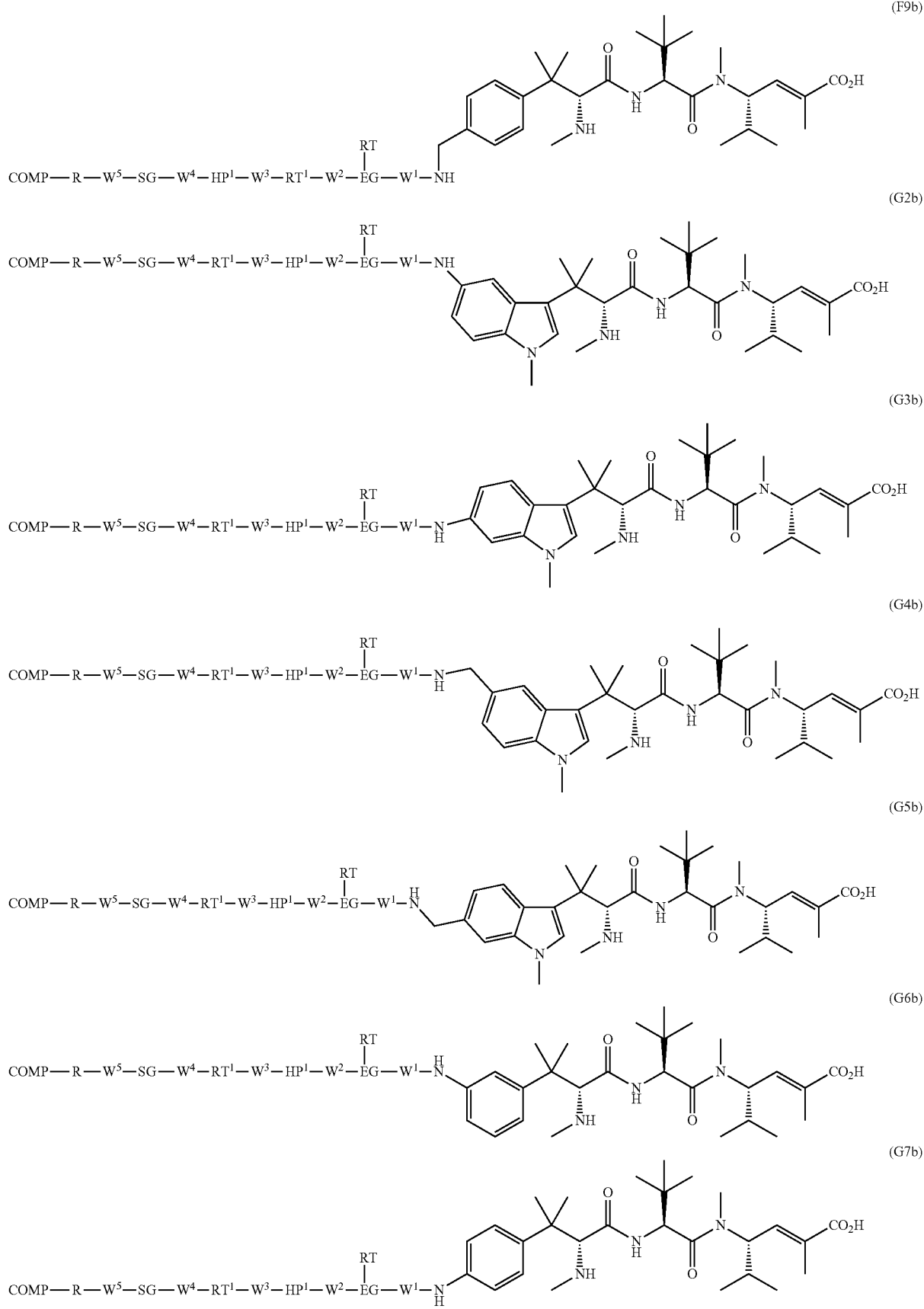

(G8b)
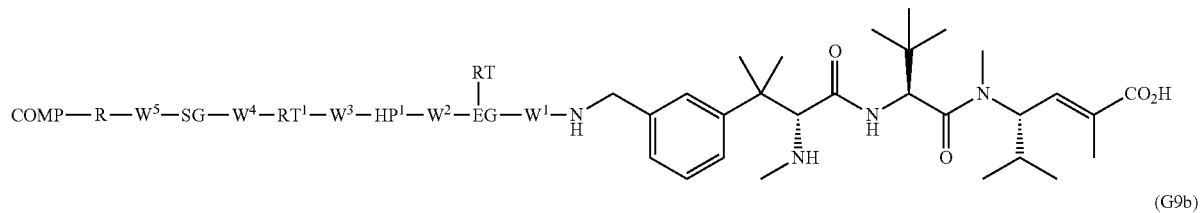
(G9b)
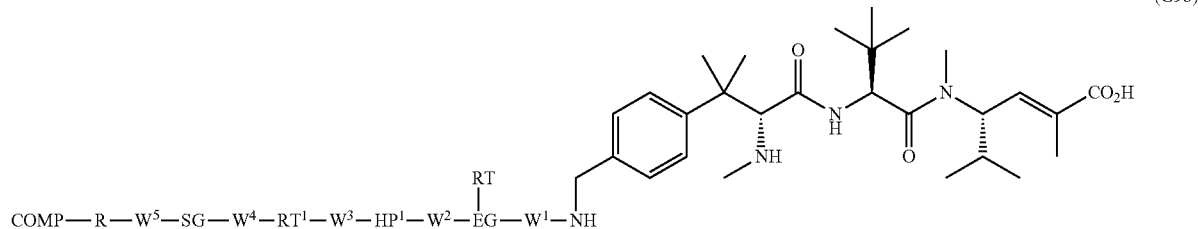
or a pharmaceutically acceptable salt, solvate, stereoisomer, or tautomer thereof, wherein all other groups are a described in the context of any of the Formulas or embodiments described herein.
In an embodiment, provided herein is a compound according to any of Formulas C10-C13:
(C10)
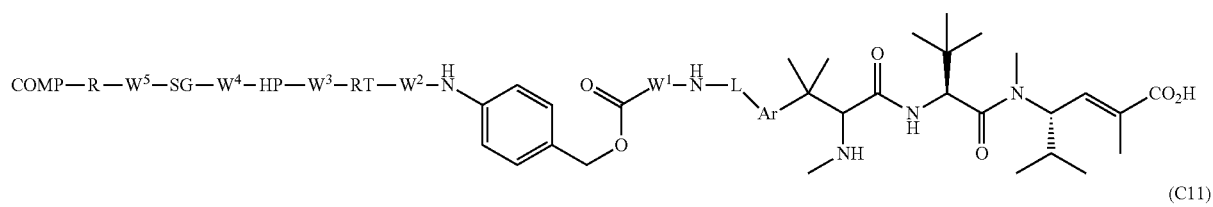
(C11)
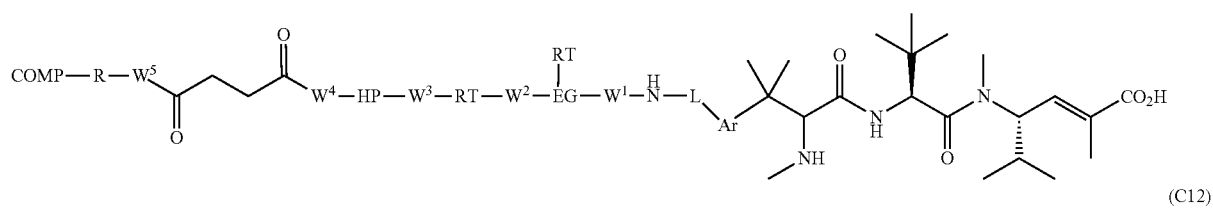
(C12)
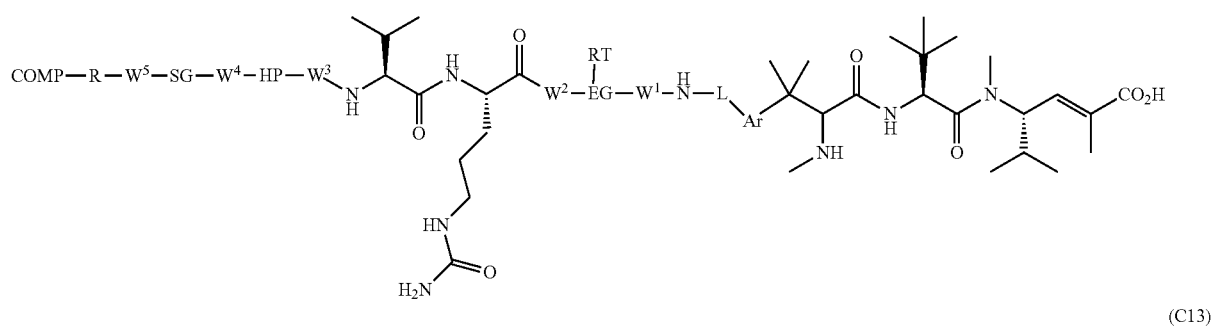
(C13)
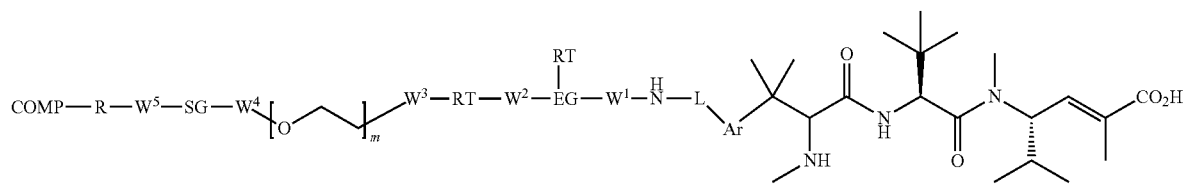

or a pharmaceutically acceptable salt, solvate, stereoisomer, or tautomer thereof, wherein COMP, R, SG, HP, RT, EG, $W^1$, $W^2$, $W^3$, $W^4$, $W^5$, L, and Ar are a described in the context of Formulas C1 and I-XVIb.

In an embodiment, provided herein is a compound according to any of the following Formula:

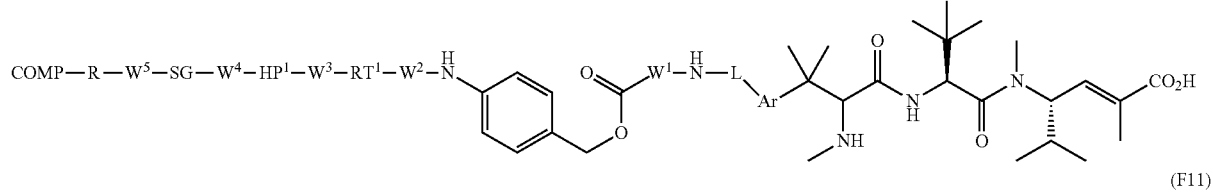
(F10)

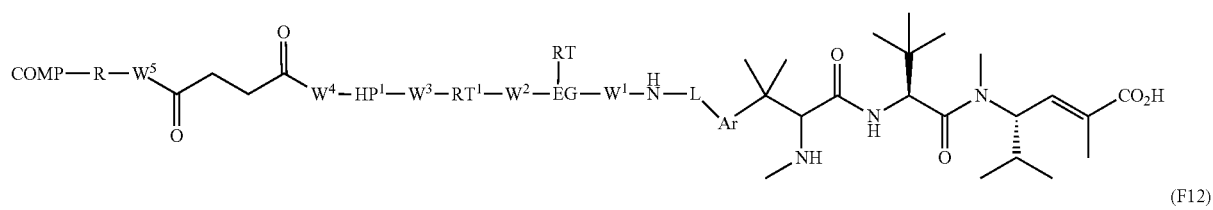
(F11)

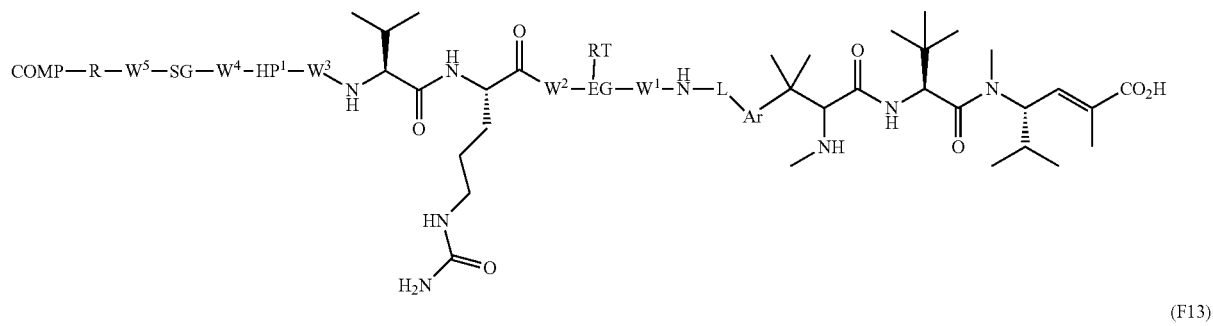
(F12)

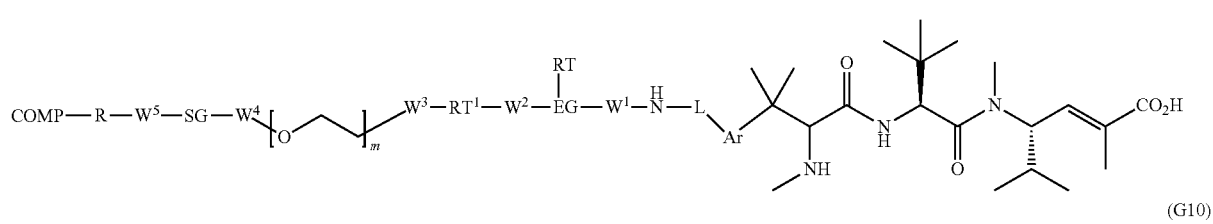
(F13)

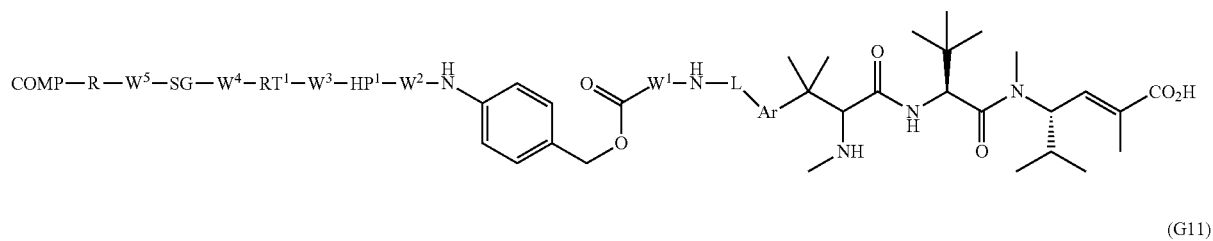
(G10)

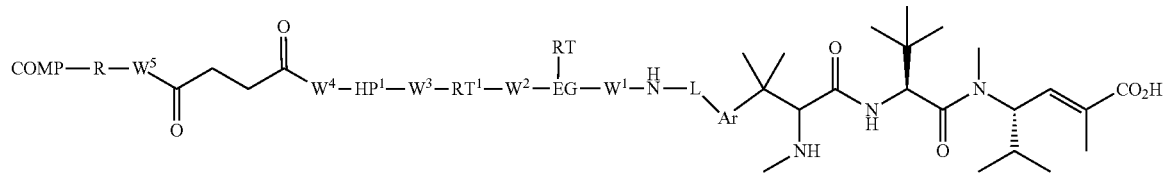
(G11)

or a pharmaceutically acceptable salt, solvate, stereoisomer, or tautomer thereof, wherein all other groups are as defined in any of the Formulas or embodiments herein.

In an embodiment, provided herein is a compound according to any of Formulas C10a-C13a:

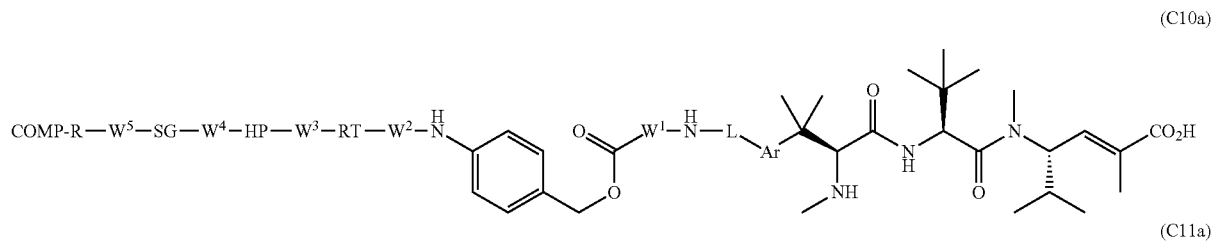
(C10a)

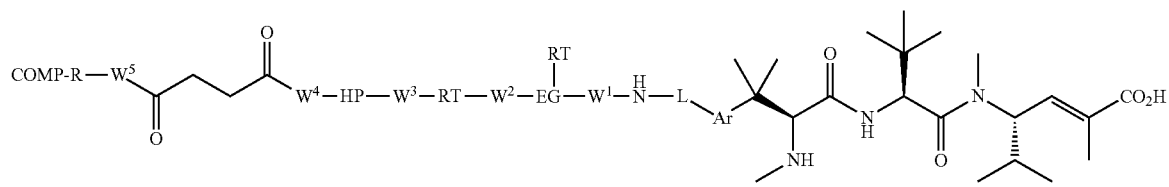
(C11a)

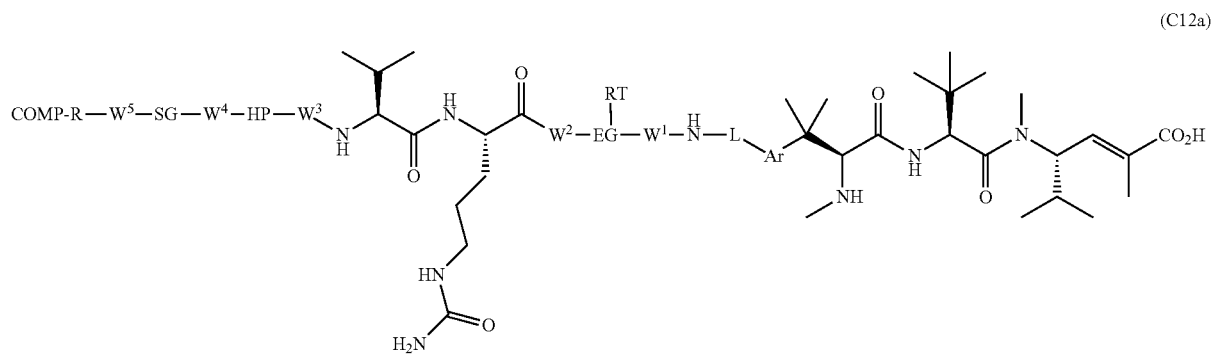
(C12a)

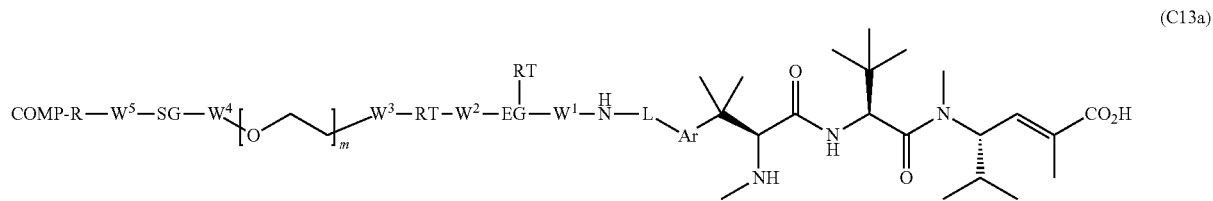
(C13a)

or a pharmaceutically acceptable salt, solvate, stereoisomer, or tautomer thereof, wherein COMP, R, SG, HP, RT, EG, $W^1$, $W^2$, $W^3$, $W^4$, $W^5$, L, and Ar are a described in the context of Formulas C1 and I-XVIb.

In an embodiment, provided herein is a compound according to any of the following Formula:

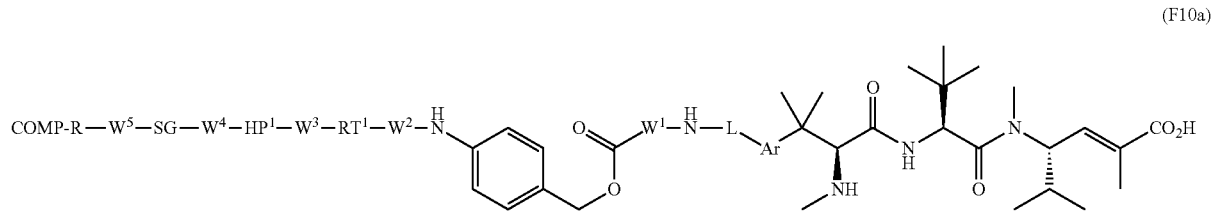
(F10a)

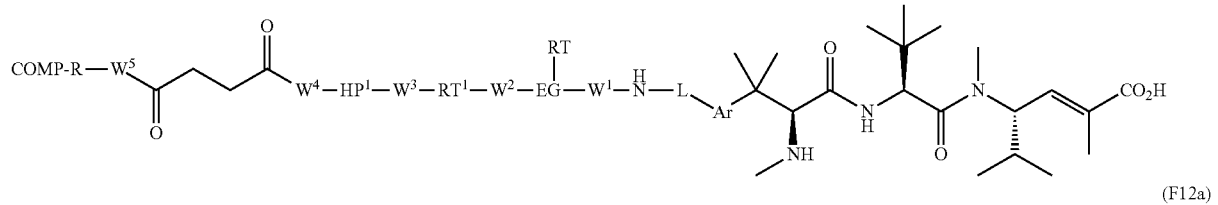
(F11a)
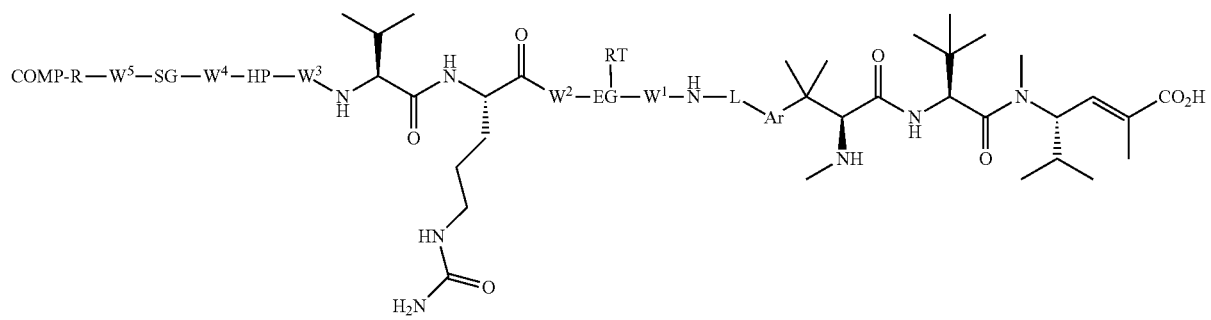
(F12a)
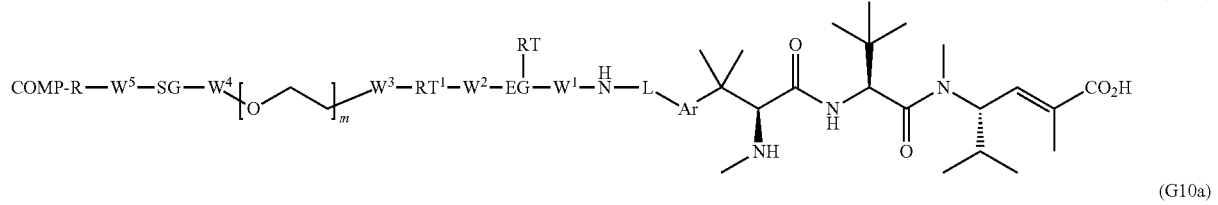
(F13a)
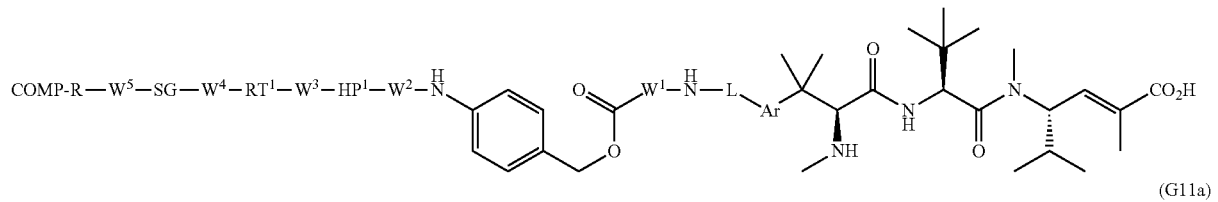
(G10a)
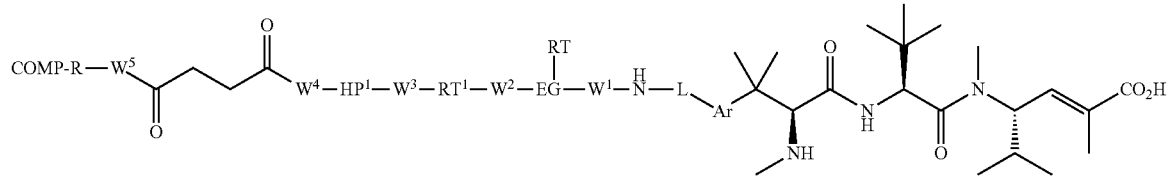
(G11a)
or a pharmaceutically acceptable salt, solvate, stereoisomer, or tautomer thereof, wherein all other groups are as defined in any of the Formulas or embodiments herein.
In an embodiment, provided herein is a compound according to any of Formulas C10b-C13b:
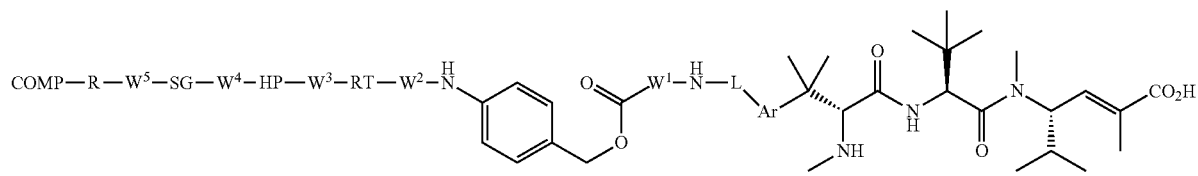
(C10b)

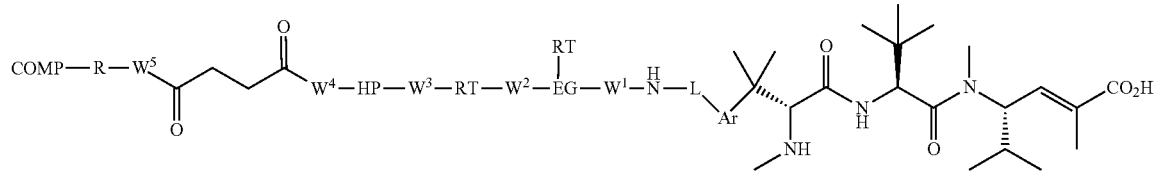
(C11b)
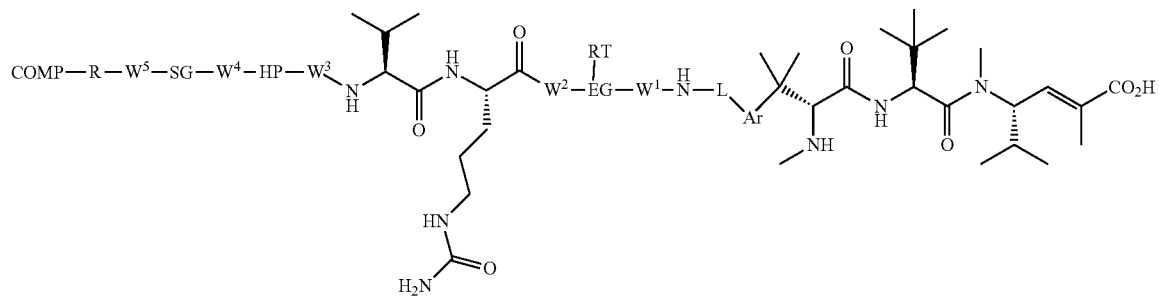
(C12b)
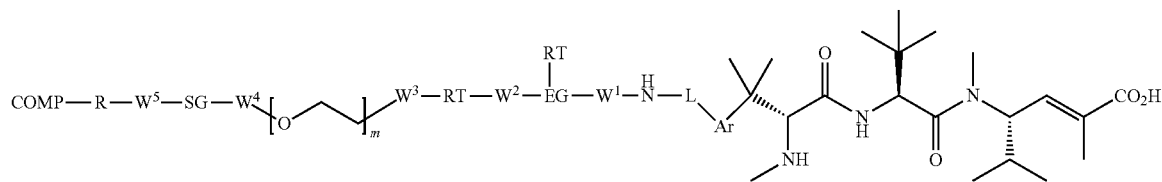
(C13b)
or a pharmaceutically acceptable salt, solvate, stereoisomer, or tautomer thereof, wherein COMP, R, SG, HP, RT, EG, $W^1$, $W^2$, $W^3$, $W^4$, $W^5$, L, and Ar are a described in the context of Formulas C1 and I-XVIb.
In an embodiment, provided herein is a compound according to any of the following Formula:
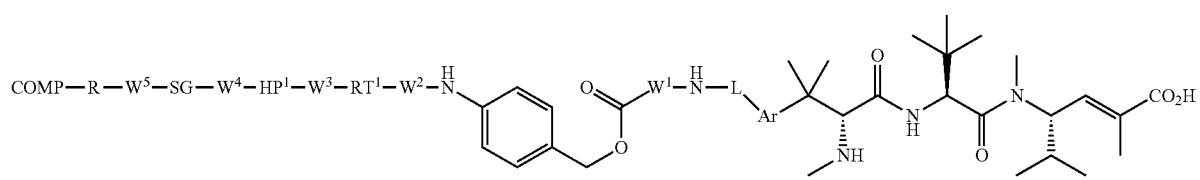
(F10b)
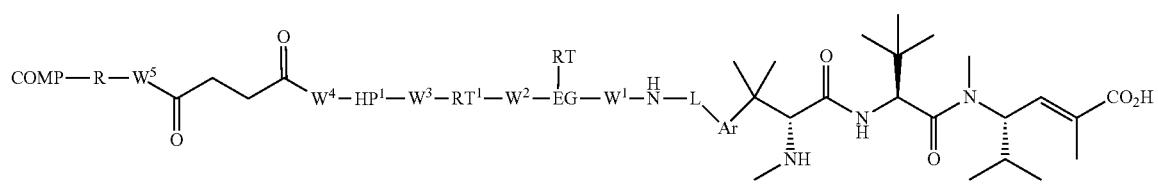
(F11b)

-continued
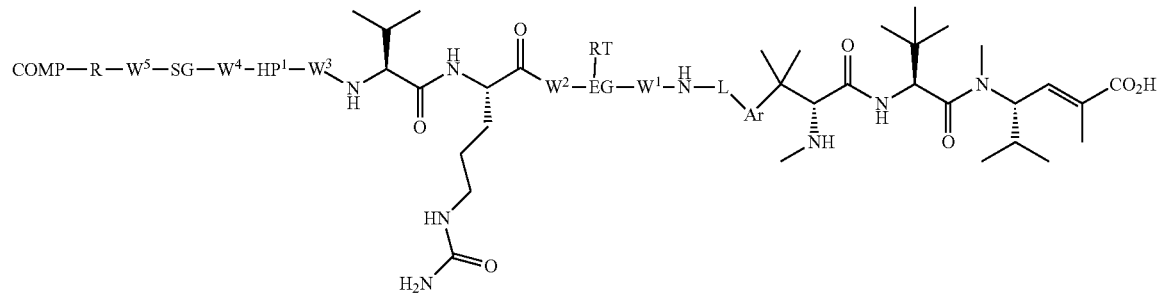
(F12b)
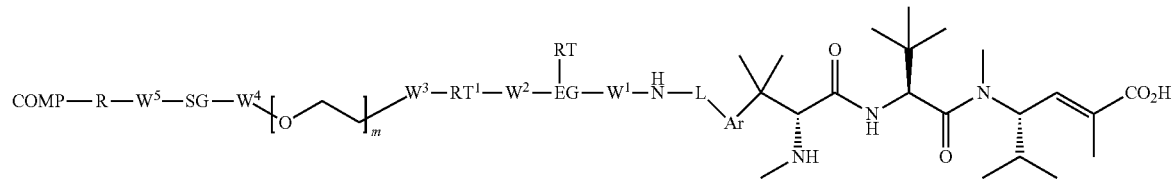
(F13b)
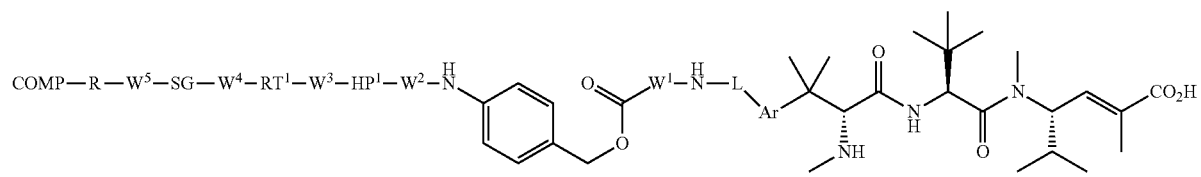
(G10b)
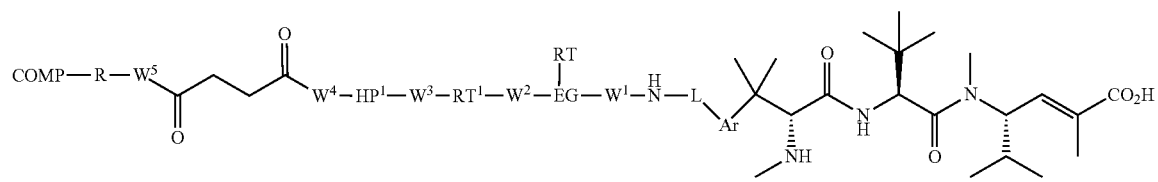
(G11b)
or a pharmaceutically acceptable salt, solvate, stereoisomer, or tautomer thereof, wherein all other groups are as defined in any of the Formulas or embodiments herein.
In an embodiment, provided herein is a compound according to any of Formula C14-C17:
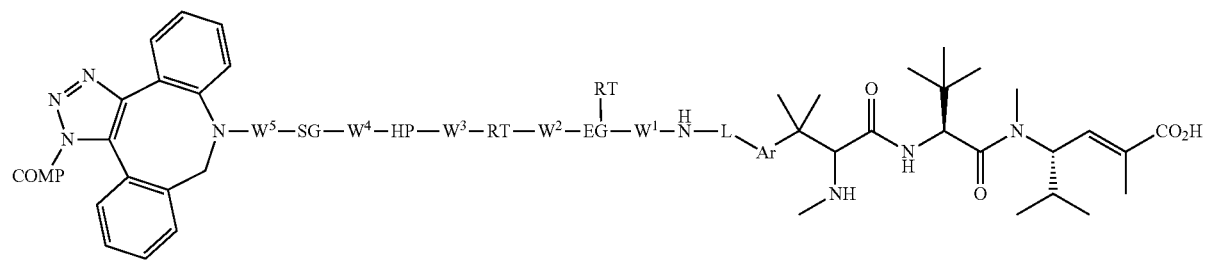
(C14)

(C15)
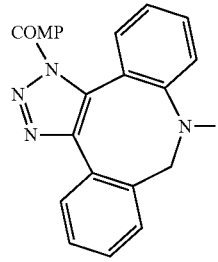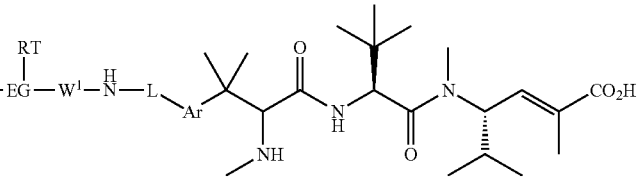
(C16)
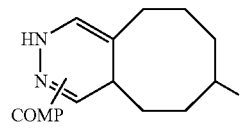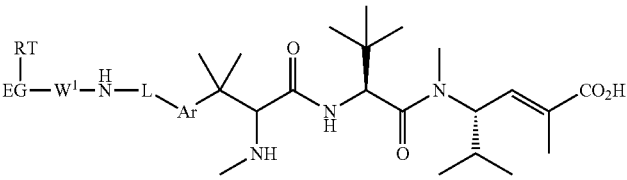
(C17)
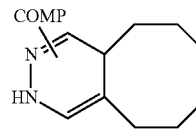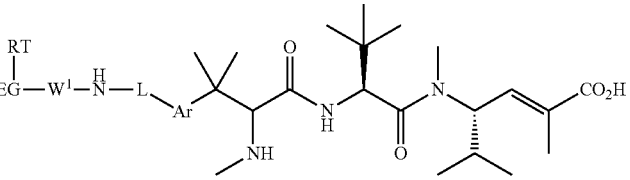
or a pharmaceutically acceptable salt, solvate, stereoisomer, or tautomer thereof, wherein COMP, SG, HP, RT, EG, $W^1$, $W^2$, $W^3$, $W^4$, $W^5$, L, and Ar are a described in the context of Formulas C1 and I-XVIb.
In an embodiment, provided herein is a compound according to any of the following Formula:
(F14)
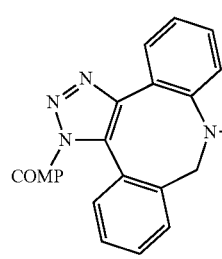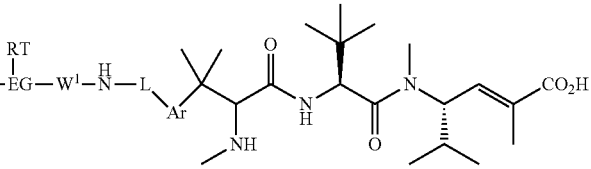
(F15)
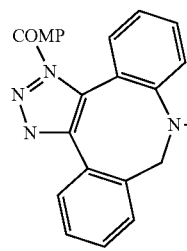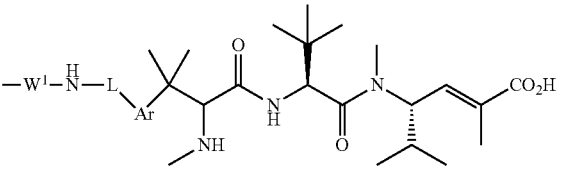

-continued
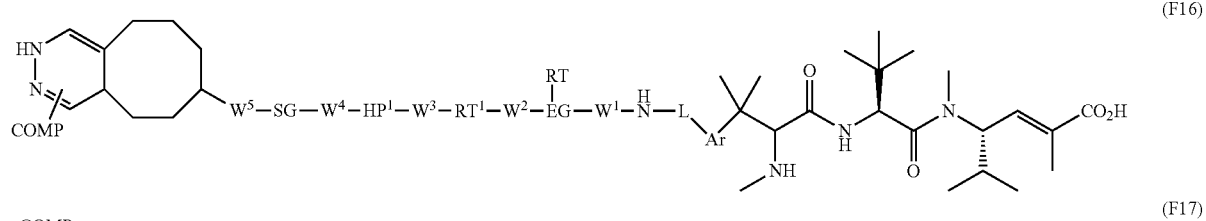
(F16)
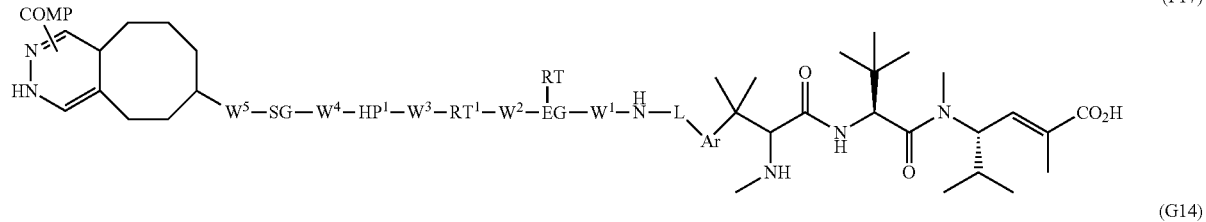
(F17)
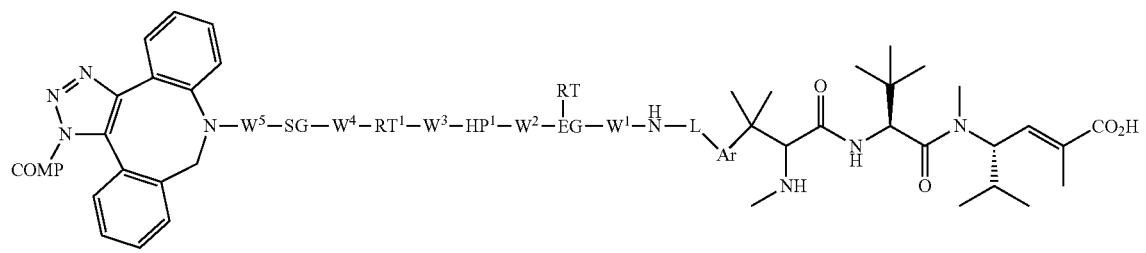
(G14)
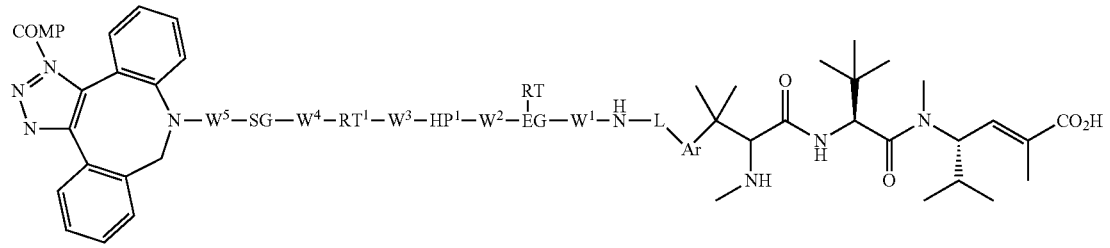
(G15)
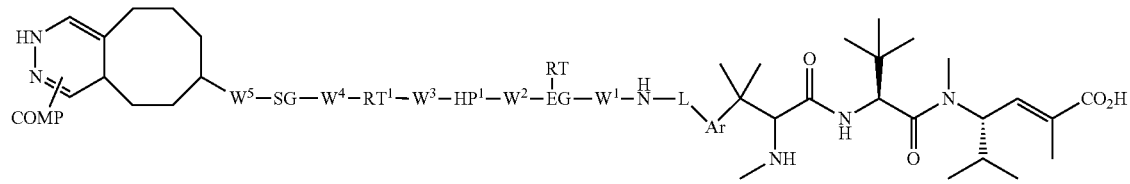
(G16)
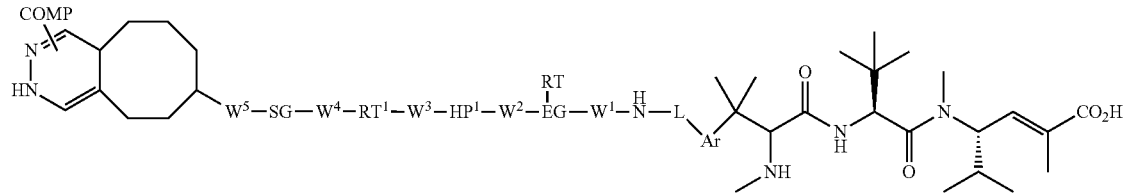
(G17)
or a pharmaceutically acceptable salt, solvate, stereoisomer, or tautomer thereof, wherein all other groups are as defined in any of the Formulas or embodiments herein.

In an embodiment, provided herein is a compound according to any of Formula C14a-C17a:

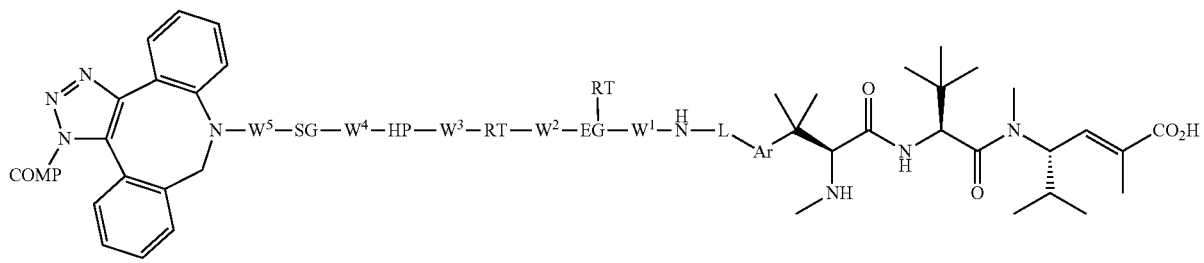

(C14a)

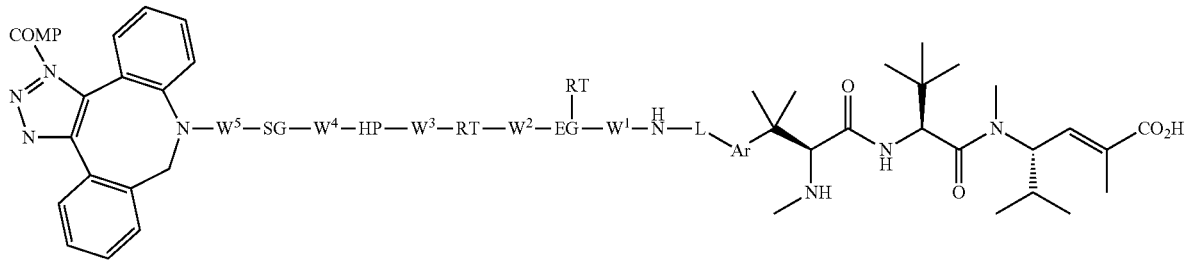

(C15a)

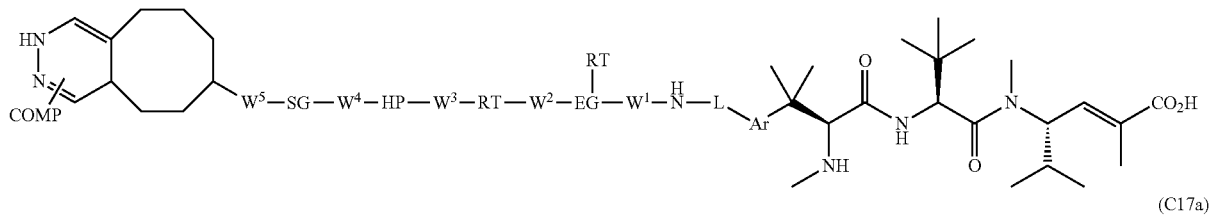

(C16a)

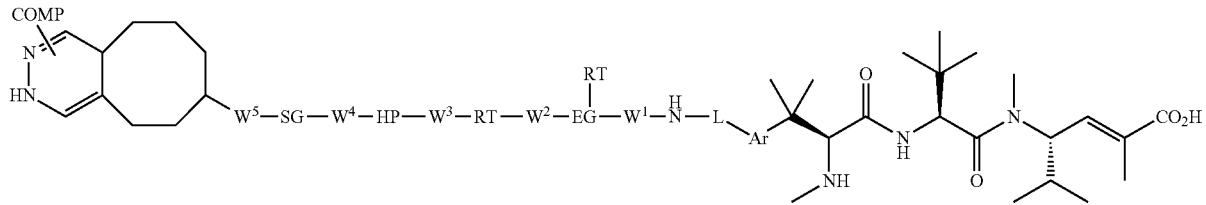

(C17a)

or a pharmaceutically acceptable salt, solvate, stereoisomer, or tautomer thereof, wherein COMP, SG, HP, RT, EG, $W^1$, $W^2$, $W^3$, $W^4$, $W^5$, L, and Ar are a described in the context of Formulas C1 and I-XVIb.

In an embodiment, provided herein is a compound according to any of the following Formula:

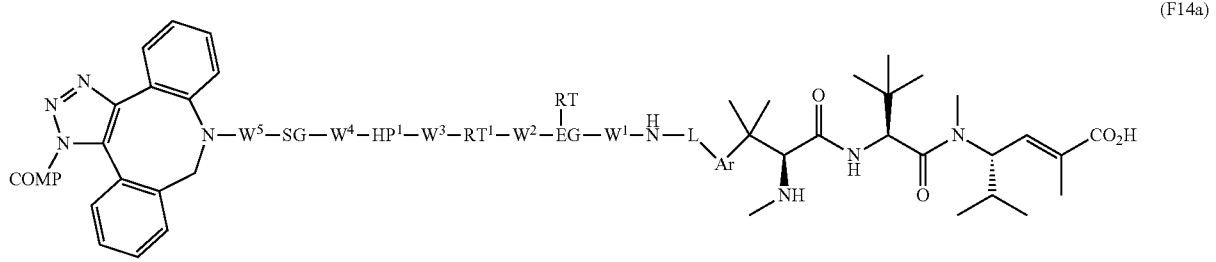

(F14a)

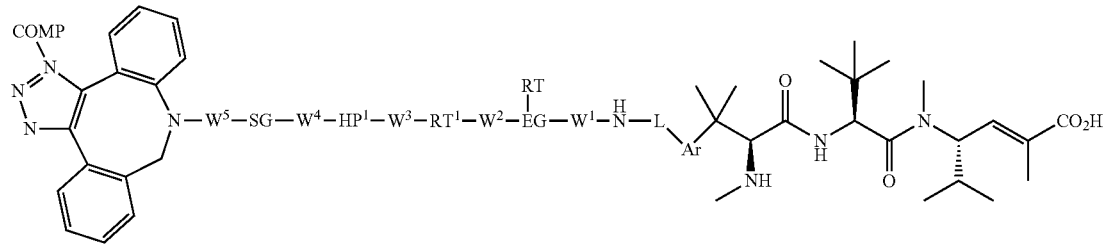
(F15a)
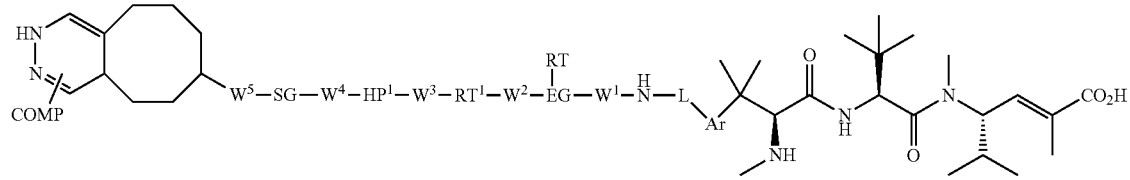
(F16a)
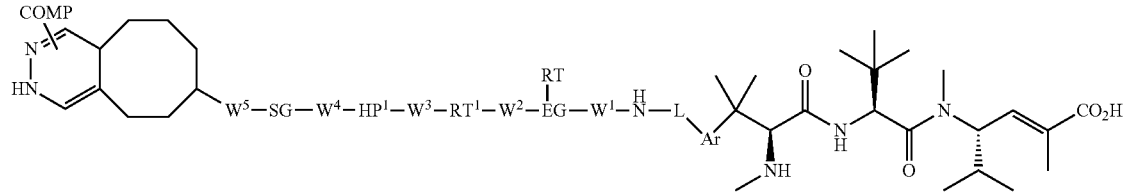
(F17a)
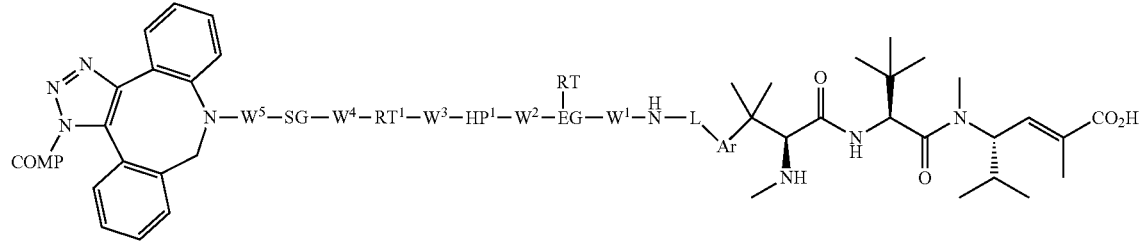
(G14a)
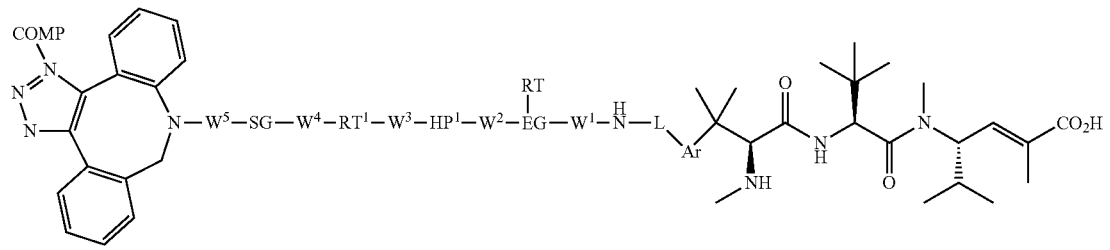
(G15a)
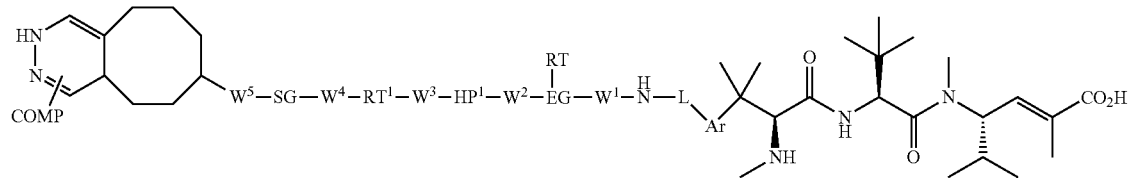
(G16a)
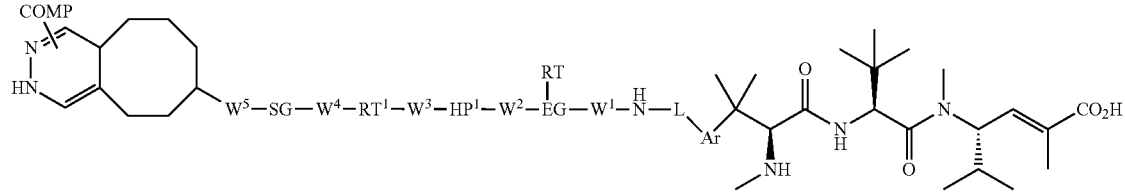
(G17a)

or a pharmaceutically acceptable salt, solvate, stereoisomer, or tautomer thereof, wherein all other groups are as defined in any of the Formulas or embodiments herein.

In an embodiment, provided herein is a compound according to any of Formula C14b-C17b:

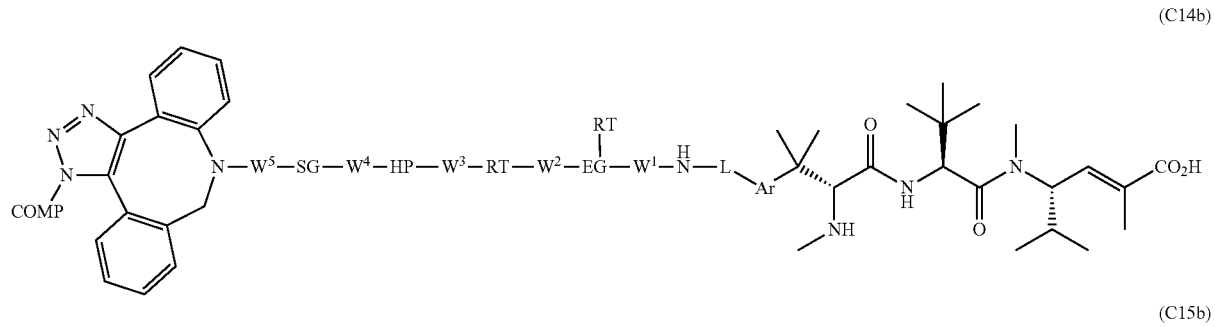

(C14b)

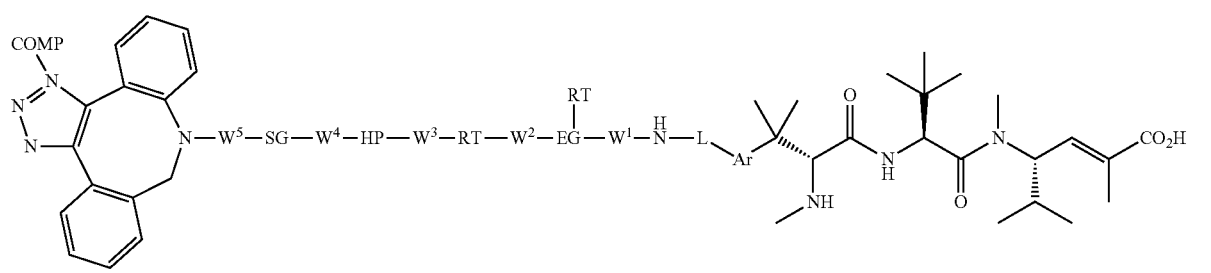

(C15b)

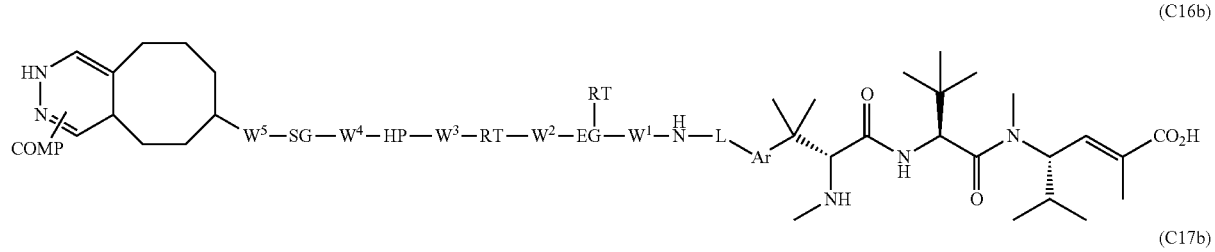

(C16b)

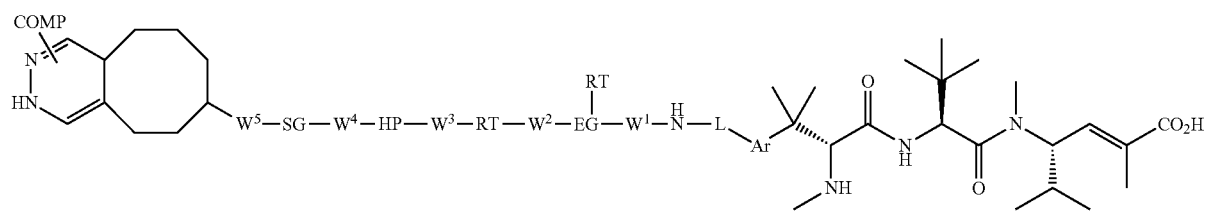

(C17b)

or a pharmaceutically acceptable salt, solvate, stereoisomer, or tautomer thereof, wherein COMP, SG, HP, RT, EG, $W^1$, $W^2$, $W^3$, $W^4$, $W^5$, L, and Ar are a described in the context of Formulas C1 and I-XVIb.

In an embodiment, provided herein is a compound according to any of the following Formula:

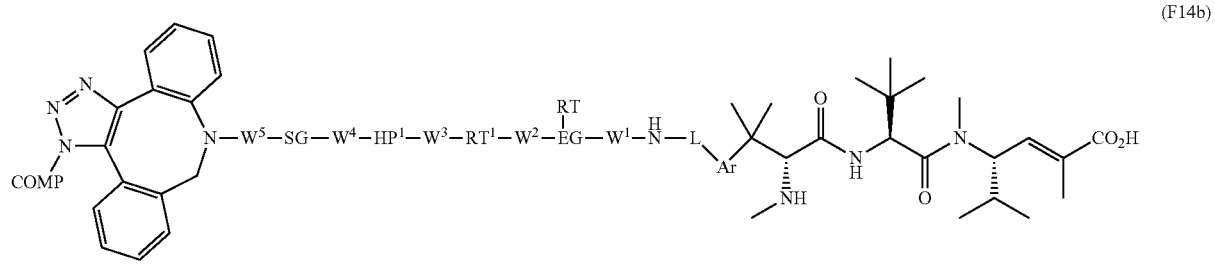

(F14b)

-continued
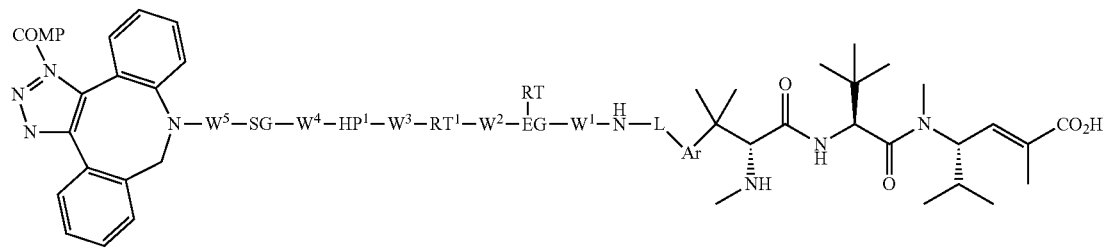
(F15b)
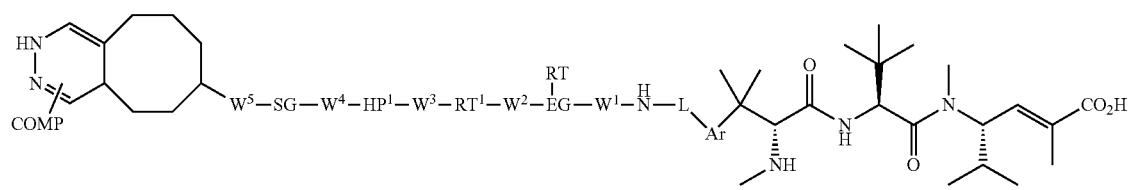
(F16b)
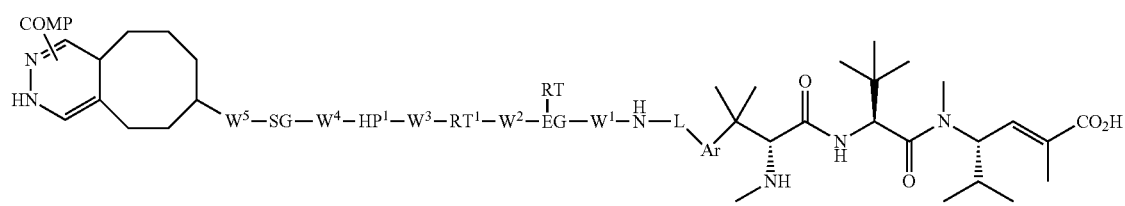
(F17b)
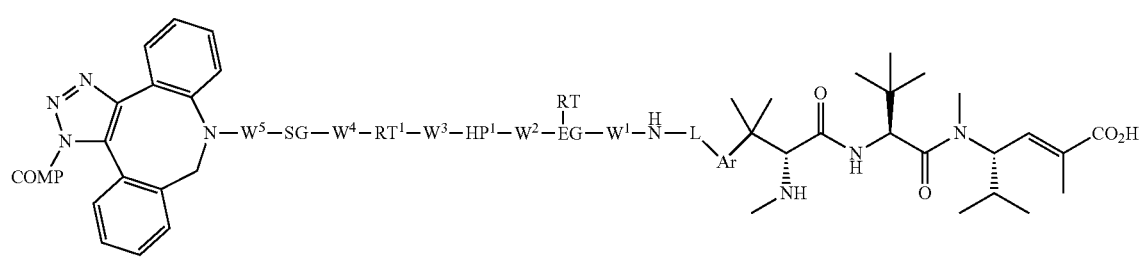
(G14b)
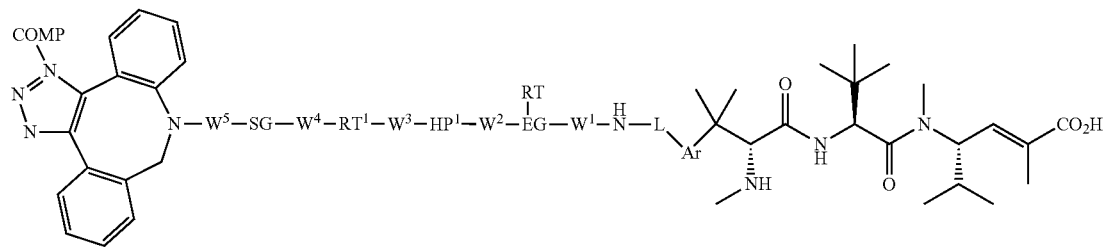
(G15b)
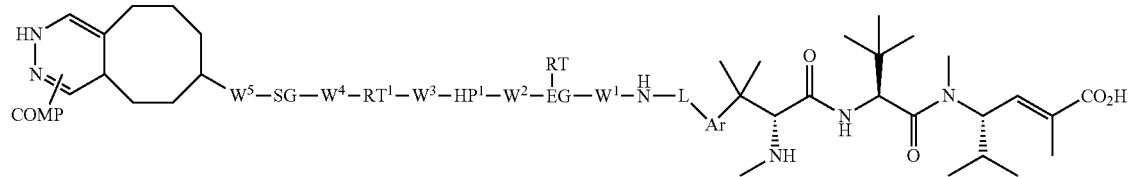
(G16b)
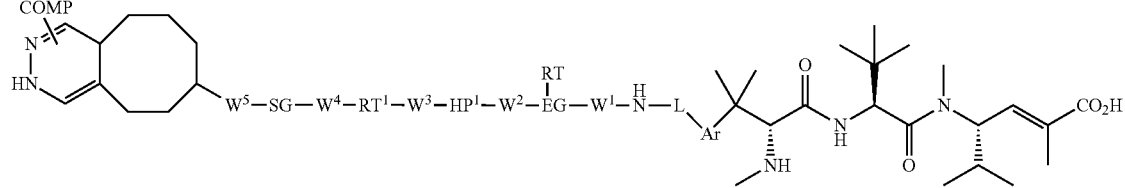
(G17b)

or a pharmaceutically acceptable salt, solvate, stereoisomer, or tautomer thereof, wherein all other groups are as defined in any of the Formulas or embodiments herein.

In an aspect, provided herein is a method of producing a conjugate (e.g., according to any of Formulas C1-C17b, E1, F1-F17b, and G1-G17b), comprising contacting a compound described herein (e.g., a compound according to any of Formulas I-XVIIIb, 101-111b, or 1-8b) with a second compound under conditions suitable for conjugating the compound described herein with the second compound; wherein the second compound comprises a modified amino acid comprising an alkyne, strained alkene, tetrazine, thiol, maleimide, carbonyl, oxyamine, or azide. In an embodiment, the second compound is a polypeptide. In an embodiment, the second compound is an antibody.

Conjugation Reactions

[3+2] Alkyne-Azide Cycloaddition Reaction

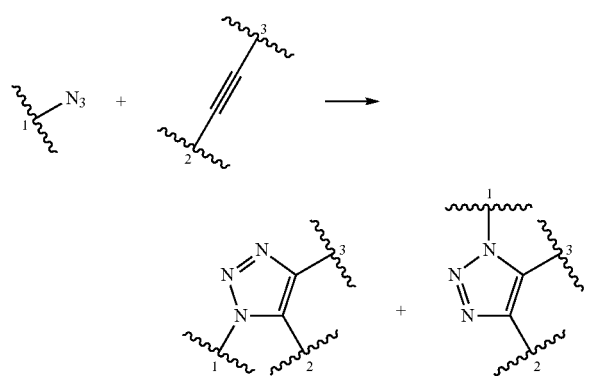

Advantageously, the compounds described herein comprising a terminal conjugating alkyne group or an azide group (e.g., a compound according to any of Formulas I-IXb, XI-XVIIb, and 101-111b) facilitate selective and efficient reactions with a second compound comprising a complementary azide group or alkyne group. It is believed the azide and alkyne groups react in a 1,3-dipolar cycloaddition reaction to form a 1,2,3-triazolylene moiety which links the compound described herein comprising an alkyne group or an azide group to the second compound. This reaction between an azide and alkyne to form a triazole is generally known to those in the art as a Huisgen cycloaddition reaction or a [3+2] alkyne-azide cycloaddition reaction.

The unique reactivity of azide and alkyne functional groups makes them useful for the selective modification of polypeptides and other biological molecules. Organic azides, particularly aliphatic azides, and alkynes are generally stable toward common reactive chemical conditions. In particular, both the azide and the alkyne functional groups are inert toward the side chains of the 20 common amino acids found in naturally-occurring polypeptides. It is believed that, when brought into close proximity, the "spring-loaded" nature of the azide and alkyne groups is revealed and they react selectively and efficiently via a [3+2] alkyne-azide cycloaddition reaction to generate the corresponding triazole. See, e.g., Chin J., et al., Science 301: 964-7 (2003); Wang, Q., et al., J. Am. Chem. Soc. 125, 3192-3193 (2003); Chin, J. W., et al., J. Am. Chem. Soc. 124:9026-9027 (2002).

Because the [3+2] alkyne-azide cycloaddition reaction involves a selective cycloaddition reaction [see, e.g., Padwa, A., in COMPREHENSIVE ORGANIC SYNTHESIS, Vol. 4, (ed. Trost, B. M., 1991), pp. 1069-1109; Huisgen, R. in 1,3-DIPOLAR CYCLOADDITION CHEMISTRY, (ed. Padwa, A., 1984), pp. 1-176] rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reactions involving azide or alkyne-containing compounds can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tornoe, C. W., et al., J. Org. Chem. 67:3057-3064 (2002); Rostovtsev, et al., Angew. Chem. Int. Ed. 41:2596-2599 (2002). Exemplary reducing agents include, but not limited to, ascorbate, metallic copper, quinine, hydroquinone, vitamin K, glutathione, cysteine, $Fe^{2+}$, $Co^{2+}$, and an applied electric potential.

Inverse Electron Demand Ligation Reaction

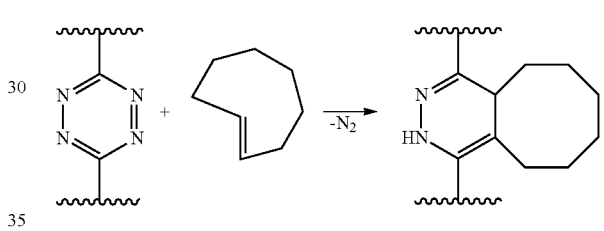

Advantageously, the compounds comprising a terminal tetrazine or strained alkene group provided herein facilitate selective and efficient reactions with a second compound comprising a strained alkene or tetrazine group. It is believed that the tetrazine and strained alkene react in an inverse-demand Diels-Alder reaction followed by a retro-Diels-Alder reaction which links the compounds comprising a terminal tetrazine or strained alkene group provided herein to the second compound. The reaction is believed to be specific, with little to no cross-reactivity with functional groups that occur on biomolecules. The reaction may be carried out under mild conditions, for example at room temperature and without a catalyst. This reaction between a tetrazine and a strained alkene is generally known to those in the art as a tetrazine ligation reaction.

Thiol Reactions

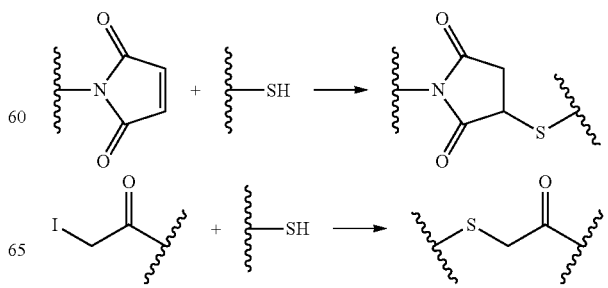

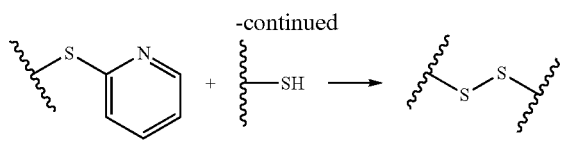

Advantageously, the compounds comprising a terminal thiol group or suitable electrophilic or disulfide-forming group provided herein facilitate selective and efficient reactions with a second compound comprising a complementary electrophilic or disulfide-forming group or thiol group. These reactions are believed to be selective with little to no cross-reactivity with functional groups that occur on biomolecules. In another embodiment, the thiol reaction does not include reaction of a maleimide group.

Carbonyl-Oxyamine Reaction

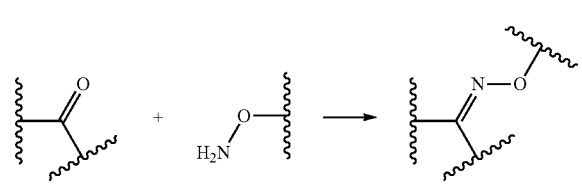

Advantageously, the compounds comprising a terminal carbonyl or oxyamine group provided herein facilitate selective and efficient reactions with a second compound comprising an oxyamine or carbonyl group. It is believed that the carbonyl and oxyamine react to form an oxime linkage. The reaction is believed to be specific, with little to no cross-reactivity with functional groups that occur on biomolecules.

Other Reactions

Other suitable conjugation reactions are described in the literature. See, for example, Lang, K. and Chin, J. 2014, Bioorthogonal Reactions for Labeling Proteins, *ACS Chem Biol* 9, 16-20; Paterson, D. M. et al. 2014, Finding the Right (Bioorthogonal) Chemistry, *ACS Chem Biol* 9, 592-605; King, M. and Wagner, A. 2014, Developments in the Field of Bioorthogonal Bond Forming Reactions—Past and Present Trends, *Bioconjugate Chem.*, 2014, 25 (5), pp 825-839; and Ramil, C. P. and Lin, Q., 2013, Bioorthogonal chemistry: strategies and recent developments, *Chem Commun* 49, 11007-11022.

Releasing Reactions

Releasing Reactions are reactions that act to release a biologically active portion of a compound or conjugate described herein from the compound or conjugate in vivo and/or in vitro. In certain embodiments, the released biologically active portion is a compound according to any of Formulas 1-8b, or a pharmaceutically acceptable salt, solvate, stereoisomer, or tautomer thereof. One example of a releasing reaction is an intramolecular reaction between an eliminator group and a release trigger group of a compound or conjugate described herein to release a biologically active portion of a compound or conjugate described herein. The eliminator group may itself devolve into two reactive components, as exemplified in these reactions where X— is a drug having a heteroatom N or O for linkage. Exemplary Releasing Reactions are depicted in the schemes below:

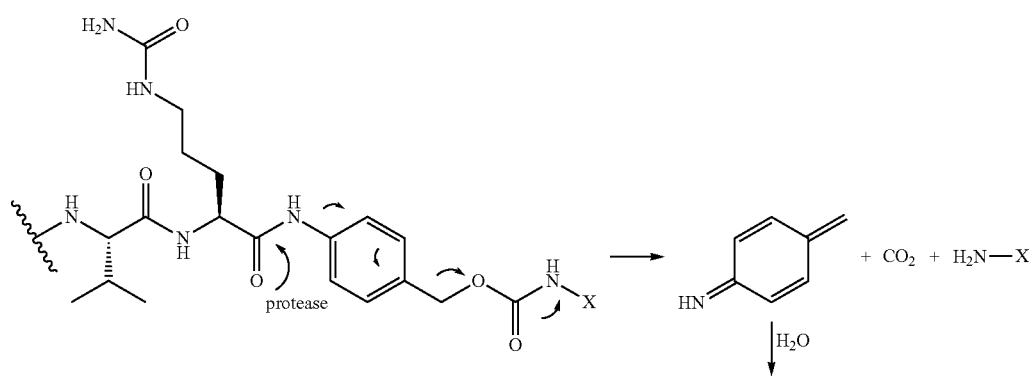

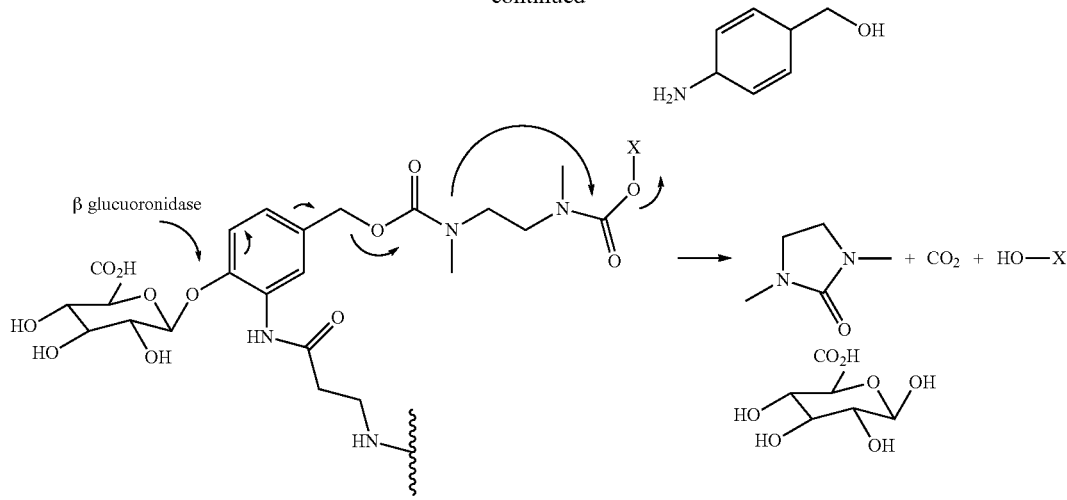

Compositions

The compounds and conjugates described herein can be formulated into compositions using methods available in the art and those disclosed herein. Any of the compounds and conjugates described herein can be provided in an appropriate pharmaceutical composition and be administered by a suitable route of administration.

In an aspect, provided herein is a pharmaceutical composition comprising:

a compound (e.g., a compound according to any of Formulas 1000-1000b, 1001-1001b, 1002-1002b, and I-XIXb-2, 101-111b, or 1-8b) or conjugate (e.g., a conjugate according to any of Formulas C1-C17b, E1, F1-F17b, and G1-G17b) as described herein; and a pharmaceutically acceptable excipient, carrier, or diluent.

In certain embodiments, the pharmaceutical compositions provided herein further comprise a pharmaceutically acceptable carrier. The carrier can be a diluent, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, or pH buffering agents. The pharmaceutical compositions can take the form of solutions, suspensions, emulsions, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in E. W. Martin, 1990, Remington's Pharmaceutical Sciences, Mack Publishing Co.

In some embodiments, the pharmaceutical composition is provided in a form suitable for administration to a human subject. In some embodiments, the pharmaceutical composition will contain a prophylactically or therapeutically effective amount of the polypeptide together with a suitable amount of carrier so as to provide the form for proper administration to the patient. The formulation should suit the mode of administration.

In some embodiments, the pharmaceutical composition is provided in a form suitable for intravenous administration. Typically, compositions suitable for intravenous administration are solutions in sterile isotonic aqueous buffer. Where necessary, the composition may also include a solubilizing agent and a local anesthetic such as lignocaine to ease pain at the site of the injection. Such compositions, however, may be administered by a route other than intravenous administration.

In particular embodiments, the pharmaceutical composition is suitable for subcutaneous administration. In particular embodiments, the pharmaceutical composition is suitable for intramuscular administration.

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, polypeptides are supplied as a water free concentrate. In some embodiments, the polypeptide is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

In another embodiment, the pharmaceutical composition is supplied in liquid form. In some embodiments, the pharmaceutical composition is provided in liquid form and is substantially free of surfactants and/or inorganic salts. In some embodiments, the polypeptide is supplied as in liquid form at a unit dosage of at least 0.1 mg/ml, at least 0.5 mg/ml, at least 1 mg/ml, at least 2.5 mg/ml, at least 3 mg/ml, at least 5 mg/ml, at least 8 mg/ml, at least 10 mg/ml, at least 15 mg/ml, at least 25 mg/ml, at least 30 mg/ml, or at least 60 mg/ml.

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In therapeutic use, the practitioner will determine the posology most appropriate according to a preventive or curative treatment and according to the age, weight, stage of the disease and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

Methods of Use for Therapy or Prophylaxis

Certain compounds, conjugates, polypeptides, and antibodies provided herein can be used for the treatment or prevention of any disease or condition deemed suitable to the practitioner of skill in the art. Generally, a method of treatment or prevention encompasses the administration of a therapeutically or prophylactically effective amount of a compound, conjugate, polypeptide, antibody, or pharmaceutical composition comprising the same to a subject in need thereof to treat or prevent the disease or condition.

In an aspect, provided herein is a method of inhibiting tubulin polymerization in a subject in need thereof comprising administering an effective amount of a compound (e.g., a compound according to any of Formulas 1000-1000b, 1001-1001b, 1002-1002b, and I-XIXb-2, 101-111b, or 1-8b), conjugate (e.g., a conjugate according to any of Formulas C1-C17b, E1, F1-F17b, and G1-G17b), or composition comprising the compound or conjugate, as described herein, to the subject.

In an aspect, provided herein is a method of treating cell proliferation or cancer in a subject in need thereof comprising administering an effective amount of a compound (e.g., a compound according to any of Formulas 1000-1000b, 1001-1001b, 1002-1002b, and I-XIXb-2, 101-111b, or 1-8b), conjugate (e.g., a conjugate according to any of Formulas C1-C17b, E1, F1-F17b, and G1-G17b), or composition comprising the compound or conjugate, as described herein, to the subject.

A therapeutically effective amount of the compound, conjugate, polypeptide, antibody, or pharmaceutical composition comprising the same is an amount that is effective to reduce the severity, the duration and/or the symptoms of a particular disease or condition. The amount of the compound, conjugate, polypeptide, antibody, or pharmaceutical composition comprising the same that will be therapeutically effective in the prevention, management, treatment and/or amelioration of a particular disease can be determined by standard clinical techniques. The precise amount of the compound, conjugate, polypeptide, antibody, or pharmaceutical composition comprising the same to be administered with depend, in part, on the route of administration, the seriousness of the particular disease or condition, and should be decided according to the judgment of the practitioner and each subject's circumstances.

In some embodiments, the effective amount of the compound, conjugate, polypeptide, antibody, or pharmaceutical composition comprising the same provided herein is between about 0.025 mg/kg and about 1000 mg/kg body weight of a human subject. In certain embodiments, the compound, conjugate, polypeptide, antibody, or pharmaceutical composition comprising the same is administered to a human subject at an amount of about 1000 mg/kg body weight or less, about 950 mg/kg body weight or less, about 900 mg/kg body weight or less, about 850 mg/kg body weight or less, about 800 mg/kg body weight or less, about 750 mg/kg body weight or less, about 700 mg/kg body weight or less, about 650 mg/kg body weight or less, about 600 mg/kg body weight or less, about 550 mg/kg body weight or less, about 500 mg/kg body weight or less, about 450 mg/kg body weight or less, about 400 mg/kg body weight or less, about 350 mg/kg body weight or less, about 300 mg/kg body weight or less, about 250 mg/kg body weight or less, about 200 mg/kg body weight or less, about 150 mg/kg body weight or less, about 100 mg/kg body weight or less, about 95 mg/kg body weight or less, about 90 mg/kg body weight or less, about 85 mg/kg body weight or less, about 80 mg/kg body weight or less, about 75 mg/kg body weight or less, about 70 mg/kg body weight or less, or about 65 mg/kg body weight or less.

In some embodiments, the effective amount of compound, conjugate, polypeptide, antibody, or pharmaceutical composition comprising the same provided herein is between about 0.025 mg/kg and about 60 mg/kg body weight of a human subject. In some embodiments, the effective amount of a compound, conjugate, polypeptide, antibody, or pharmaceutical composition comprising the same of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

The pharmaceutical composition of the method can be administered using any method known to those skilled in the art. For example, the pharmaceutical composition can be administered intramuscularly, intradermally, intraperitoneally, intravenously, subcutaneously administration, or any combination thereof. In some embodiments, the pharmaceutical composition is administered subcutaneously. In some embodiments, the composition is administered intravenously. In some embodiments, the composition is administered intramuscularly.

Cancers which can be treated using a compound, conjugate, polypeptide, antibody, or pharmaceutical composition disclosed herein include cancers where Her2 is overexpressed, CD7 is overexpressed, Her2 is not overexpressed, and CD7 is not overexpressed, In some embodiments, the cancer is small cell lung cancer, non-small cell lung cancer, ovarian cancer, platinum-resistant ovarian cancer, ovarian adenocarcinoma, endometrial cancer, breast cancer, breast cancer which overexpresses Her2, triple-negative breast cancer, a lymphoma, large cell lymphoma, diffuse mixed histiocytic and lymphocytic lymphoma, follicular B cell lymphoma, colon cancer, colon carcinoma, colon adenocarcinoma, colorectal adenocarcinoma, melanoma, prostate, or multiple myeloma. In certain embodiments, the cancer is breast cancer, lung cancer, ovarian cancer, endometrial cancer, prostate cancer, colon cancer, colorectal cancer, melanoma, prostate cancer, or multiple myeloma.

Assay Methods

Compounds, conjugates, polypeptides, antibodies, and pharmaceutical composition comprising the same described herein can be assayed for their expected activity, or for a new activity, according to any assay apparent to those of skill in the art. The compound, conjugate, polypeptide, antibody, or pharmaceutical composition comprising the same can be assayed for activity in a functional assay or by quantitating the amount of protein present in a non-functional assay, e.g. immunostaining, ELISA, quantitation on Coomasie or silver stained gel, etc., and determining the ratio of biologically active protein to total protein.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^{3}$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Preparation of Modified Hemiasterlin Compounds

The compounds provided herein can be prepared, isolated or obtained by any method apparent to those of skill in the art. Compounds provided herein can be prepared according to the General Preparation Scheme provided herein. Reaction conditions, steps and reactants not provided in the General Preparation Scheme would be apparent to, and known by, those skilled in the art in light of the Examples provided herein.

General Preparation Scheme $$R—W^5—SG—W^4—HP—W^3—RT—W^2—\underset{\underset{RT}{|}}{EG}—W^1—OH \quad +$$

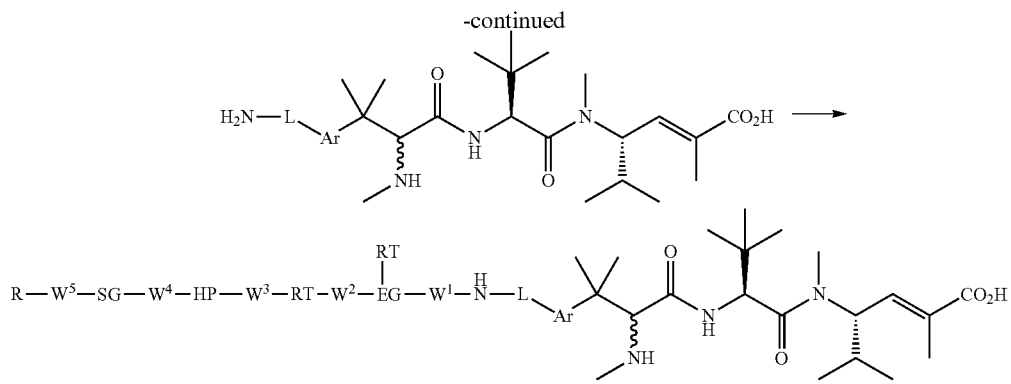

In the General Preparation Scheme R, SG, HP, RT, EG, $W^1$, $W^2$, $W^3$, $W^4$, $W^5$, L, and Ar are a described in the context of Formulas C1 and 1000-1000b, 1001-1001b, 1002-1002b, and I-XIXb-2.

EXAMPLES

As used herein, the symbols and conventions used in these processes, schemes and examples, regardless of whether a particular abbreviation is specifically defined, are consistent with those used in the contemporary scientific literature, for example, the Journal of Biological Chemistry and/or the Journal of the American Chemical Society.

For all of the following examples, standard work-up and purification methods known to those skilled in the art can be utilized. Unless otherwise indicated, all temperatures are expressed in ° C. (degrees Celsius). All methods are conducted at room temperature ("rt" or "r.t."), unless otherwise noted.

Example 1a

Synthesis of Compound 1 (Two Diastereomers)

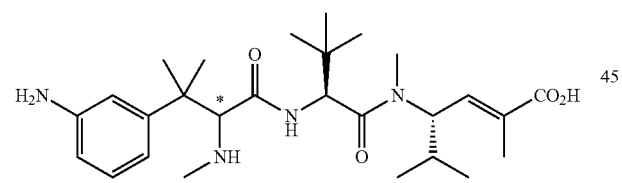

Scheme 1

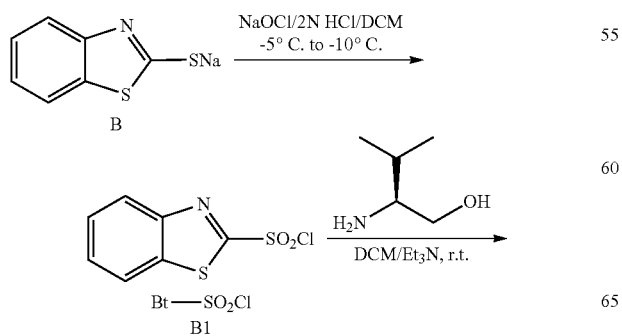

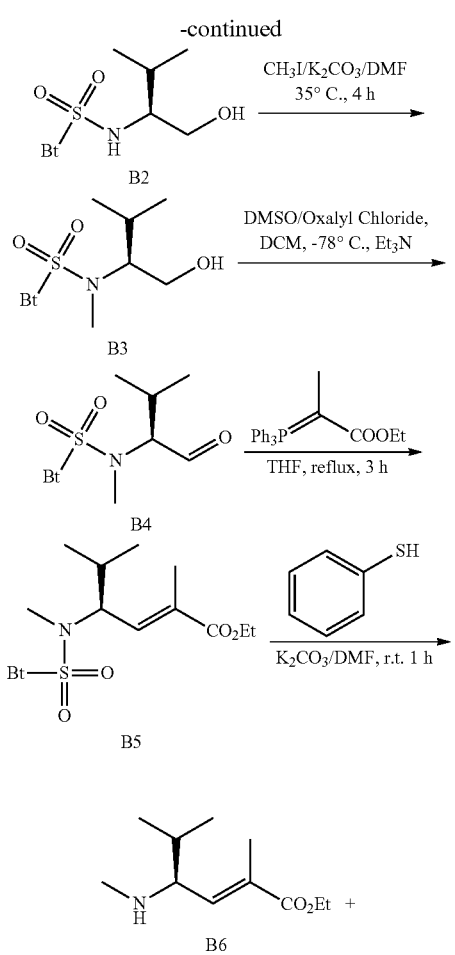

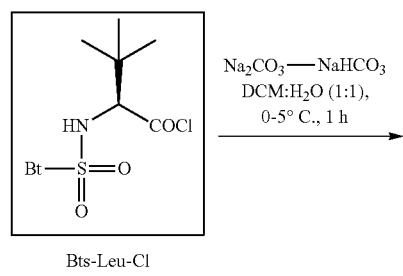

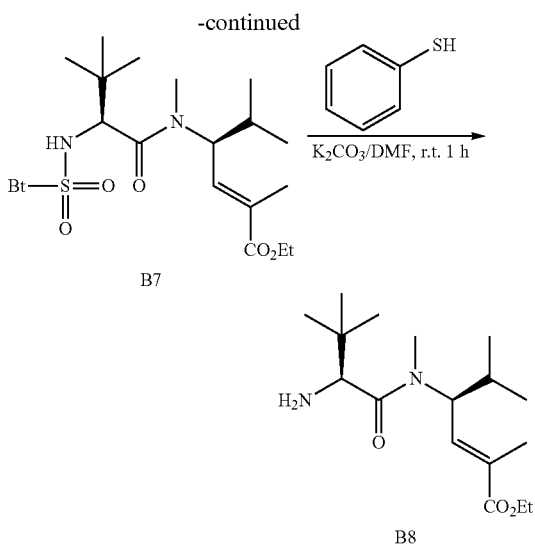

Preparation of Compound B2

To a mixed solvent of dichloromethane (100 mL) and 2N HCl (78 mL, 156 mmol) at −5° C. was added cold bleach (contain 6% NaOCl, 108 mL, 87 mmol) in portions. The mixture was stirred at 0° C. (inside temperature) for 5 min. Sodium 2-mercaptobezothioazole (B, 5 g, 26 mmol) was then added into the mixture in multi-portions. The mixture stirred at −5 to −10° C. for 20 min. The organic layer (B1, major is BtsCl) was collected and mixed with L-valinol (3.2 g, 31.2 mmol) and triethyl amine (8.7 mL, 121 mmol) in dichloromethane at r.t. The mixture allowed stirring at r.t. for 1 h. Solvent was removed and product was purified by silica gel column (Hexanes: Ethyl acetate=1:1) to give product B2 (3.1 g, 40%, two steps) as white solid.

LC-MS (ESI): 301 (M+1).
$^1$H NMR (300 MHz, CDCl$_3$) δ 8.08 (dd, J=2.1 and 7.2 Hz, 1H), 7.96 (dd, J=1.8 and 6.9 Hz, 1H), 7.58 (m, 2H), 5.46 (br s, 1H), 3.67 (d, J=4.5 Hz, 2H), 3.54 (br s, 1H), 3.23 (brs, 1H), 1.93 (m, 1H), 0.97 (d, J=6.9 Hz, 6H).

Preparation of Compound B3

To a solution of B2 (3 g, 10 mmol, 1.0 eq) in dimethylformamide (50 mL) was added potassium carbonate (2.77 g, 20 mmol, 2.0 eq) and iodomethane (1.25 mL, 20 mmol, 2.0 eq) at rt. The mixture was heated to 35° C., 4 h. The solvent was removed and the residue was worked up with ethyl acetate and water (3×), dried with Na$_2$SO$_4$ and concentrated to give product B3 (3.14 g, 100%) as white solid.

LC-MS (ESI): 315 (M+1).
$^1$H NMR (300 MHz, CDCl$_3$) δ 8.09 (dd, J=1.6 and 7.5 Hz, 1H), 7.95 (dd, J=1.8 and 6.9 Hz, 1H), 7.58 (m, 2H), 4.25 (br s, 1H), 2.90 (s, 3H), 1.93 (m, 1H), 1.02 (dd, J=2.1 and 6.6 Hz, 6H).

Preparation of Compound B4

To a mixed solvent of dichloromethane (50 mL) and DMSO (1.56 mL, 22 mmol, 2.2 eq) at −78° C. was added oxalyl chloride (1.05 mL, 12 mmol, 1.2 eq) slowly under nitrogen and stirred at this temperature for 30 min. B3 (3.14 g, 10 mmol, 1.0 eq) in 20 mL of dichloromethane was then added into this reaction mixture at −78° C. under nitrogen. The reaction mixture allowed stirring at −78° C. for 2 h. Triethylamine (7 mL, 50 mmol, 5 eq) was then added into the reaction and stirred at −78° C. for 30 min. and continued to warm up to 0° C. for another 30 min. The reaction mixture was poured into an ice-water and extracted with DCM (3×). The organic layer was washed with half saturated ammonium chloride (2×) solution, brine and dried with sodium sulfate. It was concentrated at low temperature (below 30° C.) to give product B4 (3.0 g, 96%) as white solid.

$^1$H NMR (300 MHz, CDCl$_3$) δ 9.69 (s, 1H), 8.17 (dd, J=1.5 and 8.1 Hz, 1H), 7.95 (dd, J=2.1 and 6.9 Hz, 1H), 7.58 (m, 2H), 4.30 (d, J=10.2 Hz, 1H), 3.01 (s, 3H), 2.21 (m, 1H), 1.15 (d, J=6.6 Hz, 3H), 0.98 (d, J=6.6 Hz, 3H).

Preparation of Compound B5

Product B4 (3 g, 9.58 mmol, 1.0 eq) and [(1-ethoxycaarbonyl)ethylidene]Ph$_3$P (6.95 g, 19.2 mmol, 2 eq) were dissolved in anhydrous tetrahydrofuran (60 mL) and was heated to reflux, 3 h. The reaction was cooled to r.t. and poured into ice water. Product was extracted with ethyl acetate (3×). The organic layer was washed with brine, dried with sodium sulfate and then concentrated to give crude product. It was further purified by silica gel column (Hexanes: Ethyl acetate=8:2) to give product B5 (2.9 g, 82%).

$^1$H NMR (300 MHz, CDCl$_3$) δ 8.09 (dd, J=1.2 and 7.2 Hz, 1H), 7.93 (dd, J=1.8 and 8.1 Hz, 1H), 7.53 (m, 2H), 6.39 (dd, J=1.6 and 10.5 Hz, 1H), 4.41 (t, J=10.5 Hz, 1H), 3.87 (q, J=7.2 Hz, 2H), 3.08 (s, 3H), 1.85 (s, 3H), 1.02-1.08 (m, 6H), 0.83 (d, J=6.9 Hz, 3H).

Preparation of Compound B6

To a solution of product B5 (2.9 g, 7.31 mmol, 1.0 eq) in dimethylformamide (30 mL) was added potassium carbonate (4.04 g, 29.2 mmol, 4.0 eq) and thiophenol (2.25 mL, 21.9 mmol, 3.0 eq). The reaction stirred at r.t. for 1 h. It was then worked up with diethyl ether and water (3×). The ether layer was extracted with 1% HCl, the aqueous was washed with ether. The aqueous layer was neutralized with sodium bicarbonate to pH 8 and extracted with dichloromethane (3×). The organic layer was dried with sodium sulfate and concentrated to give pure product B6 (1.2 g, 84%) as yellow oil.

LC-MS (ESI): 200 (M+1).
$^1$H NMR (300 MHz, CDCl$_3$) δ 6.48 (dd, J=1.2 and 10.2 Hz, 1H), 4.18 (q, J=7.2 Hz, 1H), 3.06 (q, J=6.3 Hz, 2H), 2.30 (s, 3H), 1.86 (d, J=1.8 Hz, 2H), 1.72 (m, 1H), 1.28 (t, J=7.2 Hz, 3H), 0.93 (d, J=6.9 Hz, 3H), 0.87 (d, J=6.9 Hz, 3H).

Preparation of Compounds Bts-Leu-C1 and B7

This synthesis is fully described in Vedejs and Kongkittingam, "A Total Synthesis of (−)-Hemiasterlin Using N-Bts Methodology," J. Org. Chem. 2001, 66(22), 7355-7364. A summary is provided below.

To a solution of Bts-Leu (2.4 g, 7.3 mmol, 1.0 eq) in anhydrous dichloromethane (30 mL) at 0° C. was added thionyl chloride (1.6 mL, 21.9 mmol, 3.0 eq) under nitrogen. The reaction mixture was refluxed at 42° C. for 2 h. It was concentrated and co-evaporated with toluene to give Bt-Leu-C1 as a crude solid and was used in the next step reaction without further purification.

To a solution of product B6 (1.2 g, 6.02 mmol) in a mixed solvent of dichloromethane and water (1:1, 40 mL) at 0° C. was added a solution of sodium carbonate (1.28 g, 12.04 mmol, 2.0 eq) and sodium bicarbonate (1.32 g, 15.7 mmol. 3.2 eq) under nitrogen. The fresh made Bts-Leu-C1 (from above) in dichloromethane (10 mL) was added into this reaction with syringe. The mixture stirred at 0-5° C. for 1 h. Product B7 was extracted with dichloromethane and water (3×), dried with sodium sulfate and concentrated to give crude product B7, which was purified by silica gel column (Hexanes: ethyl acetate=1:1) to give product B7 (1.8 g, 59%) as white solid. LC-MS (ESI): 510 (M+1).

$^1$H NMR (300 MHz, CDCl$_3$) δ 8.11 (dd, J=1.5 Hz, 8.7 Hz, 1H), 7.93 (dd, J=1.2 Hz, 8.7 Hz, 1H), 7.58 (m, 2H), 6.52 (dd, J=1.2 Hz, 9.9 Hz, 1H), 6.10 (d, J=8.7 Hz, 1H), 4.85 (t, J=10.2 Hz, 1H), 4.47 (d, J=8.7 Hz, 1H), 4.16 (m, 2H), 2.94 (s, 3H), 1.82 (d, J=1.2 Hz, 2H), 1.27 (m, 3H), 0.98 (s, 6H), 0.63 (d, J=6.6 Hz, 3H), −0.12 (d, J=6.6 Hz, 3H).

Preparation of Compound B8

To a solution of B7 (200 mg, 0.392 mmol, 1.0 eq) in DMF (2 mL) was added potassium carbonate (217 mg, 1.57 mmol, 4.0 eq) and thiophenol (121 μL, 1.18 mmol, 3.0 eq) under nitrogen at r.t. The reaction mixture was stirred at rt. for 4 h and LC-MS showed the reaction completed. The reaction was worked up with water and ether and 10% hydrochloric acid (as the literature described) and pure B8 (100 mg, 82%) obtained. LC-MS (ESI): 313 (M+1). $^1$H NMR (300 MHz, CDCl$_3$) δ 7.99 (s, 1H), 6.63 (dd, J=1.2 Hz, 9.9 Hz, 1H), 5.15 (t, J=9.9 Hz, 1H), 4.19 (m, 2H), 3.45 (s, 1H), 2.86-2.94 (m, 6H), 1.89 (m, 3H), 1.70 (s, bro, 2H), 1.28 (t, J=5.7 Hz, 3H), −0.86-1.01 (m, 12H).

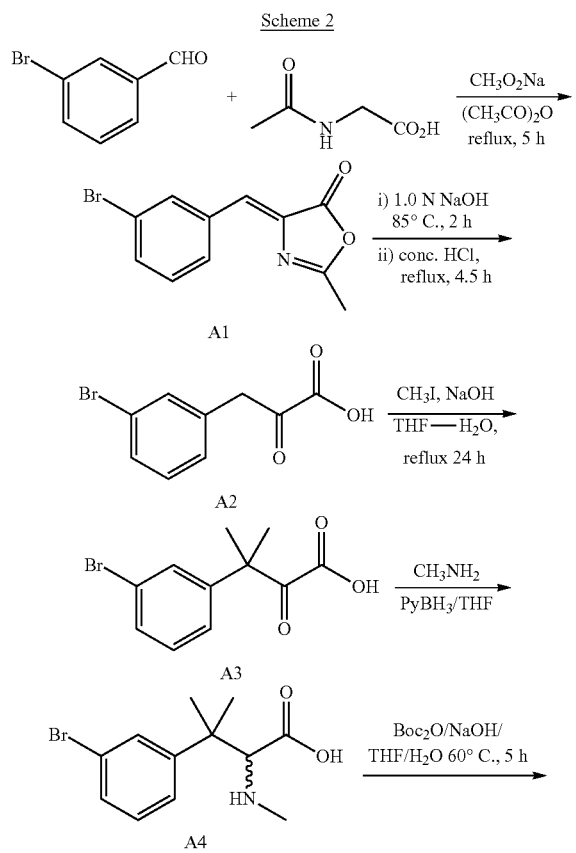

Scheme 2

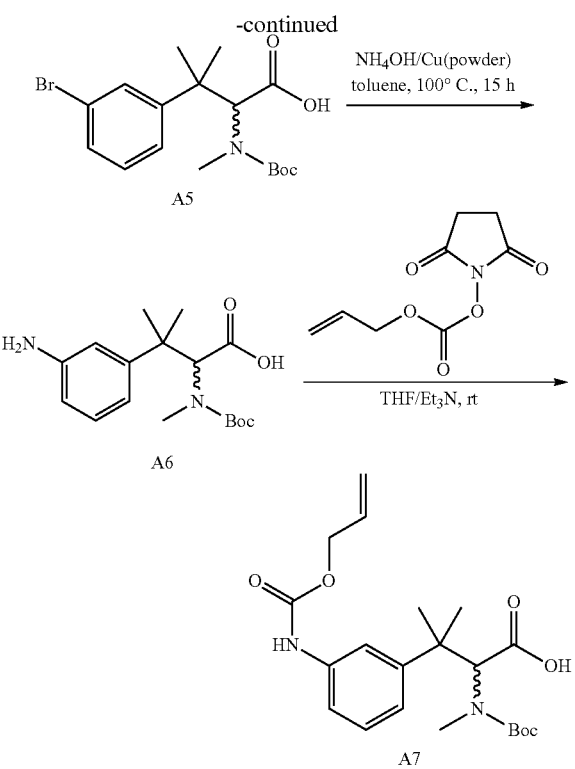

Preparation of Compound A1

A mixture of 3-bromobenzaldehyde (25.0 g, 135 mmol, 1.0 eq), N-acetyl glycine (15.8 g, 135 mmol, 1.0 eq) and sodium acetate (10.6 g, 135 mmol, 1.0 eq) were suspended in acetic anhydride (40 mL) and heated with stirring to reflux under N$_2$ for 5 hr. The resulting solution solidified upon cooling to room temperature and was quenched with ice-cold water and filtered. The solids were washed twice more with water, air dried for 4 h, then further dried in vacuo to give compound A1 (31 g, 86%).

Preparation of Compound A2

Oxazolone A1 (31 g, 117 mmol, 1.0 eq) in 1.0 N NaOH (175 mL, 175 mmol, 1.5 eq) was stirred at 85° C. until a translucent reddish solution was obtained. The reaction was cooled down to room temperature and acidified to pH 1.0 with 5 N HCl to precipitate a brown solid. Concentrated HCl (30 mL) was added to the flask, and the reaction solution diluted to about 500 mL. A reflux was maintained for another 5 hr. The solids were collected by filtration and washed with water twice, and dried under high vacuum to deliver the crude material A2 (23 g, 81%) which was used without further purification.

Preparation of Compound A3

Pyruvic acid A2 (23 g, 94.7 mmol, 1.0 eq) was dissolved in THF (100 mL) and cooled to 0° C. Methyl iodide (36 g, 256 mmol, 2.7 eq) followed by 5 N NaOH (80 mL) were slowly added, and the reaction brought to reflux overnight. The volatiles were stripped off and the residual aqueous solution was extracted with ethyl acetate, and acidified with 10% HCl at 0° C. to pH 1. The resulting aqueous layer was extracted with ethyl acetate (2×). The combined organics were washed with brine, dried over sodium sulfate, and purified by column chromatography (EtOAc/hexanes 1:1) to yield pure compound A3 (11 g, 43%).

Preparation of Compound A4

A 2 N solution of methylamine (14.4 mL, 28.8 mmol, 2.0 eq) was added into a solution of the keto-acid A3 (11 g, 40.6 mmol, 1.0 eq) in THF (100 mL) at room temperature and stirred for 4 hr. An 8 N solution of pyridine-borane complex (5 mL, 40.6 mmol, 1.0 eq) was added, and the mixture heated to 55° C. for 3 hr. The reaction was quenched with methanol, concentrated, and diluted with THF (50 mL) to form a white precipitate. The white solid precipitate was filtered and dried on vacuum to give compound A4 (5 g, 61%).

Preparation of Compound A5

To a solution of compound A4 (1.0 g, 3.5 mmol, 1.0 eq) and (Boc)$_2$O (1.15 g, 5.24 mmol, 1.5 eq) in THF and water (1:1, 20 mL) was added sodium hydroxide (280 mg, 6.99 mmol, 2.0 eq). The mixture was heated at 60° C. for 5 h. The reaction mixture was cooled and concentrated. The residual aqueous solution was acidified with 10% HCl at 0° C. to pH 1, and extracted with ethyl acetate (3×). The combined organic layers were dried over sodium sulfate, and purified with flash column chromatography to give compound A5 (420 mg, 31%).

Preparation of Compound A6

To compound A5 (1.58 g, 4.07 mmol, 1 eq) in toluene (15 mL) in a sealed tube was added ammonium hydroxide (2.7 mL, 40.7 mmol, 10 eq) and copper powder (39 mg, 0.61 mmol, 0.15 eq). The tube was heated to 100° C. overnight and concentrated to give a residue, which was diluted with aqueous NaHCO$_3$ and n-butanol. The aqueous layer was extracted with n-butanol. The organic layers were concentrated, and purified by silica gel column (DCM:MeOH:Et3N=9:1:1) to give compound A6 (680 mg, 52%).

Preparation of Compound A7

To a solution of compound A6 (1.42 g, 3.36 mmol, 1 eq) in THF (10 mL) was added Alloc-OSu (1.34 g, 6.72 mmol, 2 eq) and triethylamine (1.4 mL, 10.1 mmol, 3 eq). The mixture was stirred at rt overnight. The solvent was removed and the residue was purified by flash column chromatography (DCM: MeOH=9:1) to give compound A7 (1.01 g, 74%).

Scheme 3

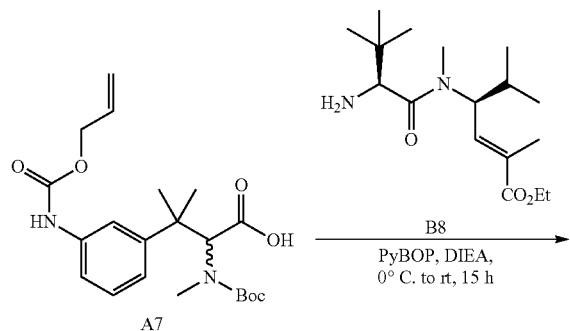

Preparation of Compound A8

To a solution of compound A7 (41 mg, 0.1 mmol, 1 eq) in dry DCM (1.5 mL) was added B8 (31 mg, 0.1 mmol, 1 eq) and PyBOP (57.2 mg, 0.11 mmol, 1.1 eq). The mixture was cooled down to 0° C., and DIEA (49 µL, 0.3 mmol, 3 eq) was added. The reaction was stirred at rt overnight, and diluted with DCM and washed with water. The aqueous was further extracted with DCM (2×). The organic layers were combined, and dried over sodium sulfate, concentrated to dryness to give a crude product. It was purified by pre-HPLC to give A8 (10 mg, 14%) as a mixture of two diastereoisomers (60:40).

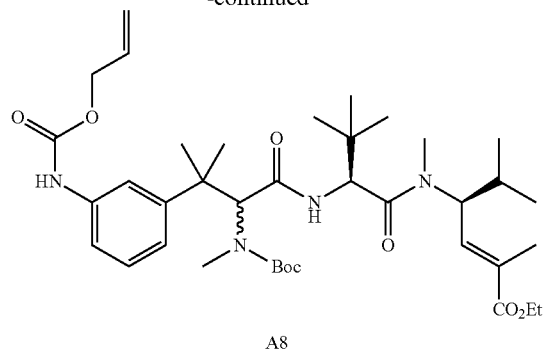

Scheme 4

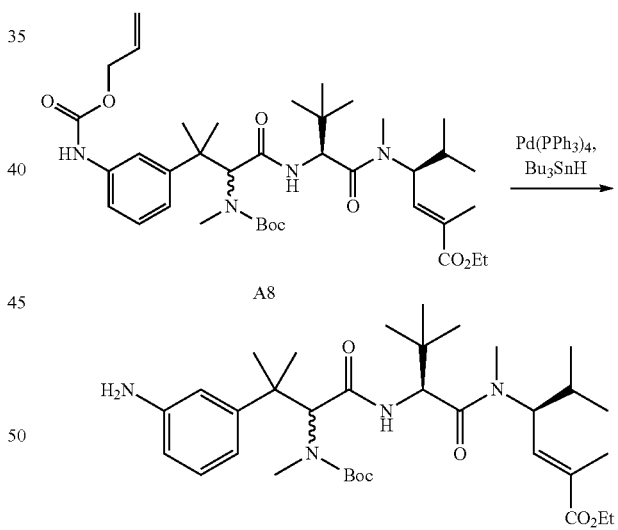

Preparation of Compound A9

To a solution of compound A8 (150 mg, 0.21 mmol, 1.0 eq) and Pd(PPh$_3$)$_4$ (12.4 mg, 0.011 mmol, 0.05 eq) in THF (10 mL) was added tri-n-butyl-tin hydride (113 µL, 0.43 mmol, 2.0 eq). The mixture was degassed and backfilled with nitrogen (3×). The reaction was stirred at rt for 6 h. The solvent was removed, and the crude product was purified by silica gel column (DCM: MeOH=9:1) to give A9 (78 mg, 60%) as a mixture of two isomers.

Scheme 5

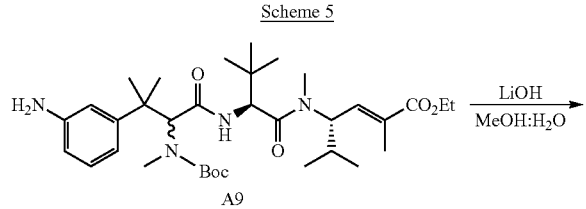

A9

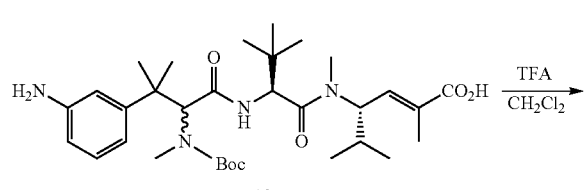

A10

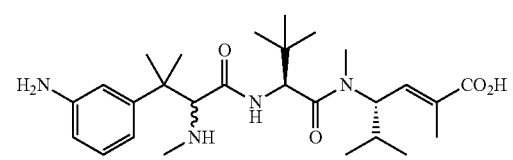

[R/S, S, S] compound 1

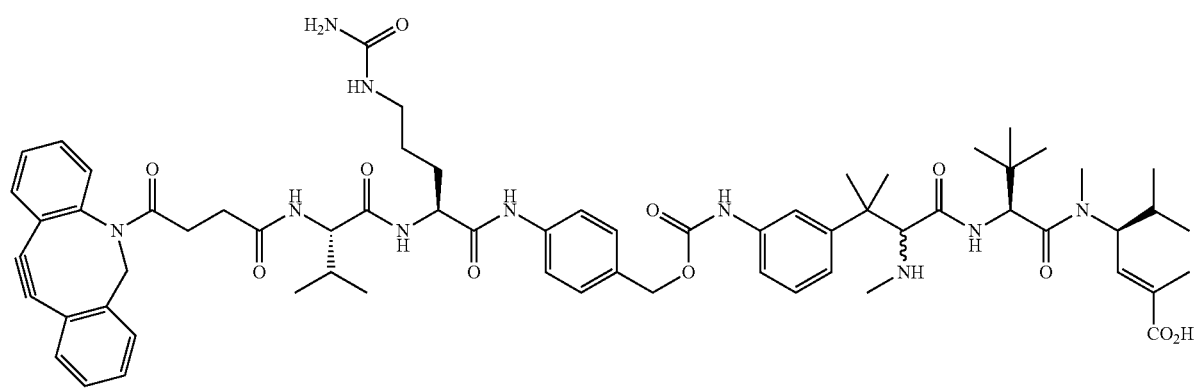

[S, S, S] compound 1

[R, S, S] compound 1

To a solution of compound A9 (28 mg, 0.046 mmol, 1 eq) in MeOH (1 mL) was added LiOH (10 mg, 0.23 mmol, 5 eq) in water (0.5 mL). The mixture was stirred at rt overnight. The product was purified by prep-HPLC to give A12 (23 mg, 85%).

To a solution of A12 (11 mg, 0.0187 mmol, 1 eq) in DCM (1 mL) was added 10% TFA in DCM (1 mL). The mixture stirred at rt for 4 h. Solvent was removed and the crude product 1 was purified by preparative RP-HPLC twice to give two isomers 1a (0.8 mg), and 1b (1 mg).

Example 1b

Synthesis of Compound 101 (Two Diastereomers)

101

Linkers synthesized from the aryl amine Compound 1 give rise to cleavable Compound 101 which releases the novel aniline parent compounds as a diastereomeric pair.

Scheme 6
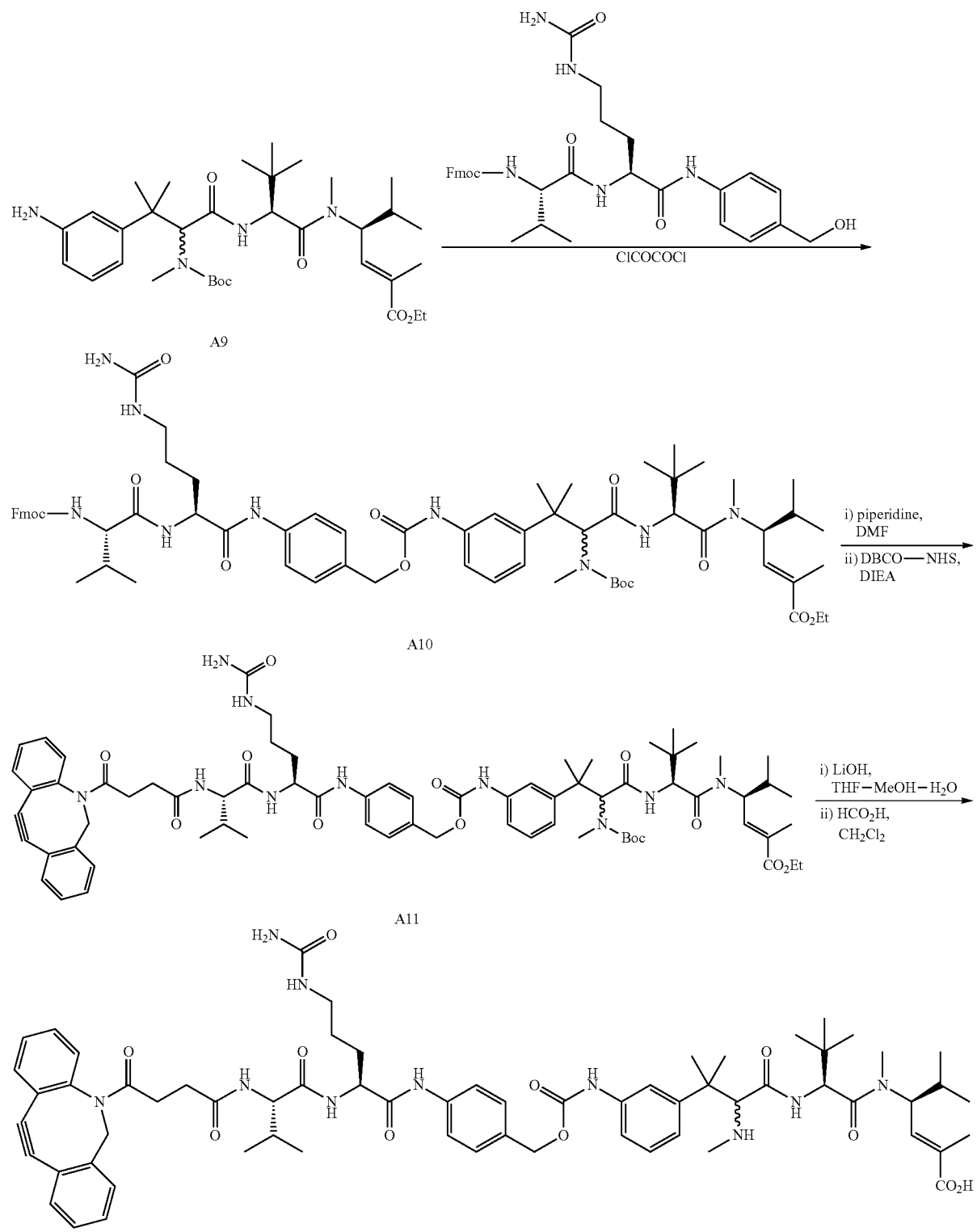
Preparation of Compound A10
To an argon-flushed solution of A9 (27 mg, 0.04 mmol) in 1 mL $CH_2Cl_2$ was added 15% w/v phosgene in toluene (0.6 mL, 0.06 mmol). The reaction mixture was heated to 50° C. in a sealed tube for 4 h, cooled to ambient temperature, and the volatiles removed in vacuo. To the residue was added a vacuum-dried solution of Fmoc-valine-citruline-p-aminobenzyl alcohol (26 mg, 0.04 mmol) in 1 mL DMF. The reaction mixture was stirred at 45° C. under argon for 6 h, then at ambient temperature for 24 hr. After removal of all volatiles in vacuo the residue was purified on silica gel (90:10 CH$_2$Cl$_2$:MeOH eluent) to give 10 mg (0.008 mmol) A10 as a white solid.

Preparation of Compound A11

To a solution of A10 in CH$_2$Cl$_2$ (1 mL) was added piperidine (0.1 mL) and the reaction mixture was stirred at ambient temperature for 1 hr. After removal of all volatiles in vacuo, to the residue was added DBCO-succinyl N-hydroxysuccinimidyl ester (3.6 mg, 0.009 mmol), DMF (1 mL), and diisopropylethylamine (0.004 mL, 0.02 mmol). The reaction mixture was stirred at ambient temperature for 24 hr. After removal of all volatiles in vacuo the residue was purified on silica gel (90:10 CH$_2$Cl$_2$:MeOH eluent) to give 7 mg (0.005 mmol) A11.

Preparation of Compound 101

Compound A11 (7 mg, 0.005 mmol) was dissolved in 3:1:1 THF:MeOH:H$_2$O (1 mL) and the solution cooled to 0° C. Solid LiOH.H$_2$O (1.7 mg, 0.4 mmol) was added and the reaction mixture stirred at ambient temperature overnight. A few microliters of glacial acetic acid were added, the volatiles removed in vacuo, and the free acid 101 was purified by reverse phase-high performance liquid chromatography (RP-HPLC) using an Ultro 120 (7 μm), 150×20 mm ID column (water-acetonitrile (10 mm NH$_4$OAc) solvent system, gradient mode from 10% ACN to 100% ACN in 50 min, 15 ml/min). LC-MS (ESI): 1282.6 (M+1), 1182.4 (M-Boc+1).

The N-protected acid of A11 (5 mg, 0.004) was dissolved in CH$_2$Cl$_2$ (1 mL) and the solution was cooled to 0° C. To this was added a 0.2 M solution of HCO$_2$H in CH$_2$Cl$_2$ (0.039 mL) and the reaction mixture allowed to stir at ambient temperature overnight. After the volatiles were removed in vacuo, the free amino acid was purified by reverse phase-high performance liquid chromatography (RP-HPLC) using Ultro 120 (7 μm), 150×20 mm ID column (water-acetonitrile (10 mm NH$_4$OAc) solvent system, gradient mode from 10% ACN to 100% ACN in 50 min, 15 ml/min) to give 3 mg (0.0025 mmol, 65%) compound 101 as white solid.

Example 1c

Chiral Synthesis of Compound A9a

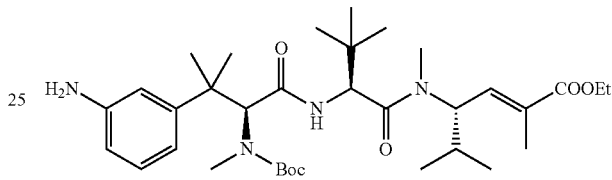

A9a

Linkers synthesized from the aryl amine Compound 1 give rise to cleavable Compound 101 which releases the novel aniline parent compounds as a diastereomeric pair.

Scheme 7

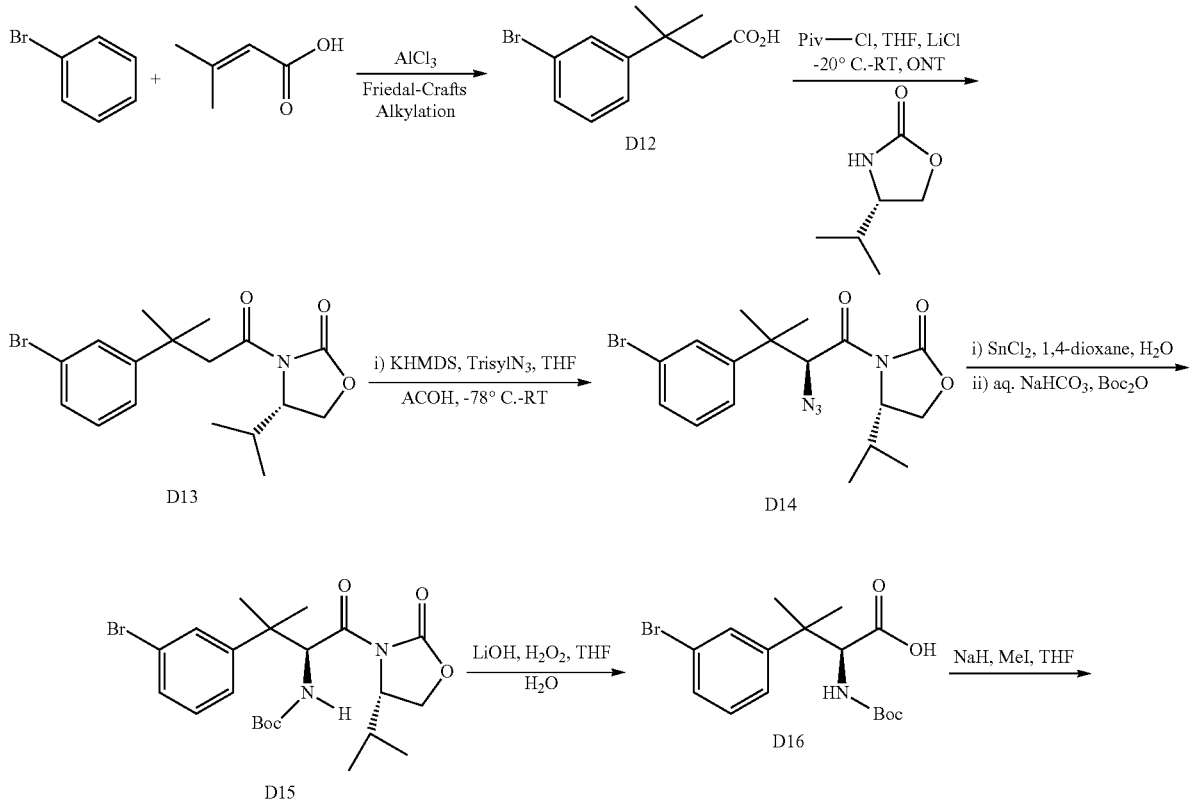

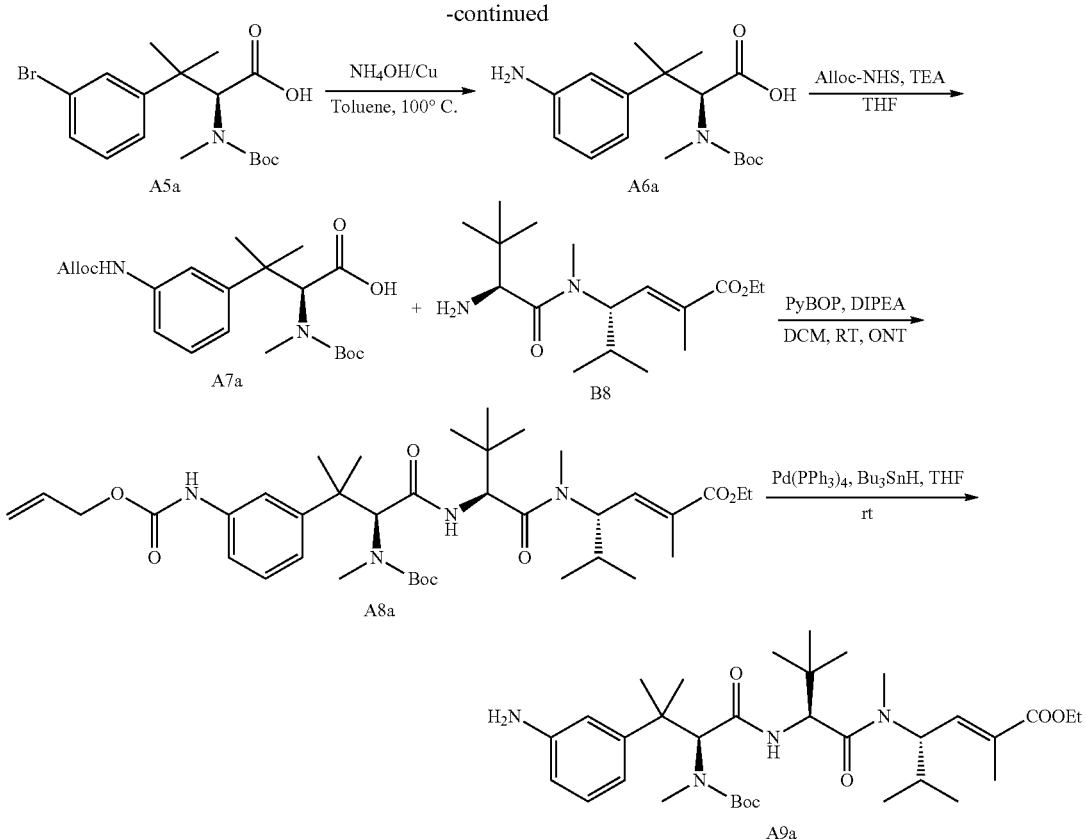

Preparation of Compound D12

3,3-Dimethylacrylic acid, (97%, 15.8 g, 157.9 mmol), AlCl$_3$ (22 g, 164.9 mmol) and DCM (100 mL) were placed in a one-neck round-bottomed flask under an argon atmosphere. Bromobenzene (31 g, 197.4 mmol) was added producing vigorous bubbling. Upon completion of the bubbling, the reaction mixture was stirred in an oil bath at 65° C. for 1 h and 30 min and overnight at rt under N$_2$ atm. Reaction was poured in HCl:H$_2$O (1:1) 200 mL slowly, EtOAc (300 mL) was added and the organic phase was separated, organics were washed with brine, dried over Na$_2$SO$_4$, and concentrated. The crude mixture $^1$H NMR data showed mixture of m,p-regioisomers. Crude material was crystallized from hexane to give pure 3-(3-bromophenyl)-3-methylbutanoicacid (meta isomer) (14 g, 54.7 mmol, 42%) as brown crystals.

$^1$H NMR (400 MHz, CDCl$_3$) δ 7.52-7.50 (m, 1H), 7.37-7.35 (m, 1H), 7.35-7.30 (m, 1H), 7.23-7.20 (m, 1H), 2.66 (s, 2H), 1.47 (s, 6H).

Preparation of Compound D13

3-(3-bromophenyl)-3-methylbutanoicacid (Compound D12, 7.7 g, 29.94 mmol) was dissolved in 170 ml of THF and cooled to −20° C. Triethylamine (8.3 ml, 59.89 mmol) and trimethylacetyl chloride (3.7 ml, 29.94 mmol) were added to the reaction flask producing a white precipitate. The resulting mixture was stirred at −20° C. for 1 h under N$_2$ atm, after which LiCl (1.27 g, 29.94 mmol) and (4S)-(−)-4-isopropyl-2oxazolidinone (3.87 g, 29.94 mmol) were added sequentially and the resulting reaction mixture was stirred at −20° C. for 2 h and overnight at rt under N$_2$ atm. Water was added and the reaction mixture was extracted with EtOAc (2×100 mL). The combined organic extracts were dried over magnesium sulfate and concentrated in vacuo. The product was purified by flash column chromatography (silica gel, hexane:EtOAc, 4:1) affording compound D13 as a clear, colorless oil in 87% yield (9.5 g, 25.79 mmol).

$^1$H NMR (400 MHz, CDCl$_3$) δ 7.52-7.50 (m, 1H), 7.36-7.31 (m, 2H), 7.21-7.18 (m, 1H), 4.25-4.21 (m, 1H, H-4), 4.17-4.09 (m, 2H), 3.42-3.31 (m, 2H, H-10), 2.22-2.10 (m, 1H), 1.50 (s, 3H), 1.49 (s, 3H), 0.86 (d, 3H, J=6.80 Hz), 0.77 (d, 3H, J=6.80 Hz)

Preparation of Compound D14

Oxazolidinone compound D13 (8.4 g, 22.8 mmol) was dissolved in THF (100 ml) under an argon atmosphere, and cooled to −78° C. Potassium bis(trimethylsilyl)amide (25.1 ml, 1 M in THF, 25.1 mmol) was added and the resulting solution was stirred at −78° C. for 1 h and 20 min. A solution of 2,4,6-triisopropylbenzenesulfonyl azide (9.2 g, 29.64 mmol) in THF (40 ml) at −78° C. was added via cannula and after 5 min, the reaction mixture was treated with glacial acetic acid (6.3 ml, 104.9 mmol), warmed to 40° C., and stirred for an additional 10 h at rt. Brine (270 ml) and Water (35 ml) were added to the light yellow mixture and the aqueous phase was extracted with (2×500 ml) diethyl ether. The combined organic extracts were washed with a saturated sodium hydrogen carbonate solution (2×110 ml), dried with magnesium sulfate, and concentrated in vacuo. The product was purified by column chromatography (3:7 EtOAc-hexanes), affording azide compound D14 as a colorless oil (8.1 g, 19.84 mmol) in 87% yield.

$^1$H NMR (400 MHz, CDCl$_3$) δ 7.55-7.52 (m, 1H), 7.41-7.39 (m, 1H), 7.23-7.20 (m, 2H), 5.67 (s, 1H), 4.21-4.07 (m, 3H), 3.61 (t, 1H, J=8.3 Hz), 2.37-2.25 (m, 1H, H-6), 1.56 (s, 3H), 1.54 (s, 3H), 0.89 (d, 3H, J=6.8 Hz), 0.85 (d, 3H, J=7.2 Hz).

Preparation of Compound D15

SnCl$_2$ (5.5 g, 29.32 mmol) was dissolved in 1,4-Dioxane:H$_2$O (2:1) 75 mL and the resulted colorless clear solution was cooled to 0° C., to which compound D14 (4 g, 9.77 mmol) dissolved in 20 mL of dioxane was added, and the reaction mixture was stirred at rt overnight. Reaction was cooled back to 0° C., NaHCO$_3$ (4.1 g, 48.86 mmol) and Boc$_2$O (6.4 g, 29.31 mmol) were added sequentially, and the reaction was stirred 1 day at rt under N$_2$ atm. Solvent was removed under reduced pressure, extracted with EtOAc (2×300 mL) and the organics layer was washed with brine, dried over Na$_2$SO$_4$, concentrated, and purified by column chromatography (3:7 EtOAc-hexanes), affording compound D15 as a colorless oil (4.1 g, 8.48 mmol) in 87.2% yield. $^1$H NMR (400 MHz, CDCl$_3$) δ 7.45 (bs, 1H), 7.35-7.31 (m, 1H), 7.32-729 (m, 1H), 6.17 (d, 1H, J=9.6 Hz), 5.15 (bs, 1H, NH), 3.89-3.80 (m, 2H), 3.52 (t, 1H, J=8.3 Hz), 2.33-2.21 (m, 1H), 1.41 (s, 3H), 1.39 (s, 9H), 1.38 (s, 3H), 0.80 (d, 3H, J=7.2 Hz), 0.78 (d, 3H, J=6.8 Hz)

Preparation of Compound D16

Oxazolidinone Compound D15 (4.1 g, 8.48 mmol) was dissolved in a mixture of 4:1 THF:H$_2$O (50 mL). The solution was cooled to 0° C. Hydrogen peroxide (2.7 ml, 30% aqueous, 25.44 mmol) and lithium hydroxide (610 mg, 25.44 mmol) were then added to the oxazolidinone solution and stirred at room temperature overnight. The excess peroxide was quenched by the slow addition of sodium hydrogen sulfite and stirring was continued for 1 hr. The mixture was diluted with EtOAc (50 mL) and H$_2$O (100 mL), the aqueous phase was separated and acidified with 1.0 M HCl at 0° C., and extracted with ethyl acetate (2×200 ml). The organic layer was washed with brine, dried over magnesium sulfate, and concentrated in vacuo to give clear colorless oil (2.9 g, 7.83 mmol, 95%) pure enough to use in the next step without further purification. $^1$H NMR (400 MHz, CDCl$_3$) δ 7.32-7.31 (m, 1H), 7.17-7.10 (m, 2H), 7.00-6.97 (m, 1H), 4.83 (d, 1H, J=8.8 Hz), 4.41 (d, 1H, J=8.8 Hz), 1.45 (s, 6H), 1.38 (s, 9H).

Preparation of Compound A5a

Under an argon atmosphere, sodium hydride (60%, 830 mg, 22.64 mmol), a catalytic amount of tetrabutylammonium iodide, followed by methyl iodide (2.0 ml, 32 mmol) were added to a vigorously stirred solution of acid compound D16 (1.2 g, 3.23 mmol) in 50 ml dry THF. The resulting suspension was stirred 1 day at room temperature. The excess sodium hydride was quenched by cautious addition of ice cold water and the mixture was acidified by drop wise addition of 1.0 M HCl to pH 3 at 0° C. The acidic mixture was extracted with ethyl acetate (3×100 mL), the combined organic layer was washed with brine, dried over magnesium sulfate, and concentrated in vacuo. Purification of acid Compound A5a was performed by silica gel column chromatography (1:2 EtOAc-hexanes with 1% acetic acid) resulting in a 77% yield (0.74 g, 1.93 mmol, 60%) of a clear colorless oil as mixture of rotamers. $^1$H NMR (400 MHz, CDCl$_3$) δ 7.50-7.49 (m, 1H), 7.37-7.27 (m, 2H), 7.13-7.07 (m, 1H), 5.15 (s, 0.65 H, H-2), 4.95 (s, 0.35H, H-2), 2.51 (s, 1H, H-6), 2.27 (s, 2H, H-6), 1.57 (s, 3H), 1.53-1.38 (m, 12H).

Preparation of Compound A6a

Compound A5a (600 mg, 1.56 mmol, 1 eq) in toluene (10 mL) in a sealed tube was added ammonium hydroxide (3 mL, 15.6 mmol, 10 eq) and copper powder (20 mg, 0.23 mmol, 0.15 eq). The tube was heated to 100° C. overnight and was cooled to rt, sealed tube cap was carefully released, concentrated to give a residue, which was diluted with aqueous NaHCO$_3$ and n-butanol. The aqueous layer was extracted with n-butanol. The organic layers were concentrated, and purified by silica gel column (DCM:MeOH:Et$_3$N=9:1:1) to give compound A6a (300 mg, 0.930 mmol, 60%). LC-MS (ESI): 323.4 (M+1), 223.5 (M-Boc+1).

Preparation of Compound A7A

To a solution of compound A6a (300 mg, 0.930 mmol, 1 eq) in THF (7 mL) was added Alloc-OSu (199.1 mg, 1.86 mmol, 2 eq) and triethylamine (0.51 mL, 3.72 mmol, 4 eq). The mixture was stirred overnight at room temperature under N$_2$ atm. The solvent was removed and the residue was purified by flash column chromatography (DCM:MeOH=9:1) to give compound A7A (284 mg, 0.70 mmol, 75%). LC-MS (ESI): 407.4 (M+1), 307.6 (M-Boc+1).

Preparation of Compound A8A

To a solution of compound A7A (220 mg, 0.54 mmol, 1 eq) in dry DCM (5 mL) was added B8 (202 mg, 0.65 mmol, 1.2 eq). The mixture was cooled to 0° C., and DIEA (49 µL, 0.3 mmol, 3 eq) and PyBop (338 mg, 0.65 mmol, 1.2 eq) were added sequentially. The reaction was stirred at rt overnight under N$_2$ atm, and diluted with DCM and washed with water. The aqueous was further extracted with DCM (2×50 mL). The organic layers were combined, dried over sodium sulfate, and concentrated to dryness to give a crude product. This crude product was purified by flash column chromatography (EtOAc:Hexane=1:1) to give compound A8A (200 mg, 0.28 mmol, 53%). LC-MS (ESI): 701.4 (M+1), 601.6 (M-Boc+1).

Preparation of Compound A9a

To a solution of compound A8A (170 mg, 0.24 mmol, 1.0 eq) and Pd(PPh$_3$)$_4$ (28 mg, 0.024 mmol, 0.1 eq) in DCM (10 mL) was added tri-n-butyl-tin hydride (78 µL, 0.29 mmol, 1.2 eq). The reaction mixture was degassed and backfilled with nitrogen. The reaction was stirred for 3-4 h at rt under N$_2$ atm. The solvent was removed, and the crude product was purified by silica gel column (EtOAc:Hexane=1:1) to give A9a (130 mg, 87%) as a clear oil. $^1$HNMR (400 MHz, CDCl$_3$) δ 7.11-7.07 (m, 1H), 6.97-6.70 (m, 2H), 6.61-6.48 (m, 2H), 6.03-5.97 (m, 1H), 5.12-4.89 (m, 1H), 4.63-4.49 (m, 1H), 4.21-4.01 (m, 2H), 2.93 (s, 3H), 2.83 (m, 3H), 1.83-1.81 (bs, 4H), 1.42 (s, 12H), 1.27-1.17 (m, 6H), 0.87-0.0.81 (m, 6H), 0.78-0.63 (m, 6H), 0.63 (s, 6H). LC-MS (ESI): 617.6 (M+1).

Example 1d
Chiral Synthesis of Compound 101a (Single Diastereomer)
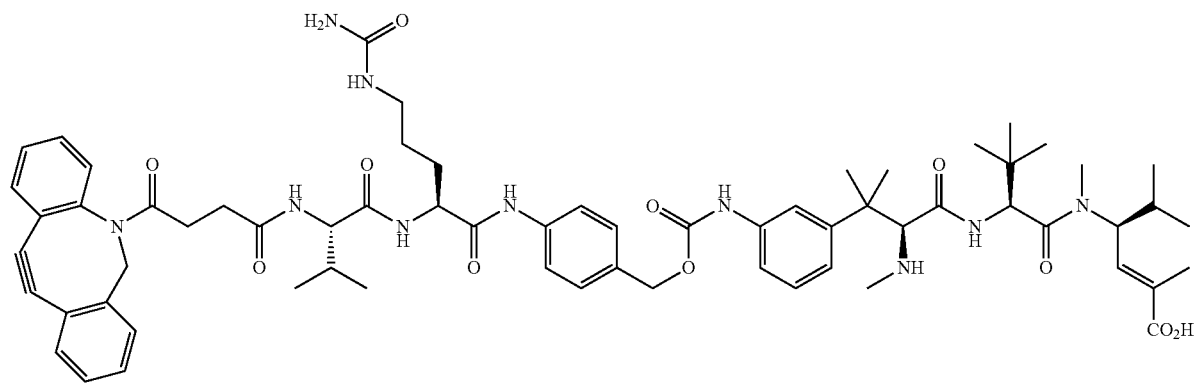
Compound 101a is produced from compound A9a according to Scheme 8.
Scheme 8
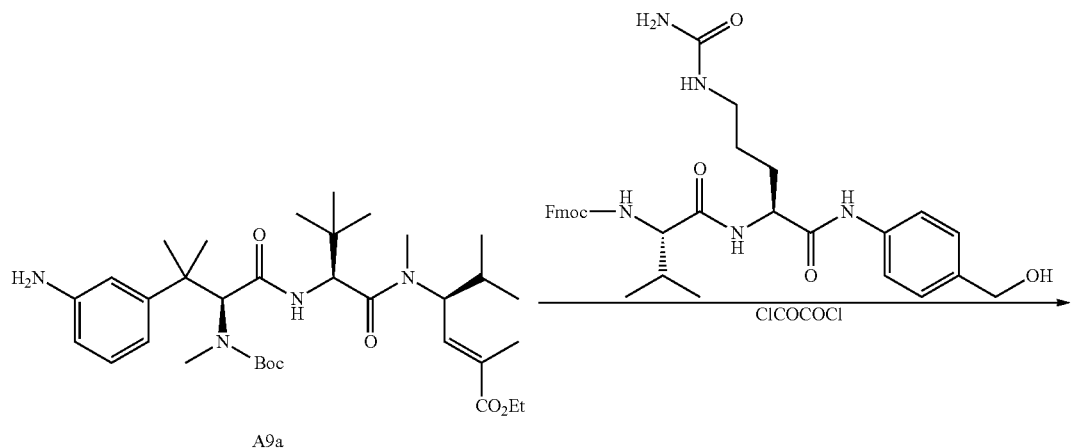
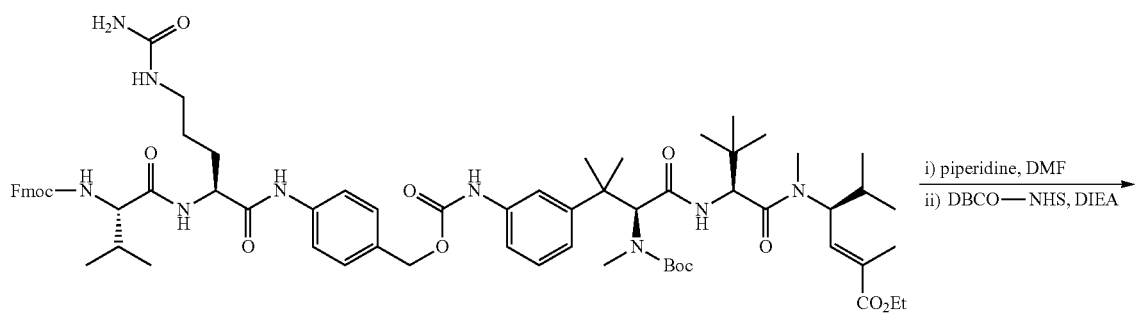

-continued

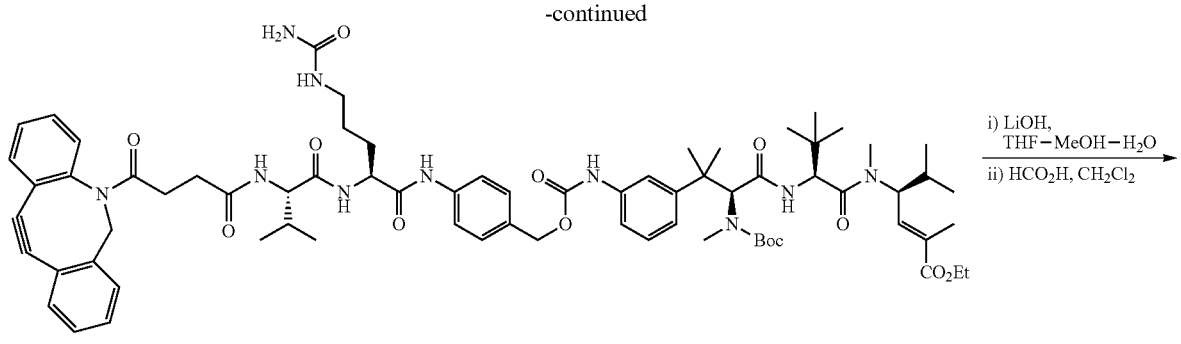

A11a

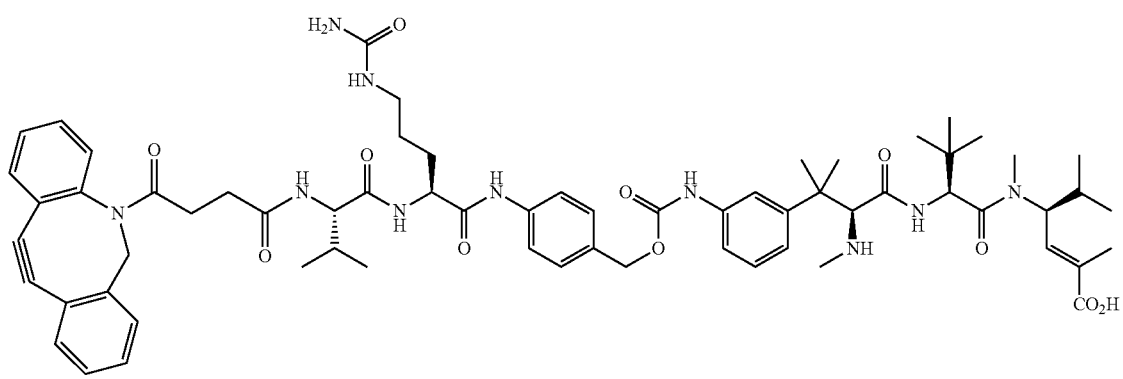

101a

Preparation of Compound A10a

To an argon-flushed solution of A9a (27 mg, 0.04 mmol) in 1 mL CH$_2$Cl$_2$ is added 15% w/v phosgene in toluene (0.6 mL, 0.06 mmol). The reaction mixture is heated to 50° C. in a sealed tube for 4 h, cooled to ambient temperature, and the volatiles removed in vacuo. To the residue is added a vacuum-dried solution of Fmoc-valine-citruline-p-aminobenzyl alcohol (26 mg, 0.04 mmol) in 1 mL DMF. The reaction mixture is stirred at 45° C. under argon for 6 h, then at ambient temperature for 24 hr. After removal of all volatiles in vacuo the residue is purified on silica gel (90:10 CH$_2$Cl$_2$:MeOH eluent) to give A10a.

Preparation of Compound A11a

To a solution of A10a in CH$_2$Cl$_2$ (1 mL) is added piperidine (0.1 mL) and the reaction mixture is stirred at ambient temperature for 1 hr. After removal of all volatiles in vacuo, to the residue is added DBCO-succinyl N-hydroxysuccinimidyl ester (3.6 mg, 0.009 mmol), DMF (1 mL), and diisopropylethylamine (0.004 mL, 0.02 mmol). The reaction mixture is stirred at ambient temperature for 24 hr. After removal of all volatiles in vacuo the residue is purified on silica gel (90:10 CH$_2$Cl$_2$:MeOH eluent) to give A11a.

Preparation of Compound 101a

Compound A11a (7 mg, 0.005 mmol) is dissolved in 3:1:1 THF:MeOH:H$_2$O (1 mL) and the solution cooled to 0° C. Solid LiOH.H$_2$O (1.7 mg, 0.4 mmol) is added and the reaction mixture stirred at ambient temperature overnight. A few microliters of glacial acetic acid are added, the volatiles removed in vacuo, and the free acid 101a is purified by reverse phase-high performance liquid chromatography (RP-HPLC) using an Ultro 120 (7 μm), 150×20 mm ID column (water-acetonitrile (10 mm NH$_4$OAc) solvent system, gradient mode from 10% ACN to 100% ACN in 50 min, 15 ml/min).

The N-protected acid of A11a (5 mg, 0.004) is dissolved in CH$_2$Cl$_2$ (1 mL) and the solution is cooled to 0° C. To this is added a 0.2 M solution of HCO$_2$H in CH$_2$Cl$_2$ (0.039 mL) and the reaction mixture is allowed to stir at ambient temperature overnight. After the volatiles are removed in vacuo, the free amino acid is purified by reverse phase-high performance liquid chromatography (RP-HPLC) using Ultro 120 (7 μm), 150×20 mm ID column (water-acetonitrile (10 mm NH$_4$OAc) solvent system, gradient mode from 10% ACN to 100% ACN in 50 min, 15 ml/min) to give compound 101a.

Example 1e
Synthesis of Compound (110a)
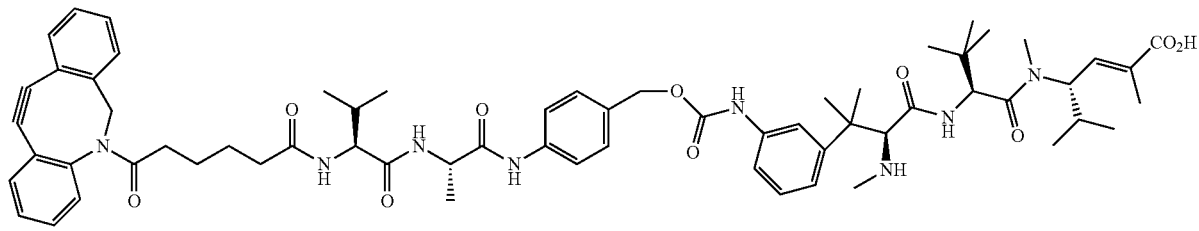 [SMILES: CN[C@H](C(=O)N[C@H](C(=O)N(C)[C@H](/C=C(\C)C(=O)O)C(C)C)C(C)(C)C)C(C)(C)c1cccc(NC(=O)OCc2ccc(NC(=O)[C@H](C)NC(=O)[C@@H](NC(=O)CCCCC(=O)N3Cc4ccccc4C#Cc4ccccc43)C(C)C)cc2)c1]
Compound (110a) is prepared according to Scheme 9.
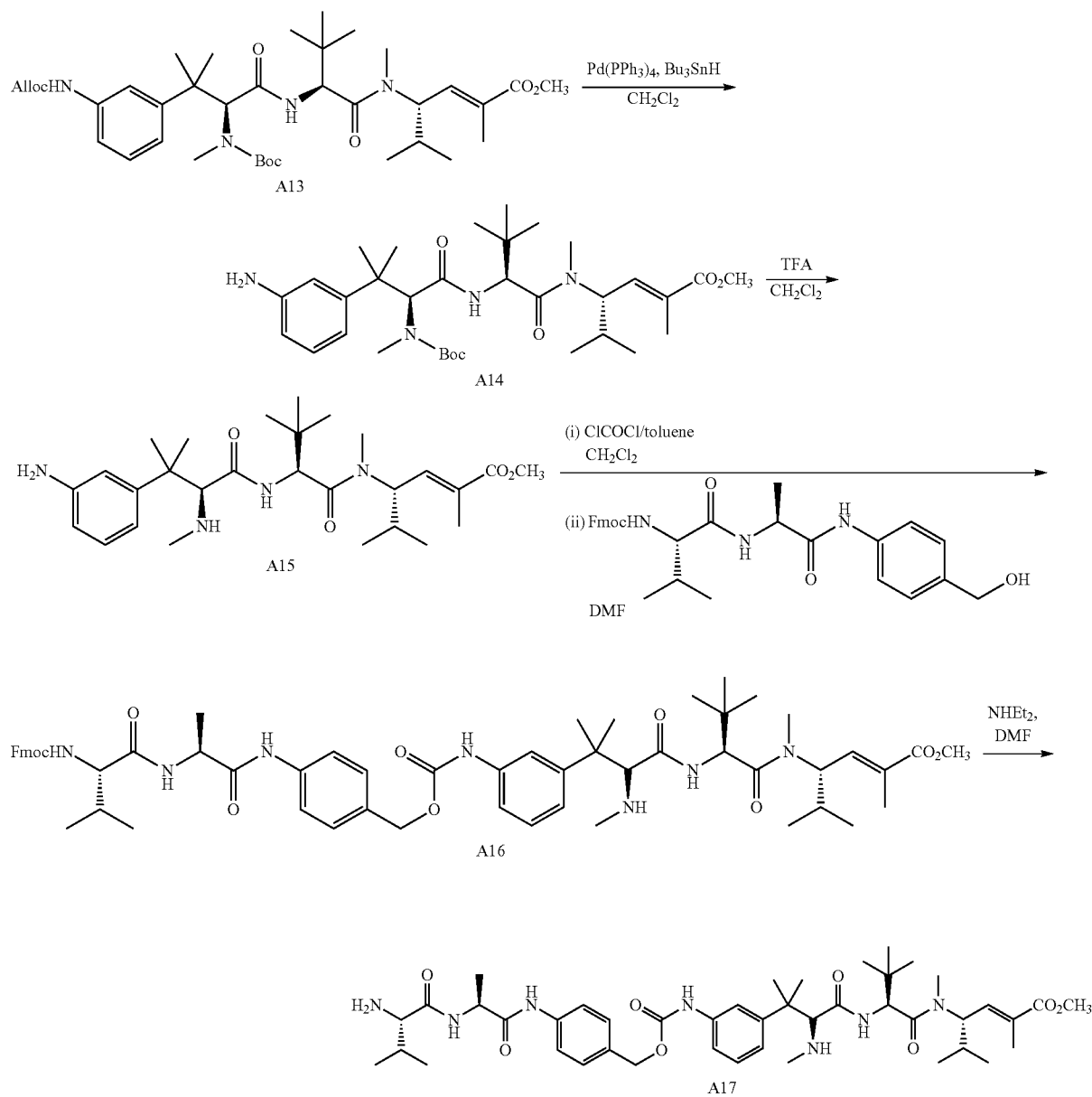

-continued

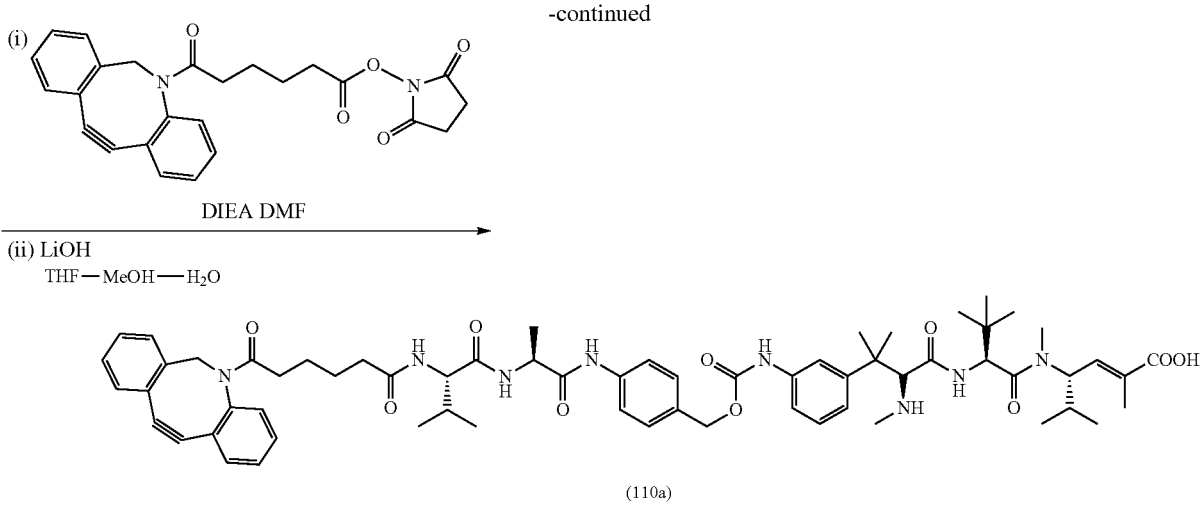

(110a)

Preparation of Compound A14

Compound A14 was prepared from compound A13 (using procedures similar to those described for compound A8a) by the method described for compound A9a. Yield: 379 mg (45%) as a white foam. MS (ESI) m/z 603 (M+H)$^+$; $^1$H NMR (400 MHz, CDCl$_3$) δ: 6.96-7.12 (m, 1H), 6.91 (br d, J=7.5 Hz, 1H), 6.83 (br s, 1H), 6.66-6.80 (m, 1H), 6.51-6.65 (m, 1H), 6.41-6.50 (m, 1H), 5.95 (br d, J=8.8 Hz, 1H), 5.33 (s, 1H), 4.94-5.11 (m, 1H), 4.92 (br s, 1H), 4.58 (br d, J=9.5 Hz, 1H), 4.48 (br d, J=8.5 Hz, 1H), 3.72 (br s, 1H), 3.67 (br s, 3H), 2.73-2.96 (m, 7H), 1.75-1.98 (m, 5H), 1.72 (br s, 1H), 1.49 (br s, 2H), 1.18-1.45 (m, 15H), 0.60-0.86 (m, 17H); $^{13}$C NMR (400 MHz, CDCl$_3$) δ: 171.2, 169.9, 168.2, 168.1, 157.1, 148.8, 146.9, 139.2, 139.0, 132.5, 132.2, 129.7, 116.6, 113.4, 79.8, 65.4, 55.9, 55.2, 52.0, 42.5, 42.5, 34.7, 34.3, 33.9, 31.0, 31.0, 30.2, 30.1, 28.3, 28.3, 26.5, 26.3, 26.2, 19.5, 19.4, 18.8, 18.5, 13.9, 13.8.

Preparation of Compound A15

To an argon-flushed, ice-cooled solution of A14 (63 mg, 0.1 mmol) in CH$_2$Cl$_2$ (0.8 mL) was added trifluoroacetic acid (0.2 mL, 2.6 mmol). The ice bath was removed, and the reaction was stirred at ambient temperature for 1 h. The volatiles were removed in vacuo to give A15 as a pale yellow glass that was used directly in the subsequent reaction. MS (ESI) m/z 503 (M+H)$^+$; $^1$H NMR (400 MHz, CDCl$_3$) δ 10.36 (br, 3H), 7.19-8.14 (m, 4H), 6.57 (br d, J=7.5 Hz, 1H), 5.02-4.45 (m, 3H), 3.68 (s, 3H), 2.97 (s, 3H), 2.38-2.48 (m, 3H), 1.74-1.80 s (m, 3H), 1.18-1.38 (m, 6H), 0.80-0.95 (m, 17H); $^{13}$C NMR (400 MHz, CDCl$_3$) δ: 170.9, 168.2, 161.5, 145.3, 139.2, 138.0, 131.5, 126.8, 122.3, 117.2, 86.9, 52.1, 40.9, 40.5, 35.3, 34.4, 33.6, 31.4, 29.7, 28.2, 28.3, 27.5, 26.5, 26.4, 26.3, 26.2, 19.1, 187, 18.4, 13.8.

Preparation of Compound A16

Compound A16 was prepared from compound A15 by the general method described for compound A10. Yield: 52 mg (50%) as a white foam. MS (ESI) m/z 1044 (M+H)$^+$; $^1$H NMR (400 MHz, CDCl$_3$) δ 9.10 (br, 1H), 7.84 (brd, J=7.8 Hz, 1H), 7.62 (d, J=7.6 Hz, 2H), 7.42-7.31 (m, 7H), 7.11-7.23 (m, 7H), 6.94-6.98 (m, 1H), 6.56 (d, J=8.0 Hz, 1H), 5.94-5.96 (m, 1H), 4.85-5.1 (m, 3H), 4.61-4.80 (m, 2H), 4.15 (t, J=7.3 Hz, 1H), 4.25 (t, J=7.0 Hz, 1H), 4.15 (t, J=7.1 Hz, 1H), 4.05 (t, J=7.0 Hz, 1H), 3.67 (s, 3H), 3.60 (d J=3.6 Hz, 1H), 2.89-3.05 (m, 5H), 1.80=2.09 (m, 10H), 1.28-1.36 (m, 10H), 0.66-0.99 (m, 17H); $^{13}$C NMR (400 MHz, CDCl$_3$) δ: 172.4, 172.0, 171.5, 170.9, 168.2, 156.7, 153.9, 147.9, 143.7, 143.6, 141.3, 138.9, 132.3, 129.2, 127.7, 127.0, 125.0, 120.67.1, 66.0, 54.7, 52.0, 49.6, 47.1, 41.2, 35.6, 35.1, 31.1, 31.0, 29.8, 29.2, 26.7, 21.7, 19.5, 19.3, 19.2, 19.0, 18.9, 18.1, 18.0, 13.8.

Preparation of compound A17

To an argon-flushed solution of A16 (52 mg, 0.05 mmol) in DMF (0.4 mL) was added N,N-diethylamine (0.2 mL, 5 mmol), and the reaction was stirred at ambient temperature 2 h. The volatiles were removed in vacuo, and the residue purified on silica gel (Biotage Isolera) using a gradient of 2-100% methanol in chloroform to yield 23 mg free amine as a white solid. This was further purified on RP-HPLC (×mm C18 5□□ using a linear gradient of 10 to 90% B in A over 20 minutes (A=10 mM NH$_4$OAc in water; B=10 mM NH$_4$OAc in CH$_3$CN) and detected at 254 and 280 nM to give A17 Yield 9.5 mg, 24%). MS (ESI) m/z 822 (M+H)$^+$; $^1$HNMR (400 MHz, CDCl$_3$) δ 9.11 (s, 1H), 7.73 (br, 1H), 7.81 (d, J=9.5 Hz, 1H), 7.48 (d, J=9.0 Hz, 2H), 7.01-7.3 (m, 4H), 6.57 (dd, J=1.4, 9.5 Hz, 1H), 5.07 (s, 2H), 5.04 (d, J=1.1 Hz, 1H), 4.72 (d, J=9.8 Hz, 1H), 4.6 (t, J=7.0 Hz, 1H), 3.6 (s, 3H), 3.63 (s, 1H), 3.24 (br, 1H), 3.05 (s, 1H), 3.01, (d J=6.3 Hz, 1H), 2.95 (s, 3H), 2.08 (br, 2H), 2.01 (s, 3H), 1.98 (s, 3H), 1.80-1.84 (m, 1H), 1.40 (d, J=6.2 Hz, 4H), 1.31 (s, 6H), 0.92-0.93 (m, 13H), 0.79 (d, J=6.6 Hz, 8H), 0.71 (d, J=6.6 Hz, 4H)

Preparation of (110a)

Under an argon atmosphere, compound A17 (9.8 mg, 0.012 mmol) was stirred with dibenzocyclooctynyladipoyl N-hydroxysuccinimidyl ester (Broadpharm 22447, 7.7 mg, 0.018 mmol) in DMF (0.150 mL). To this was added N,N-diisopropylethylamine (0.006 mL, 0.036 mmol) and the reaction was stirred at ambient temperature for 3 h. The volatiles were removed in vacuo, and the residue partially purified on silica gel using a gradient of 2 to 10% methanol in chloroform. The product-containing fractions were concentrated in vacuo to a residue MS m/z 1137.4. This residue (10.6 mg, 0.009 mmol), under an argon atmosphere, was dissolved in 3:1:1 THF: methanol: water (0.5 mL), cooled in an ice-bath, and treated with LiOH.H$_2$O (2.6 mg, 0.063 mmol). The reaction mixture was allowed to equilibrate to ambient temperature overnight. Volatiles were removed in vacuo and the residue purified by RP-HPLC as above to yield, after lyophilization, (110a), 2.1 mg, 0.002 mmol, as a flocculent white solid. MS (ESI) m/z 1123 (M+H)$^+$; $^1$HNMR (400 MHz, DMSO-d$_6$) δ: 10.02 (br d, J=3.8 Hz, 1H), 9.67 (br s, 1H), 8.25 (br d, J=6.8 Hz, 1H), 7.88 (br d, J=8.8 Hz, 1H), 7.79 (br d, J=8.3 Hz, 1H), 7.54-7.70 (m, 4H), 7.29-7.54 (m, 9H), 7.06-7.27 (m, 3H), 6.40-6.50 (m, 1H), 5.10 (s, 2H), 5.05 (br d, J=14.1 Hz, 1H), 4.91 (br t, J=10.2 Hz, 1H), 4.77 (br d, J=9.5 Hz, 1H), 4.25-4.49 (m, 2H), 4.06-4.24 (m, 2H), 3.60-2.99 (m, broad water envelope), 2.99 (m, 3H), 2.69-2.82 (m, 3H), 2.56-2.49 (m, DMSO envelope), 2.42 (br s, 1H), 2.12-2.29 (m, 3H), 1.90-2.11 (m, 6H), 1.73-1.90 (m, 6H), 1.15-0.76 (m, 18H), 0.72 (br d, J=6.3 Hz, 6H).

Example 1f

Synthesis of Compound (111a)

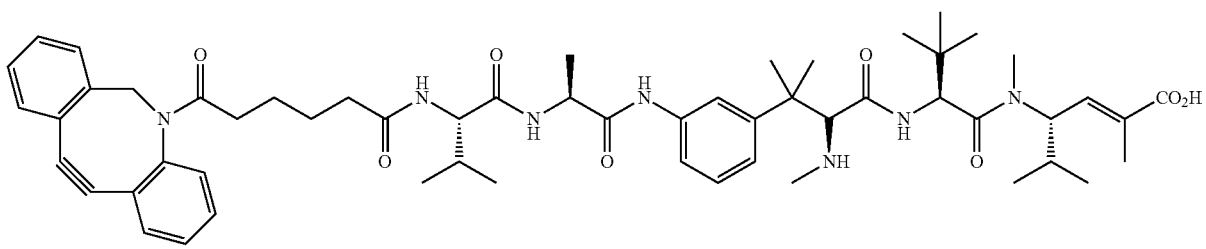

Compound (111a) was prepared according to Scheme 10.

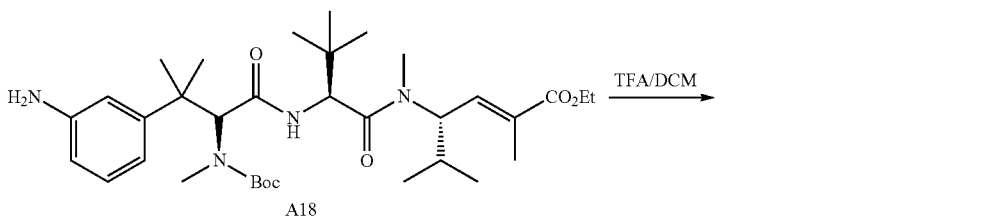

A18

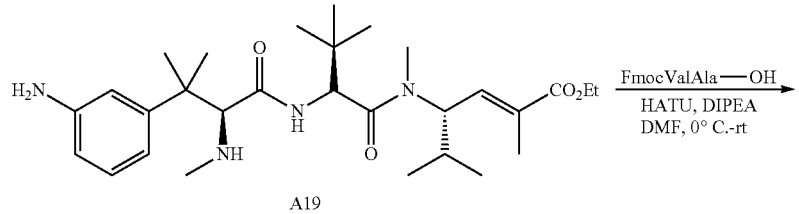

A19

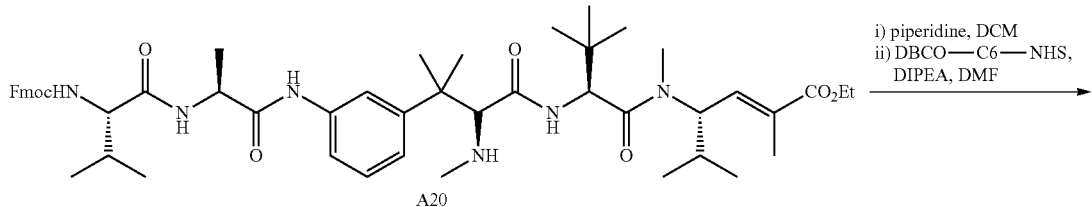

A20

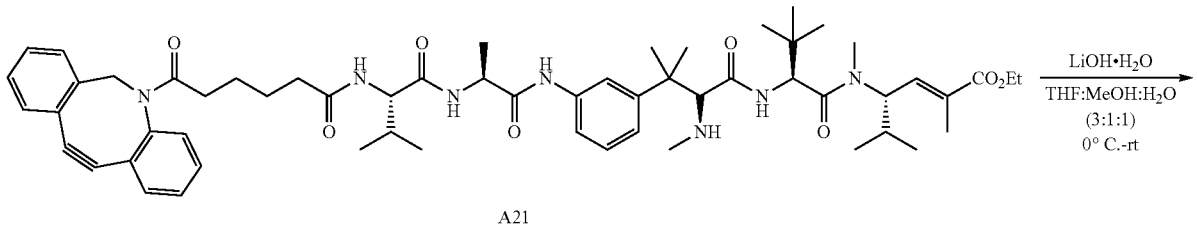

A21

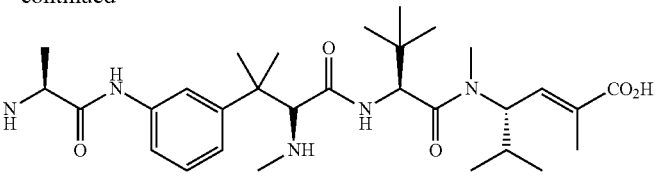

(111a)

Preparation of Compound A19: ethyl (S,E)-4-((R)-2-((S)-3-(3-aminophenyl)-3-methyl-2-(methylamino)butanamido)-N,3,3-trimethylbutanamido)-2,5-dimethylhex-2-enoate An oven-dried 50 mL single-necked round-bottomed flask equipped with a teflon-coated magnetic stir bar was charged with compound A18 (200 mg, 0.32 mmol, 1.0 eq) dry CH$_2$Cl$_2$ (3 mL) and the clear solution was cooled to 0° C. with an ice bath, to this 1 mL of Trifluoroacetic acid was added. The reaction mixture was allowed to stir 4 h at room temperature. After which LC-MS showed completion of the reaction. The solvent was removed under reduced pressure, and the crude material was lyophilized for 16 h to give compound A19 (167 mg, 100%) as an off-white solid. LC-MS (ESI): 517.5 (M+1).

Preparation of Compound A20: ethyl(S,E)-4-((S)-2-((R)-3-(3-((S)-2-((S)-2-((((9H-fluoren-9-yl)methoxy)carbonyl)amino)-3-methylbutanamido)propanamido)phenyl)-3-methyl-2-(methylamino)butanamido)-N,3,3-trimethylbutanamido)-2,5-dimethylhex-2-enoate To an oven-dried 50 mL single-necked round-bottomed flask equipped with a teflon-coated magnetic stir bar is charged with compound A19 (70 mg, 0.135 mmol, 1 eq), Fmoc-Valine-Alanine-OH (67 mg, 0.162 mmol, 1.2 eq) and 1 mL of anhydrous N,N-Dimethylformamide. The resulted clear solution was cooled to 0° C. with an ice bath, N,N-Diisopropylethylamine (72 μL, 0.405 mmol, 3 eq), 1-[Bis(dimethylamino)methylene]-1H-1,2,3-triazolo[4,5-b]pyridinium 3-oxid hexafluorophosphate (HATU) (62 mg, 0.162 mmol, 1.2 eq) were sequentially added to the reaction. The reaction mixture was allowed to stir at room temperature overnight under N$_2$ atmosphere. LC-MS showed completion of the reaction. The reaction was quenched by the addition of saturated NH$_4$Cl (10 mL) and then extracted with CH$_2$Cl$_2$ (2×100 mL). The organic layer was washed with saturated brine (50 mL), dried over anhydrous Na$_2$SO$_4$, filtered and then concentrated to dryness at reduced pressure. The crude product was purified by preparative reverse phase-high performance liquid chromatography using an Ultro 120 (7 μm) C18Q, 150×20 mm ID column. Solvent system used Solvent A: water containing 10 mm NH$_4$OAc; Solvent B: acetonitrile containing 10 mm NH$_4$OAc., Gradient mode from 10% Solvent B to 90% solvent B, over 20 minutes, 10 mL/min), pure fractions were collected and lyophilized to give the compound A20 (86 mg, 0.095 mmol, 70%) as a white solid. LC-MS (ESI): 909.5 (M+1).

Preparation of Compound A21

An oven-dried 25 mL single-necked round-bottomed flask equipped with a teflon-coated magnetic stir bar was charged with compound A20 (80 mg, 0.088 mmol), dry CH$_2$Cl$_2$ (2 mL), to this clear solution was added piperidine (0.5 mL) and the reaction mixture was stirred at ambient temperature for 1 h under N$_2$ atm. LC-MS showed completion of the reaction, all volatiles were removed under reduced pressure. The crude free amine was purified by preparative reverse phase-high performance liquid chromatography using an Ultro 120 (7 μm) C18Q, 150×20 mmID column. Solvent system used Solvent A: water containing 10 mm NH$_4$OAc; Solvent B: acetonitrile containing 10 mm NH$_4$OAc, Gradient mode from 10% Solvent B to 90% solvent B, over 20 minutes, 10 mL/min), pure fractions were collected and lyophilized to give the free amine A20a (51 mg, 0.074 mmol, 85%) as a white solid. LC-MS (ESI): 688 (M+1).

An oven-dried 25 mL single-necked round-bottomed flask equipped with a teflon-coated magnetic stir bar was charged with the free amine A20a (51 mg, 0.074 mmol). DBCO adipinyl N-hydroxysuccinimidyl ester (41 mg, 0.096 mmol), anhydrous N,N-Dimethylformamide (0.5 mL), and N,N-Diisopropylethylamine (40 μL, 0.22 mmol) were sequentially added. The reaction mixture was flushed with Argon and stirred at ambient temperature for 3 hours under N$_2$ atm. LC-MS showed completion of the reaction. After removal of all volatiles in vacuo, the residue was purified by reverse phase-high performance liquid chromatography using a Ultro 120 (7 μm) C18Q, 150×20 mm ID column Solvent system used Solvent A: water containing 10 mm NH$_4$OAc; Solvent B: acetonitrile containing 10 mm NH$_4$OAc., Gradient mode from 10% B Solvent to 90% solvent B, over 20 minutes, 10 mL/min), pure fractions were collected and lyophilized to give compound A21a (52 mg, 0.052 mmol, 70%) as a white powder. LC-MS (ESI): 1003.8 (M+1).

Preparation of Compound (111a)

An oven-dried 25 mL single-necked round-bottomed flask equipped with a teflon-coated magnetic stir bar is charged with compound A21 (50 mg, 0.05 mmoles, 1 equiv.), THF:MeOH:H$_2$O (3:1:1) (1 mL). The clear solution was cooled to 0° C. with an ice bath. Solid LiOH.H$_2$O (16 mg, 0.349 mmol, 7 eq) was added and the reaction was allowed to stir at room temperature under N$_2$ atm for 7 h, after which LC-MS showed completion of the reaction, the volatiles were removed in vacuo, and the crude material was purified by reverse phase-high performance liquid chromatography using Ultro 120 (7 μm) C18Q, 150×20 mmID column, Solvent system used Solvent A: water containing 10 mm NH$_4$OAc; Solvent B: acetonitrile containing 10 mm NH$_4$OAc., Gradient elution mode from 10% Solvent B to 90% solvent B, over 20 minutes, 10 mL/min), pure fractions were collected and lyophilized to give compound (111a) (34 mg, 0.034 mmol, 70%) as a white powder. LC-MS (ESI): 974.5 (M+1). $^1$HNMR (400 MHz, DMSO-d6) δ 9.78-9.63 (bd, 1H), 8.34-8.10 (m, 1H), 7.82-7.68 (2H), 7.58-7.35 (m, 8H), 7.34-7.18 (m, 4H), 7.16-7.08 (m, 4H), 6.53-6.52 (m, 1H) 4.98-4.93 (m, 1H), 4.85 (m, 1H), 4.71 (brd, 1H), 4.36-4.26 (m, 1.5H), 4.09-4.04 (m, 1H), 3.67-3.47 (m, 2H), 3.12 (brd, 1H), 2.91-2.87 (m, 3H), 2.13-2.02 (m, 2H), 1.96-1.78 (m, 9H), 1.74-1.61 (m, 5H), 1.31-1.03 (m, 16H), 0.90-0.67 (m, 15H).

Example 1 g

Synthesis of Compound (109a

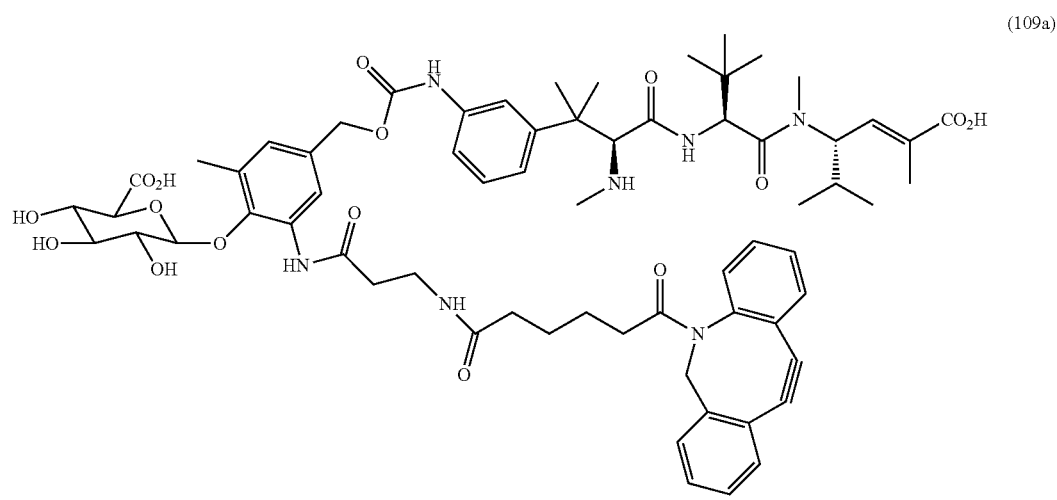 [SMILES: CN[C@H](C(=O)N[C@H](C(=O)N(C)[C@H](/C=C(\C)C(=O)O)C(C)C)C(C)(C)C)C(C)(C)c1cccc(NC(=O)OCc2cc(C)c(OC3OC(C(=O)O)C(O)C(O)C3O)c(NC(=O)CCNC(=O)CCCCC(=O)N3Cc4ccccc4C#Cc4ccccc43)c2)c1]

(109a)

Compound (109a) was prepared according to Scheme 11a and 11b.

Scheme 11a

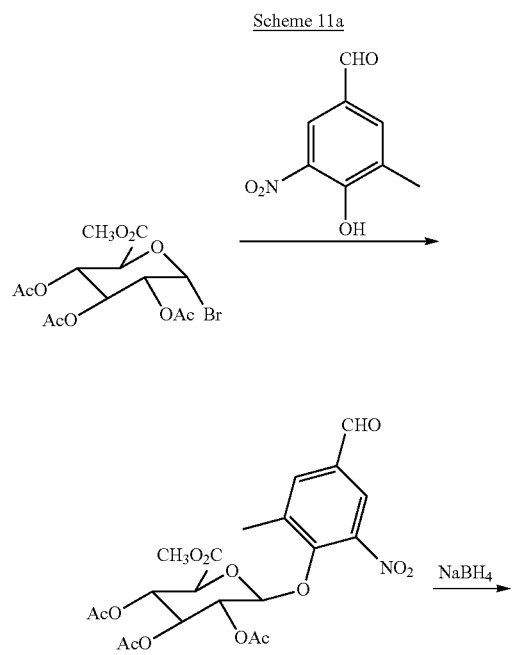

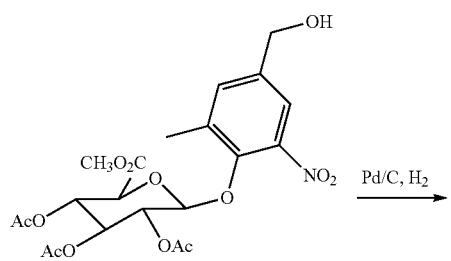

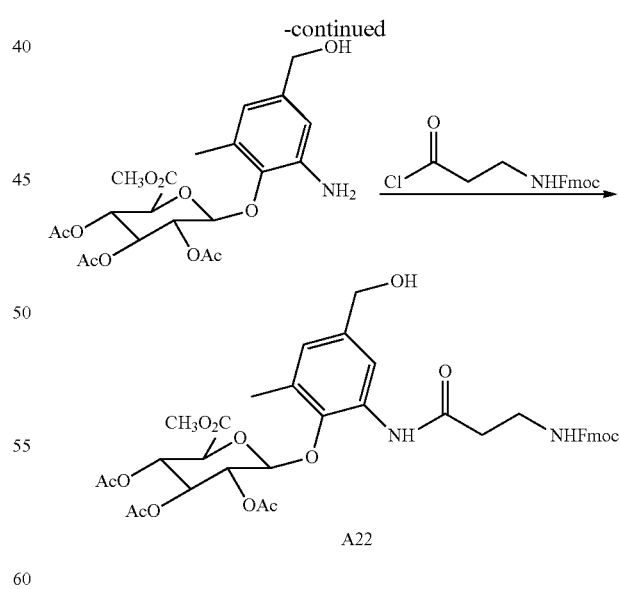

Preparation of A22

A22 was prepared by a straightforward adaptation of literature methods. (See, for example, Florent et al 1998, *J Med Chem* 41, 3572; and Jeffrey et al 2006, *Biocong Chem* 17, 831). LC-MS: $T_R$ 9.21 min. m/z 763 (M+H)$^+$.

Scheme 11b

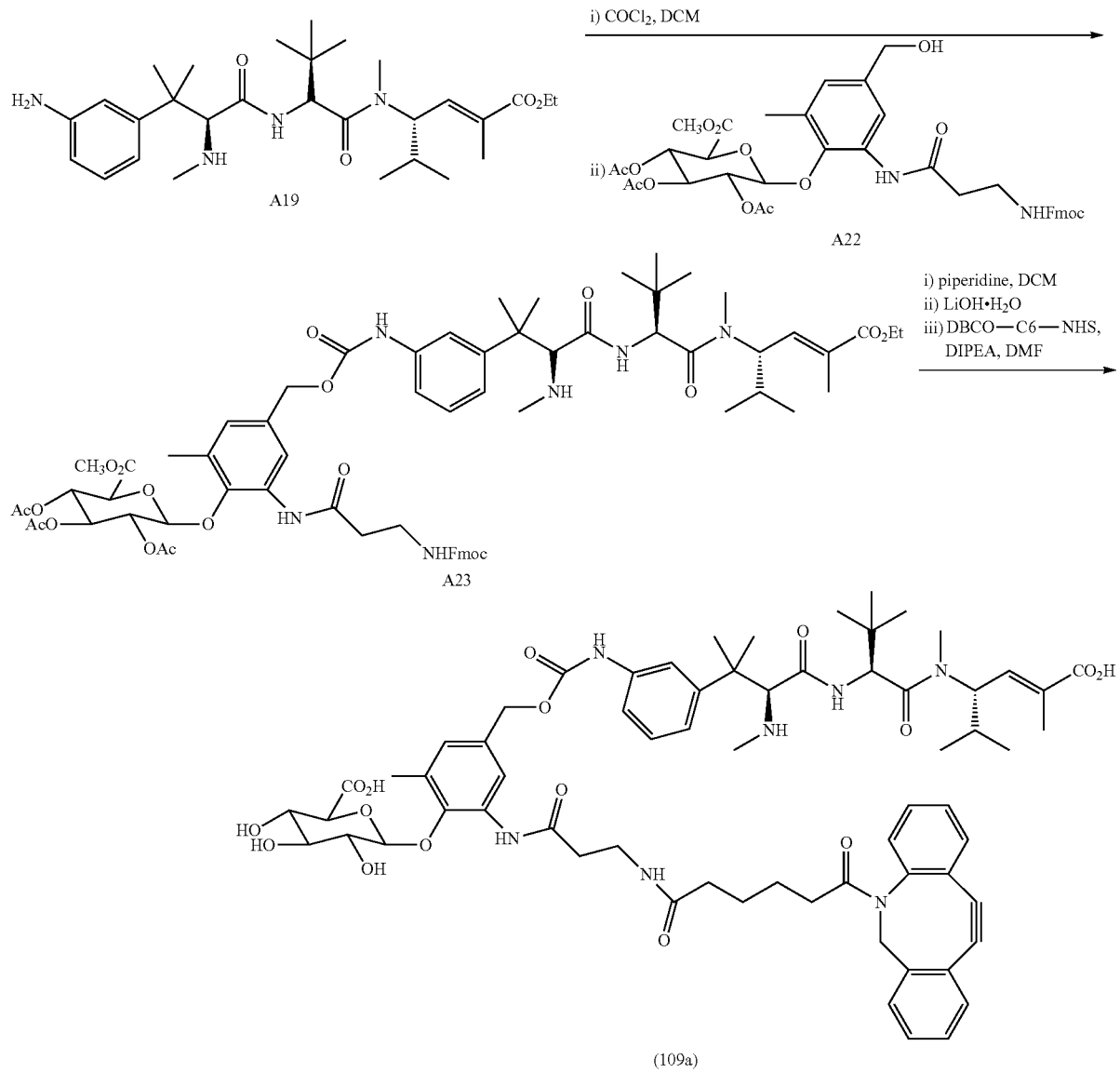

Preparation of Compound A23: (2S,3R,5S,6S)-2-(2-(3-(((((9H-fluoren-9-yl)methoxy)carbonyl)amino)propanamido)-4-((((3-((R)-4-(((S)-1-(((S,E)-6-ethoxy-2,5-dimethyl-6-oxohex-4-en-3-yl)(methyl)amino)-

3,3-dimethyl-1-oxobutan-2-yl)amino)-2-methyl-3-(methylamino)-4-oxobutan-2-yl)phenyl)carbamoyl)oxy)methyl)-6-methylphenoxy)-6-(methoxycarbonyl)tetrahydro-2H-pyran-3,4,5-triyl triacetate To an oven-dried 25 mL pressure vessel equipped with a teflon-coated magnetic stir bar is charged with compound A19 (25 mg, 0.048 mmol, 1 eq) and 1 mL of anhydrous CH$_2$Cl$_2$, to this was added 15% w/v phosgene in toluene (0.7 mL) at rt. The reaction mixture was flushed with Argon and it was stirred in a sealed vessel for 17 h at rt, then concentrated under reduced pressure to remove volatiles, and dried under high vacuum for at least 2 hours. To this residue was added compound A22 (44 mg, 0.058 mmol, 1.2 eq). This mixture was dissolved in 1 mL of anhydrous N,N-Dimethylformamide. The reaction mixture was stirred at 45° C. for 2 h, then at ambient temperature for 12 h. After removal of all volatiles in vacuo the residue was purified by reverse phase-high performance liquid chromatography using Ultro 120 (7 μm) C18Q, 150×20 mmID column, Solvent system used Solvent A: water containing 10 mm NH$_4$OAc; Solvent B: acetonitrile containing 10 mm NH$_4$OAc., Gradient elution mode from 10% Solvent B to 90% solvent B, over 20 minutes, 10 mL/min), pure fractions were collected and lyophilized to give compound A23 (25 mg, 0.019 mmol, 70%) as a white powder. LC-MS (ESI): 1305.8 (M+1).

Preparation of Compound (109a)

An oven-dried 25 mL single-necked round-bottomed flask equipped with a teflon-coated magnetic stir bar was charged with compound A23 (23 mg, 0.018 mmol), dry $CH_2Cl_2$ (0.5 mL), to this clear solution was added piperidine (0.2 mL) and the reaction mixture was stirred at ambient temperature for 1 h under $N_2$ atm, all volatiles were removed under reduced pressure. The crude product was dissolved in THF: $MeOH:H_2O$ (3:1:1) (1 mL). The clear solution was cooled to 0° C. with an ice bath. Solid $LiOH.H_2O$ (8 mg, 0.176 mmol, 10 eq) was added and the reaction was allowed to stir at room temperature under $N_2$ atm for 7 h, after which LC-MS showed completion of the reaction, the volatiles were removed in vacuo, and the crude material was purified by reverse phase-high performance liquid chromatography using Ultro 120 (7 µm) C18Q, 150×20 mmID column, Solvent system used Solvent A: water containing 10 mm $NH_4OAc$; Solvent B: acetonitrile containing 10 mm $NH_4OAc$., Gradient elution mode from 10% Solvent B to 90% solvent B, over 20 minutes, 10 mL/min), pure fractions were collected and lyophilized to give compound A23a (8 mg, 0.009 mmol, 50%) as a white powder. LC-MS (ESI): 915.7 (M+H), 897.7 (M−H$_2$O+H)

An oven-dried 10 mL single-necked round-bottomed flask equipped with a teflon-coated magnetic stir bar was charged with the free amine A23a (8 mg, 0.009 mmol). DBCO adipinyl N-hydroxysuccinimidyl ester (5 mg, 0.011 mmol), anhydrous N,N-Dimethylformamide (0.3 mL), and N,N-Diisopropylethylamine (10 µL, 0.033 mmol) were sequentially added. The reaction mixture was flushed with Argon and stirred at ambient temperature for 3 hours under $N_2$ atm. LC-MS showed completion of the reaction. After removal of all volatiles in vacuo, the residue was purified by reverse phase-high performance liquid chromatography using a Ultro 120 (7 µm) C18Q, 150×20 mmID column Solvent system used Solvent A: water containing 10 mm $NH_4OAc$; Solvent B: acetonitrile containing 10 mm $NH_4OAc$., Gradient mode from 10% B Solvent to 90% solvent B, over 20 minutes, 10 mL/min), pure fractions were collected and lyophilized to give compound (109a) (5 mg, 0.004 mmol, 50%) as a white powder. LC-MS (ESI): 1230.8 (M+H), 1212.8 (M−H$_2$O+H). $^1$HNMR (400 MHz, DMSO-d6) δ 9.61-9.55 (m, 2H), 7.85 (bs, 2H), 7.80 (bd, 1H), 7.61-6.97 (m, 15H), 6.64-6.50 (m, 2H), 6.02 (bs, 1H), 5.48 (bs, 1H), 5.17-4.89 (m, 6H), 4.85-4.76 (bt, 1H), 4.71-4.62 (m, 1H), 4.01 (bs, 1H), 3.69-3.66 (m, 3H), 3.10 (bs, 2H), 2.89 (bs, 3H), 2.29-2.26 (m, 19H), 2.13-2.00 (m, H), 1.96-1.56 (m, 18H), 1.80-1.02 (m, 14H), 0.89 (bs, 10H), 0.70 (d, 3H), 0.66 (d, 3H).

Example 1 h

Synthesis of Compound (111a)

Compound (111a) was prepared according to Schemes 12 and 13.

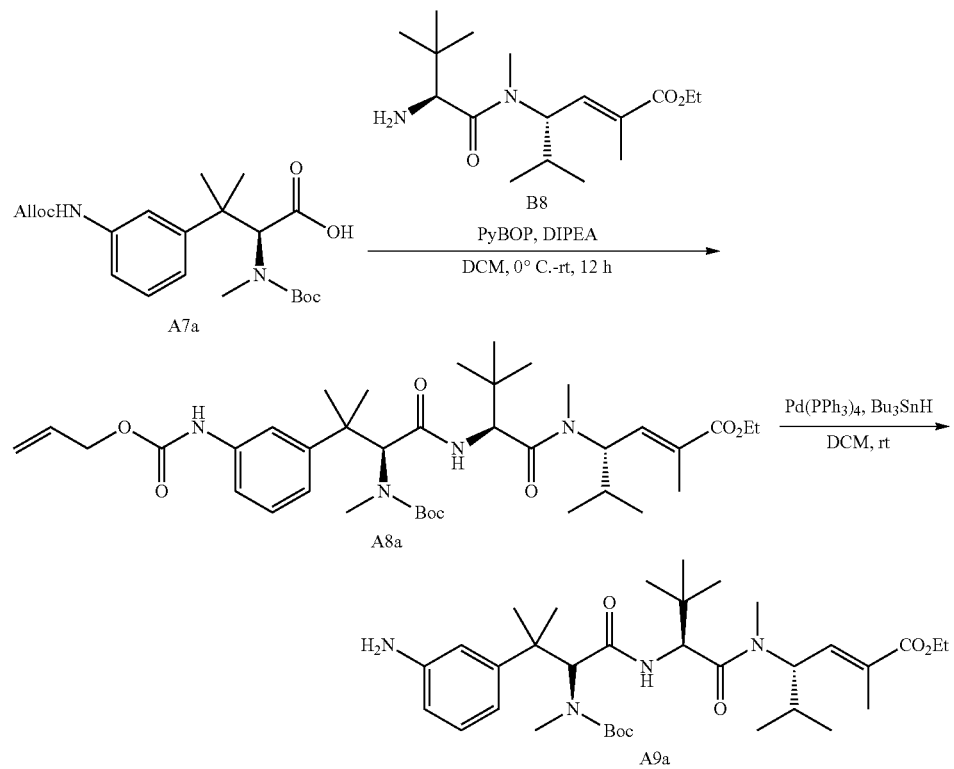

Scheme 12

Preparation of Compound A8a: ethyl (6S,9S,12S, E)-6-(2-(3-(((allyloxy)carbonyl)amino)phenyl)propan-2-yl)-9-(tert-butyl)-12-isopropyl-2,2,5,11,14-pentamethyl-4,7,10-trioxo-3-oxa-5,8,11-triazapentadec-13-en-15-oate An oven-dried 100 mL single-necked round-bottomed flask equipped with a teflon-coated magnetic stir bar is charged with compound A7a (1.1 g, 2.70 mmoles, 1 equiv, prepared internally), dry $CH_2Cl_2$ (10 mL) and compound B8

(1.00 g, 3.24 mmoles, 1.2 equiv., prepared internally) in dry CH$_2$Cl$_2$ (10 mL). The resulted clear solution was cooled to 0° C. with an ice bath, N,N-Diisopropylethylamine (1.5 mL, 8.1 mmoles, 3 equiv.,) and (benzotriazol-1-yloxy)tripyrrolidinophosphonium hexafluorophosphate (PyBOP, 1.7 g, 3.24 mmol, 1.2 equiv.,) were sequentially added to the cooled solution. The reaction mixture was allowed to stir at room temperature overnight under N$_2$ atmosphere. LC-MS showed completion of the reaction. The reaction was quenched by the dropwise addition of saturated NH$_4$Cl (10 mL) and then extracted with CH$_2$Cl$_2$ (2×200 mL). The organic layer was washed with saturated brine (50 mL), dried over anhydrous Na$_2$SO$_4$ filtered and then concentrated to dryness at reduced pressure. The crude product was purified by flash silica column chromatography on a Teledyne ISCO system (40 g silica flash column, gradient: Hexane to 30% EtOAc/Hexane) to give compound A8a (1.2 g, 1.71 mmol, 63%) as a colorless viscous oil which slowly solidifies to give an off-white solid upon standing. LC-MS (ESI): 701.5 (M+1).

Preparation of Compound A9a: Ethyl (6R,9S,12S, E)-6-(2-(3-aminophenyl)propan-2-yl)-9-(tert-butyl)-12-isopropyl-2,2,5,11,14-pentamethyl-4,7,10-trioxo-3-oxa-5,8,11-triazapentadec-13-en-15-oate An oven-dried 100 mL single-necked round-bottomed flask equipped with a teflon-coated magnetic stir bar is charged with compound A8a (1.2 g, 1.71 mmols, 1.0 equiv, prepared internally), dry CH$_2$Cl$_2$ (10 mL). To this clear solution, tetrakis(triphenylphosphine)palladium(O) (0.98 g, 0.856 mmoles, 0.5 equiv.,) and tri-n-butyl-tin hydride (0.55 mL, 2.05 mmoles, 1.2 equiv.,) were sequentially added at room temperature under N$_2$ atmosphere. Upon completion of addition, the reaction mixture was flushed with argon and then stirred at room temperature under a N$_2$ atmosphere. LC-MS & TLC (1:1 EtOAc/Hexane) showed the reaction was complete in 4 hours. The solvent was removed under reduced pressure and the resulting crude material was purified by flash column chromatography on a Teledyne ISCO system (40 g silica flash column, gradient: Hexane to 50% EtOAc/Hexane) to give compound A9a (0.95 g, 1.54 mmole, yield: 90%) as a foamy off-white solid. LC-MS (ESI): 617.3 (M+1).

Scheme 12

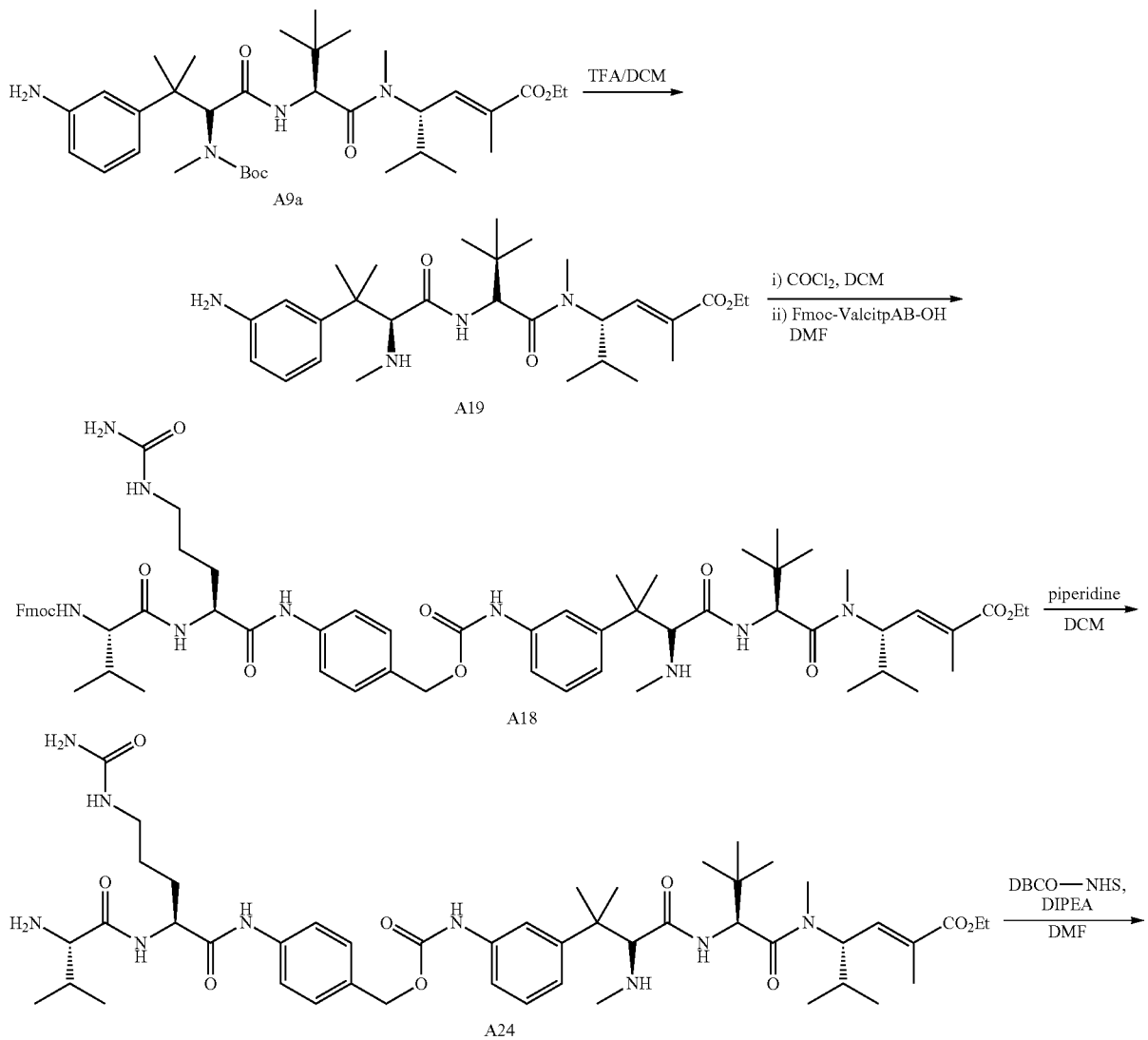

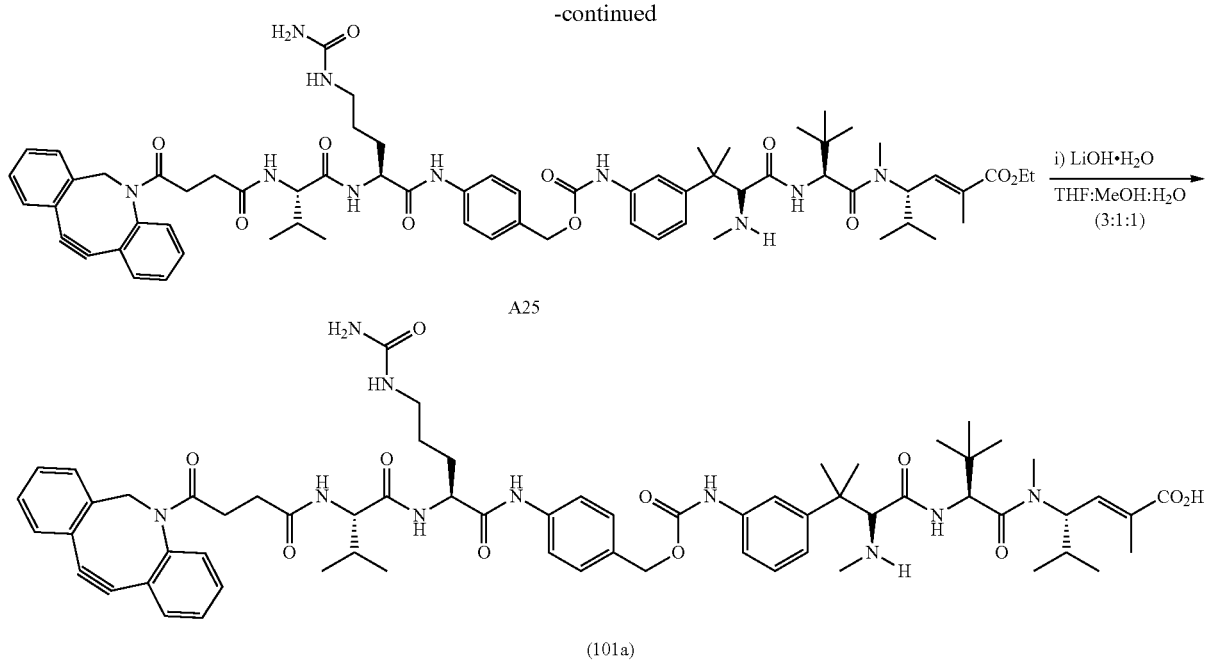

A25

(101a)

Preparation of Compound A19: ethyl (S,E)-4-((R)-2-((S)-3-(3-aminophenyl)-3-methyl-2-(methylamino)butanamido)-N,3,3-trimethylbutanamido)-2,5-dimethylhex-2-enoate An oven-dried 50 mL single-necked round-bottomed flask equipped with a teflon-coated magnetic stir bar was charged with compound A9a (200 mg, 0.32 mmol, 1.0 eq) dry $CH_2Cl_2$ (3 mL) and the clear solution was cooled to 0° C. with an ice bath, to this 1 mL of Trifluoroacetic acid was added. The reaction mixture was allowed to stir 4 h at room temperature. After which LC-MS showed completion of the reaction. The solvent was removed under reduced pressure, and the crude material was lyophilized for 16 h to give compound A19 (167 mg, 100%) as an off-white solid. LC-MS (ESI): 517.5 (M+1).

Preparation of Compound A18: ethyl (S,E)-4-((S)-2-((R)-3-(3-((((4-((S)-2-((S)-2-((((9H-fluoren-9-yl)methoxy)carbonyl)amino)-3-methylbutanamido)-5-ureidopentanamido)benzyl)oxy)carbonyl)amino)phenyl)-3-methyl-2-(methylamino)butanamido)-N,3,3-trimethylbutanamido)-2,5-dimethylhex-2-enoate To an oven-dried 50 mL pressure vessel equipped with a teflon-coated magnetic stir bar is charged with compound A19 (167 mg, 0.323 mmol, 1 eq) (**Note: compound A19 was dried under lyophilizer pump for 15 h prior to use) and 4 mL of anhydrous $CH_2Cl_2$ to this was added 15% w/v phosgene in toluene (5 mL) at rt. The reaction mixture was flushed with Argon and it was stirred in a sealed vessel for 17 h at rt, then concentrated under reduced pressure to remove volatiles, and dried under high vacuum for at least 2 hours. To this residue was added Fmoc valine-citruline-p-aminobenzyl alcohol (253 mg, 0.42 mmol, 1.3 eq). This mixture was dissolved in 3 mL of anhydrous N,N-Dimethylformamide. The reaction mixture was stirred at 45° C. for 2 h, then at ambient temperature for 12 h. After removal of all volatiles in vacuo the residue was purified by flash column chromatography on a Teledyne ISCO (24 g silica flash column, gradient: $CH_2Cl_2$ to 12% $MeOH/CH_2Cl_2$) to give compound A18 (247 mg, 0.215 mmol, 67%) as an off-white solid. LC-MS (ESI): 1144.7 (M+1).

Preparation of Compound A25

An oven-dried 50 mL single-necked round-bottomed flask equipped with a teflon-coated magnetic stir bar was charged with compound A18 (240 mg, 0.209 mmol), dry $CH_2Cl_2$ (5 mL), to this clear solution was added piperidine (1.5 mL) and the reaction mixture was stirred at ambient temperature for 1 h under $N_2$ atm. LC-MS showed completion of the reaction, all volatiles were removed under reduced pressure. The crude free amine was purified by preparative reverse phase-high performance liquid chromatography using an Ultro 120 (7 µm) C18Q, 150×20 mmID column. Solvent system used Solvent A: water containing 10 mm $NH_4OAc$; Solvent B: acetonitrile containing 10 mm $NH_4OAc.$, Gradient mode from 10% Solvent B to 90% solvent B, over 20 minutes, 10 mL/min), pure fractions were collected and lyophilized to give the free amine A24 (164 mg, 0.177 mmol, 85%) as a white solid.

An oven-dried 50 mL single-necked round-bottomed flask equipped with a teflon-coated magnetic stir bar was charged with the free amine A24 (164 mg, 0.177 mmol). DBCO succinyl N-hydroxysuccinimidyl ester (126 mg, 0.313 mmol), anhydrous N,N-Dimethylformamide (3 mL), and N,N-Diisopropylethylamine (110 µL, 0.627 mmol) were sequentially added. The reaction mixture was flushed with Argon and stirred at ambient temperature for 3 hours under $N_2$ atm. LC-MS showed completion of the reaction. After removal of all volatiles in vacuo, the residue was purified by reverse phase-high performance liquid chromatography using a Ultro 120 (7 µm) C18Q, 150×20 mmID column Solvent system used Solvent A: water containing 10 mm $NH_4OAc$; Solvent B: acetonitrile containing 10 mm $NH_4OAc.$, Gradient mode from 10% B Solvent to 90% solvent B, over 20 minutes, 10 mL/min), pure fractions were collected and lyophilized to give compound A25 (177 mg, 0.146 mmol, 70%) as a white powder. LC-MS (ESI): 1209.6 (M+1).

An oven-dried 25 mL single-necked round-bottomed flask equipped with a teflon-coated magnetic stir bar is charged with compound A25 (177 mg, 0.146 mmoles, 1 equiv.), THF:MeOH:H$_2$O (3:1:1) (5 mL). The clear solution was cooled to 0° C. with an ice bath. Solid LiOH.H$_2$O (46 mg, 1.022 mmol, 7 eq) was added and the reaction was allowed to stir at room temperature under N$_2$ atm for 7 h, after which LC-MS showed completion of the reaction, the volatiles were removed in vacuo, and the crude material was purified by reverse phase-high performance liquid chromatography using Ultro 120 (7 μm) C18Q, 150×20 mmID column, Solvent system used Solvent A: water containing 10 mm NH$_4$OAc; Solvent B: acetonitrile containing 10 mm NH$_4$OAc., Gradient elution mode from 10% Solvent B to 90% solvent B, over 20 minutes, 10 mL/min), pure fractions were collected and lyophilized to give compound (101a) (138 mg, 0.117 mmol, 80%) as a white powder. LC-MS (ESI): 1181.5 (M+1).

Example 1i

Antibodies were expressed in a Xpress CF™ reaction using procedures know to one of skill in the art. (See, for example, Cai et al. Biotechnol. 2015, 31(3), 823; and Zimmerman et al. Bioconjugate Chem. 2014, 25, 351.) The cell free extract for this work were created from an OmpT sensitive RF1 attenuated E. coli strain engineered to over-express E. coli DsbC and FkpA as well as an orthogonal tRNA containing the CUA anti-codon for decoding the Amber Stop Codon. Extract was treated with 75 μM iodo-acetamide for 45 min at RT (20° C.) and added to a premix containing all other components, except for IgG heavy and light chain DNA. The final concentration in the protein synthesis reaction was 30% (v/v) cell extract, 2 mM para-azidomethylphenylalanine (pAMF) (RSP Amino Acids), 5 uM engineered pAMF-specific amino-acyl tRNA synthetase (FRS variant), 2 mM GSSG, 8 mM magnesium glutamate, 10 mM ammonium glutamate, 130 mM potassium gluta-mate, 35 mM sodium pyruvate, 1.2 mM AMP, 0.86 mM each of GMP, UMP, and CMP, 2 mM amino acids (except 0.5 mM for Tyrosine and Phenylalanine), 4 mM sodium oxalate, 1 mM putrescine, 1.5 mM spermidine, 15 mM potassium phosphate, 100 nM T7 RNAP, 1 μg/mL antiCD74 light chain DNA, and 4 μg/mL antiCD74 heavy chain DNA. Site directed mutagenesis was used to introduce an amber stop codon (TAG) into the nucleotide sequence to encode for the pAMF non-natural amino acid at positions S7 and F404 (light and heavy chains respectively, kabat numbering). Cell free reactions were initiated by addition of plasmid DNA and incubated at 30° C. for 16 h in 100×10 mm petri dishes containing 10 mL.

The cell free reactions were clarified by centrifugation at 10,000 rpm's for 30 minutes. The clarified supernatant was applied to Protein A MabSelect SuRe (GE Healthcare) with standard wash and low pH elution. Impurities such as aggregates were removed via preparative SEC (Sepax SRT-10C) equilibrated in 50 mM sodium phosphate, 200 mM arginine, pH 6.5. Final formulation of the sample was done in Dulbecco's Phosphate Buffered Saline (1×DPBS).

Purified IgGs containing pAMF were conjugated to a cytotoxic test compound using copper-free click chemistry with strained cyclooctyne reagent (SpAAC, strain-promoted alkyne azide cycloaddition). In brief, test compounds were dissolved in DMSO to a final concentration of 5 mM. Each compound was added to 1 mg/mL purified protein in PBS at a drug-linker to antibody molar ratio of 12 to 1. The reaction mixture was incubated at RT (20° C.) for 17 hours. Excess free drug was removed by Zeba plate (Thermo Scientific) equilibrated in PBS. DAR analysis was done by MALDI-TOF (Bruker AutoFlex Speed). The conjugated protein was reduced for 10 min at 37° C. with 10 mM TCEP in water and diluted to a final concentration of 50 μg/mL in 30% acetoni-trile, 0.1% trifluoroacetic acid. Samples were combined 1:1 with S-DHB MALDI matrix (50 mg/mL in 50% acetonitrile, 0.1% trifluoroacetic acid) and 1 μL was applied to the MALDI target and dried under vacuum. Each MALDI spectra was accumulated for 5000 shots at full laser power in linear mode and the final DAR analysis was calculated by comparing the relative peak intensity for conjugated and unconjugated species.

Example 1j

Conjugates of Compound 1 with trastuzumab were pre-pared as described below.

Compound 101 or 101a was dissolved in DMSO to a concentration of 5 mM. The solution was added to purified C225 HC C-term antibody in PBS buffer to a final com-pound concentration of 200 μM and a final antibody con-centration of 3 mg/mL (20 μM) for a 10:1 molar ratio of compound:antibody. The mixture was incubated at ambient temperature (25° C.) for 16 h. The excess compound was removed using zeba plates (Thermo Scientific) equilibrated in 1×PBS.

This procedure was used to conjugate compounds 101 and 101a to trastuzumab HC at F404 and to trastuzumab LC at S7.

To make trastuzumab containing a reactive azide group for conjugation, DNA encoding the molecule's, heavy and light chains were cloned into pUG expression vector. A TAG codon was inserted at the indicated positions by overlapping PCR. Stop codon TAA was used to terminate translation.

To express protein, cell-free extracts were thawed to room temperature and incubated with 50 μM iodoacetamide for 30 min. Cell-free reactions were run at 30 C for up to 16 h containing 30% (v/v) iodoacetamide-treated extract with 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids for all 18 amino acids except tyrosine and phenylalanine which were added at 0.5 mM, 4 mM sodium oxalate, 1 mM putrescine, 1.5 mM spermidine, 15 mM potassium phosphate,100 nM T7 RNAP, 2 mM oxidized (GSSG) glutathione, 2 mM pAzidoMethylPhenylanine (pAMF), 2.5 μM amber suppressor tRNA synthetase. The concentrations of heavy chain TAG variant plasmid and wild type light chain plasmid were 7.5 ug/mL and 2.5 ug/mL respectively.

The antibodies containing non natural amino acids were purified by MabSelect and polished by Capto adhere and stored in PBS buffer before use.

The anti-CD74 cell free reactions were clarified by cen-trifugation at 10,000 rpm's for 30 minutes. The clarified supernatant was applied to Protein A MabSelect SuRe (GE Healthcare) with standard wash and low pH elution. Impu-rities such as aggregates were removed via preparative SEC (Sepax SRT-10C) equilibrated in 50 mM sodium phosphate, 200 mM arginine, pH 6.5. Final formulation of the sample was done in Dulbecco's Phosphate Buffered Saline (1×DPBS).

Example 1k

Production of Anti-CD74 Antibodies with Non-Natural Amino Acids

Antibodies were expressed in an Xpress CF™ reaction as described previously with the following modifications. The cell free extract for this work were created from an OmpT sensitive RF1 attenuated *E. coli* strain engineered to overexpress *E. coli* DsbC and FkpA as well as an orthogonal tRNA containing the CUA anti-codon for decoding the Amber Stop Codon. Extract was treated with 75 μM iodoacetamide for 45 min at RT (20° C.) and added to a premix containing all other components, except for IgG heavy and light chain DNA. The final concentration in the protein synthesis reaction was 30% (v/v) cell extract, 2 mM para-azidomethylphenylalanine (pAMF) (RSP Amino Acids), 5 uM engineered pAMF-specific amino-acyl tRNA synthetase (FRS variant), 2 mM GSSG, 8 mM magnesium glutamate, 10 mM ammonium glutamate, 130 mM potassium glutamate, 35 mM sodium pyruvate, 1.2 mM AMP, 0.86 mM each of GMP, UMP, and CMP, 2 mM amino acids (except 0.5 mM for Tyrosine and Phenylalanine), 4 mM sodium oxalate, 1 mM putrescine, 1.5 mM spermidine, 15 mM potassium phosphate, 100 nM T7 RNAP, 1 μg/mL antiCD74 light chain DNA, and 4 μg/mL antiCD74 heavy chain DNA. Site directed mutagenesis was used to introduce an amber stop codon (TAG) into the nucleotide sequence to encode for the pAMF non-natural amino acid at positions S7 and F404 (light and heavy chains respectively, kabat numbering). Cell free reactions were initiated by addition of plasmid DNA and incubated at 30° C. for 16 h in 100×10 mm petri dishes containing 10 mL.

The anti-CD74 cell free reactions were clarified by centrifugation at 10,000 rpm's for 30 minutes. The clarified supernatant was applied to Protein A MabSelect SuRe (GE Healthcare) with standard wash and low pH elution. Impurities such as aggregates were removed via preparative SEC (Sepax SRT-10C) equilibrated in 50 mM sodium phosphate, 200 mM arginine, pH 6.5. Final formulation of the sample was done in Dulbecco's Phosphate Buffered Saline (1×DPBS).

Antibodies prepared having non-natural amino acids at positions heavy chain residues 404, 241, and 222, according to the EU number scheme, and at light chain residue 7, according to the Kabat or Chothia numbering scheme. One antibody comprised residue (56), above, at position 404, and four antibodies comprised residue (30), above, at each of postions 404, 241, 222 (heavy chain) and 7 (light chain). Each antibody was expressed at a total yield of at least 400 mg/L as shown in FIG. 2A, and intact IgG were detected by SDS-PAGE as shown in FIG. 2B.

Production of Antibody-PEG$_4$-Maytansine Conjugate

Purified anti-CD74 IgG containing modified amino acid residue 30 (i.e. para-azido-methyl-L-phenylalanine, or pAMF) at EU position 404 in its heavy chains was obtained according to Example 2. The anti-CD74 IgG was conjugated to a hemiasterlin, using a strained cyclooctyne reagent to yield Conjugate A.

In brief, DBCO-val-cit-pAB-hemiasterlin according to the following:

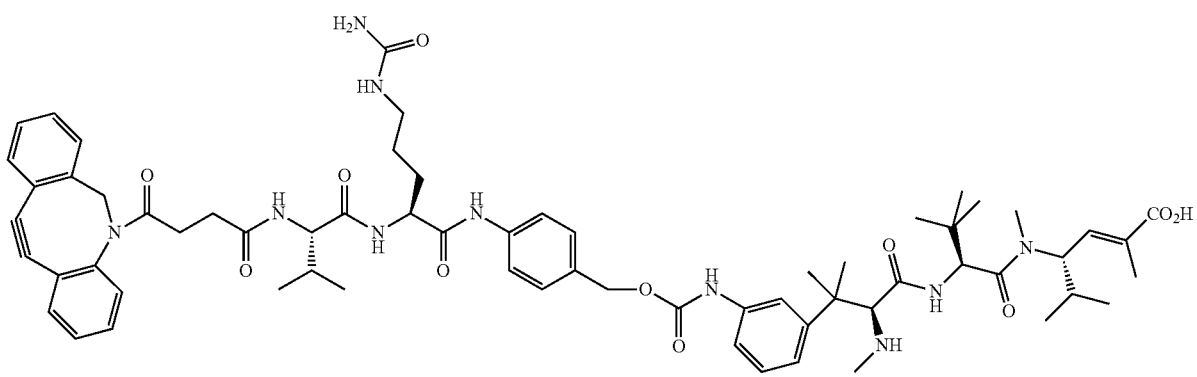 [SMILES: CN[C@H](C(=O)N[C@H](C(=O)N(C)[C@H](/C=C(\C)C(=O)O)C(C)C)C(C)(C)C)C(C)(C)c1cccc(NC(=O)OCc2ccc(NC(=O)[C@H](CCCNC(N)=O)NC(=O)[C@@H](NC(=O)CCC(=O)N3Cc4ccccc4C#Cc4ccccc43)C(C)C)cc2)c1]

was dissolved in DMSO to a final concentration of 5 mM. The compound was added to 1 mg/mL purified protein in PBS at a drug to antibody molar ratio of 12 to 1. The reaction mixture was incubated at RT (20° C.) for 17 hours. Excess free drug was removed by Zeba plate (Thermo Scientific) equilibrated in PBS.

DAR analysis was done by MALDI-TOF (Broker AutoFlex Speed). The conjugated protein was reduced for 10 min at 37° C. with 10 mM TCEP in water and diluted to a final concentration of 50 μg/mL in 30% acetonitrile, 0.1% trifluoroacetic acid. Samples were combined 1:1 with S-DHB MALDI matrix (50 mg/mL in 50% acetonitrile, 0.1% trifluoroacetic acid) and 1 uL was applied to the MALDI target and dried under vacuum. Each MALDI spectra was accumulated for 5000 shots at full laser power in linear mode and the final DAR analysis was calculated by comparing the relative peak heights for conjugated and unconjugated masses for both the heavy and light chains.

By peak intensity, MALDI-TOF showed a drug to antibody ratio (DAR) of 1.88. Conjugate A, as two regioisomers:

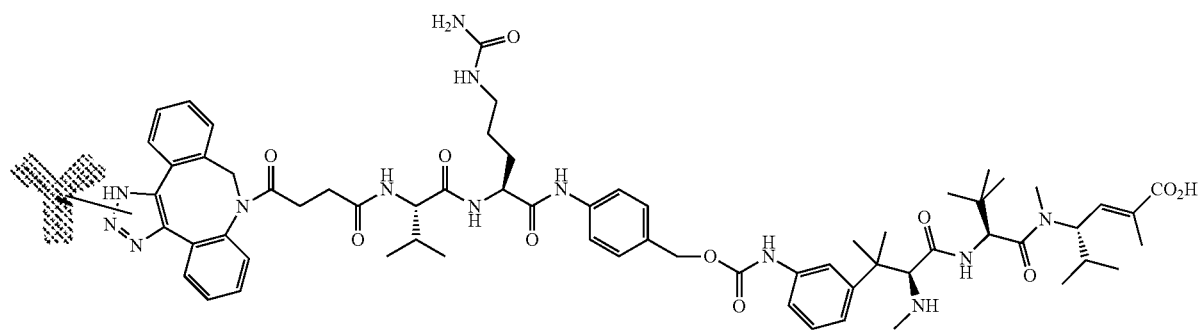

Example 2a

Tumor Cell Line Assay

SUMMARY

The two diastereomers of Compound 1, [S,S,S] and [R,S,S] were assayed against breast cancer cell lines expressing Her2, CD74 expressing and non-expressing cell lines, and CD30 expressing and non-expressing cell lines. Her2 expressing cell lines included SKBR3, MDA-MB-453, and MDA-MB-468 which are respectively high-, medium-, and low-Her2 expressing. CD74 expressing and non-expressing cell lines included SU-DHL6 and OPM2, which are respectively CD74 expressing and non-expressing. CD30 expressing and non-expressing cell lines included L540 and Raji cells, which are respectively CD30 expressing and non-expressing.

[S,S,S] Compound 1 was found to be 20-fold more potent (average $IC_{50}$ ca 1 nM) against a panel of these tumor cell lines when compared to [R,S,S] Compound 1.

Methods

Cytotoxicity effects of test compounds were evaluated with a cell proliferation assay. Adherent cancer cell lines (SKBR3, MDA-MB435, MDA-MB-468, HCT116, HT29, Skcol, and MDA-MB-453) were obtained from ATCC and maintained in high glucose DMEM/F12 (50/50) medium (Cellgro-Mediatech; Manassas, Va.) supplemented with 10% heat-inactivated fetal bovine serum (Hyclone; Thermo Scientific; Waltham, Mass.), 2 mM glutamax (Invitrogen; Carlsbad, Calif.) and 1× Pencillin/streptomycin (Cellgro-Mediatech; Manassas, Va.). Suspension cell lines (SU-DHL-6 and OPM-2) were obtained from ATCC and maintained in high glucose RPMI medium (Cellgro-Mediatech; Manassas, Va.) supplemented with 20% heat-inactivated fetal bovine serum (Hyclone; Thermo Scientific; Waltham, Mass.), 2 mM glutamax (Invitrogen; Carlsbad, Calif.) and 1× Pencillin/streptomycin (Cellgro-Mediatech; Manassas, Va.).

For adherent cells, a total of 1000 cells in a volume of 40 µL were seeded in a 96-well half area flat bottom white polystyrene plate the day before the assay. For suspension cells, a total of 20000 cells in a volume of 40 µL were seeded in a 96-well half area flat bottom white polystyrene plate on the day of assay.

Testing compounds were formulated at 2× concentration in culture medium and filtered through MultiScreen HTS 96-Well Filter Plates (Millipore; Billerica, Mass.). Filter sterilized compounds were serial diluted in culture medium and 40 µL of the compounds were added into treatment wells. For adherent cells, plates were cultured at 37° C. in a $CO_2$ incubator for 96 hours. For suspension cells, the incubation time was 72 hours. For cell viability measurements, 80 µL of Cell Titer-Glo® reagent (Promega Corp.; Madison, Wis.) was added into each well, and plates processed as per product instructions.

Relative luminescence was measured on an ENVISION® plate reader (Perkin-Elmer; Waltham, Mass.). Relative luminescence readings were converted to percent viability using untreated cells as controls. Data was fitted with non-linear regression analysis, using log(inhibitor) vs. response, variable slope, 4 parameter fit equation using GraphPad Prism (GraphPad v 5.00, Software; San Diego, Calif.). Data was expressed as percent relative cell viability vs. dose of compounds in nM. Cell killing IC50 calculated by Prism was used to evaluate the potency of each compound on each cell line.

Results

For all the cancer cell lines tested, [S,S,S] Compound 1 (cell killing IC50 ranged from 0.74 nM to 9.18 nM) was found to be 10 to 20-fold more potent when compared to [R,S,S] Compound 1 (cell killing IC50 ranged from 12.21 nM to 91.53 nM).

Results for trastuzumab conjugates are provided in FIG. 1 and Table 1. Results for hemiasterlin derivatives [S,S,S] and [R,S,S] Compound 1, are provided in FIGS. 2a-c and Table 2.

TABLE 1

Tumor Cell Line Assay with Trastuzumab Conjugates

| Test Conjugate | IC50 (nM) | Span (%) |
| --- | --- | --- |
| Trastuzumab | 10.0 | 66 |
| Trastuzumab F404 [S,S,S] Compound 1, Conjugate | 0.2 | 91 |
| Trastuzumab heavy chain F404 racemic [R/S,S,S] Compound 1 conjugate | 0.4 | 87 |
| Trastuzumab light chain S7 racemic [R/S,S,S] Compound 1 conjugate | 0.4 | 86 |
| Trastuzumab heavy chain F404 MMAF Conjugate | 0.1 | 88 |

TABLE 2

Tumor Cell Line Assay with Hemiasterlin Derivatives

| | | | Cell Killing IC50 (nM) | |
|---|---|---|---|---|
| Origin | Cell Line | Markers | [S,S,S] Compound 1 | [R,S,S] Compound 1 |
| Breast | SKBR3 | Her2 High | 1.42 | 19.97 |
| | MDA-MB-453 | Her2 Medium | 1.80 | 27.63 |
| | MDA-MB-468 | Her2 Low | 0.74 | 16.71 |
| Colon | HCT116 | EpCAM High | 3.18 | 62.18 |
| | HT29 | EpCAM Medium | 9.18 | 91.53 |
| | Skco1 | EpCAM Low | 3.59 | 46.88 |
| Melanoma | MDA-MB-435 | — | 2.29 | 33.74 |
| Multiple Myeloma | OPM-2 | CD74 Negative | 2.42 | 14.35 |
| Lymphoma | SU-DHL-6 | CD74 Positive | 1.42 | 12.21 |

Example 2b

Tumor Cell Line Assay

Cytotoxicity effects of test compounds on target positive and target negative cells were measured with a cell proliferation assay. Tumor cell lines were obtained from American Type Culture Collection (ATCC) and maintained in Ham's F-12: high glucose DMEM (50:50) glucose medium supplemented with 10% heat-inactivated fetal bovine serum, 1% Penicillin/Streptomcin and 2 mmol/L L-glutamax. Target positive and negative cells (a total of 625 cells per well) were seeded in a volume of 25 μL in a 384-well flat bottom white polystyrene plate. The cells were allowed to adhere overnight at 37° C. in a $CO_2$ incubator. ADC variants were formulated at 2× concentration in DMEM/F12 medium and filtered through MultiScreen HTS 96-Well Filter Plates. Filter sterilized ADCs were serial diluted (1:3) and 25 μL of diluted samples were added into each treatment wells. Plates were then cultured at 37° C. in a $CO_2$ incubator for 120 hrs. For cell viability measurement, 30 μL of Cell Titer-Glo® reagent (Promega Corp) was added into each well, and plates processed as per product instructions. Relative luminescence was measured on an ENVISION® plate reader (Perkin-Elmer; Waltham, Mass.). Relative luminescence readings were converted to % viability using untreated cells as controls. Data was fitted with non-linear regression analysis, using log(inhibitor) vs. response, variable slope, 4 parameter fit equation using GraphPad Prism (GraphPad v 5.00, Software; San Diego, Calif.). Data was expressed as % relative cell viability vs. dose of ADC in nM.

Results

TABLE 3

Tumor Cell Line Assay with Hemiasterlin Derivatives

| | Target Positive Cell | | Target Negative Cell | |
|---|---|---|---|---|
| Compound | IC50 (nM) | Span (%) | IC50 (nM) | Span (%) |
| 1a | 2.2 | =90 | 6.8 | =88 |
| 101a | 222 | 93 | 2011 | 110 |
| 110a | 26 | 93 | 337 | 90 |
| 109a | 661 | 92 | 2440 | 95 |
| 111a | 65 | 92 | 717 | 91 |

TABLE 4

Tumor Cell Line Assay with Antibody Conjugates

| | Target Positive Cell | | Target Negative Cell | |
|---|---|---|---|---|
| Conjugate | IC50 (nM) | Span (%) | IC50 (nM) | Span (%) |
| Antibody HC-Y180/F404-110a | 0.016 | 74 | IA | IA |
| Antibody HC-Y180/F404-109a | 0.039 | 77 | IA | IA |
| Antibody HC-Y180/F404-111a | IA | IA | IA | IA |
| Antibody HC-Y180/F404-101a | 0.11 | 73 | IA | IA |

IA means not active as tested.

Example 2c

Cell Binding and Cell Killing

Conjugate A was evaluated for the ability to bind and kill cells expressing CD74 by the methods below. Cell lines tested included B-lymphoma, multiple myeloma, and leukemia cells. Controls included unconjugated anti-CD74 antibody.

Cell Binding Assay

Cell lines were maintained in RPMI, high glucose (Cellgro-Mediatech; Manassas, Va.) supplemented with 20% heat-inactivated fetal bovine serum (Hyclone; Thermo Scientific; Waltham, Mass.), 2 mM glutamax (Invitrogen; Carlsbad, Calif.) and 1× Pencillin/streptomycin (Cellgro-Mediatech; Manassas, Va.). Cells were harvested and re-suspended in FACS buffer (DPBS buffer supplemented with 1% bovine serum albumin). A total of 200,000 cells per well were incubated on ice with serial dilutions of anti-CD74 lead SP7919 without conjugation for 60 minutes. Cells were washed twice with ice-cold FACS buffer and incubated with 5 ug/ml Alexa 647 labeled donkey anti-human IgG antibody (Jackson Immune-Research) on ice for another 60 mins. Unstained cells and cells stained with secondary antibody alone were used as controls. Samples were then washed twice using FACS buffer and analyzed using a BD FACS Canto system. Mean fluorescence intensities were fitted using non-linear regression analysis with one site specific binding equation on GraphPad Prism. Data was expressed as geometric mean fluorescent intensity vs. antibody concentration in nM.

Cell Killing Assay

Cytotoxicity effects of the free drug linkers and conjugates were measured with a cell proliferation assay. A total of 12500 cells in a volume of 25 μl were seeded in a 384-well flat bottom white polystyrene plate on the day of assay. Free drug-linkers and conjugates were formulated at 2× starting concentration (1000 nM for free drug linkers and 100 nM for ADCs) in RPMI medium and filtered through MultiScreen HTS 96-Well Filter Plates (Millipore). Filter sterilized conjugated leads were serial diluted (1:3) under sterile conditions and added into treatment wells. Plates were cultured at 37° C. in a $CO_2$ incubator for 72 hrs. For cell viability measurement, 30 μl of Cell Titer-Glo® reagent (Promega Corp.) was added into each well, and plates processed as per product instructions. Relative luminescence was measured on an ENVISION® plate reader (Perkin-Elmer; Waltham, Mass.). Relative luminescence readings were converted to % viability using untreated cells as controls. Data was fitted with non-linear regression analysis, using log(inhibitor) vs. response, variable slope, 4 parameter fit equation using GraphPad Prism. Data was expressed as % relative cell viability vs. dose of free drug-linker or conjugate in nM.

Conjugate A was evaluated for the ability to bind and kill cells expressing CD74. Cell lines tested included B-lymphoma, multiple myeloma, and leukemia cells. Controls included unconjugated anti-CD74 antibody. The results are summarized in the following table:

| Disease | Cell Lines Tested | Cell Binding anti-CD74 | | Cell Killing Activity Conjugate A | |
|---|---|---|---|---|---|
| | | Bmax | Kd (nM) | IC50 (nM) | Span (%) |
| B-Lymphoma | RPMI-6666 (HL) | 3879 | 2.3 | 0.9 | 84 |
| | SU-DHL-6 (NHL) | 1565 | 2.0 | 0.3 | 97 |
| Multiple Myeloma | ARD (MM) | 190 | 2.6 | 26.0 | 74 |
| | ARP (MM) | | | 7.6 | 87 |
| | RPMI-8226 (MM) | 119 | 3.6 | 17.0 | 43 |
| | OPM-2 (MM) | NB | NB | NK | NK |
| Leukemia | BDCM (AML) | 3059 | 4.5 | 1.1 | 89 |
| | SUP-B15 (ALL) | 680 | 3.5 | 2.8 | 68 |
| | JVM-13 (CLL) | 447 | 2.5 | 0.9 | 54 |
| | K562 (CML) | NB | NB | NK | NK |

While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A compound according to Formula 1000:

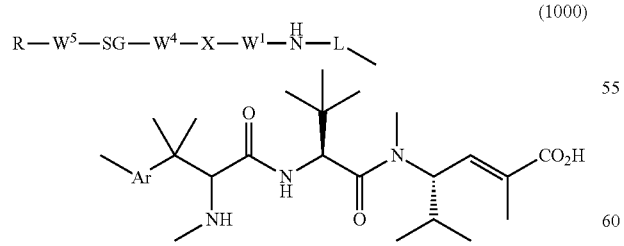

(1000)

or a pharmaceutically acceptable salt, stereoisomer, or tautomer thereof, wherein:

Ar is a divalent six-membered, substituted or unsubstituted, monocyclic aryl; a divalent five- or six-membered, substituted or unsubstituted, monocyclic heteroaryl; a divalent nine- or ten-membered, substituted or unsubstituted, fused bicyclic aryl; or a divalent eight-, nine- or ten-membered, substituted or unsubstituted, fused bicyclic heteroaryl;

L is absent or —$CH_2$—;

X is

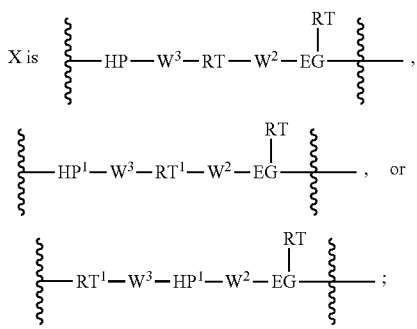

$W^1$, $W^2$, $W^3$, $W^4$, $W^5$ are each independently, a single bond, absent, or a divalent attaching group;

EG is;

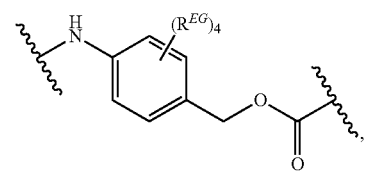

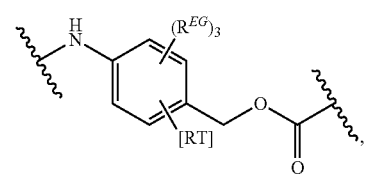

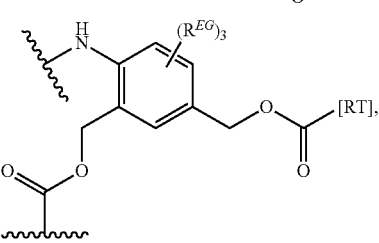

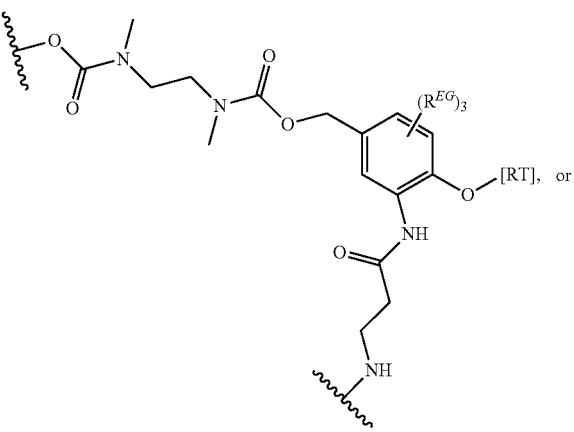

-continued

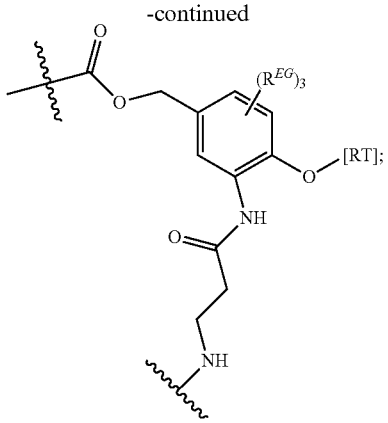

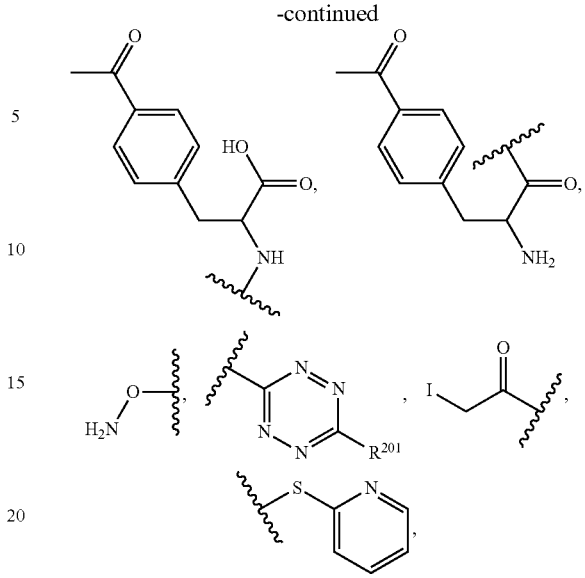

wherein each $R^{EG}$ is independently selected from the group consisting of hydrogen, alkyl, biphenyl, —$CF_3$, —$NO_2$, —CN, fluoro, bromo, chloro, alkoxyl, alkylamino, dialkylamino, alkyl-C(O)O—, alkylamino-C(O)— and dialkylaminoC(O)-;

each RT is a release trigger group, in the backbone of Formula 1000 or bonded to EG, wherein each RT is optional;

$RT^1$ is a release trigger group, or a cleavable linker, or $RT^1$ is absent;

—$N_3$, or —SH;

wherein $R^{201}$ is lower alkyl.

2. The compound of claim 1 according to Formula I:

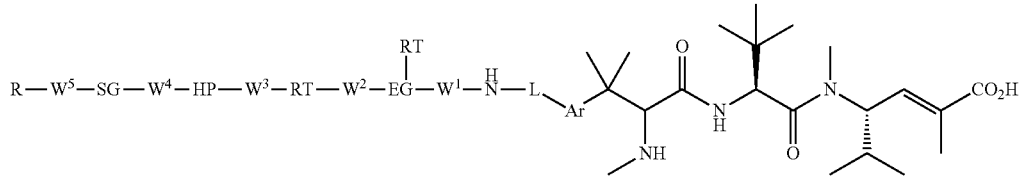

(I)

HP is a single bond, absent, or a divalent hydrophilic group;

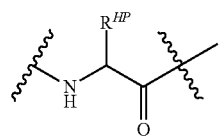

$HP^1$ is a single bond, absent, a divalent hydrophilic group, or where $R^{HP}$ is a monovalent hydrophilic group;

SG is a single bond, absent, or a divalent spacer group; and

R is:

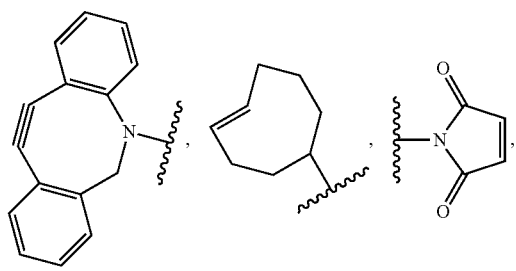

or a pharmaceutically acceptable salt, or tautomer thereof.

3. The compound of claim 2, wherein one RT is optional and RT comprises a natural or non-natural amino acid or a sugar; or a pharmaceutically acceptable salt, or tautomer thereof.

4. The compound of claim 2, wherein one RT is optional and RT is:

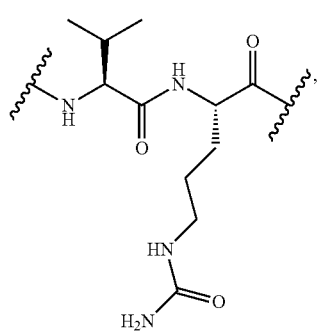

-continued

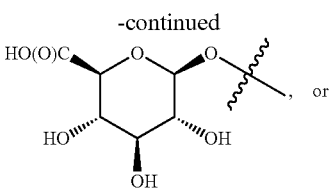

, or

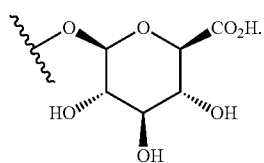

or a pharmaceutically acceptable salt, or tautomer thereof.

5. The compound of claim 4, wherein SG comprises $C_1$—$C_{10}$ alkylene, —C(O)—, or a combination thereof; or a pharmaceutically acceptable salt, or tautomer thereof.

6. The compound of claim 2, wherein SG is:

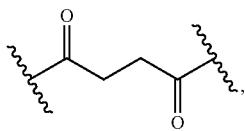

,

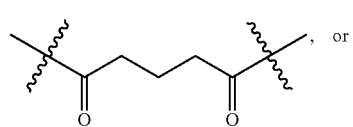

, or

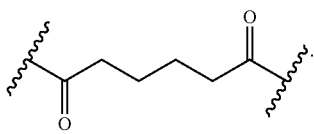

or a pharmaceutically acceptable salt, or tautomer thereof.

7. The compound of claim 2, wherein HP is:

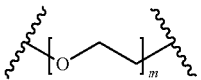

wherein m is an integer selected from 1 to 12; or a pharmaceutically acceptable salt, or tautomer thereof.

8. The compound of claim 2 where $W^1$, $W^2$, $W^3$, $W^4$ and $W^5$ are independently absent or a bond; or a pharmaceutically acceptable salt, or tautomer thereof.

9. The compound of claim 2 wherein Ar is a divalent six-membered, substituted or unsubstituted, monocyclic aryl or a divalent six-membered, substituted or unsubstituted, monocyclic heteroaryl; or a pharmaceutically acceptable salt, or tautomer thereof.

10. The compound of claim 1 according to Formula 1001 or 1002:

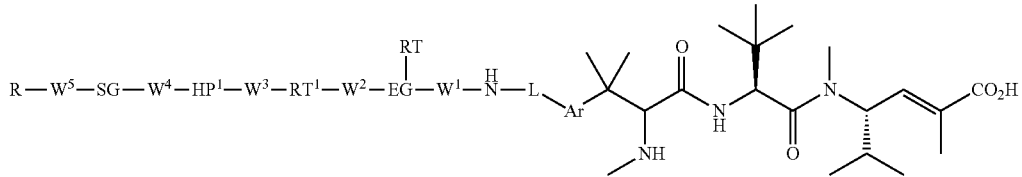
(1001)

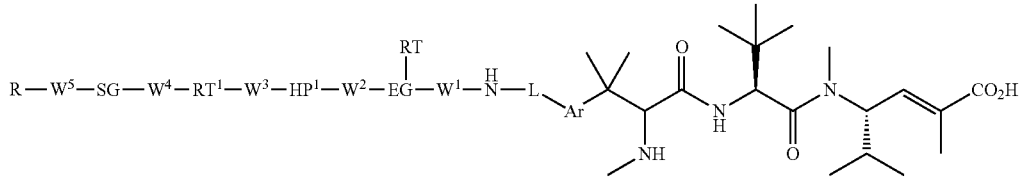
(1002)

or a pharmaceutically acceptable salt, or tautomer thereof, wherein $RT^1$ is a release trigger group or a cleavable linker; and RT is optional.

11. The compound of claim 1, wherein $RT^1$ is absent;

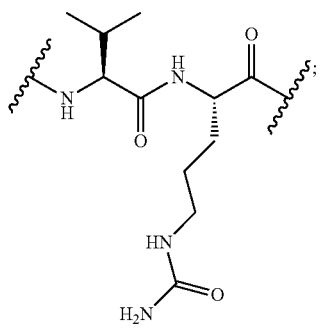 [SMILES: *N[C@H](C(=O)N[C@@H](CCCNC(N)=O)C(*)=O)C(C)C]

valine-alanine; valine-glutamic acid; alanine-phenylalanine; phenylalanine-lysine; phenylalanine-homolysine; glycine-glycine-glycine;

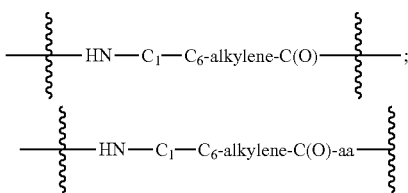

where aa is a natural or non-natural amino acid residue; or

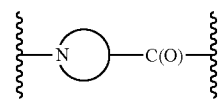

where the ring is a 4-7 membered heterocyclic ring comprising 3-6 carbon atoms; or a pharmaceutically acceptable salt, or tautomer thereof.

12. The compound of claim 1, wherein $R^{201}$ is methyl, ethyl, or propyl; or a pharmaceutically acceptable salt, or tautomer thereof.

13. The compound of claim 1, wherein $W^1$, $W^2$, $W^3$, $W^4$, and $W^5$ are each independently a single bond, absent, or comprise C(O)—, —O—, —C(O)NH—, —C(O)NH-alkyl—, —OC(O)NH—, —SC(O)NH—, —NH—, —NH-alkyl—, —N(CH$_3$)CH$_2$CH$_2$N(CH$_3$)—, —S—, —S—S—, —OCH$_2$CH$_2$O—, or a combination thereof; or a pharmaceutically acceptable salt, or tautomer thereof.

14. The compound of claim 1, wherein Ar is a divalent nine-membered, substituted or unsubstituted, fused bicyclic heteroaryl; or a pharmaceutically acceptable salt, or tautomer thereof.

15. The compound of claim 1, wherein L is absent; or a pharmaceutically acceptable salt, or tautomer thereof.

16. The compound of claim 1, according to any of the following Formulas:

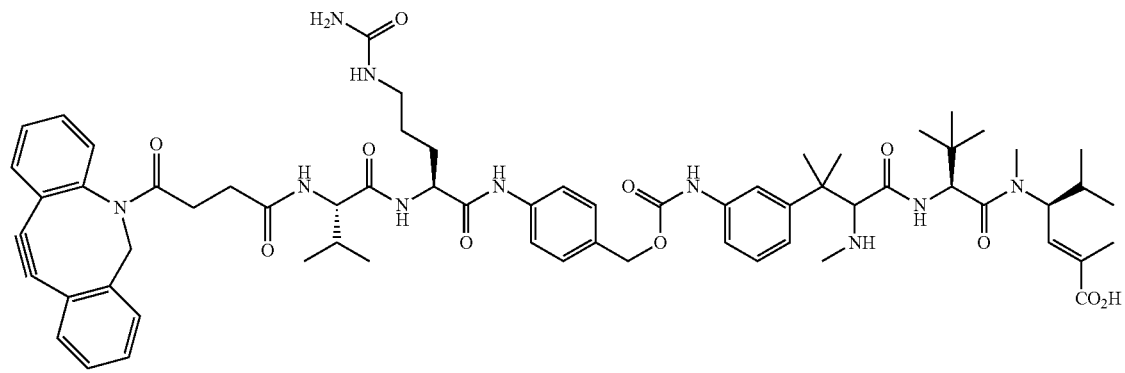

(101)

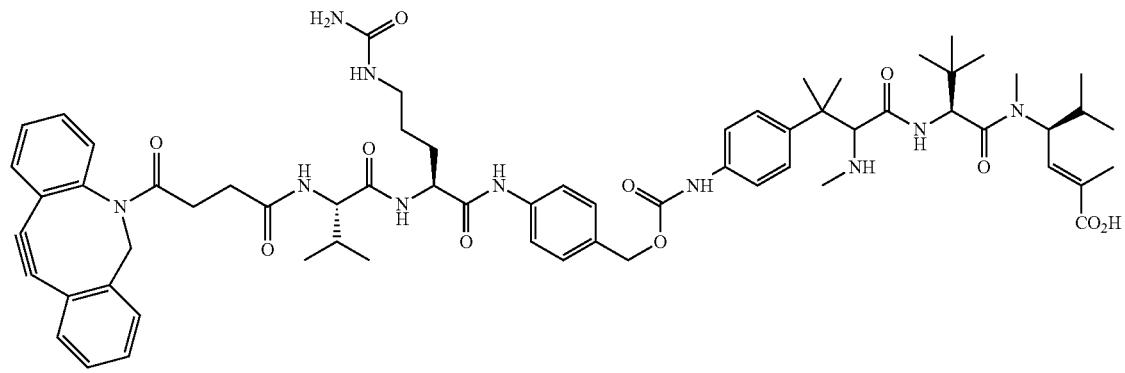

(102)

(103)
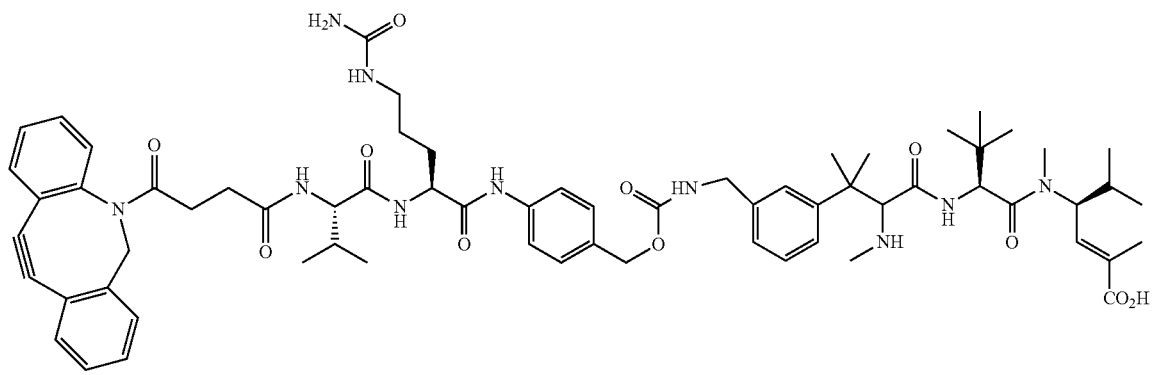
(104)
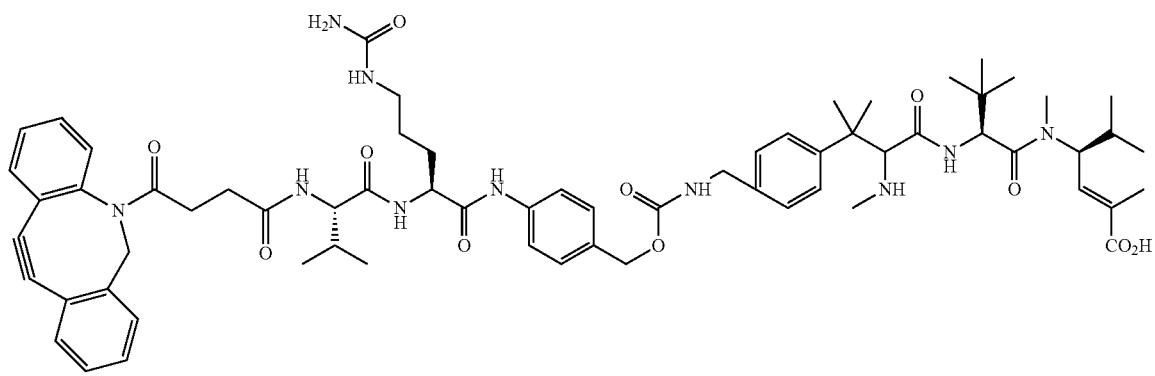
(105)
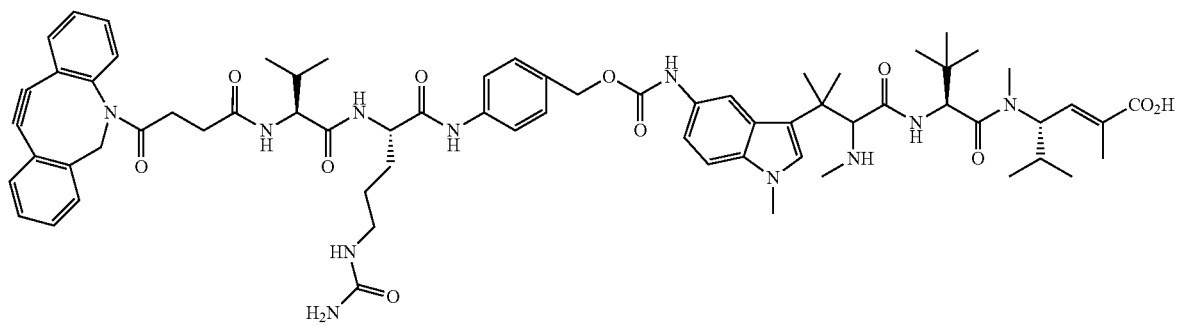
(106)
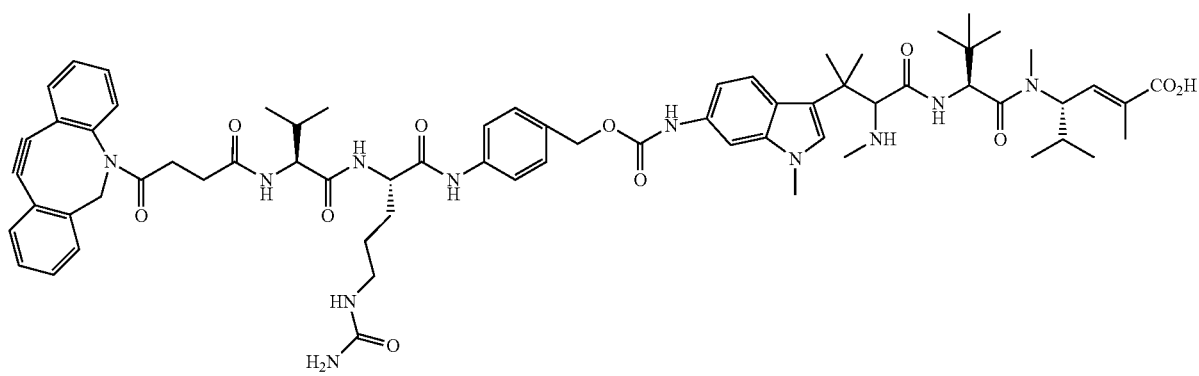

(107)
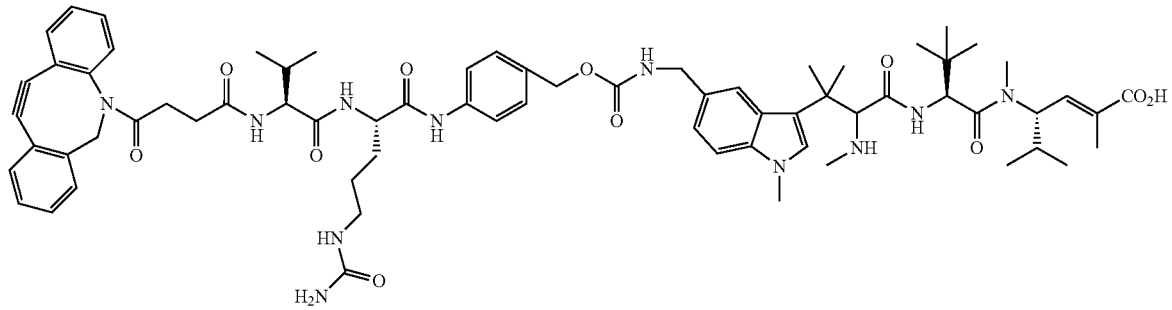
(108)
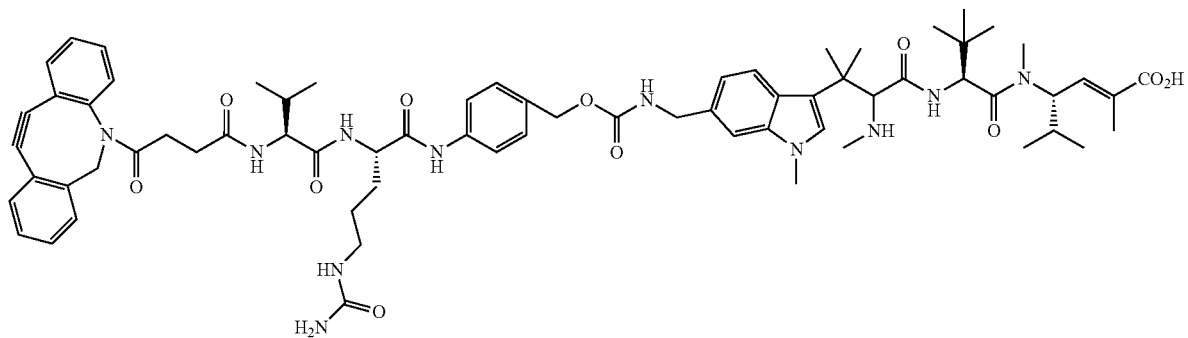
(109)
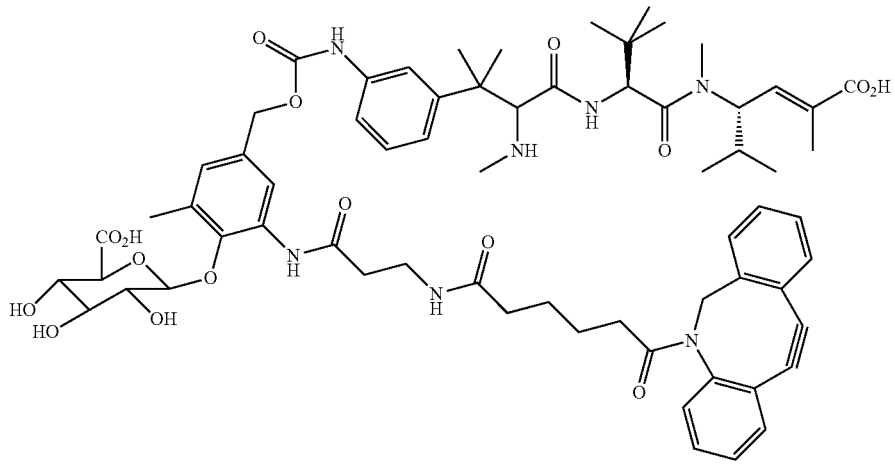
and
(110)
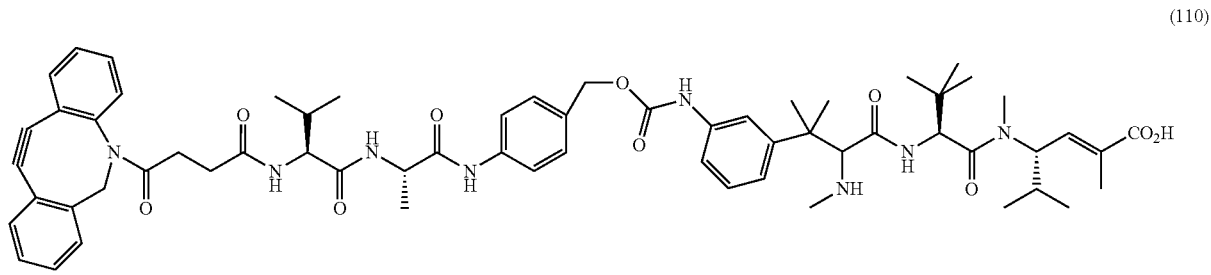
or a pharmaceutically acceptable salt, or tautomer thereof.